(12) United States Patent
D'Auria et al.

(10) Patent No.: US 11,931,625 B2
(45) Date of Patent: *Mar. 19, 2024

(54) USER INTERFACES FOR GROUP WORKOUTS

(71) Applicant: Apple Inc., Cupertino, CA (US)

(72) Inventors: Anthony D'Auria, San Francisco, CA (US); Jae Woo Chang, Cupertino, CA (US); Edward Chao, Palo Alto, CA (US); Nathan De Vries, Alameda, CA (US); Michael D. Ford, Portola Valley, CA (US); Colin G. McKinstry, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/952,027

(22) Filed: Sep. 23, 2022

(65) Prior Publication Data

US 2023/0012755 A1 Jan. 19, 2023

Related U.S. Application Data

(63) Continuation of application No. 17/744,500, filed on May 13, 2022.

(Continued)

(51) Int. Cl.
*G06F 3/0482* (2013.01)
*A63B 24/00* (2006.01)
(Continued)

(52) U.S. Cl.
CPC ...... *A63B 24/0075* (2013.01); *A63B 71/0622* (2013.01); *G06F 3/0481* (2013.01); *G06F 3/04817* (2013.01); *G06F 3/0482* (2013.01); *G06F 3/04842* (2013.01); *G06F 3/1454* (2013.01); *H04N 7/15* (2013.01);
(Continued)

(58) Field of Classification Search
CPC ............ A63B 24/0075; A63B 71/0622; A63B 2024/0081; A63B 2071/0675; G06F 3/0481; G06F 3/04817; G06F 3/0482; G06F 3/04842; G06F 3/1454; H04N 7/15; H04N 7/155; H04L 67/141; G16H 40/63; G16H 40/67; G16H 30/20
See application file for complete search history.

(56) References Cited

U.S. PATENT DOCUMENTS 4,205,628 A 6/1980 Null
4,842,266 A 6/1989 Sweeney et al.
(Continued)

FOREIGN PATENT DOCUMENTS

AU 2011302438 A1 5/2013
CA 2815518 A1 5/2012
(Continued)

OTHER PUBLICATIONS

Applicant-Initiated Interview Summary received for U.S. Appl. No. 17/031,854, dated Jan. 24, 2023, 6 pages.
(Continued)

*Primary Examiner* — Jennifer N Welch
*Assistant Examiner* — Amy P Hoang
(74) *Attorney, Agent, or Firm* — DLA Piper LLP (US)

(57) ABSTRACT

The present disclosure generally relates to sharing workout content on electronic devices.

51 Claims, 57 Drawing Sheets

Related U.S. Application Data

(60) Provisional application No. 63/243,576, filed on Sep. 13, 2021, provisional application No. 63/189,085, filed on May 15, 2021.

(51) Int. Cl.

| | |
|---|---|
| *A63B 71/06* | (2006.01) |
| *G06F 3/0481* | (2022.01) |
| *G06F 3/04817* | (2022.01) |
| *G06F 3/04842* | (2022.01) |
| *G06F 3/14* | (2006.01) |
| *H04N 7/15* | (2006.01) |
| *H04L 67/141* | (2022.01) |

(52) U.S. Cl.
CPC ...... *H04N 7/155* (2013.01); *A63B 2024/0081* (2013.01); *A63B 2071/0675* (2013.01); *H04L 67/141* (2013.01)

(56) References Cited

U.S. PATENT DOCUMENTS

| | | |
|---|---|---|
| 5,349,962 A | 9/1994 | Lockard et al. |
| 5,423,863 A | 6/1995 | Felblinger et al. |
| 5,458,548 A | 10/1995 | Crossing et al. |
| 5,474,077 A | 12/1995 | Suga |
| 5,642,731 A | 7/1997 | Kehr |
| 5,685,723 A | 11/1997 | Ladin et al. |
| 5,730,141 A | 3/1998 | Fain et al. |
| 5,788,655 A | 8/1998 | Yoshimura et al. |
| 5,944,633 A | 8/1999 | Wittrock |
| 6,013,008 A | 1/2000 | Fukushima |
| 6,061,592 A | 5/2000 | Nigam |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,199,012 B1 | 3/2001 | Hasegawa |
| 6,244,988 B1 | 6/2001 | Delman |
| 6,302,789 B2 | 10/2001 | Harada et al. |
| 6,416,471 B1 | 7/2002 | Kumar et al. |
| 6,594,654 B1 | 7/2003 | Salam et al. |
| 6,603,477 B1 | 8/2003 | Tittle |
| 6,639,584 B1 | 10/2003 | Li |
| 6,662,023 B1 | 12/2003 | Helle |
| 6,705,972 B1 | 3/2004 | Takano et al. |
| 6,837,827 B1 | 1/2005 | Lee |
| 6,866,613 B1 | 3/2005 | Brown et al. |
| 6,912,694 B1 | 6/2005 | Harrison et al. |
| 7,020,514 B1 | 3/2006 | Wiesel |
| 7,128,693 B2 | 10/2006 | Brown et al. |
| 7,251,454 B2 | 7/2007 | White |
| 7,302,272 B2 | 11/2007 | Ackley |
| 7,302,650 B1 | 11/2007 | Allyn et al. |
| 7,662,065 B1 | 2/2010 | Kahn et al. |
| 7,695,406 B2 | 4/2010 | Waters |
| 7,739,148 B2 | 6/2010 | Suzuki et al. |
| 7,771,320 B2 | 8/2010 | Riley et al. |
| 7,773,460 B2 | 8/2010 | Holt |
| 7,870,013 B1 | 1/2011 | Allemann et al. |
| 7,970,827 B1 | 6/2011 | Cumberbatch et al. |
| 8,060,229 B2 | 11/2011 | Gupta et al. |
| 8,105,208 B2 | 1/2012 | Oleson et al. |
| 8,152,694 B2 | 4/2012 | Srinivasan et al. |
| 8,200,323 B2 | 6/2012 | Dibenedetto et al. |
| 8,321,006 B1 | 11/2012 | Snyder et al. |
| 8,341,557 B2 | 12/2012 | Pisula et al. |
| 8,462,997 B2 | 6/2013 | Soldan et al. |
| 8,467,770 B1 | 6/2013 | Ben |
| 8,475,339 B2 | 7/2013 | Hwang et al. |
| 8,496,563 B2 | 7/2013 | Komatsu et al. |
| 8,543,081 B2 | 9/2013 | Scott et al. |
| 8,566,403 B2 | 10/2013 | Pascal et al. |
| 8,595,798 B2 | 11/2013 | Anand et al. |
| 8,624,836 B1 | 1/2014 | Miller et al. |
| 8,666,361 B2 | 3/2014 | Chu et al. |
| 8,676,170 B2 | 3/2014 | Porrati et al. |
| 8,700,158 B2 | 4/2014 | Mass et al. |
| 8,768,648 B2 | 7/2014 | Panther et al. |
| 8,784,115 B1 | 7/2014 | Chuang |
| 8,784,271 B2 | 7/2014 | Brumback et al. |
| 8,825,445 B2 | 9/2014 | Hoffman et al. |
| 8,849,610 B2 | 9/2014 | Molettiere et al. |
| 8,934,963 B1 | 1/2015 | Farazi |
| 8,947,239 B1 | 2/2015 | Park |
| 8,948,819 B2 | 2/2015 | Yun et al. |
| 8,990,006 B1 | 3/2015 | Wallace et al. |
| 9,011,292 B2 | 4/2015 | Weast et al. |
| 9,020,538 B1 | 4/2015 | White et al. |
| 9,063,164 B1 | 6/2015 | Yuen et al. |
| 9,087,234 B2 | 7/2015 | Hoffman et al. |
| 9,125,566 B2 | 9/2015 | Libbus et al. |
| 9,148,483 B1 | 9/2015 | Molettiere et al. |
| 9,164,663 B1 | 10/2015 | Berard |
| 9,173,576 B2 | 11/2015 | Yuen et al. |
| 9,224,291 B2 | 12/2015 | Moll-carrillo et al. |
| 9,230,076 B2 | 1/2016 | King et al. |
| 9,338,242 B1 | 5/2016 | Suchland et al. |
| 9,449,365 B2 | 9/2016 | Roberts |
| 9,532,734 B2 | 1/2017 | Hoffman et al. |
| 9,557,881 B1 | 1/2017 | Jain et al. |
| 9,582,165 B2 | 2/2017 | Wilson et al. |
| 9,589,445 B2 | 3/2017 | White et al. |
| 9,600,178 B2 | 3/2017 | Yun et al. |
| 9,600,630 B2 | 3/2017 | Keegan et al. |
| 9,712,629 B2 | 7/2017 | Molettiere et al. |
| 9,723,381 B2 | 8/2017 | Swanson |
| 9,730,621 B2 | 8/2017 | Cohen et al. |
| 9,734,477 B2 | 8/2017 | Weast et al. |
| 9,798,443 B1 | 10/2017 | Gray |
| 9,800,525 B1 | 10/2017 | Lerner et al. |
| 9,813,642 B1 | 11/2017 | Chen et al. |
| 9,817,481 B2 | 11/2017 | Pantelopoulos et al. |
| 9,854,653 B1 | 12/2017 | Ackmann et al. |
| 9,880,805 B1 | 1/2018 | Guralnick |
| 9,904,906 B2 | 2/2018 | Kim et al. |
| 9,910,571 B2 | 3/2018 | Chen et al. |
| 9,931,539 B1 | 4/2018 | De Pablos et al. |
| 9,940,682 B2 | 4/2018 | Hoffman et al. |
| 10,019,136 B1 | 7/2018 | Ozog |
| 10,051,103 B1 | 8/2018 | Gordon et al. |
| 10,056,006 B1 | 8/2018 | Hsu-hoffman et al. |
| 10,220,258 B2 | 3/2019 | Gu et al. |
| 10,226,195 B2 | 3/2019 | Briante et al. |
| 10,270,898 B2 | 4/2019 | Soli et al. |
| 10,275,116 B2 | 4/2019 | Decker et al. |
| 10,300,334 B1 | 5/2019 | Chuang |
| 10,304,347 B2 | 5/2019 | Wilson et al. |
| 10,339,830 B2 | 7/2019 | Han et al. |
| 10,398,381 B1 | 9/2019 | Heneghan et al. |
| 10,425,284 B2 | 9/2019 | Dellinger et al. |
| 10,489,508 B2 | 11/2019 | Zhai et al. |
| 10,500,441 B2 | 12/2019 | Lagree |
| 10,639,521 B2 | 5/2020 | Foley et al. |
| 10,736,543 B2 | 8/2020 | Chen et al. |
| 10,777,314 B1 | 9/2020 | Williams et al. |
| 10,873,786 B2 | 12/2020 | Folse et al. |
| 10,978,195 B2 | 4/2021 | Blahnik et al. |
| 11,103,161 B2 | 8/2021 | Williams et al. |
| 11,107,569 B1 | 8/2021 | Devoto |
| 11,152,100 B2 | 10/2021 | Crowley et al. |
| 11,202,598 B2 | 12/2021 | Soli et al. |
| 11,209,957 B2 | 12/2021 | Dryer et al. |
| 11,216,119 B2 | 1/2022 | De Vries et al. |
| 11,317,833 B2 | 5/2022 | Williams et al. |
| 11,446,548 B2 | 9/2022 | Devine et al. |
| 11,452,915 B2 | 9/2022 | Devine et al. |
| 2001/0031622 A1 | 10/2001 | Kivela et al. |
| 2001/0049470 A1 | 12/2001 | Mault et al. |
| 2002/0045960 A1 | 4/2002 | Phillips et al. |
| 2002/0068600 A1 | 6/2002 | Chihara et al. |
| 2002/0086774 A1 | 7/2002 | Warner |
| 2002/0118121 A1 | 8/2002 | Lehrman et al. |
| 2002/0142734 A1 | 10/2002 | Wickstead |

(56) References Cited

U.S. PATENT DOCUMENTS

| | | |
|---|---|---|
| 2003/0002391 A1 | 1/2003 | Biggs et al. |
| 2003/0023178 A1 | 1/2003 | Bischoff et al. |
| 2003/0064860 A1 | 4/2003 | Yamashita et al. |
| 2003/0134714 A1 | 7/2003 | Oishi et al. |
| 2003/0179229 A1 | 9/2003 | Van et al. |
| 2003/0181291 A1 | 9/2003 | Ogawa |
| 2003/0182628 A1 | 9/2003 | Lira |
| 2003/0216971 A1 | 11/2003 | Sick et al. |
| 2003/0226695 A1 | 12/2003 | Mault |
| 2004/0014567 A1 | 1/2004 | Mendel |
| 2004/0077462 A1 | 4/2004 | Brown et al. |
| 2004/0083474 A1 | 4/2004 | Mckinlay et al. |
| 2004/0128286 A1 | 7/2004 | Yasushi et al. |
| 2004/0168107 A1 | 8/2004 | Sharp et al. |
| 2004/0181771 A1 | 9/2004 | Anonsen et al. |
| 2004/0218472 A1 | 11/2004 | Narayanaswami et al. |
| 2004/0225966 A1 | 11/2004 | Besharat et al. |
| 2004/0236189 A1 | 11/2004 | Hawthorne et al. |
| 2004/0246607 A1 | 12/2004 | Watson et al. |
| 2005/0015803 A1 | 1/2005 | Macrae et al. |
| 2005/0066325 A1 | 3/2005 | Mori et al. |
| 2005/0075214 A1 | 4/2005 | Brown et al. |
| 2005/0079905 A1 | 4/2005 | Martens |
| 2005/0113650 A1 | 5/2005 | Pacione et al. |
| 2005/0124324 A1 | 6/2005 | Thomas et al. |
| 2005/0130802 A1 | 6/2005 | Kinnunen et al. |
| 2005/0139852 A1 | 6/2005 | Chen et al. |
| 2005/0156873 A1 | 7/2005 | Walter et al. |
| 2005/0165627 A1 | 7/2005 | Fotsch et al. |
| 2005/0172311 A1 | 8/2005 | Hjelt et al. |
| 2005/0197063 A1 | 9/2005 | White et al. |
| 2005/0202846 A1 | 9/2005 | Glass et al. |
| 2005/0215848 A1 | 9/2005 | Lorenzato et al. |
| 2005/0216867 A1 | 9/2005 | Marvit et al. |
| 2005/0228735 A1 | 10/2005 | Duquette |
| 2005/0272564 A1 | 12/2005 | Pyles et al. |
| 2005/0278757 A1 | 12/2005 | Grossman et al. |
| 2006/0010098 A1 | 1/2006 | Goodnow et al. |
| 2006/0010435 A1 | 1/2006 | Jhanwar et al. |
| 2006/0020174 A1 | 1/2006 | Matsumura et al. |
| 2006/0048076 A1 | 3/2006 | Vronay et al. |
| 2006/0052727 A1 | 3/2006 | Palestrant |
| 2006/0098109 A1 | 5/2006 | Ooki |
| 2006/0106741 A1 | 5/2006 | Janarthanan |
| 2006/0117014 A1 | 6/2006 | Qi |
| 2006/0122748 A1 | 6/2006 | Nou |
| 2006/0155578 A1 | 7/2006 | Eisenberger et al. |
| 2006/0160090 A1 | 7/2006 | Macina et al. |
| 2006/0184800 A1 | 8/2006 | Rosenberg |
| 2006/0217104 A1 | 9/2006 | Cho |
| 2006/0218500 A1 | 9/2006 | Sauve et al. |
| 2006/0240959 A1 | 10/2006 | Huang |
| 2006/0242259 A1 | 10/2006 | Vallabh et al. |
| 2006/0250524 A1 | 11/2006 | Roche |
| 2006/0271605 A1 | 11/2006 | Petruzzo |
| 2006/0277118 A1 | 12/2006 | Keohane et al. |
| 2006/0277469 A1 | 12/2006 | Chaudhri et al. |
| 2007/0016091 A1 | 1/2007 | Butt et al. |
| 2007/0021269 A1 | 1/2007 | Shum |
| 2007/0032733 A1 | 2/2007 | Burton |
| 2007/0033069 A1 | 2/2007 | Rao et al. |
| 2007/0056727 A1 | 3/2007 | Newman |
| 2007/0067733 A1 | 3/2007 | Moore et al. |
| 2007/0071256 A1 | 3/2007 | Ito |
| 2007/0101279 A1 | 5/2007 | Chaudhri et al. |
| 2007/0113726 A1 | 5/2007 | Oliver et al. |
| 2007/0135043 A1 | 6/2007 | Hayes et al. |
| 2007/0136093 A1 | 6/2007 | Rankin et al. |
| 2007/0143433 A1 | 6/2007 | Daigle |
| 2007/0143495 A1 | 6/2007 | Porat |
| 2007/0169614 A1 | 7/2007 | Sasaki et al. |
| 2007/0239801 A1 | 10/2007 | Lee et al. |
| 2007/0249949 A1 | 10/2007 | Hadley |
| 2007/0261537 A1 | 11/2007 | Eronen et al. |
| 2007/0271065 A1 | 11/2007 | Gupta et al. |
| 2007/0271340 A1 | 11/2007 | Goodman et al. |
| 2008/0005734 A1 | 1/2008 | Kendra et al. |
| 2008/0020803 A1 | 1/2008 | Rios et al. |
| 2008/0027586 A1 | 1/2008 | Hern et al. |
| 2008/0027673 A1 | 1/2008 | Trumm |
| 2008/0051919 A1 | 2/2008 | Sakai et al. |
| 2008/0052945 A1 | 3/2008 | Matas et al. |
| 2008/0058626 A1 | 3/2008 | Miyata et al. |
| 2008/0076637 A1 | 3/2008 | Gilley et al. |
| 2008/0077026 A1 | 3/2008 | Banet et al. |
| 2008/0077936 A1 | 3/2008 | Goel et al. |
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0122796 A1 | 5/2008 | Jobs et al. |
| 2008/0141135 A1 | 6/2008 | Mason et al. |
| 2008/0150731 A1 | 6/2008 | Laukkanen et al. |
| 2008/0161161 A1 | 7/2008 | Pipinich et al. |
| 2008/0161707 A1 | 7/2008 | Farringdon et al. |
| 2008/0183909 A1 | 7/2008 | Lim et al. |
| 2008/0200312 A1 | 8/2008 | Tagliabue |
| 2008/0229226 A1 | 9/2008 | Rowbottom et al. |
| 2008/0247519 A1 | 10/2008 | Abella et al. |
| 2008/0254767 A1 | 10/2008 | Jin |
| 2008/0259829 A1 | 10/2008 | Rosenblatt |
| 2008/0262946 A1 | 10/2008 | Wren |
| 2008/0278333 A1 | 11/2008 | Fennell et al. |
| 2008/0300110 A1 | 12/2008 | Smith et al. |
| 2009/0007017 A1 | 1/2009 | Anzures et al. |
| 2009/0012821 A1 | 1/2009 | Besson et al. |
| 2009/0012988 A1 | 1/2009 | Brown |
| 2009/0047645 A1 | 2/2009 | Dibenedetto et al. |
| 2009/0054743 A1 | 2/2009 | Stewart |
| 2009/0060170 A1 | 3/2009 | Coughlan et al. |
| 2009/0070675 A1 | 3/2009 | Li |
| 2009/0075782 A1 | 3/2009 | Joubert et al. |
| 2009/0106685 A1 | 4/2009 | Care et al. |
| 2009/0113315 A1 | 4/2009 | Fisher et al. |
| 2009/0118100 A1 | 5/2009 | Oliver et al. |
| 2009/0144639 A1 | 6/2009 | Nims et al. |
| 2009/0149299 A1 | 6/2009 | Tchao et al. |
| 2009/0158167 A1 | 6/2009 | Wang et al. |
| 2009/0164567 A1 | 6/2009 | Hara |
| 2009/0170532 A1 | 7/2009 | Lee et al. |
| 2009/0192823 A1 | 7/2009 | Hawkins et al. |
| 2009/0195497 A1 | 8/2009 | Fitzgerald et al. |
| 2009/0198581 A1 | 8/2009 | Lidestri |
| 2009/0205041 A1 | 8/2009 | Michalske |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0222761 A1 | 9/2009 | Hayashi |
| 2009/0231960 A1 | 9/2009 | Hutcheson |
| 2009/0233771 A1 | 9/2009 | Quatrochi et al. |
| 2009/0249076 A1 | 10/2009 | Reed et al. |
| 2009/0253516 A1 | 10/2009 | Hartmann et al. |
| 2009/0259134 A1 | 10/2009 | Levine |
| 2009/0262088 A1 | 10/2009 | Moll-carrillo et al. |
| 2009/0268949 A1 | 10/2009 | Ueshima et al. |
| 2009/0276463 A1 | 11/2009 | Miller et al. |
| 2009/0287103 A1 | 11/2009 | Pillai |
| 2009/0291805 A1 | 11/2009 | Blum et al. |
| 2009/0292561 A1 | 11/2009 | Itoh |
| 2009/0300598 A1 | 12/2009 | Choi |
| 2009/0311993 A1 | 12/2009 | Horodezky |
| 2009/0313579 A1 | 12/2009 | Poulson et al. |
| 2009/0319243 A1 | 12/2009 | Suarez-rivera et al. |
| 2009/0319467 A1 | 12/2009 | Berg et al. |
| 2010/0030094 A1 | 2/2010 | Lundback |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0054519 A1 | 3/2010 | Mulvey et al. |
| 2010/0060586 A1 | 3/2010 | Pisula et al. |
| 2010/0062818 A1 | 3/2010 | Haughay et al. |
| 2010/0062905 A1 | 3/2010 | Rottler et al. |
| 2010/0063840 A1 | 3/2010 | Hoyme et al. |
| 2010/0064255 A1 | 3/2010 | Rottler et al. |
| 2010/0076331 A1 | 3/2010 | Chan et al. |

(56) References Cited

U.S. PATENT DOCUMENTS

| | | |
|---|---|---|
| 2010/0079291 A1 | 4/2010 | Kroll et al. |
| 2010/0103101 A1 | 4/2010 | Song et al. |
| 2010/0121700 A1 | 5/2010 | Wigder et al. |
| 2010/0125785 A1 | 5/2010 | Moore et al. |
| 2010/0130890 A1 | 5/2010 | Matsumura et al. |
| 2010/0137106 A1 | 6/2010 | Oshima et al. |
| 2010/0145209 A1 | 6/2010 | Lee et al. |
| 2010/0151908 A1 | 6/2010 | Skarby et al. |
| 2010/0151918 A1 | 6/2010 | Annambhotla et al. |
| 2010/0152600 A1 | 6/2010 | Droitcour et al. |
| 2010/0157742 A1 | 6/2010 | Relyea et al. |
| 2010/0179832 A1 | 7/2010 | Van et al. |
| 2010/0179833 A1 | 7/2010 | Roizen et al. |
| 2010/0184564 A1 | 7/2010 | Molyneux et al. |
| 2010/0190468 A1 | 7/2010 | Scott et al. |
| 2010/0194692 A1 | 8/2010 | Orr et al. |
| 2010/0197463 A1 | 8/2010 | Haughay et al. |
| 2010/0198453 A1 | 8/2010 | Dorogusker et al. |
| 2010/0202368 A1 | 8/2010 | Hans |
| 2010/0211685 A1 | 8/2010 | Mcdowall et al. |
| 2010/0222645 A1 | 9/2010 | Nadler et al. |
| 2010/0222859 A1 | 9/2010 | Govari et al. |
| 2010/0223563 A1 | 9/2010 | Green |
| 2010/0225962 A1 | 9/2010 | Okigami et al. |
| 2010/0226213 A1 | 9/2010 | Drugge |
| 2010/0231612 A1 | 9/2010 | Chaudhri et al. |
| 2010/0264097 A1 | 10/2010 | Sun et al. |
| 2010/0269055 A1* | 10/2010 | Daikeler ............ G06Q 10/10 715/757 |
| 2010/0269157 A1 | 10/2010 | Experton |
| 2010/0273610 A1 | 10/2010 | Johnson |
| 2010/0281374 A1 | 11/2010 | Schulz et al. |
| 2010/0292599 A1 | 11/2010 | Oleson et al. |
| 2010/0292600 A1 | 11/2010 | Dibenedetto et al. |
| 2010/0295795 A1 | 11/2010 | Wilairat |
| 2010/0298899 A1 | 11/2010 | Donnelly et al. |
| 2010/0299601 A1 | 11/2010 | Kaplan et al. |
| 2010/0305965 A1 | 12/2010 | Benjamin et al. |
| 2010/0309149 A1 | 12/2010 | Blumenberg et al. |
| 2010/0331145 A1 | 12/2010 | Lakovic et al. |
| 2011/0003665 A1 | 1/2011 | Burton et al. |
| 2011/0004835 A1 | 1/2011 | Yanchar et al. |
| 2011/0010195 A1 | 1/2011 | Cohn et al. |
| 2011/0016120 A1 | 1/2011 | Haughay et al. |
| 2011/0029750 A1 | 2/2011 | Jang et al. |
| 2011/0032105 A1 | 2/2011 | Hoffman et al. |
| 2011/0052005 A1 | 3/2011 | Selner |
| 2011/0059769 A1 | 3/2011 | Brunolli |
| 2011/0061010 A1 | 3/2011 | Wasko et al. |
| 2011/0066051 A1 | 3/2011 | Moon et al. |
| 2011/0071869 A1 | 3/2011 | Obrien et al. |
| 2011/0074699 A1 | 3/2011 | Marr et al. |
| 2011/0083111 A1 | 4/2011 | Forutanpour et al. |
| 2011/0087076 A1 | 4/2011 | Brynelsen et al. |
| 2011/0088086 A1 | 4/2011 | Swink et al. |
| 2011/0093728 A1 | 4/2011 | Das |
| 2011/0098928 A1 | 4/2011 | Hoffman et al. |
| 2011/0106553 A1 | 5/2011 | Tanaka et al. |
| 2011/0106954 A1 | 5/2011 | Chatterjee et al. |
| 2011/0112418 A1 | 5/2011 | Feild et al. |
| 2011/0113337 A1 | 5/2011 | Liu et al. |
| 2011/0113430 A1 | 5/2011 | Fuse |
| 2011/0125041 A1 | 5/2011 | Fischell et al. |
| 2011/0130168 A1 | 6/2011 | Vendrow et al. |
| 2011/0137678 A1 | 6/2011 | Williams |
| 2011/0137836 A1 | 6/2011 | Kuriyama et al. |
| 2011/0159469 A1 | 6/2011 | Hwang et al. |
| 2011/0167369 A1 | 7/2011 | Van |
| 2011/0193878 A1 | 8/2011 | Seo et al. |
| 2011/0197165 A1 | 8/2011 | Filippov et al. |
| 2011/0201911 A1 | 8/2011 | Johnson et al. |
| 2011/0202883 A1 | 8/2011 | Oh et al. |
| 2011/0205851 A1 | 8/2011 | Harris |
| 2011/0213276 A1 | 9/2011 | Sarussi et al. |
| 2011/0218765 A1 | 9/2011 | Rogers et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0234152 A1 | 9/2011 | Frossen et al. |
| 2011/0246509 A1 | 10/2011 | Migita et al. |
| 2011/0248992 A1 | 10/2011 | Van et al. |
| 2011/0257638 A1 | 10/2011 | Boukhny et al. |
| 2011/0261079 A1 | 10/2011 | Ingrassia et al. |
| 2011/0271223 A1 | 11/2011 | Cruz Moreno et al. |
| 2011/0275940 A1 | 11/2011 | Nims et al. |
| 2011/0296324 A1 | 12/2011 | Goossens et al. |
| 2011/0304685 A1 | 12/2011 | Khedouri et al. |
| 2011/0306389 A1 | 12/2011 | Nagayama |
| 2011/0307821 A1 | 12/2011 | Martens |
| 2011/0307880 A1 | 12/2011 | Hilerio et al. |
| 2012/0001922 A1 | 1/2012 | Escher et al. |
| 2012/0015778 A1 | 1/2012 | Lee et al. |
| 2012/0015779 A1 | 1/2012 | Powch et al. |
| 2012/0022884 A1 | 1/2012 | Chillemi |
| 2012/0030623 A1 | 2/2012 | Hoellwarth |
| 2012/0034897 A1 | 2/2012 | Kreitzer et al. |
| 2012/0036220 A1 | 2/2012 | Dare et al. |
| 2012/0036460 A1 | 2/2012 | Cieplinski et al. |
| 2012/0041767 A1 | 2/2012 | Hoffman et al. |
| 2012/0042039 A1 | 2/2012 | Mark |
| 2012/0044062 A1 | 2/2012 | Jersa et al. |
| 2012/0046784 A1 | 2/2012 | Malina et al. |
| 2012/0047447 A1 | 2/2012 | Haq |
| 2012/0059664 A1 | 3/2012 | Georgiev et al. |
| 2012/0059787 A1 | 3/2012 | Brown et al. |
| 2012/0060092 A1 | 3/2012 | Hill et al. |
| 2012/0066628 A1 | 3/2012 | Ens et al. |
| 2012/0071770 A1 | 3/2012 | Grey et al. |
| 2012/0079122 A1 | 3/2012 | Brown et al. |
| 2012/0083258 A1 | 4/2012 | Rabii et al. |
| 2012/0092379 A1 | 4/2012 | Tsuji et al. |
| 2012/0092383 A1 | 4/2012 | Hysek et al. |
| 2012/0105225 A1 | 5/2012 | Valtonen |
| 2012/0116550 A1 | 5/2012 | Hoffman et al. |
| 2012/0116684 A1 | 5/2012 | Ingrassia et al. |
| 2012/0117507 A1 | 5/2012 | Tseng et al. |
| 2012/0131441 A1 | 5/2012 | Jitkoff et al. |
| 2012/0143013 A1 | 6/2012 | Davis et al. |
| 2012/0143094 A1 | 6/2012 | Jallon |
| 2012/0150446 A1 | 6/2012 | Chang et al. |
| 2012/0150759 A1 | 6/2012 | Tarjan |
| 2012/0159380 A1 | 6/2012 | Kocienda et al. |
| 2012/0169608 A1 | 7/2012 | Forutanpour et al. |
| 2012/0169882 A1 | 7/2012 | Millar et al. |
| 2012/0171649 A1 | 7/2012 | Wander et al. |
| 2012/0179319 A1 | 7/2012 | Gilman et al. |
| 2012/0197523 A1 | 8/2012 | Kirsch |
| 2012/0209829 A1 | 8/2012 | Thomas et al. |
| 2012/0232414 A1 | 9/2012 | Mollicone et al. |
| 2012/0251079 A1 | 10/2012 | Meschter et al. |
| 2012/0253485 A1 | 10/2012 | Weast et al. |
| 2012/0253488 A1 | 10/2012 | Shaw et al. |
| 2012/0254263 A1 | 10/2012 | Hiestermann et al. |
| 2012/0258684 A1 | 10/2012 | Franz et al. |
| 2012/0274508 A1 | 11/2012 | Brown et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0302843 A1 | 11/2012 | Otsubo et al. |
| 2012/0310389 A1 | 12/2012 | Martin |
| 2012/0310674 A1 | 12/2012 | Faulkner et al. |
| 2012/0313776 A1 | 12/2012 | Utter, II |
| 2012/0317167 A1 | 12/2012 | Rahman et al. |
| 2012/0317430 A1 | 12/2012 | Rahman et al. |
| 2012/0323129 A1 | 12/2012 | Fujita et al. |
| 2012/0324390 A1 | 12/2012 | Tao et al. |
| 2012/0326873 A1 | 12/2012 | Utter, II |
| 2013/0013327 A1 | 1/2013 | Horseman |
| 2013/0017846 A1 | 1/2013 | Schoppe |
| 2013/0027341 A1 | 1/2013 | Mastandrea |
| 2013/0031490 A1 | 1/2013 | Joo et al. |
| 2013/0044072 A1 | 2/2013 | Kobayashi et al. |
| 2013/0050263 A1 | 2/2013 | Khoe et al. |
| 2013/0053990 A1 | 2/2013 | Ackland |

(56) References Cited

U.S. PATENT DOCUMENTS

| | | |
|---|---|---|
| 2013/0054150 A1 | 2/2013 | Sacks et al. |
| 2013/0054634 A1 | 2/2013 | Chakraborty et al. |
| 2013/0054720 A1 | 2/2013 | Kang et al. |
| 2013/0055147 A1 | 2/2013 | Vasudev et al. |
| 2013/0063383 A1 | 3/2013 | Anderssonreimer et al. |
| 2013/0067050 A1 | 3/2013 | Kotteri et al. |
| 2013/0069893 A1 | 3/2013 | Brinda et al. |
| 2013/0081083 A1 | 3/2013 | Yu et al. |
| 2013/0093715 A1 | 4/2013 | Marsden et al. |
| 2013/0103814 A1 | 4/2013 | Carrasco et al. |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0111579 A1 | 5/2013 | Newman et al. |
| 2013/0115583 A1 | 5/2013 | Gordon et al. |
| 2013/0117696 A1 | 5/2013 | Robertson et al. |
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0143512 A1 | 6/2013 | Hernandez et al. |
| 2013/0151285 A1 | 6/2013 | Mclaren et al. |
| 2013/0158367 A1 | 6/2013 | Pacione et al. |
| 2013/0184613 A1 | 7/2013 | Homsi et al. |
| 2013/0185097 A1 | 7/2013 | Saria et al. |
| 2013/0187923 A1 | 7/2013 | Yoshimoto et al. |
| 2013/0188322 A1 | 7/2013 | Lowe et al. |
| 2013/0190083 A1 | 7/2013 | Toy et al. |
| 2013/0197679 A1 | 8/2013 | Balakrishnan et al. |
| 2013/0198672 A1 | 8/2013 | Yoon et al. |
| 2013/0203475 A1 | 8/2013 | Shin et al. |
| 2013/0205210 A1 | 8/2013 | Jeon et al. |
| 2013/0215119 A1 | 8/2013 | Vanhoecke |
| 2013/0217253 A1 | 8/2013 | Golko et al. |
| 2013/0217979 A1 | 8/2013 | Blackadar et al. |
| 2013/0222270 A1 | 8/2013 | Winkler et al. |
| 2013/0223707 A1 | 8/2013 | Stephenson |
| 2013/0225118 A1 | 8/2013 | Jang et al. |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0238287 A1 | 9/2013 | Hoffman et al. |
| 2013/0239063 A1 | 9/2013 | Ubillos et al. |
| 2013/0245966 A1 | 9/2013 | Burroughs et al. |
| 2013/0254685 A1 | 9/2013 | Batraski et al. |
| 2013/0254705 A1 | 9/2013 | Mooring et al. |
| 2013/0260896 A1 | 10/2013 | Miura et al. |
| 2013/0262155 A1 | 10/2013 | Hinkamp |
| 2013/0263719 A1 | 10/2013 | Watterson et al. |
| 2013/0290013 A1 | 10/2013 | Forrester et al. |
| 2013/0295872 A1 | 11/2013 | Guday et al. |
| 2013/0304276 A1 | 11/2013 | Flies |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0325758 A1 | 12/2013 | Alphin et al. |
| 2013/0330694 A1 | 12/2013 | Watterson |
| 2013/0332286 A1 | 12/2013 | Medelius et al. |
| 2013/0332856 A1 | 12/2013 | Sanders et al. |
| 2013/0345978 A1 | 12/2013 | Lush et al. |
| 2014/0006769 A1 | 1/2014 | Chory et al. |
| 2014/0022183 A1 | 1/2014 | Ayoub et al. |
| 2014/0025737 A1 | 1/2014 | Kruglick |
| 2014/0035761 A1 | 2/2014 | Burton et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0059493 A1 | 2/2014 | Kim |
| 2014/0067096 A1 | 3/2014 | Aibara |
| 2014/0068520 A1 | 3/2014 | Missig et al. |
| 2014/0073298 A1 | 3/2014 | Rossmann |
| 2014/0074570 A1 | 3/2014 | Hope et al. |
| 2014/0075234 A1 | 3/2014 | Stekkelpak et al. |
| 2014/0081666 A1 | 3/2014 | Teller et al. |
| 2014/0082383 A1 | 3/2014 | De Cesare et al. |
| 2014/0082384 A1 | 3/2014 | De Cesare et al. |
| 2014/0089836 A1 | 3/2014 | Damani et al. |
| 2014/0107524 A1 | 4/2014 | Brull et al. |
| 2014/0108998 A1 | 4/2014 | Chaudhri et al. |
| 2014/0128021 A1 | 5/2014 | Walker et al. |
| 2014/0129255 A1 | 5/2014 | Woodson et al. |
| 2014/0135955 A1 | 5/2014 | Burroughs |
| 2014/0139637 A1 | 5/2014 | Mistry et al. |
| 2014/0143678 A1 | 5/2014 | Mistry et al. |
| 2014/0156292 A1 | 6/2014 | Kozicki et al. |
| 2014/0172864 A1 | 6/2014 | Shum |
| 2014/0176346 A1 | 6/2014 | Brumback et al. |
| 2014/0176475 A1 | 6/2014 | Myers et al. |
| 2014/0179272 A1 | 6/2014 | Zhang et al. |
| 2014/0180786 A1 | 6/2014 | Sullivan |
| 2014/0181205 A1 | 6/2014 | Sherrets et al. |
| 2014/0181558 A1 | 6/2014 | Taha et al. |
| 2014/0187314 A1 | 7/2014 | Perry et al. |
| 2014/0187323 A1 | 7/2014 | Perry |
| 2014/0189584 A1 | 7/2014 | Weng et al. |
| 2014/0195826 A1 | 7/2014 | Wojcik et al. |
| 2014/0200691 A1 | 7/2014 | Lee et al. |
| 2014/0208250 A1 | 7/2014 | Ording et al. |
| 2014/0213415 A1 | 7/2014 | Parker et al. |
| 2014/0218369 A1 | 8/2014 | Yuen et al. |
| 2014/0221790 A1 | 8/2014 | Pacione et al. |
| 2014/0228647 A1 | 8/2014 | Sakamoto et al. |
| 2014/0236459 A1 | 8/2014 | Boesch et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0245177 A1 | 8/2014 | Maklouf et al. |
| 2014/0250391 A1 | 9/2014 | Jong et al. |
| 2014/0257537 A1 | 9/2014 | Stroupe et al. |
| 2014/0266731 A1 | 9/2014 | Malhotra |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278229 A1 | 9/2014 | Hong et al. |
| 2014/0280498 A1 | 9/2014 | Frankel et al. |
| 2014/0282103 A1 | 9/2014 | Jerry |
| 2014/0282153 A1 | 9/2014 | Christiansen et al. |
| 2014/0282207 A1 | 9/2014 | Wouhaybi et al. |
| 2014/0287821 A1 | 9/2014 | Barclay et al. |
| 2014/0288680 A1 | 9/2014 | Hoffman et al. |
| 2014/0289660 A1 | 9/2014 | Min |
| 2014/0293755 A1 | 10/2014 | Geiser et al. |
| 2014/0304738 A1 | 10/2014 | Nakaoka et al. |
| 2014/0310598 A1 | 10/2014 | Sprague et al. |
| 2014/0310618 A1 | 10/2014 | Venkatesh |
| 2014/0310643 A1 | 10/2014 | Karmanenko et al. |
| 2014/0317543 A1 | 10/2014 | Kim |
| 2014/0325384 A1 | 10/2014 | Kobayashi |
| 2014/0325408 A1 | 10/2014 | Leppanen et al. |
| 2014/0331314 A1 | 11/2014 | Fujioka |
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0344693 A1 | 11/2014 | Reese et al. |
| 2014/0344723 A1 | 11/2014 | Malik et al. |
| 2014/0344951 A1 | 11/2014 | Brewer |
| 2014/0358473 A1 | 12/2014 | Goel et al. |
| 2014/0358584 A1 | 12/2014 | Worden et al. |
| 2014/0362056 A1 | 12/2014 | Zambetti et al. |
| 2014/0371887 A1 | 12/2014 | Hoffman et al. |
| 2015/0004578 A1 | 1/2015 | Gilley et al. |
| 2015/0018632 A1 | 1/2015 | Khair |
| 2015/0026615 A1 | 1/2015 | Choi et al. |
| 2015/0033149 A1* | 1/2015 | Kuchoor ............ H04N 21/4782 715/753 |
| 2015/0046814 A1 | 2/2015 | Haughay et al. |
| 2015/0057942 A1 | 2/2015 | Self et al. |
| 2015/0057943 A1 | 2/2015 | Self et al. |
| 2015/0057945 A1 | 2/2015 | White et al. |

(56) References Cited

U.S. PATENT DOCUMENTS

| | | |
|---|---|---|
| 2015/0058093 A1 | 2/2015 | Jakobs |
| 2015/0058263 A1 | 2/2015 | Landers |
| 2015/0065095 A1 | 3/2015 | Seo et al. |
| 2015/0065302 A1 | 3/2015 | Ou et al. |
| 2015/0066172 A1 | 3/2015 | Yi |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0081060 A1 | 3/2015 | Hwang et al. |
| 2015/0081529 A1 | 3/2015 | Lee et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0100982 A1 | 4/2015 | Sirpal et al. |
| 2015/0106025 A1 | 4/2015 | Keller et al. |
| 2015/0112700 A1 | 4/2015 | Sublett et al. |
| 2015/0112990 A1 | 4/2015 | Van Os et al. |
| 2015/0113553 A1 | 4/2015 | Pan |
| 2015/0118657 A1 | 4/2015 | Shrake et al. |
| 2015/0124067 A1 | 5/2015 | Bala et al. |
| 2015/0130830 A1 | 5/2015 | Nagasaki et al. |
| 2015/0133748 A1 | 5/2015 | Edmonds et al. |
| 2015/0142689 A1 | 5/2015 | Squires |
| 2015/0153943 A1 | 6/2015 | Wang |
| 2015/0160856 A1 | 6/2015 | Jang et al. |
| 2015/0164349 A1 | 6/2015 | Gopalakrishnan et al. |
| 2015/0180746 A1 | 6/2015 | Day et al. |
| 2015/0180980 A1 | 6/2015 | Welinder et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0185995 A1 | 7/2015 | Shoemaker et al. |
| 2015/0193805 A1 | 7/2015 | Filipiak |
| 2015/0196804 A1 | 7/2015 | Koduri et al. |
| 2015/0196805 A1 | 7/2015 | Koduri et al. |
| 2015/0199494 A1 | 7/2015 | Koduri et al. |
| 2015/0205492 A1 | 7/2015 | Nobil |
| 2015/0205509 A1 | 7/2015 | Scriven et al. |
| 2015/0205930 A1 | 7/2015 | Shaanan et al. |
| 2015/0217163 A1 | 8/2015 | Amis et al. |
| 2015/0220523 A1 | 8/2015 | Lagree |
| 2015/0220883 A1 | 8/2015 | Bfar et al. |
| 2015/0227782 A1 | 8/2015 | Salvador et al. |
| 2015/0251053 A1 | 9/2015 | Hoffman et al. |
| 2015/0253740 A1 | 9/2015 | Nishijima et al. |
| 2015/0256491 A1 | 9/2015 | Eatough et al. |
| 2015/0262497 A1 | 9/2015 | Landau et al. |
| 2015/0269848 A1 | 9/2015 | Yuen et al. |
| 2015/0286391 A1 | 10/2015 | Jacobs et al. |
| 2015/0293592 A1 | 10/2015 | Cheong et al. |
| 2015/0295901 A1 | 10/2015 | Woodward et al. |
| 2015/0297134 A1 | 10/2015 | Albert et al. |
| 2015/0301506 A1 | 10/2015 | Koumaiha |
| 2015/0301691 A1 | 10/2015 | Qin |
| 2015/0317147 A1 | 11/2015 | Nachimuthu et al. |
| 2015/0324751 A1 | 11/2015 | Orenstein et al. |
| 2015/0331589 A1 | 11/2015 | Kawakita |
| 2015/0334546 A1 | 11/2015 | Diamond |
| 2015/0341695 A1 | 11/2015 | Pattan |
| 2015/0343709 A1 | 12/2015 | Gerstle et al. |
| 2015/0347711 A1 | 12/2015 | Soli et al. |
| 2015/0350141 A1 | 12/2015 | Yang et al. |
| 2015/0350861 A1 | 12/2015 | Soli et al. |
| 2015/0351655 A1 | 12/2015 | Coleman |
| 2015/0355804 A1 | 12/2015 | Nguyen et al. |
| 2015/0364057 A1 | 12/2015 | Catani et al. |
| 2015/0374310 A1 | 12/2015 | Lee |
| 2016/0000379 A1 | 1/2016 | Pougatchev et al. |
| 2016/0004393 A1 | 1/2016 | Faaborg et al. |
| 2016/0004432 A1 | 1/2016 | Bernstein et al. |
| 2016/0014266 A1 | 1/2016 | Bhatt |
| 2016/0015275 A1 | 1/2016 | Samadani et al. |
| 2016/0019360 A1 | 1/2016 | Pahwa et al. |
| 2016/0022202 A1 | 1/2016 | Peterson et al. |
| 2016/0027282 A1 | 1/2016 | Lee |
| 2016/0027420 A1 | 1/2016 | Eronen |
| 2016/0028869 A1 | 1/2016 | Bhatt |
| 2016/0034148 A1 | 2/2016 | Wilson et al. |
| 2016/0044269 A1 | 2/2016 | Kang |
| 2016/0048298 A1 | 2/2016 | Choi et al. |
| 2016/0058331 A1 | 3/2016 | Keen et al. |
| 2016/0058336 A1 | 3/2016 | Blahnik et al. |
| 2016/0058337 A1 | 3/2016 | Blahnik et al. |
| 2016/0062464 A1 | 3/2016 | Moussette et al. |
| 2016/0062582 A1 | 3/2016 | Wilson et al. |
| 2016/0062589 A1 | 3/2016 | Wan et al. |
| 2016/0065505 A1 | 3/2016 | Iskander |
| 2016/0066005 A1 | 3/2016 | Davis et al. |
| 2016/0070275 A1 | 3/2016 | Anderson et al. |
| 2016/0072896 A1 | 3/2016 | Petersen et al. |
| 2016/0073034 A1 | 3/2016 | Mukherjee et al. |
| 2016/0085937 A1 | 3/2016 | Dettinger et al. |
| 2016/0098137 A1 | 4/2016 | Kim et al. |
| 2016/0107031 A1 | 4/2016 | Palatsi et al. |
| 2016/0135731 A1 | 5/2016 | Drennan |
| 2016/0140828 A1 | 5/2016 | Deforest |
| 2016/0150063 A1 | 5/2016 | Choi et al. |
| 2016/0156584 A1 | 6/2016 | Hum et al. |
| 2016/0180568 A1 | 6/2016 | Bullivant et al. |
| 2016/0187995 A1 | 6/2016 | Rosewall |
| 2016/0188181 A1 | 6/2016 | Smith |
| 2016/0196635 A1 | 7/2016 | Cho et al. |
| 2016/0197773 A1 | 7/2016 | Pandrangi et al. |
| 2016/0202889 A1 | 7/2016 | Shin et al. |
| 2016/0210099 A1 | 7/2016 | Hampapuram et al. |
| 2016/0210568 A1 | 7/2016 | Krupa et al. |
| 2016/0217601 A1 | 7/2016 | Tsuda et al. |
| 2016/0220225 A1 | 8/2016 | Wang et al. |
| 2016/0226713 A1 | 8/2016 | Pitschel et al. |
| 2016/0235374 A1 | 8/2016 | Miller et al. |
| 2016/0239724 A1 | 8/2016 | Arfvidsson et al. |
| 2016/0246880 A1 | 8/2016 | Battiah et al. |
| 2016/0249864 A1 | 9/2016 | Kang et al. |
| 2016/0250517 A1 | 9/2016 | Tilvis et al. |
| 2016/0253864 A1 | 9/2016 | Weber et al. |
| 2016/0256082 A1 | 9/2016 | Ely et al. |
| 2016/0256741 A1 | 9/2016 | Holma et al. |
| 2016/0261675 A1 | 9/2016 | Block et al. |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0296798 A1 | 10/2016 | Balakrishnan et al. |
| 2016/0301794 A1 | 10/2016 | Schlakman et al. |
| 2016/0302680 A1 | 10/2016 | Narusawa et al. |
| 2016/0302717 A1 | 10/2016 | Tawa et al. |
| 2016/0321932 A1 | 11/2016 | Mitchell et al. |
| 2016/0324457 A1 | 11/2016 | Dagum |
| 2016/0327911 A1 | 11/2016 | Eim et al. |
| 2016/0328736 A1 | 11/2016 | Wang et al. |
| 2016/0332025 A1 | 11/2016 | Repka |
| 2016/0346607 A1 | 12/2016 | Rapfogel |
| 2016/0357363 A1 | 12/2016 | Decker et al. |
| 2016/0371464 A1 | 12/2016 | Bricker |
| 2016/0373631 A1 | 12/2016 | Titi et al. |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0007882 A1 | 1/2017 | Werner |
| 2017/0011210 A1 | 1/2017 | Cheong et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0026430 A1 | 1/2017 | Beckhardt et al. |
| 2017/0032168 A1 | 2/2017 | Kim |
| 2017/0039535 A1 | 2/2017 | Park et al. |
| 2017/0041549 A1 | 2/2017 | Kim et al. |
| 2017/0045866 A1 | 2/2017 | Hou et al. |
| 2017/0046108 A1 | 2/2017 | Kang et al. |
| 2017/0053542 A1 | 2/2017 | Wilson et al. |
| 2017/0056722 A1 | 3/2017 | Singh et al. |
| 2017/0063753 A1 | 3/2017 | Probasco et al. |

(56) References Cited

U.S. PATENT DOCUMENTS

| | | |
|---|---|---|
| 2017/0065224 A1 | 3/2017 | Rahko et al. |
| 2017/0087469 A1 | 3/2017 | Hardee et al. |
| 2017/0093769 A1 | 3/2017 | Lind et al. |
| 2017/0093780 A1 | 3/2017 | Lieb et al. |
| 2017/0095695 A1 | 4/2017 | Mangusson et al. |
| 2017/0123571 A1 | 5/2017 | Huang et al. |
| 2017/0124276 A1 | 5/2017 | Tee |
| 2017/0134321 A1 | 5/2017 | Ushio et al. |
| 2017/0140143 A1 | 5/2017 | Ahmad et al. |
| 2017/0143262 A1 | 5/2017 | Kurunmäki et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0249417 A1 | 8/2017 | Gosieski et al. |
| 2017/0255169 A1 | 9/2017 | Lee et al. |
| 2017/0266494 A1 | 9/2017 | Crankson et al. |
| 2017/0266531 A1 | 9/2017 | Elford et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0301039 A1 | 10/2017 | Dyer et al. |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0333752 A1 | 11/2017 | Korkala et al. |
| 2017/0337033 A1 | 11/2017 | Duyan et al. |
| 2017/0344257 A1 | 11/2017 | Gnedin et al. |
| 2017/0348562 A1 | 12/2017 | Jung et al. |
| 2017/0354845 A1 | 12/2017 | Williams et al. |
| 2017/0357520 A1 | 12/2017 | De Vries et al. |
| 2017/0359623 A1 | 12/2017 | Folse et al. |
| 2018/0000426 A1 | 1/2018 | Li |
| 2018/0001184 A1 | 1/2018 | Tran et al. |
| 2018/0032234 A1 | 2/2018 | Michalske |
| 2018/0034765 A1 | 2/2018 | Keszler et al. |
| 2018/0039406 A1 | 2/2018 | Kong et al. |
| 2018/0053200 A1 | 2/2018 | Cronin et al. |
| 2018/0056132 A1 | 3/2018 | Foley et al. |
| 2018/0065025 A1 | 3/2018 | Toda et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0081515 A1 | 3/2018 | Block et al. |
| 2018/0121060 A1 | 5/2018 | Jeong et al. |
| 2018/0126248 A1 | 5/2018 | Dion et al. |
| 2018/0137937 A1 | 5/2018 | Gass et al. |
| 2018/0140211 A1 | 5/2018 | Nakazawa et al. |
| 2018/0140903 A1 | 5/2018 | Poure et al. |
| 2018/0140927 A1 | 5/2018 | Kito et al. |
| 2018/0143761 A1 | 5/2018 | Choi et al. |
| 2018/0150709 A1 | 5/2018 | Ha |
| 2018/0157452 A1 | 6/2018 | Nelson et al. |
| 2018/0177437 A1 | 6/2018 | Yoshioka |
| 2018/0182491 A1 | 6/2018 | Belliveau et al. |
| 2018/0189077 A1 | 7/2018 | Gupta et al. |
| 2018/0206766 A1 | 7/2018 | Blahnik et al. |
| 2018/0247706 A1 | 8/2018 | Riley et al. |
| 2018/0272190 A1 | 9/2018 | Miura et al. |
| 2018/0294053 A1 | 10/2018 | Runyon et al. |
| 2018/0300037 A1 | 10/2018 | Takeda et al. |
| 2018/0316783 A1 | 11/2018 | Ye et al. |
| 2018/0316964 A1* | 11/2018 | Dillon .................. G06F 3/04817 |
| 2018/0318647 A1 | 11/2018 | Foley et al. |
| 2018/0329584 A1 | 11/2018 | Williams et al. |
| 2018/0339195 A1 | 11/2018 | Bernotas |
| 2018/0345078 A1 | 12/2018 | Blahnik et al. |
| 2018/0367484 A1* | 12/2018 | Rodriguez .................. H04L 67/75 |
| 2019/0008467 A1 | 1/2019 | Averina et al. |
| 2019/0025995 A1 | 1/2019 | Williams |
| 2019/0026011 A1 | 1/2019 | Wang et al. |
| 2019/0034049 A1 | 1/2019 | Williams et al. |
| 2019/0034050 A1 | 1/2019 | Williams et al. |
| 2019/0089701 A1 | 3/2019 | Mercury et al. |
| 2019/0102049 A1 | 4/2019 | Anzures et al. |
| 2019/0104951 A1 | 4/2019 | Valys et al. |
| 2019/0126099 A1 | 5/2019 | Hoang |
| 2019/0143194 A1 | 5/2019 | Evancha et al. |
| 2019/0184234 A1* | 6/2019 | Packles .............. A63B 24/0075 |
| 2019/0209777 A1 | 7/2019 | O'connell et al. |
| 2019/0220243 A1 | 7/2019 | Decker et al. |
| 2019/0232110 A1 | 8/2019 | Williams et al. |
| 2019/0232111 A1 | 8/2019 | Williams et al. |
| 2019/0250813 A1 | 8/2019 | Block et al. |
| 2019/0268771 A1 | 8/2019 | Seo et al. |
| 2019/0274565 A1 | 9/2019 | Soli et al. |
| 2019/0279520 A1 | 9/2019 | Wilson et al. |
| 2019/0334782 A1 | 10/2019 | Dellinger et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339822 A1 | 11/2019 | Devine et al. |
| 2019/0339849 A1 | 11/2019 | Williams et al. |
| 2019/0339860 A1 | 11/2019 | Chen et al. |
| 2019/0342616 A1 | 11/2019 | Domm et al. |
| 2019/0349463 A1 | 11/2019 | Soli et al. |
| 2019/0364120 A1 | 11/2019 | Bandela et al. |
| 2019/0387982 A1 | 12/2019 | Buller |
| 2020/0014967 A1 | 1/2020 | Putnam |
| 2020/0026398 A1 | 1/2020 | Kim |
| 2020/0054931 A1 | 2/2020 | Martin et al. |
| 2020/0098278 A1 | 3/2020 | Doti et al. |
| 2020/0101365 A1 | 4/2020 | Wilson et al. |
| 2020/0110814 A1 | 4/2020 | Abuelsaad et al. |
| 2020/0149921 A1 | 5/2020 | Hoffman et al. |
| 2020/0160961 A1 | 5/2020 | Wadhawan et al. |
| 2020/0213437 A1 | 7/2020 | Bhatt |
| 2020/0261763 A1 | 8/2020 | Park et al. |
| 2020/0297249 A1 | 9/2020 | Williams et al. |
| 2020/0356242 A1 | 11/2020 | Wilson et al. |
| 2020/0357522 A1 | 11/2020 | Pahwa et al. |
| 2020/0381100 A1 | 12/2020 | Williams et al. |
| 2020/0382613 A1 | 12/2020 | Sundstrom et al. |
| 2021/0007632 A1 | 1/2021 | Blahnik et al. |
| 2021/0007633 A1 | 1/2021 | Blahnik et al. |
| 2021/0042028 A1 | 2/2021 | Block et al. |
| 2021/0042132 A1* | 2/2021 | Park ........................ G06F 9/452 |
| 2021/0092488 A1 | 3/2021 | Folse et al. |
| 2021/0093919 A1 | 4/2021 | Lyke et al. |
| 2021/0110908 A1 | 4/2021 | Blahnik et al. |
| 2021/0113116 A1 | 4/2021 | Chen et al. |
| 2021/0113137 A1 | 4/2021 | Soli et al. |
| 2021/0145321 A1 | 5/2021 | Chen et al. |
| 2021/0191584 A1 | 6/2021 | Williams et al. |
| 2021/0193293 A1 | 6/2021 | Blahnik et al. |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255758 A1 | 8/2021 | Devine et al. |
| 2021/0255826 A1 | 8/2021 | Devine et al. |
| 2021/0263700 A1 | 8/2021 | Decker et al. |
| 2021/0289067 A1 | 9/2021 | Dellinger et al. |
| 2021/0294438 A1 | 9/2021 | Yang et al. |
| 2021/0316185 A1 | 10/2021 | Mckenna et al. |
| 2021/0350900 A1 | 11/2021 | Blahnik et al. |
| 2021/0352118 A1 | 11/2021 | Ahn et al. |
| 2021/0379447 A1 | 12/2021 | Lee |
| 2021/0394020 A1 | 12/2021 | Killen et al. |
| 2022/0047918 A1 | 2/2022 | Williams et al. |
| 2022/0062707 A1 | 3/2022 | Bedekar et al. |
| 2022/0066902 A1 | 3/2022 | Narra et al. |
| 2022/0121299 A1 | 4/2022 | De Vries et al. |
| 2022/0157184 A1 | 5/2022 | Wilson et al. |
| 2022/0160258 A1 | 5/2022 | Williams et al. |
| 2022/0262485 A1 | 8/2022 | Meschter et al. |
| 2022/0262509 A1 | 8/2022 | Pahwa et al. |

(56) References Cited

U.S. PATENT DOCUMENTS

| | | |
|---|---|---|
| 2022/0264184 A1 | 8/2022 | Folse et al. |
| 2022/0328161 A1 | 10/2022 | Gilravi et al. |
| 2022/0386901 A1 | 12/2022 | Chen et al. |
| 2023/0013809 A1 | 1/2023 | D'auria et al. |
| 2023/0013932 A1 | 1/2023 | Blahnik et al. |
| 2023/0014053 A1 | 1/2023 | Devine et al. |
| 2023/0014290 A1 | 1/2023 | Davydov et al. |
| 2023/0017793 A1 | 1/2023 | Williams et al. |
| 2023/0019337 A1 | 1/2023 | D'auria et al. |
| 2023/0024084 A1 | 1/2023 | D'auria et al. |
| 2023/0025724 A1 | 1/2023 | Gilravi et al. |
| 2023/0027358 A1 | 1/2023 | Williams et al. |
| 2023/0031103 A1 | 2/2023 | Decker et al. |
| 2023/0066552 A1 | 3/2023 | Van Os et al. |
| 2023/0119253 A1 | 4/2023 | Sundstrom et al. |
| 2023/0136700 A1 | 5/2023 | Williams et al. |
| 2023/0179700 A1 | 6/2023 | Bhatt |
| 2023/0260416 A1 | 8/2023 | Wilson et al. |
| 2023/0390606 A1 | 12/2023 | Bolton et al. |
| 2023/0390626 A1 | 12/2023 | Bolton et al. |
| 2023/0390627 A1 | 12/2023 | Bolton et al. |
| 2023/0393723 A1 | 12/2023 | Arney et al. |

FOREIGN PATENT DOCUMENTS

| | | |
|---|---|---|
| CA | 2897539 A1 | 10/2014 |
| CA | 2826239 C | 1/2017 |
| CN | 1337638 A | 2/2002 |
| CN | 1397904 A | 2/2003 |
| CN | 1443427 A | 9/2003 |
| CN | 1523500 A | 8/2004 |
| CN | 1536511 A | 10/2004 |
| CN | 1585943 A | 2/2005 |
| CN | 1628609 A | 6/2005 |
| CN | 1767789 A | 5/2006 |
| CN | 1782685 A | 6/2006 |
| CN | 1824358 A | 8/2006 |
| CN | 1997050 A | 7/2007 |
| CN | 101061484 A | 10/2007 |
| CN | 101150810 A | 3/2008 |
| CN | 101219046 A | 7/2008 |
| CN | 101444419 A | 6/2009 |
| CN | 101505320 A | 8/2009 |
| CN | 101541387 A | 9/2009 |
| CN | 101651870 A | 2/2010 |
| CN | 101658423 A | 3/2010 |
| CN | 101668482 A | 3/2010 |
| CN | 101822020 A | 9/2010 |
| CN | 101827363 A | 9/2010 |
| CN | 101828411 A | 9/2010 |
| CN | 101836894 A | 9/2010 |
| CN | 101890217 A | 11/2010 |
| CN | 101910992 A | 12/2010 |
| CN | 101939740 A | 1/2011 |
| CN | 101978374 A | 2/2011 |
| CN | 102339201 A | 2/2012 |
| CN | 102438521 A | 5/2012 |
| CN | 102448555 | 5/2012 |
| CN | 102449560 A | 5/2012 |
| CN | 102449566 A | 5/2012 |
| CN | 102549590 A | 7/2012 |
| CN | 102646081 A | 8/2012 |
| CN | 102804238 A | 11/2012 |
| CN | 102814037 A | 12/2012 |
| CN | 102834079 A | 12/2012 |
| CN | 102989159 A | 3/2013 |
| CN | 103154954 A | 6/2013 |
| CN | 103182175 A | 7/2013 |
| CN | 103210355 A | 7/2013 |
| CN | 103212197 A | 7/2013 |
| CN | 103270540 A | 8/2013 |
| CN | 103294124 A | 9/2013 |
| CN | 103297610 A | 9/2013 |
| CN | 103370924 A | 10/2013 |
| CN | 103403627 A | 11/2013 |
| CN | 203276086 U | 11/2013 |
| CN | 103577108 A | 2/2014 |
| CN | 103581456 A | 2/2014 |
| CN | 103646570 A | 3/2014 |
| CN | 103682785 A | 3/2014 |
| CN | 103701504 A | 4/2014 |
| CN | 103902808 A | 7/2014 |
| CN | 103914238 A | 7/2014 |
| CN | 103973899 A | 8/2014 |
| CN | 104288983 A | 1/2015 |
| CN | 104501043 A | 4/2015 |
| CN | 104508426 A | 4/2015 |
| CN | 104815428 A | 8/2015 |
| CN | 105187282 A | 12/2015 |
| CN | 105320454 A | 2/2016 |
| CN | 105681328 A | 6/2016 |
| CN | 105874447 A | 8/2016 |
| CN | 106310638 A | 1/2017 |
| CN | 106510719 A | 3/2017 |
| CN | 106537397 A | 3/2017 |
| CN | 106709235 A | 5/2017 |
| CN | 106878550 A | 6/2017 |
| CN | 107469327 A | 12/2017 |
| CN | 107710197 A | 2/2018 |
| EP | 943290 A1 | 9/1999 |
| EP | 1559372 A1 | 8/2005 |
| EP | 1705883 A1 | 9/2006 |
| EP | 1935339 A1 | 6/2008 |
| EP | 2025368 A2 | 2/2009 |
| EP | 2426902 A1 | 3/2012 |
| EP | 2529663 A1 | 12/2012 |
| EP | 2631830 A2 | 8/2013 |
| EP | 2632139 A2 | 8/2013 |
| EP | 2728680 A1 | 5/2014 |
| EP | 3117767 A1 | 1/2017 |
| EP | 3122038 A1 | 1/2017 |
| EP | 3130997 A1 | 2/2017 |
| GB | 2550639 A | 11/2017 |
| JP | 5-288869 A | 11/1993 |
| JP | 6-187118 A | 7/1994 |
| JP | 7-334463 A | 12/1995 |
| JP | 8-126632 A | 5/1996 |
| JP | 10-90333 A | 4/1998 |
| JP | 10-202715 A | 8/1998 |
| JP | 2001-76078 A | 3/2001 |
| JP | 2001-133293 A | 5/2001 |
| JP | 2002-73486 A | 3/2002 |
| JP | 2002-190007 A | 7/2002 |
| JP | 2002-346013 A | 12/2002 |
| JP | 2003-102868 A | 4/2003 |
| JP | 2003-157323 A | 5/2003 |
| JP | 2003-248721 A | 9/2003 |
| JP | 2003-296246 A | 10/2003 |
| JP | 2003-319912 A | 11/2003 |
| JP | 2003-337863 A | 11/2003 |
| JP | 2004-102609 A | 4/2004 |
| JP | 2004-113466 A | 4/2004 |
| JP | 2004-174006 A | 6/2004 |
| JP | 2005-79814 A | 3/2005 |
| JP | 3635663 B2 | 4/2005 |
| JP | 2005-339017 A | 12/2005 |
| JP | 2006-155104 A | 6/2006 |
| JP | 2006-180899 A | 7/2006 |
| JP | 2006-230679 A | 9/2006 |
| JP | 2007-260288 A | 10/2007 |
| JP | 2007-330513 A | 12/2007 |
| JP | 2008-104758 A | 5/2008 |
| JP | 2008-183339 A | 8/2008 |
| JP | 2008-272301 A | 11/2008 |
| JP | 2009-78134 A | 4/2009 |
| JP | 2009-88989 A | 4/2009 |
| JP | 2009-112731 A | 5/2009 |
| JP | 2009-88989 A | 7/2009 |
| JP | 2009-147889 A | 7/2009 |
| JP | 2009-211241 A | 9/2009 |
| JP | 2009-282670 A | 12/2009 |
| JP | 2010-12335 A | 1/2010 |
| JP | 2010-517725 A | 5/2010 |
| JP | 2010-122901 A | 6/2010 |

(56) References Cited

FOREIGN PATENT DOCUMENTS

| | | |
|---|---|---|
| JP | 2010-162297 A | 7/2010 |
| JP | 2010-181280 A | 8/2010 |
| JP | 2010-182287 A | 8/2010 |
| JP | 2010-186249 A | 8/2010 |
| JP | 2010-206668 A | 9/2010 |
| JP | 2011-514192 A | 5/2011 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011-210119 A | 10/2011 |
| JP | 2011-229141 A | 11/2011 |
| JP | 2011-259253 A | 12/2011 |
| JP | 2012-20134 A | 2/2012 |
| JP | 2012-35071 A | 2/2012 |
| JP | 2012-53642 A | 3/2012 |
| JP | 2012-59264 A | 3/2012 |
| JP | 2012-86088 A | 5/2012 |
| JP | 2012-203537 A | 10/2012 |
| JP | 2012-524640 A | 10/2012 |
| JP | 2012-230503 A | 11/2012 |
| JP | 2012-232114 A | 11/2012 |
| JP | 2012-533117 A | 12/2012 |
| JP | 2013-29925 A | 2/2013 |
| JP | 2013-54468 A | 3/2013 |
| JP | 2013-103020 A | 5/2013 |
| JP | 2013-117690 A | 6/2013 |
| JP | 2013-146557 A | 8/2013 |
| JP | 2013-530776 A | 8/2013 |
| JP | 2013-543156 A | 11/2013 |
| JP | 5346115 B1 | 11/2013 |
| JP | 2013-544140 A | 12/2013 |
| JP | 2014-500740 A | 1/2014 |
| JP | 2014-45782 A | 3/2014 |
| JP | 2014-104139 A | 6/2014 |
| JP | 2014-143473 A | 8/2014 |
| JP | 2014-168685 A | 9/2014 |
| JP | 2014-171831 A | 9/2014 |
| JP | 2014-216868 A | 11/2014 |
| JP | 2015-58218 A | 3/2015 |
| JP | 2015-507811 A | 3/2015 |
| JP | 2015-509019 A | 3/2015 |
| JP | 2015-509755 A | 4/2015 |
| JP | 2015-531916 A | 11/2015 |
| JP | 2016-17331 A | 2/2016 |
| JP | 2016-502875 A | 2/2016 |
| JP | 2016-52512 A | 4/2016 |
| JP | 2016-517329 A | 6/2016 |
| JP | 2016-158867 A | 9/2016 |
| JP | 2016-528016 A | 9/2016 |
| JP | 2016-177151 A | 10/2016 |
| JP | 2016-185288 A | 10/2016 |
| JP | 2016-202751 A | 12/2016 |
| JP | 2017-83978 A | 5/2017 |
| JP | 2016-17331 A | 8/2017 |
| JP | 2017-134689 A | 8/2017 |
| JP | 2018-202174 A | 8/2017 |
| JP | 2017-156267 A | 9/2017 |
| JP | 2017-531235 A | 10/2017 |
| JP | 2017-211994 A | 11/2017 |
| JP | 2017-532069 A | 11/2017 |
| JP | 2018-102908 A | 7/2018 |
| JP | 2018-202174 A | 12/2018 |
| JP | 2019-3670 A | 1/2019 |
| JP | 2019-3670 A | 7/2020 |
| KR | 10-2006-0117570 A | 11/2006 |
| KR | 10-2009-0112132 A | 10/2009 |
| KR | 10-2011-0017076 A | 2/2011 |
| KR | 10-2011-0121394 A | 11/2011 |
| KR | 10-2012-0023657 A | 3/2012 |
| KR | 10-2012-0076559 A | 7/2012 |
| KR | 10-2012-0098854 A | 9/2012 |
| KR | 10-2012-0132732 A | 12/2012 |
| KR | 10-2013-0043698 A | 5/2013 |
| KR | 10-2013-0109466 A | 10/2013 |
| KR | 10-2013-0111569 A | 10/2013 |
| KR | 10-2013-0111570 A | 10/2013 |
| KR | 10-2013-0135282 A | 12/2013 |
| KR | 10-2015-0026635 A | 3/2015 |
| KR | 10-2016-0027943 A | 3/2016 |
| KR | 10-2016-0105129 A | 9/2016 |
| KR | 10-2016-0142418 A | 12/2016 |
| KR | 10-2017-0003608 A | 1/2017 |
| KR | 10-2017-0020085 A | 2/2017 |
| KR | 10-2017-0029014 A | 3/2017 |
| KR | 10-2017-0032471 A | 3/2017 |
| KR | 10-2019-0022883 A | 3/2019 |
| KR | 10-2019-0141702 A | 12/2019 |
| TW | 498240 B | 8/2002 |
| TW | 200512616 A | 4/2005 |
| TW | 201210368 A | 3/2012 |
| TW | 201240499 A | 10/2012 |
| WO | 97/38626 A1 | 10/1997 |
| WO | 1999/41682 A2 | 8/1999 |
| WO | 2002/27530 A2 | 4/2002 |
| WO | 2005/029242 A2 | 3/2005 |
| WO | 2005/070289 A1 | 8/2005 |
| WO | 2007/081629 A2 | 7/2007 |
| WO | 2007/142703 A1 | 12/2007 |
| WO | 2007/149731 A1 | 12/2007 |
| WO | 2008/114491 A1 | 9/2008 |
| WO | 2009/129402 A1 | 10/2009 |
| WO | 2009/152608 A1 | 12/2009 |
| WO | 2010/126821 A1 | 11/2010 |
| WO | 2010/126825 A1 | 11/2010 |
| WO | 2011/072111 A2 | 6/2011 |
| WO | 2011/108335 A1 | 9/2011 |
| WO | 2012/021507 A2 | 2/2012 |
| WO | 2012/036891 A2 | 3/2012 |
| WO | 2012/061438 A2 | 5/2012 |
| WO | 2012/061440 A2 | 5/2012 |
| WO | 2012/075322 A2 | 6/2012 |
| WO | 2012/078079 A2 | 6/2012 |
| WO | 2012/086910 A1 | 6/2012 |
| WO | 2012/095712 A1 | 7/2012 |
| WO | 2013/052789 A1 | 4/2013 |
| WO | 2013/109762 A1 | 7/2013 |
| WO | 2013/109776 A1 | 7/2013 |
| WO | 2013/109777 A1 | 7/2013 |
| WO | 2013/109916 A1 | 7/2013 |
| WO | 2013/157307 A1 | 10/2013 |
| WO | 2013/169870 A1 | 11/2013 |
| WO | 2013/173838 A2 | 11/2013 |
| WO | 2014/002711 A1 | 1/2014 |
| WO | 2014/022711 A1 | 2/2014 |
| WO | 2014/059259 A1 | 4/2014 |
| WO | 2014/105276 A1 | 7/2014 |
| WO | 2014/200730 A1 | 12/2014 |
| WO | 2014/207294 A1 | 12/2014 |
| WO | 2015/027133 A1 | 2/2015 |
| WO | 2015/029313 A1 | 3/2015 |
| WO | 2015/179592 A1 | 11/2015 |
| WO | 2015/198488 A1 | 12/2015 |
| WO | 2016/022203 A1 | 2/2016 |
| WO | 2016/025036 A1 | 2/2016 |
| WO | 2016/036472 A1 | 3/2016 |
| WO | 2016/036582 A1 | 3/2016 |
| WO | 2016/126733 A1 | 8/2016 |
| WO | 2017/037242 A1 | 3/2017 |
| WO | 2018/048510 A1 | 3/2018 |
| WO | 2018/213066 A1 | 11/2018 |
| WO | 2018/222313 A1 | 12/2018 |
| WO | 2018/236291 A1 | 12/2018 |
| WO | 2019/017508 A1 | 1/2019 |
| WO | 2019/024383 A1 | 2/2019 |
| WO | 2019/024603 A1 | 2/2019 |
| WO | 2019/183422 A1 | 9/2019 |

(56) References Cited

FOREIGN PATENT DOCUMENTS

| WO | 2019/217249 A2 | 11/2019 |
|---|---|---|
| WO | 2019/231982 A1 | 12/2019 |

OTHER PUBLICATIONS

Applicant-Initiated Interview Summary received for U.S. Appl. No. 17/031,859, dated Dec. 27, 2022, 5 pages.
Applicant-Initiated Interview Summary received for U.S. Appl. No. 17/031,874, dated Jan. 24, 2023, 5 pages.
Applicant-Initiated Interview Summary received for U.S. Appl. No. 17/892,534, dated Feb. 6, 2023, 2 pages.
Brief Communication Regarding Oral Proceedings received for European Patent Application No. 20203526.7, mailed on Dec. 23, 2022, 4 pages.
Brief Communication Regarding Oral Proceedings received for European Patent Application No. 20203526.7, mailed on Jan. 18, 2023, 1 page.
Decision to Grant received for Danish Patent Application No. PA202070815, dated Dec. 23, 2022, 1 page.
Extended European Search Report received for European Patent Application No. 22194355.8, dated Dec. 23, 2022, 10 pages.
Final Office Action received for U.S. Appl. No. 17/591,184, dated Dec. 23, 2022, 10 pages.
Non-Final Office Action received for U.S. Appl. No. 17/068,386, dated Jan. 30, 2023, 20 pages.
Non-Final Office Action received for U.S. Appl. No. 17/862,097, dated Feb. 1, 2023, 16 pages.
Non-Final Office Action received for U.S. Appl. No. 17/892,534, dated Dec. 19, 2022, 20 pages.
Non-Final Office Action received for U.S. Appl. No. 17/951,875, dated Jan. 23, 2023, 12 pages.
Notice of Allowance received for Chinese Patent Application No. 202210238202.4, dated Jan. 13, 2023, 7 pages (3 pages of English Translation and 4 pages of Official Copy).
Notice of Allowance received for Japanese Patent Application No. 2020-160053, dated Jan. 16, 2023, 4 pages (1 page of English Translation and 3 pages of Official Copy).
Notice of Allowance received for Korean Patent Application No. 10-2022-0061486, dated Nov. 22, 2022, 7 pages (2 pages of English Translation and 5 pages of Official Copy).
Notice of Allowance received for U.S. Appl. No. 17/030,318, dated Jan. 25, 2023, 10 pages.
Notice of Allowance received for U.S. Appl. No. 17/030,337, dated Dec. 23, 2022, 9 pages.
Notice of Allowance received for U.S. Appl. No. 17/030,343, dated Dec. 15, 2022, 9 pages.
Notice of Allowance received for U.S. Appl. No. 17/516,537, dated Dec. 27, 2022, 7 pages.
Notice of Allowance received for U.S. Appl. No. 17/739,664, dated Dec. 7, 2022, 8 pages.
Office Action received for Australian Patent Application No. 2022200514, dated Jan. 17, 2023, 3 pages.
Office Action received for Chinese Patent Application No. 201811303556.2, dated Nov. 28, 2022, 18 pages (7 pages of English Translation and 11 pages of Official Copy).
Office Action received for Chinese Patent Application No. 201880032190.1, dated Nov. 14, 2022, 23 pages (12 pages of English Translation and 11 pages of Official Copy).
Office Action received for Chinese Patent Application No. 201911401161.0, dated Dec. 15, 2022, 14 pages (7 pages of English Translation and 7 pages of Official Copy).
Office Action received for Chinese Patent Application No. 202110783860.7, dated Nov. 15, 2022, 8 pages (2 pages of English Translation and 6 pages of Official Copy).
Office Action received for Japanese Patent Application No. 2021-131726, dated Dec. 2, 2022, 4 pages (2 pages of English Translation and 2 pages of Official Copy).

Office Action received for Japanese Patent Application No. 2021-153558, dated Nov. 21, 2022, 8 pages (4 pages of English Translation and 4 pages of Official Copy).
Office Action received for Japanese Patent Application No. 2021-565912, dated Jan. 12, 2023, 9 pages (5 pages of English Translation and 4 pages of Official Copy).
Office Action received for Japanese Patent Application No. 2021-571468, dated Jan. 5, 2023, 14 pages (7 pages of English Translation & 7 pages of Official Copy).
Office Action received for Korean Patent Application No. 10-2020-0123840, dated Nov. 21, 2022, 18 pages (8 pages of English Translation and 10 pages of Official Copy).
Office Action received for Korean Patent Application No. 10-2022-7031866, dated Nov. 18, 2022, 11 pages (5 pages of English Translation and 6 pages of Official Copy).
Result of Consultation received for European Patent Application No. 20203526.7, mailed on Jan. 13, 2023, 3 pages.
Supplemental Notice of Allowance received for U.S. Patent Application No. 17/030,343, dated Jan. 6, 2023, 2 pages.
Updated Notice of Allowance received for U.S. Appl. No. 17/030,340, dated Dec. 2, 2022, 2 pages.
Li-Yu et al., "Influence of exercise prescription on body composition of college students", Clinical Rehabilitation in China, vol. 9 Issue 24, Jun. 28, 2005, pp. 147-149. (Official Copy only). {(See Communication under Rule 37 Cfr § 1.98(a) (3))}.
Advisory Action received for U.S. Appl. No. 16/144,864, dated Jul. 29, 2019, 6 pages.
Adeniyi Samuel, "How to connect a second PS4 controller to a PlayStation 4 console", Online available on:—https://www.youtube.com/watch?v=mOZX_SrNISE, May 28, 2017, 2 pages.
Advisory Action received for U.S. Appl. No. 14/841,606, dated Feb. 28, 2019, 3 pages.
Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 14/839,922, dated Mar. 24, 2017, 4 pages.
Advisory Action received for U.S. Appl. No. 14/863,099, dated Sep. 8, 2016, 3 pages.
Advisory Action received for U.S. Appl. No. 15/554,204, dated Mar. 12, 2020, 3 pages.
Advisory Action received for U.S. Appl. No. 16/144,849, dated Aug. 12, 2019, 5 pages.
Advisory Action received for U.S. Appl. No. 16/144,864, dated Jul. 6, 2020, 6 pages.
Advisory Action received for U.S. Appl. No. 16/145,033, dated Nov. 2, 2021, 5 pages.
Advisory Action received for U.S. Appl. No. 16/377,892, dated Apr. 9, 2021, 4 pages.
Advisory Action received for U.S. Appl. No. 16/378,136, dated Apr. 12, 2021, 4 pages.
Advisory Action received for U.S. Appl. No. 16/389,722, dated Mar. 9, 2021, 5 pages.
Allison Conor, "Working out with Fiit's wearable-powered boutique fitness classes", Online available at:—<https://www.wareable.com/wearable-tech/fiit-fitness-classes-review-3849>, May 14, 2018, 8 pages.
Apple Inc., "iPhone User Guide for IOS 7.1 Software", available online at <https://manuals.info.apple.com/MANUALS/1000/MA1681/en_US/iphone_ios7_user_guide.pdf>, Mar. 10, 2014, pp. 1-162.
Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Applicant Initiated Interview Summary received for U.S. Appl. No. 16/994,352, dated Nov. 2, 2021, 4 pages.
Applicant Initiated Interview Summary received for U.S. Appl. No. 15/608,848, dated Apr. 13, 2021, 4 pages.
Applicant Initiated Interview Summary received for U.S. Appl. No. 15/608,848, dated May 12, 2020, 5 pages.
Applicant Initiated Interview Summary received for U.S. Appl. No. 15/608,848, dated Oct. 26, 2020, 3 pages.

(56) References Cited

OTHER PUBLICATIONS

Applicant Initiated Interview Summary received for U.S. Appl. No. 15/627,069, dated Nov. 4, 2019, 6 pages.
Applicant Initiated Interview Summary received for U.S. Appl. No. 16/144,735, dated Jun. 18, 2020, 3 pages.
Applicant Initiated Interview Summary received for U.S. Appl. No. 16/144,753, dated Jun. 18, 2020, 3 pages.
Applicant Initiated Interview Summary received for U.S. Appl. No. 16/144,849, dated Jan. 21, 2020, 6 pages.
Applicant Initiated Interview Summary received for U.S. Appl. No. 16/144,864, dated Apr. 29, 2020, 4 pages.
Applicant Initiated Interview Summary received for U.S. Appl. No. 16/363,945, dated Aug. 13, 2020, 5 pages.
Applicant Initiated Interview Summary received for U.S. Appl. No. 16/389,722, dated Jul. 7, 2020, 5 pages.
Applicant Initiated Interview Summary received for U.S. Appl. No. 16/894,309, dated Jan. 26, 2021, 3 pages.
Applicant Initiated Interview Summary received for U.S. Appl. No. 17/030,318, dated Jul. 30, 2021, 4 pages.
Applicant Initiated Interview Summary received for U.S. Appl. No. 17/030,321, dated Jul. 30, 2021, 2 pages.
Applicant Initiated Interview Summary received for U.S. Appl. No. 17/327,204, dated Jan. 25, 2022, 5 pages.
Applicant Initiated Interview Summary received for U.S. Appl. No. 17/381,570, dated Apr. 26, 2022, 5 pages.
Applicant-Initiated Interview Summary received for U.S. Appl. No. 15/554,204, dated Jan. 31, 2020, 3 pages.
Applicant-Initiated Interview Summary received for U.S. Appl. No. 15/554,204, dated Oct. 11, 2019, 5 pages.
Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Applicant-Initiated Interview Summary received for U.S. Appl. No. 15/614,121, dated Feb. 13, 2020, 4 pages.
Applicant-Initiated Interview Summary received for U.S. Appl. No. 15/627,069, dated Jan. 22, 2021, 4 pages.
Applicant-Initiated Interview Summary received for U.S. Appl. No. 15/627,069, dated Jul. 20, 2020, 5 pages.
Applicant-Initiated Interview Summary received for U.S. Appl. No. 15/705,849, dated Feb. 14, 2020, 3 pages.
Applicant-Initiated Interview Summary received for U.S. Appl. No. 15/705,849, dated Jun. 29, 2020, 3 pages.
Applicant-Initiated Interview Summary received for U.S. Appl. No. 15/925,652, dated Nov. 3, 2020, 4 pages.
Applicant-Initiated Interview Summary received for U.S. Appl. No. 16/138,809, dated Dec. 16, 2020, 7 pages.
Applicant-Initiated Interview Summary received for U.S. Appl. No. 16/138,809, dated Jun. 9, 2020, 4 pages.
Applicant-Initiated Interview Summary received for U.S. Appl. No. 16/144,753, dated Nov. 4, 2020, 3 pages.
Applicant-Initiated Interview Summary received for U.S. Appl. No. 16/144,864, dated Jun. 22, 2020, 3 pages.
Applicant-Initiated Interview Summary received for U.S. Appl. No. 16/145,033, dated Apr. 30, 2021, 4 pages.
Applicant-Initiated Interview Summary received for U.S. Appl. No. 16/145,033, dated Jun. 29, 2020, 5 pages.
Applicant-Initiated Interview Summary received for U.S. Appl. No. 16/145,033, dated Nov. 24, 2020, 4 pages.
Applicant-Initiated Interview Summary received for U.S. Appl. No. 16/145,033, dated Oct. 7, 2021, 4 pages.
Applicant-Initiated Interview Summary received for U.S. Appl. No. 16/377,892, dated Mar. 26, 2021, 2 pages.
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Mar. 26, 2021, 2 pages.
Applicant-Initiated Interview Summary received for U.S. Appl. No. 16/378,136, dated Oct. 13, 2020, 4 pages.
Applicant-Initiated Interview Summary received for U.S. Appl. No. 16/388,493, dated Feb. 17, 2022, 2 pages.
Applicant-Initiated Interview Summary received for U.S. Appl. No. 16/389,722, dated Feb. 11, 2021, 4 pages.
Applicant-Initiated Interview Summary received for U.S. Appl. No. 16/389,722, dated Feb. 18, 2022, 5 pages.
Applicant-Initiated Interview Summary received for U.S. Appl. No. 16/389,722, dated Sep. 7, 2021, 4 pages.
Applicant-Initiated Interview Summary received for U.S. Appl. No. 16/407,590, dated Jun. 5, 2020, 3 pages.
Applicant-Initiated Interview Summary received for U.S. Appl. No. 16/407,590, dated Nov. 17, 2020, 6 pages.
Applicant-Initiated Interview Summary received for U.S. Appl. No. 16/418,786, dated Mar. 30, 2021, 4 pages.
Applicant-Initiated Interview Summary received for U.S. Appl. No. 16/418,786, dated May 9, 2022, 2 pages.
Applicant-Initiated Interview Summary received for U.S. Appl. No. 16/679,967, dated Feb. 10, 2022, 2 pages.
Applicant-Initiated Interview Summary received for U.S. Appl. No. 16/679,967, dated Jun. 1, 2022, 2 pages.
Applicant-Initiated Interview Summary received for U.S. Appl. No. 16/679,967, dated Oct. 25, 2021, 2 pages.
Applicant-Initiated Interview Summary received for U.S. Appl. No. 16/820,383, dated Mar. 11, 2021, 2 pages.
Applicant-Initiated Interview Summary received for U.S. Appl. No. 16/820,383, dated May 10, 2022, 2 pages.
Applicant-Initiated Interview Summary received for U.S. Appl. No. 16/888,629, dated Aug. 4, 2021, 5 pages.
Applicant-Initiated Interview Summary received for U.S. Appl. No. 16/894,309, dated Jun. 25, 2021, 4 pages.
Applicant-Initiated Interview Summary received for U.S. Appl. No. 16/987,275, dated Feb. 3, 2022, 4 pages.
Applicant-Initiated Interview Summary received for U.S. Appl. No. 17/031,543, dated Apr. 21, 2022, 2 pages.
Applicant-Initiated Interview Summary received for U.S. Appl. No. 17/031,854, dated Feb. 25, 2022, 5 pages.
Applicant-Initiated Interview Summary received for U.S. Appl. No. 17/031,859, dated Feb. 25, 2022, 4 pages.
Applicant-Initiated Interview Summary received for U.S. Appl. No. 17/031,859, dated Feb. 26, 2021, 4 pages.
Applicant-Initiated Interview Summary received for U.S. Appl. No. 17/031,859, dated Jun. 30, 2021, 4 pages.
Applicant-Initiated Interview Summary received for U.S. Appl. No. 17/031,874, dated Feb. 25, 2022, 4 pages.
Applicant-Initiated Interview Summary received for U.S. Appl. No. 17/031,874, dated Feb. 26, 2021, 4 pages.
Applicant-Initiated Interview Summary received for U.S. Appl. No. 17/031,874, dated Jun. 30, 2021, 4 pages.
Applicant-Initiated Interview Summary received for U.S. Appl. No. 17/068,386, dated Jan. 13, 2022, 2 pages.
Applicant-Initiated Interview Summary received for U.S. Appl. No. 17/068,386, dated Sep. 21, 2021, 2 pages.
Applicant-Initiated Interview Summary received for U.S. Appl. No. 17/116,775, dated Nov. 3, 2021, 4 pages.
Applicant-Initiated Interview Summary received for U.S. Appl. No. 17/126,571, dated Jan. 27, 2022, 4 pages.
Applicant-Initiated Interview Summary received for U.S. Appl. No. 17/157,728, dated Feb. 3, 2022, 5 pages.
Applicant-Initiated Interview Summary received for U.S. Appl. No. 17/192,161, dated Dec. 24, 2021, 4 pages.
Applicant-Initiated Interview Summary received for U.S. Appl. No. 17/192,161, dated Jun. 29, 2021, 4 pages.
Applicant-Initiated Interview Summary received for U.S. Appl. No. 17/192,161, dated Sep. 29, 2021, 3 pages.
Bagala et al., "Evaluation of Accelerometer-Based Fall Detection Algorithms on Real-World Falls", PloS ONE, vol. 7, No. 5, May 16, 2012, 9 pages.
Board Decision received for Chinese Patent Application No. 201380081349.6, mailed on Nov. 23, 2020, 2 pages.
Board Decision received for Chinese Patent Application No. 201510284850.3, mailed on Mar. 3, 2022, 27 pages.
Board Opinion received for Chinese Patent Application No. 201510284850.3, mailed on Jul. 2, 2021, 13 pages.

(56) References Cited

OTHER PUBLICATIONS

Brief Communication Regarding Oral Proceedings received for European Patent Application No. 19724963.4, mailed on Jun. 22, 2021, 2 pages.
Brief Communication Regarding Oral Proceedings received for European Patent Application No. 20182116.2, mailed on Apr. 13, 2022, 3 pages.
CBS This Morning, "This smart mirror puts a personal trainer in your reflection", Available on: https://www.youtube.com/watch?v=nSmTTZcpVGg, Oct. 13, 2018, 4 pages.
Certificate of Examination received for Australian Patent Application No. 2018101855, dated Aug. 6, 2019, 2 pages.
Certificate of Examination received for Australian Patent Application No. 2019100490, dated Oct. 16, 2019, 2 pages.
Certification of Examination received for Australian Patent Application No. 2018100158, dated Oct. 23, 2018, 2 pages.
Cho H.S. , "Satisfactory Innovative Smart-watch (fitbit force) . . . review after seven days of use, such as the amount of sleep and movement (improving sleep is the object of X-Blue", Online Available at: <https://x-blueuv.blogspot.com/2013/12/fitbit-force.html>, Dec. 3, 2013, 8 pages (2 pages of English Translation and 6 pages.
CNET, "Google Fit's automatic activity tracking is getting smarter on Android Wear", Available online at: https://www.youtube.com/watch?v=IttzlCid_d8, May 18, 2016, 1 page.
Codrington Simon, "Intuitive Scrolling Interfaces with CSS Scroll Snap Points", Online Available at: https://www.sitepoint.com/intuitive-scrolling-interfaces-with-css-scroll-snap-points/, Dec. 08, 2015, 14 pages.
Communication of the Board of Appeal received for European Patent Application No. 15771747.1, mailed on Aug. 25, 2021, 9 pages.
Corrected Notice of Allowance received for U.S. Appl. No. 14/732,773, dated Feb. 10, 2020, 3 pages.
Corrected Notice of Allowance received for U.S. Appl. No. 14/732,773, dated Mar. 24, 2020, 3 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.
Corrected Notice of Allowance received for U.S. Appl. No. 15/554,204, dated Aug. 19, 2020, 3 pages.
Corrected Notice of Allowance received for U.S. Appl. No. 15/600,243, dated Feb. 5, 2020, 3 pages.
Corrected Notice of Allowance received for U.S. Appl. No. 15/600,243, dated Mar. 13, 2020, 3 pages.
Corrected Notice of Allowance received for U.S. Appl. No. 15/600,243, dated Mar. 31, 2020, 5 pages.
Corrected Notice of Allowance received for U.S. Appl. No. 16/377,892, dated Aug. 11, 2021, 3 pages.
Corrected Notice of Allowance received for U.S. Appl. No. 16/378,136, dated Aug. 11, 2021, 2 pages.
Corrected Notice of Allowance received for U.S. Appl. No. 16/378,136, dated Jun. 11, 2021, 2 pages.
Corrected Notice of Allowance received for U.S. Appl. No. 16/418,786, dated Jan. 5, 2022, 3 pages.
Corrected Notice of Allowance received for U.S. Appl. No. 16/820,383, dated Aug. 13, 2021, 2 pages.
Corrected Notice of Allowance received for U.S. Appl. No. 16/820,383, dated Aug. 19, 2021, 2 pages.
Corrected Notice of Allowance received for U.S. Appl. No. 16/820,383, dated Oct. 5, 2021, 2 pages.
Corrected Notice of Allowance received for U.S. Appl. No. 16/888,629, dated Jan. 21, 2022, 2 pages.
Corrected Notice of Allowance received for U.S. Appl. No. 16/987,275, dated Jun. 8, 2022, 3 pages.
Corrected Notice of Allowance received for U.S. Appl. No. 17/030,318, dated Jan. 24, 2022, 2 pages.
Corrected Notice of Allowance received for U.S. Appl. No. 17/031,543, dated Jun. 8, 2022, 3 pages.
Corrected Notice of Allowance received for U.S. Appl. No. 17/116,775, dated Jan. 28, 2022, 2 pages.
Corrected Notice of Allowance received for U.S. Appl. No. 17/157,728, dated Apr. 4, 2022, 3 pages.
Corrected Notice of Allowance received for U.S. Appl. No. 17/157,728, dated Apr. 14, 2022, 6 pages.
Corrected Notice of Allowance received for U.S. Appl. No. 17/192,161, dated Apr. 22, 2022, 2 pages.
Corrected Notice of Allowance received for U.S. Appl. No. 17/192,161, dated Mar. 23, 2022, 2 pages.
Corrected Notice of Allowance received for U.S. Appl. No. 17/197,628, dated Apr. 27, 2022, 3 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Dc Rainmaker, "Garmin Fenix3 New Auto Climb Functionality", Available online at: https://www.youtube.com/watch?v=ivavOSNpVRc, Feb. 19, 2015, 1 page.
Decision of Appeal received for European Patent Application No. 15771747.1, mailed on Dec. 14, 2021, 21 pages.
Decision on Appeal received for Korean Patent Application No. 10-2019-7025538, mailed on Feb. 24, 2021, 20 pages.
Decision on Appeal received for U.S. Appl. No. 14/774,664, mailed on Sep. 12, 2019, 8 pages.
Decision on Appeal received for U.S. Appl. No. 14/863,099, mailed on Aug. 22, 2019, 9 pages.
Decision to Grant received for Danish Patent Application No. PA201670656, mailed on Jun. 21, 2021, 2 pages.
Decision to Grant received for Danish Patent Application No. PA201870379, mailed on Jul. 5, 2019, 2 pages.
Decision to Grant received for Danish Patent Application No. PA201870385, mailed on Mar. 26, 2020, 2 pages.
Decision to Grant received for European Patent Application No. 16706081.3, mailed on Nov. 29, 2018, 2 pages.
Decision to Grant received for European Patent Application No. 16762356.0, mailed on Apr. 26, 2022, 2 pages.
Decision to Grant received for European Patent Application No. 18213157.3, mailed on Feb. 24, 2022, 2 pages.
Decision to Grant received for European Patent Application No. 19724963.4, mailed on Feb. 3, 2022, 2 pages.
Decision to Grant received for German Patent Application No. 112015002326.7, mailed on Jun. 15, 2021, 10 pages.
Decision to Refuse received for European Patent Application No. 13811085.3, dated Sep. 11, 2018, 21 pages.
Decision to Refuse received for European Patent Application No. 15771747.1, dated Aug. 10, 2018, 22 pages.
Decision to Refuse received for European Patent Application No. 17810749.6, dated Jan. 29, 2021, 24 pages.
Decision to Refuse received for European Patent Application No. 18154145.9, dated Feb. 17, 2021, 20 pages.
Dharmasena Anusha, "iMessage-send as text message Option", YouTube, Available online at: <https://www.youtube.com/watch?v=hXG-MdIW6FA>, Feb. 18, 2013, 1 page.
DwProgressBar v2: Stepping and Events, davidwalsh.name/dwprogressbar-2-stepping-events-mootools-progress-bar, retrieved from the Wayback Machine, Aug. 31, 2008, 4 pages.
European Search Report received for European Patent Application No. 20182116.2, dated Oct. 21, 2020, 4 pages.
European Search Report received for European Patent Application No. 21165295.3, dated Jun. 18, 2021, 4 pages.
European Search Report received for European Patent Application No. 21168916.1, dated Jul. 14, 2021, 5 pages.
Evergreen et al., "Bar Chart", Better Evaluation, Available Online at: https://www.betterevaluation.org/en/evaluation-options/BarChart, Oct. 31, 2014, 8 pages.
Examiner's Answer to Appeal Brief received for U.S. Appl. No. 14/774,664, mailed on May 31, 2018, 28 pages.
Examiner's Answer to Appeal Brief received for U.S. Appl. No. 14/863,099, mailed on Jul. 28, 2017, 31 pages.
Extended European Search Report received for European Patent Application No. 16762356.0, dated Nov. 9, 2018, 10 pages.
Extended European Search Report received for European Patent Application No. 16837432.0, dated Mar. 11, 2019, 10 pages.

(56) References Cited

OTHER PUBLICATIONS

Extended European Search Report received for European Patent Application No. 18154145.9, dated Mar. 2, 2018, 8 pages.
Extended European Search Report received for European Patent Application No. 18213157.3, dated Apr. 12, 2019, 8 pages.
Extended European Search Report received for European Patent Application No. 19163212.4, dated Jun. 25, 2019, 11 pages.
Extended European Search Report received for European Patent Application No. 20203526.7, dated Jan. 29, 2021, 13 pages.
Extended European Search Report received for European Patent Application No. 22150207.3, dated Apr. 11, 2022, 11 pages.
Extended European Search Report received for European Patent Application No. 22152524.9, dated May 2, 2022, 10 pages.
Extended European Search Report received for European Patent Application No. 17813824.4, dated Dec. 5, 2019, 7 pages.
Final Office Action received for U.S. Appl. No. 16/994,352, dated Dec. 6, 2021, 14 pages.
Final Office Action received for U.S. Appl. No. 12/205,847, dated Apr. 25, 2012, 42 pages.
Final Office Action received for U.S. Appl. No. 14/599,424, dated Jun. 28, 2018, 12 pages.
Final Office Action received for U.S. Appl. No. 14/599,425, dated Jun. 12, 2018, 45 pages.
Final Office Action received for U.S. Appl. No. 14/599,425, dated May 19, 2017, 24 pages.
Final Office Action received for U.S. Appl. No. 14/599,425, dated Oct. 8, 2015, 20 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 14/774,664, dated Aug. 25, 2017, 23 pages.
Final Office Action received for U.S. Appl. No. 14/839,922, dated Dec. 14, 2016, 22 pages.
Final Office Action received for U.S. Appl. No. 14/841,606, dated Sep. 7, 2018, 34 pages.
Final Office Action received for U.S. Appl. No. 14/863,069, dated Jul. 5, 2018, 19 pages.
Final Office Action received for U.S. Appl. No. 14/863,099, dated Apr. 21, 2016, 20 pages.
Final Office Action received for U.S. Appl. No. 14/864,759, dated Sep. 4, 2018, 24 pages.
Final Office Action received for U.S. Appl. No. 15/554,204, dated Oct. 31, 2019, 22 pages.
Final Office Action received for U.S. Appl. No. 15/608,848, dated Aug. 21, 2020, 15 pages.
Final Office Action received for U.S. Appl. No. 15/608,848, dated Jun. 26, 2019, 27 pages.
Final Office Action received for U.S. Appl. No. 15/614,121, dated Apr. 8, 2019, 32 pages.
Final Office Action received for U.S. Appl. No. 15/627,069, dated Mar. 2, 2020, 22 pages.
Final Office Action received for U.S. Appl. No. 15/627,069, dated Oct. 20, 2020, 25 pages.
Final Office Action received for U.S. Appl. No. 15/705,849, dated May 1, 2020, 17 pages.
Final Office Action received for U.S. Appl. No. 15/925,652, dated Aug. 1, 2019, 30 pages.
Final Office Action received for U.S. Appl. No. 16/138,809, dated Aug. 27, 2020, 24 pages.
Final Office Action received for U.S. Appl. No. 16/144,735, dated May 4, 2020, 12 pages.
Final Office Action received for U.S. Appl. No. 16/144,753, dated Sep. 22, 2020, 9 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Final Office Action received for U.S. Appl. No. 16/144,864, dated May 28, 2020, 29 pages.
Final Office Action received for U.S. Appl. No. 16/145,033, dated Jul. 6, 2021, 113 pages.
Final Office Action received for U.S. Appl. No. 16/145,033, dated Sep. 22, 2020, 49 pages.
Final Office Action received for U.S. Appl. No. 16/377,892, dated Jan. 28, 2021, 11 pages.
Final Office Action received for U.S. Appl. No. 16/378,136, dated Jan. 28, 2021, 9 pages.
Final Office Action received for U.S. Appl. No. 16/389,722, dated Dec. 6, 2021, 19 pages.
Final Office Action received for U.S. Appl. No. 16/389,722, dated Dec. 8, 2020, 18 pages.
Final Office Action received for U.S. Appl. No. 16/407,590, dated Aug. 25, 2020, 14 pages.
Final Office Action received for U.S. Appl. No. 16/418,786, dated Jan. 13, 2021, 14 pages.
Final Office Action received for U.S. Appl. No. 16/679,967, dated Nov. 10, 2021, 14 pages.
Final Office Action received for U.S. Appl. No. 16/894,309, dated Feb. 24, 2021, 30 pages.
Final Office Action received for U.S. Appl. No. 17/030,318, dated Sep. 30, 2021, 28 pages.
Final Office Action received for U.S. Appl. No. 17/030,321, dated Apr. 2, 2021, 28 pages.
Final Office Action received for U.S. Appl. No. 17/031,859, dated Apr. 16, 2021, 14 pages.
Final Office Action received for U.S. Appl. No. 17/031,874, dated Apr. 16, 2021, 17 pages.
Final Office Action received for U.S. Appl. No. 17/031,874, dated Jun. 2, 2022, 19 pages.
Final Office Action received for U.S. Appl. No. 17/068,386, dated Mar. 3, 2022, 29 pages.
Final Office Action received for U.S. Appl. No. 17/192,161, dated Aug. 16, 2021, 22 pages.
Final Office Action received for U.S. Appl. No. 17/192,161, dated Oct. 18, 2021, 22 pages.
Fitbit App, Available online at: <http://web.archive.org/web/20180114083150/https://www.fitbit.com/au/app>, Jan. 14, 2018, 8 pages.
Garmin Edge 520, Owner's Manual, Online available at: https://www8.garmin.com/manuals/webhelp/edge520/EN-US/Edge_520_OM_EN-US.pdf, 2015, 24 pages.
Garmin, "Fenix 5x Owner's Manual", Online Available at:—https://web.archive.org/web/20180127170640/https://static.garmin.com/pumac/fenix5x_OM_EN.pdf, Jan. 27, 2018, 42 pages.
Graphs and Charts, online available at: <https://www.teachervision.com/lesson-planning/graph-chart-teacher-resources, retrieved on Dec. 12, 2018, 4 pages.
Gym Book—Strength Training Planner, Logger and Analyzer, GymBookApp, Available Online at: https://web.archive.org/web/20160401104508/https://gymbookapp.com/, Apr. 1, 2016, 10 pages.
Hamilton Jim, "Peloton Tips", Online available on:—<https://www.youtube.com/watch?app=desktop&v=OneXtBOkaD4>, Oct. 22, 2015, 3 pages.
How to Send and Receive files over Bluetooth on an Android Phone, Online Available at: <https://web.archive.org/web/20160529062240/http://www.androidtipsandhacks.com/android/send-receive-files-bluetooth-android-phone/, May 29, 2016, 7 pages.
Intention to Grant received for Danish Patent Application No. PA201570668, dated Mar. 27, 2017, 2 pages.
Intention to Grant received for Danish Patent Application No. PA201670656, dated Jan. 18, 2021, 2 pages.
Intention to Grant received for Danish Patent Application No. PA201870379, dated May 2, 2019, 2 pages.
Intention to Grant received for Danish Patent Application No. PA201870385, dated Jan. 24, 2020, 2 pages.
Intention to Grant received for Danish Patent Application No. PA202070615, dated Jan. 27, 2022, 2 pages.
Intention to Grant received for European Patent Application No. 16706081.3, dated Jul. 18, 2018, 8 pages.

(56) References Cited

OTHER PUBLICATIONS

Intention to Grant received for European Patent Application No. 16706081.3, dated Jun. 11, 2018, 7 pages.
Intention to Grant received for European Patent Application No. 16762356.0, dated Dec. 23, 2021, 8 pages.
Intention to Grant received for European Patent Application No. 18213157.3, dated May 19, 2021, 8 pages.
Intention to Grant received for European Patent Application No. 18213157.3, dated Oct. 27, 2021, 8 pages.
Intention to Grant received for European Patent Application No. 19724963.4, dated Sep. 20, 2021, 7 pages.
Intention to Grant received for European Patent Application No. 20182116.2, dated Jun. 2, 2022, 8 pages.
International Preliminary Report on Patentability received for PCT Application No. PCT/US2016/037686, dated Mar. 1, 2018, 12 pages.
International Preliminary Report on Patentability received for PCT Patent Application No. PCT/US2020/035199, dated Dec. 16, 2021, 14 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2014/027882, dated Sep. 24, 2015, 8 pages.
International Preliminary Report on Patentability received for PCT Patent Application No. PCT/US2015/032474, dated Dec. 15, 2016, 7 pages.
International Preliminary Report on Patentability received for PCT Patent Application No. PCT/US2015/047282, dated Mar. 16, 2017, 26 pages.
International Preliminary Report on Patentability received for PCT Patent Application No. PCT/US2015/053353, dated Sep. 21, 2017, 15 pages.
International Preliminary Report on Patentability received for PCT Patent Application No. PCT/US2016/014997, dated Dec. 21, 2017, 16 pages.
International Preliminary Report on Patentability received for PCT Patent Application No. PCT/US2016/016216, dated May 4, 2017, 14 pages.
International Preliminary Report on Patentability received for PCT Patent Application No. PCT/US2016/021403, dated Sep. 21, 2017, 21 pages.
International Preliminary Report on Patentability received for PCT Patent Application No. PCT/US2017/035554, dated Dec. 20, 2018, 39 pages.
International Preliminary Report on Patentability received for PCT Patent Application No. PCT/US2017/036608, dated Dec. 27, 2018, 12 pages.
International Preliminary Report on Patentability received for PCT Patent Application No. PCT/US2018/031662, dated Nov. 28, 2019, 12 pages.
International Preliminary Report on Patentability received for PCT Patent Application No. PCT/US2019/024570, dated Nov. 19, 2020, 10 pages.
International Preliminary Report on Patentability received for PCT Patent Application No. PCT/US2019/024790, dated Nov. 19, 2020, 11 pages.
International Preliminary Report on Patentability received for PCT Patent Application No. PCT/US2020/025997, dated Nov. 18, 2021, 10 pages.
International Search Report & Written Opinion received for PCT Patent Application No. PCT/US2016/014997, dated Aug. 31, 2016, 21 pages.
International Search Report and Written Opinion received for PCT Patent Application No. PCT/US2013/032498, dated Feb. 10, 2014, 18 pages.
International Search Report and Written Opinion received for PCT Patent Application No. PCT/US2014/027882, dated Oct. 10, 2014, 11 pages.
International Search Report and Written Opinion received for PCT Patent Application No. PCT/US2015/032474, dated Aug. 19, 2015, 8 pages.
International Search Report and Written Opinion received for PCT Patent Application No. PCT/US2015/047282, dated May 9, 2016, 33 pages.
International Search Report and Written Opinion received for PCT Patent Application No. PCT/US2015/053353, dated May 9, 2016, 21 pages.
International Search Report and Written Opinion received for PCT Patent Application No. PCT/US2016/016216, dated Jun. 27, 2016, 18 pages.
International Search Report and Written Opinion received for PCT Patent Application No. PCT/US2016/021403, dated May 12, 2016, 23 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2017/035554, dated Sep. 22, 2017, 42 pages.
International Search Report and Written Opinion received for PCT Patent Application No. PCT/US2017/036608, dated Oct. 20, 2017, 15 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2019/024570, dated Aug. 8, 2019, 18 pages.
International Search Report and Written Opinion received for PCT Patent Application No. PCT/US2019/024790, dated Sep. 11, 2019, 18 pages.
International Search Report and written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
International Search Report and Written Opinion received for PCT Patent Application No. PCT/US2020/035199, dated Oct. 30, 2020, 20 pages.
International Search Report and Written Opinion received for PCT Patent Application No. PCT/US2021/017736, dated Sep. 2, 2021, 25 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Internet Blog Post,"[Pc] Pre-Customization of Black Desert's Characters", Online Available at:—<https://blog.naver.com/hsh6051/220209813968>, Dec. 14, 2014, 41 pages.
Invitation to Pay Addition Fees and Partial International Search Report received for PCT Patent Application No. PCT/US2018/031662, dated Jul. 16, 2018, 13 pages.
Invitation to Pay Additional Fee received for PCT Patent Application No. PCT/US2019/024790, dated Jul. 18, 2019, 10 pages.
Invitation to Pay Additional Fees received for PCT Patent Application No. PCT/US2014/027882, dated Aug. 5, 2014, 2 pages.
Invitation to Pay Additional Fees received for PCT Patent Application No. PCT/US2015/047282, dated Dec. 22, 2015, 7 pages.
Invitation to Pay Additional fees received for PCT Patent Application No. PCT/US2015/053353, dated Jan. 21, 2016, 7 pages.
Invitation to Pay Additional Fees received for PCT Patent Application No. PCT/US2016/014997, dated May 2, 2016, 5 pages.
Invitation to Pay Additional Fees received for PCT Patent Application No. PCT/US2016/016216, dated Apr. 20, 2016, 6 pages.
Invitation to Pay Additional Fees received for PCT Patent Application No. PCT/US2017/035554, dated Jul. 20, 2017, 2 pages.
Invitation to Pay Additional Fees received for PCT Patent Application No. PCT/US2017/036608, dated Aug. 14, 2017, 2 pages.
Invitation to Pay Additional Fees received for PCT Patent Application No. PCT/US2020/035199, dated Sep. 8, 2020, 12 pages.

(56) References Cited

OTHER PUBLICATIONS

Invitation to Pay Additional Fees received for PCT Patent Application No. PCT/US2021/017736, dated Jun. 15, 2021, 14 pages.
Invitation to Restrict or Pay Additional Fees received for PCT Patent Application No. PCT/US2016/016216, dated Dec. 19, 2016, 9 pages.
Jenbsjourney, "Wondering About a Fitbit?", Available at: https://jenbsjourney.blogspot.kr/2013/08/wondering-about-fitbit.html, Aug. 6, 2013, 12 pages.
Jurick et al., "iPhone Hacks", Tips & Tools for Unlocking the Power of Your iPhone & iPod touch, Online: URL: https://api.pageplace.de/preview/DT0400.9780596550974_A23629666/preview-9780596550974_A23629666.pdf >, Apr. 2009, 49 pages.
Kamcord—Wikipedia, Online Available at: <https://en.wikipedia.org/w/index.php?title=Kamcord&oldid=712263010>, Mar. 28, 2016, 2 pages.
Kamcord Developers—Quick Start Guide, Online Available at: <https://web.archive.org/web/20140801055705/https://www.kamcord.com/developers/doc s/ios/features-and-settings/, Aug. 1, 2014, 10 pages.
Kamcord Developers, Online Available at: <https://web.archive.org/web/20140827043641/http://www.kamcord.com/developers/>, Aug. 27, 2014, 7 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
Minutes of Oral Proceedings received for European Patent Application No. 16762356.0, mailed on Dec. 17, 2021, 5 pages.
Minutes of the Oral Proceedings received for European Patent Application No. 15771747.1, mailed on Dec. 1, 2021, 4 pages.
Minutes of the Oral Proceedings received for European Patent Application No. 17810749.6, mailed on Jan. 26, 2021, 8 pages.
Minutes of the Oral Proceedings received for European Patent Application No. 18154145.9, mailed on Feb. 12, 2021, 8 pages.
Minutes of the Oral Proceedings received for European Patent Application No. 19724963.4, mailed on Sep. 3, 2021, 6 pages.
Minutes of the Oral Proceedings received for European Patent Application No. 20182116.2, mailed on May 24, 2022, 7 pages.
Mugs, Online Available at: https://web.archive.org/web/20151029034349/http://le-mugs.com/, Oct. 29, 2015, 14 pages.
Multi-Set Bar Chart, the Data Visualization Catalogue, Available Online at: https://datavizcatalogue.com/methods/multiset_barchart.html, Feb. 8, 2014, 3 pages.
My CalStep, http://www.surprisesoftware.com/mycalstep/, retireved from the Wayback Machine, May 9, 2007, 2 pages.
Non-Final Office Action Received for U.S. Appl. No. 16/144,864, dated Dec. 18, 2018, 19 pages.
Non-Final Office Action received for U.S. Appl. No. 15/554,204, dated Apr. 17, 2019, 19 pages.
Non-Final Office Action received for U.S. Appl. No. 16/679,967, dated Sep. 2, 2021, 12 pages.
Non-Final Office Action received for U.S. Appl. No. 16/994,352, dated Jul. 30, 2021, 11 pages.
Non-Final Office Action received for U.S. Appl. No. 12/205,847, dated Oct. 3, 2011, 59 pages.
Non-Final Office Action received for U.S. Appl. No. 14/503,372, dated Dec. 5, 2014, 11 pages.
Non-Final Office Action received for U.S. Appl. No. 14/599,424, dated Jan. 17, 2018, 13 pages.
Non-Final Office Action received for U.S. Appl. No. 14/599,425, dated Jan. 11, 2018, 42 pages.
Non-Final Office Action received for U.S. Appl. No. 14/599,425, dated Mar. 17, 2015, 16 pages.
Non-Final Office Action received for U.S. Appl. No. 14/599,425, dated Oct. 26, 2016, 22 pages.
Non-Final Office Action received for U.S. Appl. No. 14/732,773, dated Feb. 8, 2019, 32 pages.
Non-Final Office Action received for U.S. Appl. No. 14/732,773, dated Jan. 19, 2018, 45 pages.
Non-Final Office Action received for U.S. Appl. No. 14/774,664, dated Mar. 7, 2017, 23 pages.
Non-Final Office Action received for U.S. Appl. No. 14/839,916, dated Feb. 4, 2016, 19 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 14/839,922, dated Feb. 25, 2016, 20 pages.
Non-Final Office Action received for U.S. Appl. No. 14/841,606, dated Dec. 7, 2017, 30 pages.
Non-Final Office Action received for U.S. Appl. No. 14/841,606, dated May 8, 2019, 28 pages.
Non-Final Office Action received for U.S. Appl. No. 14/863,069, dated Oct. 5, 2017, 19 pages.
Non-Final Office Action received for U.S. Appl. No. 14/863,099, dated Dec. 2, 2015, 12 pages.
Non-Final Office Action received for U.S. Appl. No. 14/864,759, dated Mar. 20, 2018, 20 pages.
Non-Final Office Action received for U.S. Appl. No. 15/183,663, dated Jul. 9, 2018, 13 pages.
Non-Final Office Action received for U.S. Appl. No. 15/600,243, dated Jun. 27, 2019, 17 pages.
Non-Final Office Action received for U.S. Appl. No. 15/608,848, dated Feb. 6, 2020, 12 pages.
Non-Final Office Action received for U.S. Appl. No. 15/608,848, dated Feb. 12, 2021, 14 pages.
Non-Final Office Action received for U.S. Appl. No. 15/608,848, dated Nov. 2, 2018, 21 pages.
Non-Final Office Action received for U.S. Appl. No. 15/614,121, dated Nov. 4, 2019, 44 pages.
Non-Final Office Action received for U.S. Appl. No. 15/614,121, dated Nov. 30, 2018, 28 pages.
Non-Final Office Action received for U.S. Appl. No. 15/627,069, dated Jun. 21, 2019, 22 pages.
Non-Final Office Action received for U.S. Appl. No. 15/627,069, dated May 26, 2020, 25 pages.
Non-Final Office Action received for U.S. Appl. No. 15/705,849, dated Nov. 12, 2019, 15 pages.
Non-Final Office Action received for U.S. Appl. No. 15/925,652, dated Apr. 5, 2019, 28 pages.
Non-Final Office Action received for U.S. Appl. No. 15/925,652, dated Aug. 7, 2020, 39 pages.
Non-Final Office Action received for U.S. Appl. No. 16/138,809, dated Feb. 28, 2020, 22 pages.
Non-Final Office Action received for U.S. Appl. No. 16/144,735, dated Feb. 19, 2020, 10 pages.
Non-Final Office Action received for U.S. Appl. No. 16/144,753, dated Mar. 5, 2020, 9 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action received for U.S. Appl. No. 16/144,864, dated Jan. 31, 2020, 29 pages.
Non-Final Office Action received for U.S. Appl. No. 16/145,033, dated Feb. 9, 2021, 55 pages.
Non-Final Office Action received for U.S. Appl. No. 16/145,033, dated Mar. 4, 2020, 50 pages.
Non-Final Office Action received for U.S. Appl. No. 16/363,945, dated Apr. 24, 2020, 13 pages.
Non-Final Office Action received for U.S. Appl. No. 16/377,892, dated May 21, 2020, 9 pages.
Non-Final Office Action received for U.S. Appl. No. 16/378,136, dated Jun. 2, 2020, 8 pages.
Non-Final Office Action received for U.S. Appl. No. 16/388,493, dated Dec. 9, 2021, 7 pages.
Non-Final Office Action received for U.S. Appl. No. 16/389,722, dated Apr. 3, 2020, 15 pages.
Non-Final Office Action received for U.S. Appl. No. 16/389,722, dated Jun. 3, 2021, 17 pages.

(56) References Cited

OTHER PUBLICATIONS

Non-Final Office Action received for U.S. Appl. No. 16/407,590, dated Apr. 10, 2020, 12 pages.
Non-Final Office Action received for U.S. Appl. No. 16/418,786, dated Apr. 24, 2020, 16 pages.
Non-Final Office Action received for U.S. Appl. No. 16/418,786, dated Mar. 28, 2022, 14 pages.
Non-Final Office Action received for U.S. Appl. No. 16/418,786, dated Oct. 4, 2021, 10 pages.
Non-Final Office Action received for U.S. Appl. No. 16/679,967, dated Apr. 19, 2022, 13 pages.
Non-Final Office Action received for U.S. Appl. No. 16/820,383, dated Dec. 14, 2020, 11 pages.
Non-Final Office Action received for U.S. Appl. No. 16/820,383, dated Jan. 10, 2022, 18 pages.
Non-Final Office Action received for U.S. Appl. No. 16/888,629, dated Mar. 31, 2021, 14 pages.
Non-Final Office Action received for U.S. Appl. No. 16/894,309, dated Oct. 15, 2020, 24 pages.
Non-Final Office Action received for U.S. Appl. No. 16/987,275, dated Nov. 23, 2021, 17 pages.
Non-Final Office Action received for U.S. Appl. No. 17/030,318, dated Apr. 2, 2021, 28 pages.
Non-Final Office Action received for U.S. Appl. No. 17/030,318, dated Dec. 3, 2020, 22 pages.
Non-Final Office Action received for U.S. Appl. No. 17/030,321, dated Dec. 15, 2020, 25 pages.
Non-Final Office Action received for U.S. Appl. No. 17/030,321, dated Oct. 18, 2021, 28 pages.
Non-Final Office Action received for U.S. Appl. No. 17/031,543, dated Apr. 1, 2022, 9 pages.
Non-Final Office Action received for U.S. Appl. No. 17/031,854, dated Dec. 27, 2021, 13 pages.
Non-Final Office Action received for U.S. Appl. No. 17/031,859, dated Dec. 15, 2020, 13 pages.
Non-Final Office Action received for U.S. Appl. No. 17/031,859, dated Dec. 24, 2021, 16 pages.
Non-Final Office Action received for U.S. Appl. No. 17/031,874, dated Dec. 28, 2020, 14 pages.
Non-Final Office Action received for U.S. Appl. No. 17/031,874, dated Jan. 24, 2022, 18 pages.
Non-Final Office Action received for U.S. Appl. No. 17/068,386, dated Jul. 15, 2021, 16 pages.
Non-Final Office Action received for U.S. Appl. No. 17/068,386, dated Oct. 28, 2021, 20 pages.
Non-Final Office Action received for U.S. Appl. No. 17/116,775, dated Aug. 24, 2021, 20 pages.
Non-Final Office Action received for U.S. Appl. No. 17/126,571, dated Dec. 21, 2021, 19 pages.
Non-Final Office Action received for U.S. Appl. No. 17/157,728, dated Nov. 26, 2021, 18 pages.
Non-Final Office Action received for U.S. Appl. No. 17/192,161, dated May 13, 2021, 28 pages.
Non-Final Office Action received for U.S. Appl. No. 17/327,204, dated Nov. 26, 2021, 13 pages.
Non-Final Office Action received for U.S. Appl. No. 17/381,570, dated Apr. 1, 2022, 29 pages.
Non-Final Office Action received for U.S. Appl. No. 17/516,537, dated May 5, 2022, 8 pages.
Notice of Acceptance received for Australian Patent Application No. 2015267240, dated Apr. 10, 2018, 3 pages.
Notice of Acceptance received for Australian Patent Application No. 2015312215, dated Oct. 9, 2017, 3 pages.
Notice of Acceptance received for Australian Patent Application No. 2016215440, dated Feb. 28, 2019, 3 pages.
Notice of Acceptance received for Australian Patent Application No. 2016229847, dated Sep. 12, 2018, 3 pages.
Notice of Acceptance received for Australian Patent Application No. 2017277971, dated Feb. 17, 2021, 3 pages.
Notice of Acceptance received for Australian Patent Application No. 2017286296, dated May 1, 2020, 3 pages.
Notice of Acceptance received for Australian Patent Application No. 2018206772, dated Mar. 17, 2020, 3 pages.
Notice of Acceptance received for Australian Patent Application No. 2018268972, dated Dec. 18, 2020, 3 pages.
Notice of Acceptance received for Australian Patent Application No. 2018279037, dated May 13, 2020, 3 pages.
Notice of Acceptance received for Australian Patent Application No. 2019201583, dated Jul. 15, 2019, 3 pages.
Notice of Acceptance received for Australian Patent Application No. 2019222943, dated May 5, 2020, 3 pages.
Notice of Acceptance received for Australian Patent Application No. 2019250251, dated Feb. 18, 2021, 3 pages.
Notice of Acceptance received for Australian Patent Application No. 2019266054, dated Nov. 25, 2021, 3 pages.
Notice of Acceptance received for Australian Patent Application No. 2020204153, dated Jul. 6, 2020, 3 pages.
Notice of Acceptance received for Australian Patent Application No. 2020204259, dated Jun. 11, 2021, 3 pages.
Notice of Acceptance received for Australian Patent Application No. 2020204506, dated Apr. 8, 2021, 3 pages.
Notice of Acceptance received for Australian Patent Application No. 2020210234, dated Feb. 3, 2022, 3 pages.
Notice of Acceptance received for Australian Patent Application No. 2020239743, dated Jan. 13, 2022, 3 pages.
Notice of Acceptance received for Australian Patent Application No. 2020239752, dated Jan. 31, 2022, 3 pages.
Notice of Acceptance received for Australian Patent Application No. 2020256383, dated Aug. 3, 2021, 3 pages.
Notice of Acceptance received for Australian Patent Application No. 2021200787, dated Mar. 19, 2021, 3 pages.
Notice of Acceptance received for Australian Patent Application No. 2021201130, dated Mar. 28, 2022, 3 pages.
Notice of Acceptance received for Australian Patent Application No. 2021203636, dated Apr. 14, 2022, 3 pages.
Notice of Allowance received for Australian Patent Application No. 2020239748, dated Mar. 7, 2022, 3 pages.
Notice of Allowance received for Chinese Patent Application No. 201380081349.6, dated Dec. 17, 2021, 2 pages.
Notice of Allowance received for Chinese Patent Application No. 201520358505.5, dated Jan. 13, 2016, 3 pages.
Notice of Allowance received for Chinese Patent Application No. 201580028677.9, dated Apr. 2, 2019, 2 pages.
Notice of Allowance received for Chinese Patent Application No. 201580037927.5, dated Oct. 17, 2019, 3 pages.
Notice of Allowance received for Chinese Patent Application No. 201680008151.9, dated Jun. 16, 2020, 2 pages.
Notice of Allowance received for Chinese Patent Application No. 201680013193.1, dated May 7, 2021, 5 pages.
Notice of Allowance received for Chinese Patent Application No. 201680047983.1, dated Apr. 28, 2021, 3 pages.
Notice of Allowance received for Chinese Patent Application No. 201710439448.7, dated Jan. 26, 2021, 2 pages.
Notice of Allowance received for Chinese Patent Application No. 201780034193.4, dated Oct. 20, 2021, 4 pages.
Notice of Allowance received for Chinese Patent Application No. 201780034203.4, dated Jan. 17, 2022, 2 pages.
Notice of Allowance received for Chinese Patent Application No. 201810105846.X, dated Feb. 18, 2020, 2 pages.
Notice of Allowance received for Chinese Patent Application No. 201811136445.7, dated Aug. 11, 2021, 2 pages.
Notice of Allowance received for Chinese Patent Application No. 202010606407.4, dated Jan. 24, 2022, 2 pages.
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages.
Notice of Allowance received for Japanese Patent Application No. 2016-557650, dated Apr. 9, 2019, 4 pages.

(56) References Cited

OTHER PUBLICATIONS

Notice of Allowance received for Japanese Patent Application No. 2016-569945, dated Jan. 7, 2020, 4 pages.
Notice of Allowance received for Japanese Patent Application No. 2017-545918, dated Jul. 22, 2019, 4 pages.
Notice of Allowance received for Japanese Patent Application No. 2018-014096, dated Jan. 5, 2021, 3 pages.
Notice of Allowance received for Japanese Patent Application No. 2018-068846, dated Dec. 9, 2019, 4 pages.
Notice of Allowance received for Japanese Patent Application No. 2018-184532, dated Jan. 17, 2022, 4 pages.
Notice of Allowance received for Japanese Patent Application No. 2019-151358, dated Jan. 22, 2021, 4 pages.
Notice of Allowance received for Japanese Patent Application No. 2019-162293, dated Apr. 9, 2021, 4 pages.
Notice of Allowance received for Japanese Patent Application No. 2019-563407, dated Aug. 20, 2021, 4 pages.
Notice of Allowance received for Japanese Patent Application No. 2020-000492, dated Jul. 16, 2021, 4 pages.
Notice of Allowance received for Japanese Patent Application No. 2020-010239, dated Sep. 3, 2021, 4 pages.
Notice of Allowance received for Japanese Patent Application No. 2020-104679, dated Jan. 4, 2021, 4 pages.
Notice of Allowance received for Japanese Patent Application No. 2020-115940, dated Oct. 22, 2021, 4 pages.
Notice of Allowance received for Japanese Patent Application No. 2020-160054, dated Apr. 4, 2022, 4 pages.
Notice of Allowance received for Korean Patent Application No. 10-2016-7014577, dated May 30, 2019, 5 pages.
Notice of Allowance received for Korean Patent Application No. 10-2016-7033638, dated May 31, 2017, 5 pages.
Notice of Allowance received for Korean Patent Application No. 10-2019-7025538, dated Mar. 10, 2021, 5 pages.
Notice of Allowance received for Korean Patent Application No. 10-2019-7025781, dated Jun. 29, 2021, 5 pages.
Notice of Allowance received for Korean Patent Application No. 10-2019-7029673, dated Aug. 3, 2021, 3 pages.
Notice of Allowance received for Korean Patent Application No. 10-2019-7033834, dated Jul. 3, 2021, 4 pages.
Notice of Allowance received for Korean Patent Application No. 10-2020-7026035, dated Aug. 23, 2021, 4 pages.
Notice of Allowance received for Korean Patent Application No. 10-2021-7031939, dated Apr. 5, 2022, 4 pages.
Notice of Allowance received for Korean Patent Application No. 10-2021-7038005, dated Dec. 14, 2021, 4 pages.
Notice of Allowance received for Korean Patent Application No. 10-2022-7008569, dated May 19, 2022, 5 pages.
Notice of Allowance received for Taiwanese Patent Application No. 104117509, dated Mar. 31, 2017, 3 pages.
Notice of Allowance received for Taiwanese Patent Application No. 104128685, dated May 3, 2017, 3 pages.
Notice of Allowance received for U.S. Appl. No. 12/205,847, dated Aug. 20, 2012, 13 pages.
Notice of Allowance received for U.S. Appl. No. 14/599,424, dated Dec. 13, 2018, 6 pages.
Notice of Allowance received for U.S. Appl. No. 14/599,425, dated Dec. 19, 2018, 9 pages.
Notice of Allowance received for U.S. Appl. No. 14/732,773, dated Dec. 18, 2019, 21 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 14/863,069, dated Feb. 6, 2019, 6 pages.
Notice of Allowance received for U.S. Appl. No. 14/863,069, dated Jun. 18, 2019, 6 pages.
Notice of Allowance received for U.S. Appl. No. 14/864,759, dated Dec. 14, 2018, 10 pages.
Notice of Allowance received for U.S. Appl. No. 15/183,663, dated Jan. 17, 2019, 6 pages.
Notice of Allowance received for U.S. Appl. No. 15/554,204, dated Jul. 13, 2020, 10 pages.
Notice of Allowance received for U.S. Appl. No. 15/600,243, dated Dec. 12, 2019, 7 pages.
Notice of Allowance received for U.S. Appl. No. 15/608,848, dated Aug. 25, 2021, 9 pages.
Notice of Allowance received for U.S. Appl. No. 15/608,848, dated Oct. 29, 2021, 7 pages.
Notice of Allowance received for U.S. Appl. No. 15/614,121, dated Aug. 27, 2020, 8 pages.
Notice of Allowance received for U.S. Appl. No. 15/614,121, dated Mar. 6, 2020, 8 pages.
Notice of Allowance received for U.S. Appl. No. 15/616,480, dated Jan. 3, 2019, 8 pages.
Notice of Allowance received for U.S. Appl. No. 15/627,069, dated Jun. 17, 2021, 14 pages.
Notice of Allowance received for U.S. Appl. No. 15/705,849, dated Jul. 28, 2020, 10 pages.
Notice of Allowance received for U.S. Appl. No. 15/705,849, dated Oct. 16, 2020, 14 pages.
Notice of Allowance received for U.S. Appl. No. 15/925,652, dated Mar. 9, 2021, 9 pages.
Notice of Allowance received for U.S. Appl. No. 15/925,652, dated Nov. 20, 2020, 9 pages.
Notice of Allowance received for U.S. Appl. No. 16/138,809, dated Apr. 16, 2021, 11 pages.
Notice of Allowance received for U.S. Appl. No. 16/138,809, dated Jul. 20, 2021, 6 pages.
Notice of Allowance received for U.S. Appl. No. 16/144,671, dated Feb. 10, 2020, 17 pages.
Notice of Allowance received for U.S. Appl. No. 16/144,735, dated Jul. 21, 2020, 13 pages.
Notice of Allowance received for U.S. Appl. No. 16/144,735, dated Oct. 28, 2020, 13 pages.
Notice of Allowance received for U.S. Appl. No. 16/144,753, dated Dec. 4, 2020, 22 pages.
Notice of Allowance received for U.S. Appl. No. 16/144,753, dated Feb. 10, 2021, 8 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Notice of Allowance received for U.S. Appl. No. 16/144,864, dated Feb. 9, 2021, 13 pages.
Notice of Allowance received for U.S. Appl. No. 16/144,864, dated Jul. 28, 2020, 27 pages.
Notice of Allowance received for U.S. Appl. No. 16/144,864, dated Mar. 12, 2021, 2 pages.
Notice of Allowance received for U.S. Appl. No. 16/144,864, dated Mar. 30, 2021, 2 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/144,864, dated Sep. 29, 2020, 2 pages.
Notice of Allowance received for U.S. Appl. No. 16/363,945, dated Sep. 23, 2020, 10 pages.
Notice of Allowance received for U.S. Appl. No. 16/377,892, dated May 24, 2021, 9 pages.
Notice of Allowance received for U.S. Appl. No. 16/377,892, dated Sep. 9, 2021, 9 pages.
Notice of Allowance received for U.S. Appl. No. 16/378,136, dated Jun. 3, 2021, 7 pages.

(56) References Cited

OTHER PUBLICATIONS

Notice of Allowance received for U.S. Appl. No. 16/378,136, dated Sep. 22, 2021, 7 pages.
Notice of Allowance received for U.S. Appl. No. 16/407,590, dated Apr. 9, 2021, 3 pages.
Notice of Allowance received for U.S. Appl. No. 16/407,590, dated Dec. 16, 2020, 6 pages.
Notice of Allowance received for U.S. Appl. No. 16/407,590, dated Mar. 22, 2021, 6 pages.
Notice of Allowance received for U.S. Appl. No. 16/418,786, dated Dec. 9, 2021, 9 pages.
Notice of Allowance received for U.S. Appl. No. 16/556,023, dated Jan. 13, 2021, 8 pages.
Notice of Allowance received for U.S. Appl. No. 16/556,023, dated Oct. 15, 2020, 8 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Notice of Allowance received for U.S. Appl. No. 16/820,383, dated Jul. 21, 2021, 11 pages.
Notice of Allowance received for U.S. Appl. No. 16/820,383, dated Mar. 31, 2021, 11 pages.
Notice of Allowance received for U.S. Appl. No. 16/888,629, dated Nov. 9, 2021, 11 pages.
Notice of Allowance received for U.S. Appl. No. 16/894,309, dated Feb. 25, 2022, 9 pages.
Notice of Allowance received for U.S. Appl. No. 16/894,309, dated Nov. 5, 2021, 12 pages.
Notice of Allowance received for U.S. Appl. No. 16/987,275, dated May 16, 2022, 7 pages.
Notice of Allowance received for U.S. Appl. No. 16/994,352, dated Jun. 3, 2022, 9 pages.
Notice of Allowance received for U.S. Appl. No. 16/994,352, dated Mar. 2, 2022, 14 pages.
Notice of Allowance received for U.S. Appl. No. 17/030,318, dated Jan. 5, 2022, 8 pages.
Notice of Allowance received for U.S. Appl. No. 17/030,321, dated Apr. 1, 2022, 8 pages.
Notice of Allowance received for U.S. Appl. No. 17/031,543, dated May 11, 2022, 6 pages.
Notice of Allowance received for U.S. Appl. No. 17/116,775, dated Jan. 18, 2022, 10 pages.
Notice of Allowance received for U.S. Appl. No. 17/126,571, dated Mar. 11, 2022, 9 pages.
Notice of Allowance received for U.S. Appl. No. 17/157,728, dated Feb. 24, 2022, 7 pages.
Notice of Allowance received for U.S. Appl. No. 17/192,161, dated Feb. 16, 2022, 8 pages.
Notice of Allowance received for U.S. Appl. No. 17/192,161, dated May 27, 2022, 8 pages.
Notice of Allowance received for U.S. Appl. No. 17/197,628, dated Mar. 23, 2022, 35 pages.
Notice of Allowance received for U.S. Appl. No. 17/327,204, dated May 18, 2022, 18 pages.
Office Action received for Australian Patent Application No. 2015100734, dated Jul. 29, 2015, 5 pages.
Office Action received for Australian Patent Application No. 2015267240, dated Apr. 10, 2017, 5 pages.
Office Action received for Australian Patent Application No. 2015267240, dated Mar. 21, 2018, 5 pages.
Office Action received for Australian Patent Application No. 2015312215, dated Oct. 13, 2016, 3 pages.
Office Action received for Australian Patent Application No. 2016215440, dated Jan. 22, 2019, 2 pages.
Office Action received for Australian Patent Application No. 2016215440, dated Mar. 13, 2018, 3 pages.
Office Action received for Australian Patent Application No. 2016229847, dated Jul. 3, 2018, 4 pages.
Office Action received for Australian Patent Application No. 2017100667, dated Aug. 3, 2017, 9 pages.
Office Action received for Australian Patent Application No. 2017277971, dated Aug. 12, 2020, 3 pages.
Office Action received for Australian Patent Application No. 2017277971, dated Jun. 3, 2020, 3 pages.
Office Action received for Australian Patent Application No. 2017286296, dated May 8, 2019, 4 pages.
Office Action received for Australian Patent Application No. 2018100158, dated Apr. 23, 2018, 5 pages.
Office Action received for Australian Patent Application No. 2018101855, dated Feb. 22, 2019, 4 pages.
Office Action received for Australian Patent Application No. 2018200428, dated Mar. 7, 2018, 4 pages.
Office Action received for Australian Patent Application No. 2018200428, dated Nov. 15, 2018, 4 pages.
Office Action received for Australian Patent Application No. 2018206772, dated Apr. 1, 2019, 4 pages.
Office Action received for Australian Patent Application No. 2018206772, dated Feb. 6, 2020, 4 pages.
Office Action received for Australian Patent Application No. 2018206772, dated Nov. 6, 2019, 4 pages.
Office Action received for Australian Patent Application No. 2018268972, dated Jul. 9, 2020, 4 pages.
Office Action received for Australian Patent Application No. 2018279037, dated Jan. 17, 2020, 4 pages.
Office Action received for Australian Patent Application No. 2018279037, dated Jun. 18, 2019, 5 pages.
Office Action received for Australian Patent Application No. 2019100490, dated Jul. 26, 2019, 4 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Australian Patent Application No. 2019250251, dated Aug. 6, 2020, 3 pages.
Office Action received for Australian Patent Application No. 2019266054, dated Aug. 23, 2021, 4 pages.
Office Action received for Australian Patent Application No. 2019266054, dated Jun. 29, 2021, 3 pages.
Office Action received for Australian Patent Application No. 2020204259, dated Nov. 30, 2020, 8 pages.
Office Action received for Australian Patent Application No. 2020204506, dated Dec. 7, 2020, 6 pages.
Office Action received for Australian Patent Application No. 2020210234, dated Jul. 30, 2021, 7 pages.
Office Action received for Australian Patent Application No. 2020239743, dated Mar. 25, 2021, 8 pages.
Office Action received for Australian Patent Application No. 2020239743, dated Sep. 3, 2021, 4 pages.
Office Action received for Australian Patent Application No. 2020239748, dated Apr. 21, 2021, 6 pages.
Office Action received for Australian Patent Application No. 2020239748, dated Feb. 11, 2022, 2 pages.
Office Action received for Australian Patent Application No. 2020239748, dated Sep. 1, 2021, 4 pages.
Office Action received for Australian Patent Application No. 2020239752, dated Jun. 4, 2021, 8 pages.
Office Action received for Australian Patent Application No. 2020239752, dated Oct. 25, 2021, 5 pages.
Office Action received for Australian Patent Application No. 2020256383, dated Jun. 4, 2021, 3 pages.
Office Action received for Australian Patent Application No. 2021201130, dated Jan. 27, 2022, 2 pages.
Office Action received for Australian Patent Application No. 2021203216, dated Mar. 7, 2022, 8 pages.
Office Action received for Australian Patent Application No. 2021203636, dated Mar. 23, 2022, 3 pages.

(56) References Cited

OTHER PUBLICATIONS

Office Action received for Australian Patent Application No. 2021204422, dated May 31, 2022, 2 pages.
Office Action received for Chinese Patent Application No. 201380081349.6, dated Feb. 26, 2019, 12 pages.
Office Action received for Chinese Patent Application No. 201380081349.6, dated Jan. 5, 2021, 16 pages.
Office Action received for Chinese Patent Application No. 201380081349.6, dated Jan. 16, 2020, 11 pages.
Office Action received for Chinese Patent Application No. 201380081349.6, dated Jul. 15, 2019, 10 pages.
Office Action received for Chinese Patent Application No. 201380081349.6, dated Jul. 15, 2020, 9 pages.
Office Action received for Chinese Patent Application No. 201380081349.6, dated Jun. 2, 2021, 17 pages.
Office Action received for Chinese Patent Application No. 201510284850.3, dated Jul. 9, 2018, 11 pages.
Office Action received for Chinese Patent Application No. 201510284850.3, dated Jun. 21, 2019, 10 pages.
Office Action received for Chinese Patent Application No. 201510284850.3, dated Nov. 28, 2017, 15 pages.
Office Action received for Chinese Patent Application No. 201580028677.9, dated May 25, 2018, 14 pages.
Office Action received for Chinese Patent Application No. 201580037927.5, dated Apr. 22, 2019, 9 pages.
Office Action received for Chinese Patent Application No. 201580037927.5, dated Jul. 20, 2018, 21 pages.
Office Action received for Chinese Patent Application No. 201680008151.9, dated Apr. 20, 2020, 6 pages.
Office Action received for Chinese Patent Application No. 201680008151.9, dated Aug. 27, 2019, 24 pages.
Office Action received for Chinese Patent Application No. 201680013193.1, dated Feb. 1, 2021, 8 pages.
Office Action received for Chinese Patent Application No. 201680013193.1, dated Mar. 25, 2020, 21 pages.
Office Action received for Chinese Patent Application No. 201680013193.1, dated Sep. 7, 2020, 6 pages.
Office Action received for Chinese Patent Application No. 201680047983.1, dated Feb. 1, 2021, 6 pages.
Office Action received for Chinese Patent Application No. 201680047983.1, dated Jul. 1, 2020, 6 pages.
Office Action received for Chinese Patent Application No. 201680047983.1, dated Mar. 18, 2019, 18 pages.
Office Action received for Chinese Patent Application No. 201680047983.1, dated Nov. 28, 2019, 9 pages.
Office Action received for Chinese Patent Application No. 201710439448.7, dated Mar. 27, 2020, 13 pages.
Office Action received for Chinese Patent Application No. 201710439448.7, dated Oct. 10, 2020, 19 pages.
Office Action received for Chinese Patent Application No. 201780034193.4, dated Jun. 8, 2021, 16 pages.
Office Action received for Chinese Patent Application No. 201780034203.4, dated Jul. 14, 2021, 12 pages.
Office Action received for Chinese Patent Application No. 201780034203.4, dated Sep. 24, 2021, 7 pages.
Office Action received for Chinese Patent Application No. 201810105846.X, dated Aug. 27, 2019, 12 pages.
Office Action received for Chinese Patent Application No. 201810105846.X, dated Feb. 25, 2019, 10 pages.
Office Action received for Chinese Patent Application No. 201810105846.X, dated Nov. 28, 2019, 9 pages.
Office Action received for Chinese Patent Application No. 201811136445.7, dated Apr. 14, 2021, 7 pages.
Office Action received for Chinese Patent Application No. 201811136445.7, dated Oct. 28, 2020, 17 pages.
Office Action received for Chinese Patent Application No. 201910858933.7, dated Aug. 18, 2020, 14 pages.
Office Action received for Chinese Patent Application No. 201910858933.7, dated Dec. 30, 2021, 9 pages.
Office Action received for Chinese Patent Application No. 201910858933.7, dated Jun. 29, 2021, 8 pages.
Office Action received for Chinese Patent Application No. 201911401161.0, dated Jan. 24, 2022, 6 pages.
Office Action received for Chinese Patent Application No. 202010606407.4, dated Jan. 27, 2021, 16 pages.
Office Action received for Chinese Patent Application No. 202010606407.4, dated Jun. 2, 2021, 12 pages.
Office Action received for Chinese Patent Application No. 202010606407.4, dated Nov. 18, 2021, 6 pages.
Office Action received for Chinese Patent Application No. 202110363565.6, dated Nov. 16, 2021, 16 pages.
Office Action received for Chinese Patent Application No. 202110783860.7, dated Mar. 10, 2022, 15 pages.
Office Action received for Danish Patent Application No. PA 2020 70612, dated Mar. 1, 2022, 2 pages.
Office Action received for Danish Patent Application No. PA201570666, dated Feb. 2, 2016, 9 pages.
Office Action received for Danish Patent Application No. PA201570666, dated Jun. 27, 2016, 4 pages.
Office Action received for Danish Patent Application No. PA201570668, dated Apr. 8, 2016, 8 pages.
Office Action received for Danish Patent Application No. PA201570668, dated Sep. 9, 2016, 3 pages.
Office Action Received for Danish Patent Application No. PA201670656, dated Jul. 1, 2020, 4 pages.
Office Action received for Danish Patent Application No. PA201670656, dated Jun. 14, 2017, 3 pages.
Office Action Received for Danish Patent Application No. PA201670656, dated May 2, 2019, 4 pages.
Office Action Received for Danish Patent Application No. PA201670656, dated May 30, 2018, 5 pages.
Office Action Received for Danish Patent Application No. PA201670656, dated Nov. 3, 2016, 8 pages.
Office Action received for Danish Patent Application No. PA201770191, dated Jan. 25, 2018, 3 pages.
Office Action received for Danish Patent Application No. PA201770191, dated Nov. 21, 2018, 4 pages.
Office Action received for Danish Patent Application No. PA201770191, dated Oct. 25, 2019, 4 pages.
Office Action received for Danish Patent Application No. PA201770423, dated Jun. 12, 2018, 7 pages.
Office Action received for Danish Patent Application No. PA201770423, dated Mar. 29, 2019, 6 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201870385, dated Aug. 23, 2019, 3 pages.
Office Action received for Danish Patent Application No. PA201970532, dated May 29, 2020, 3 pages.
Office Action received for Danish Patent Application No. PA202070612, dated May 10, 2022, 2 pages.
Office Action received for Danish Patent Application No. PA202070613, dated May 10, 2022, 2 pages.
Office Action received for Danish Patent Application No. PA202070613, dated Sep. 30, 2021, 4 pages.
Office Action received for Danish Patent Application No. PA202070614, dated Apr. 28, 2022, 4 pages.
Office Action received for Danish Patent Application No. PA202070614, dated Sep. 28, 2021, 4 pages.
Office Action received for Danish Patent Application No. PA202070615, dated Nov. 16, 2021, 4 pages.

(56) References Cited

OTHER PUBLICATIONS

Office Action received for Danish Patent Application No. PA202070616, dated Jan. 27, 2022, 2 pages.
Office Action received for Danish Patent Application No. PA202070616, dated May 5, 2022, 3 pages.
Office Action received for Danish Patent Application No. PA202070815, dated Oct. 18, 2021, 2 pages.
Office Action received for Danish Patent Application No. PA202170113, dated Apr. 15, 2021, 2 pages.
Office Action received for Danish Patent Application No. PA202170113, dated May 3, 2022, 2 pages.
Office Action received for European Patent Application No. 13811085.3, dated Apr. 20, 2018, 15 pages.
Office Action received for European Patent Application No. 15730890.9, dated Aug. 3, 2017, 4 pages.
Office Action received for European Patent Application No. 16762356.0, dated Dec. 11, 2020, 7 pages.
Office Action received for European Patent Application No. 16837432.0, dated Jan. 10, 2020, 7 pages.
Office Action received for European Patent Application No. 16837432.0, dated Jan. 27, 2021, 7 pages.
Office Action received for European Patent Application No. 17810749.6, dated Aug. 20, 2019, 9 pages.
Office Action received for European Patent Application No. 17813824.4, dated Nov. 30, 2021, 8 pages.
Office Action received for European Patent Application No. 18154145.9, dated Apr. 3, 2018, 6 pages.
Office Action received for European Patent Application No. 18213157.3, dated May 15, 2020, 7 pages.
Office Action received for European Patent Application No. 18727543.3, dated Mar. 26, 2021, 7 pages.
Office Action received for European Patent Application No. 19163212.4, dated Oct. 12, 2020, 4 pages.
Office Action received for European Patent Application No. 19721883.7, dated Jan. 10, 2020, 4 pages.
Office Action received for European Patent Application No. 19721883.7, dated Jun. 15, 2021, 9 pages.
Office Action received for European Patent Application No. 19721883.7, dated May 28, 2020, 11 pages.
Office Action received for European Patent Application No. 19724963.4, dated Jul. 28, 2020, 6 pages.
Office Action received for European Patent Application No. 20182116.2, dated May 25, 2021, 9 pages.
Office Action received for European Patent Application No. 20182116.2, dated Nov. 6, 2020, 9 pages.
Office Action received for European Patent Application No. 20203526.7, dated Nov. 23, 2021, 9 pages.
Office Action received for European Patent Application No. 20721342.2, dated Nov. 4, 2021, 9 pages.
Office Action received for European Patent Application No. 21165295.3, dated Jul. 1, 2021, 10 pages.
Office Action received for European Patent Application No. 21168916.1, dated Aug. 23, 2021, 8 pages.
Office Action received for European Patent Application No. 15771747.1, dated Oct. 31, 2017, 7 pages.
Office Action received for German Patent Application No. 112015002326.7, dated Feb. 20, 2019, 7 pages.
Office Action received for Indian Patent Application No. 202014041563, dated Dec. 30, 2021, 6 pages.
Office Action received for Indian Patent Application No. 202014041571, dated Dec. 17, 2021, 5 pages.
Office Action received for Japanese Patent Application No. 2016-535045, dated May 12, 2017, 10 pages.
Office Action received for Japanese Patent Application No. 2016-557650, dated Apr. 13, 2018, 9 pages.
Office Action received for Japanese Patent Application No. 2016-557650, dated Aug. 10, 2017, 10 pages.
Office Action received for Japanese Patent Application No. 2016-557650, dated Nov. 9, 2018, 6 pages.
Office Action received for Japanese Patent Application No. 2016-569945, dated Jul. 29, 2019, 6 pages.
Office Action received for Japanese Patent Application No. 2016-569945, dated Nov. 10, 2017, 8 pages.
Office Action received for Japanese Patent Application No. 2016-569945, dated Sep. 10, 2018, 11 pages.
Office Action received for Japanese Patent Application No. 2017-545918, dated Sep. 14, 2018, 12 pages.
Office Action received for Japanese Patent Application No. 2018-014096, dated Aug. 28, 2020, 4 pages.
Office Action received for Japanese Patent Application No. 2018-014096, dated Jan. 6, 2020, 17 pages.
Office Action received for Japanese Patent Application No. 2018-014096, dated Jun. 29, 2018, 20 pages.
Office Action received for Japanese Patent Application No. 2018-014096, dated May 8, 2019, 14 pages.
Office Action received for Japanese Patent Application No. 2018-014096, dated Nov. 6, 2018, 15 pages.
Office Action received for Japanese Patent Application No. 2018-068846, dated Jan. 8, 2019, 6 pages.
Office Action received for Japanese Patent Application No. 2018-184532, dated Mar. 1, 2021, 11 pages.
Office Action received for Japanese Patent Application No. 2019-044107, dated Jul. 30, 2021, 9 pages.
Office Action received for Japanese Patent Application No. 2019-044107, dated May 29, 2020, 6 pages.
Office Action received for Japanese Patent Application No. 2019-151358, dated Oct. 2, 2020, 5 pages.
Office Action received for Japanese Patent Application No. 2019-162293, dated Jan. 31, 2020, 8 pages.
Office Action received for Japanese Patent Application No. 2019-162293, dated Jul. 27, 2020, 9 pages.
Office Action received for Japanese Patent Application No. 2019-563407, dated Feb. 5, 2021, 5 pages.
Office Action received for Japanese Patent Application No. 2020-000492, dated Dec. 11, 2020, 6 pages.
Office Action received for Japanese Patent Application No. 2020-010239, dated Jan. 4, 2021, 6 pages.
Office Action received for Japanese Patent Application No. 2020-104679, dated Sep. 18, 2020, 13 pages.
Office Action received for Japanese Patent Application No. 2020-115940, dated May 7, 2021, 3 pages.
Office Action received for Japanese Patent Application No. 2020-160052, dated Dec. 17, 2021, 10 pages.
Office Action received for Japanese Patent Application No. 2020-160053, dated Jan. 31, 2022, 8 pages.
Office Action received for Japanese Patent Application No. 2020-160054, dated Jan. 21, 2022, 8 pages.
Office Action received for Japanese Patent Application No. 2021-023661, dated Feb. 25, 2022, 6 pages.
Office Action received for Korean Patent Application No. 10-2016-7014577, dated Dec. 26, 2017, 14 pages.
Office Action received for Korean Patent Application No. 10-2016-7014577, dated Oct. 31, 2018, 11 pages.
Office Action received for Korean Patent Application No. 10-2016-7033638, dated Jan. 31, 2017, 6 pages.
Office Action received for Korean Patent Application No. 10-2017-7024570, dated Jul. 10, 2019, 6 pages.
Office Action received for Korean Patent Application No. 10-2017-7024570, dated Sep. 28, 2018, 14 pages.
Office Action received for Korean Patent Application No. 10-2019-7025538, dated Aug. 15, 2020, 8 pages.
Office Action received for Korean Patent Application No. 10-2019-7025538, dated Feb. 17, 2020, 12 pages.
Office Action received for Korean Patent Application No. 10-2019-7025781, dated Nov. 26, 2019, 10 pages.
Office Action received for Korean Patent Application No. 10-2019-7025781, dated Oct. 30, 2020, 10 pages.
Office Action received for Korean Patent Application No. 10-2019-7029673, dated Apr. 8, 2021, 7 pages.
Office Action received for Korean Patent Application No. 10-2019-7029673, dated Nov. 5, 2019, 10 pages.

(56) References Cited

OTHER PUBLICATIONS

Office Action received for Korean Patent Application No. 10-2019-7029673, dated Sep. 3, 2020, 9 pages.
Office Action received for Korean Patent Application No. 10-2019-7033834, dated Jan. 22, 2021, 13 pages.
Office Action received for Korean Patent Application No. 10-2020-7026035, dated Feb. 19, 2021, 13 pages.
Office Action received for Korean Patent Application No. 10-2021-7026284, dated Aug. 31, 2021, 10 pages.
Office Action received for Korean Patent Application No. 10-2021-7031939, dated Oct. 19, 2021, 11 pages.
Office Action received for Korean Patent Application No. 10-2021-7036016, dated Nov. 10, 2021, 13 pages.
Office Action received for Taiwanese Patent Application No. 104117509, dated Aug. 22, 2016, 6 pages.
Office Action received for Taiwanese Patent Application No. 104128685, dated Jan. 4, 2017, 40 pages.
Office Action received for Taiwanese Patent Application No. 104132636, dated Dec. 13, 2018, 26 pages.
Office Action received for Taiwanese Patent Application No. 104132636, dated Mar. 23, 2017, 25 pages.
Office Action received for Taiwanese Patent Application No. 104132636, dated Oct. 31, 2017, 10 pages.
Partial Supplementary European Search Report received for European Patent Application No. 17810749.6, dated Apr. 25, 2019, 8 pages.
Phandroid, "How to record & stream using YouTube Gaming", Available online at: https://www.youtube.com/watch?v=8H5Q1L9M_ql, Jun. 1, 2016, 3 pages.
Preliminary Opinion received for European Patent Application No. 15730890.9, dated Mar. 7, 2019, 4 pages.
Razykdreviews, "In Depth Review of Apple Watch Activity and Workout App", available at <URL: https://www.youtube.com/watch?v=GkKI3qlK0ow>, Category: X Claims: 1-5 Category: L Reason: Internet citation/video, May 11, 2015, 1 page.
Result of Consultation received for European Patent Application No. 16762356.0, mailed on Nov. 29, 2021, 3 pages.
Result of Consultation received for European Patent Application No. 17810749.6, mailed on Dec. 15, 2020, 3 pages.
Result of Consultation received for European Patent Application No. 17810749.6, mailed on Jan. 18, 2021, 3 pages.
Result of Consultation received for European Patent Application No. 17810749.6, mailed on Jan. 21, 2021, 18 pages.
Result of Consultation received for European Patent Application No. 18154145.9, mailed on Nov. 30, 2020, 17 pages.
Result of Consultation received for European Patent Application No. 18154145.9, mailed on Sep. 4, 2020, 3 pages.
Result of Consultation received for European Patent Application No. 19721883.7, mailed on Oct. 7, 2020, 3 pages.
Result of Consultation received for European Patent Application No. 19724963.4, mailed on Jul. 8, 2021, 3 pages.
Result of Consultation received for European Patent Application No. 19724963.4, mailed on May 31, 2021, 3 pages.
Rizknows, "Garmin Connect Mobile App—Review #2", https://www.youtube.com/watch?v=7my3wMpeRbE, Category: X Claims: 1-5, Category: L Reason: Internet citation/video, Oct. 22, 2015, 1 page.
Rizknows, "TomTom Multisport Cardio Review", Online available at: https://www.youtube.com/watch?v=WoVCzLrSN9A, Sep. 4, 2015, 1 page.
Sansford Steve, "Streaming Android Games with OBS on Linux", Available online at: https://www.youtube.com/watch?v=twyh32Ud8vQ, May 20, 2016, 3 pages.
Search report and opinion received for Danish Patent Application No. PA201770191, dated Jun. 30, 2017, 9 pages.
Search Report and Opinion received for Danish Patent Application No. PA201770423, dated Oct. 4, 2017, 10 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201870385, dated Nov. 16, 2018, 10 pages.
Search Report and Opinion received for Danish Patent Application No. PA201970532, dated Nov. 8, 2019, 9 pages.
Search Report and Opinion received for Danish Patent Application No. PA202070612, dated Jun. 7, 2021, 9 pages.
Search Report and Opinion received for Danish Patent Application No. PA202070613, dated Jan. 22, 2021, 9 pages.
Search Report and Opinion received for Danish Patent Application No. PA202070614, dated Jan. 14, 2021, 9 pages.
Search Report and Opinion received for Danish Patent Application No. PA202070615, dated Jan. 22, 2021, 9 pages.
Search Report and Opinion received for Danish Patent Application No. PA202070616, dated Feb. 3, 2021, 8 pages.
Search Report and Opinion received for Danish Patent Application No. PA202070815, dated Mar. 16, 2021, 8 pages.
Search Report and Opinion received for Danish Patent Application No. PA202170113, dated Nov. 30, 2021, 9 pages.
Smith, "Garmin Fenix 5 Activity/Smart Watch Review", Online Available at: https://www.youtube.com/watch?v=6PkQxXQxpoU, Sep. 2, 2017, 1 page.
Sportstechguides, "Garmin Fenix 5: How to Add Power Data Fields", Online Available at: https://www.youtube.com/watch?v=ZkPptnnXEiQ, Apr. 29, 2017, 2 pages.
Sportstechguides, "Garmin Fenix 5: How to Set Up Run Alerts", Online Available at: https://www.youtube.com/watch?v=gSMwv8vlhB4, May 13, 2017, 2 pages.
Summons to attend oral proceedings received for European Patent Application No. 13811085.3, mailed on Jan. 26, 2018, 14 pages.
Summons to Attend Oral Proceedings received for European Patent Application No. 13811085.3, mailed on Mar. 3, 2022, 3 pages.
Summons to Attend Oral Proceedings received for European Patent Application No. 15730890.9, mailed on Sep. 10, 2018, 11 pages.
Summons to Attend Oral Proceedings received for European Patent Application No. 16762356.0, mailed on May 10, 2021, 10 pages.
Summons to Attend Oral Proceedings received for European Patent Application No. 17810749.6, mailed on Aug. 12, 2020, 11 pages.
Summons to Attend Oral Proceedings received for European Patent Application No. 18154145.9, mailed on Sep. 17, 2020, 11 pages.
Summons to Attend Oral Proceedings received for European Patent Application No. 19163212.4, mailed on Dec. 15, 2021, 9 pages.
Summons to Attend Oral Proceedings received for European Patent Application No. 19724963.4, mailed on Dec. 23, 2020, 8 pages.
Summons to Attend Oral Proceedings received for European Patent Application No. 20182116.2, mailed on Dec. 21, 2021, 7 pages.
Summons to Attend Oral Proceedings received for European Patent Application No. 20721342.2, mailed on May 20, 2022, 11 pages.
Summons to Attend Oral Proceedings received for European Patent Application no. 15771747.1, mailed on May 25, 2018, 17 pages.
Summons to Oral Proceedings received for European Patent Application No. 15771747.1, mailed on Apr. 29, 2021, 8 pages.
Supplemental Notice of Allowance received for U.S. Appl. No. 14/863,069, dated Aug. 15, 2019, 3 pages.
Supplemental Notice of Allowance received for U.S. Appl. No. 14/863,069, dated Mar. 1, 2019, 3 pages.
Supplemental Notice of Allowance received for U.S. Appl. No. 14/863,069, dated Mar. 29, 2019, 3 pages.
Supplemental Notice of Allowance received for U.S. Appl. No. 15/616,480, dated Mar. 28, 2019, 2 pages.
Supplemental Notice of Allowance received for U.S. Appl. No. 15/627,069, dated Jul. 12, 2021, 2 pages.
Supplemental Notice of Allowance received for U.S. Appl. No. 15/925,652, dated Feb. 17, 2021, 3 pages.
Supplemental Notice of Allowance received for U.S. Appl. No. 15/925,652, dated Jan. 6, 2021, 3 pages.
Supplemental Notice of Allowance received for U.S. Appl. No. 15/925,652, dated Jan. 26, 2021, 3 pages.
Supplemental Notice of Allowance received for U.S. Appl. No. 16/144,849, dated Mar. 31, 2020, 2 pages.
Supplemental Notice of Allowance received for U.S. Appl. No. 16/556,023, dated Feb. 3, 2021, 2 pages.

(56) References Cited

OTHER PUBLICATIONS

Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Supplemental Notice of Allowance received for U.S. Appl. No. 16/894,309, dated Apr. 8, 2022, 3 pages.
Supplemental Notice of Allowance received for U.S. Appl. No. 16/894,309, dated Dec. 24, 2021, 2 pages.
Supplemental Notice of Allowance received for U.S. Appl. No. 16/894,309, dated Jan. 25, 2022, 2 pages.
Supplemental Notice of Allowance received for U.S. Appl. No. 17/030,318, dated Apr. 4, 2022, 2 pages.
Supplemental Notice of Allowance received for U.S. Appl. No. 17/030,318, dated Feb. 22, 2022, 2 pages.
Supplemental Notice of Allowance received for U.S. Appl. No. 17/030,318, dated Mar. 16, 2022, 2 pages.
Supplemental Notice of Allowance received for U.S. Appl. No. 17/030,321, dated Apr. 15, 2022, 2 pages.
Supplemental Notice of Allowance received for U.S. Appl. No. 17/030,321, dated May 27, 2022, 2 pages.
Supplemental Notice of Allowance received for U.S. Appl. No. 17/192,161, dated May 13, 2022, 2 pages.
Supplementary European Search Report received for European Patent Application No. 17810749.6, dated Aug. 6, 2019, 6 pages.
Suunto Spartan Trainer Wrist Hr 1.12, Online Available at:—https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto,"Suunto Spartan—Heart Rate Zones", Online Available at:—https://www.youtube.com/watch?v=aixfoCnS0OU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
Tomtom, "TomTom Runner & Multi-Sport Reference Guide", Online available at:—https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Tweedie Steven, "Create and Customize Your Own Emojis with 'Makemoji' for iPhone", Available online at:—http://www.businessinsider.com/create-custom-emojis-with-makemoji-app-2014-8, Aug. 19, 2014, 6 pages.
Utilization of Galaxy S4—S Health, ChatOn and Samsung Hub, Available at: http://seeit.kr/1263, Jun. 12, 2013, 25 pages.
Vicky's Blog, "How to Log in to PS4 Automatically with Particular User?", Online available on:—https://www.youtube.com/watch?v=kqdlzXAvOkY, May 30, 2018, 3 pages.
Visual Pace Alarm app, Available Online at: https://apps.garmin.com/en-US/apps/3940f3a2-4847-4078-a911-d77422966c82, Oct. 19, 2016, 1 page.
Wesley, "Apple Watch Series 1", online available at:—http://toolbox.info/blog/archives/1737-unknown.html, May 28, 2015, 5 pages.
Whitwam Ryan, "Facer is Fast Becoming the De Facto Custom Watch Face Maker for Android Wear", Available online at: http://www.androidpolice.com/2014/09/19/facer-is-fast-becoming-the-de-facto-custom-watch-face-maker-for-android-wear, Sep. 19, 2014, 11 pages.
Wikipedia, "Emoji", Available online at: https://en.wikipedia.org/w/index.php?title=Emoji&oldid=648831795, Feb. 25, 2015, 12 pages.
Wikipedia, "Emoticon", Available online at: https://en.wikipedia.org/w/index.php?title=Emoticon&oldid=648776142, Feb. 25, 2015, 9 pages.
Wikipedia, "Enhanced Multi-Level Precedence and Pre-emption Service", Available online at: https://de.wikipedia.org/w/index.php?%20title=Enhanced%20Multi%E3%83%BCLevel_Precedence_And_Pre-emption_Service&oldid=123047429, Oct. 2013, 2 pages.
Written Opinion Issued from International Preliminary Examining Authority for PCT Application No. PCT/US2016/016216, dated Feb. 20, 2017, 12 pages.
Xzulas,"PS4 to Twitch—How to Broadcast Gameplay—Camera and Audio Settings", Available online at: https://www.youtube.com/watch?v=TyTR64RF0wl, Nov. 3, 2014, 4 pages.
Youtube, "Apple Watch Series 3", Online available at:—https://www.youtube.com/watch?v=iBPr9gEfkK8, Nov. 21, 2017, 15 pages.
Yoyodavid, "How to Use Multiple Accounts on the PlayStation 4", Online available at:—https://www.youtube.com/watch?v=5V21obRMeKE, Jan. 9, 2014, 3 pages.
Zlelik, "Garmin Fenix 5 Open Water Swimming Activity Demo", Online Available at:—https://www.youtube.com/watch?v=iSVhdvw2dcs, Jun. 9, 2017, 1 page.
Brief Communication Regarding Oral Proceedings received for European Patent Application No. 20721342.2, mailed on Oct. 18, 2022, 1 page.
Notice of Allowance received for U.S. Appl. No. 16/679,967, dated Nov. 2, 2022, 7 pages.
Result of Consultation received for European Patent Application No. 20721342.2, dated Oct. 18, 2022, 3 pages.
Summons to Attend Oral Proceedings received for European Patent Application No. 18727543.3, mailed on Oct. 25, 2022, 8 pages.
Updated Notice of Allowance received for U.S. Appl. No. 17/030,340, dated Nov. 2, 2022, 2 pages.
Applicant-Initiated Interview Summary received for U.S. Appl. No. 16/418,786, dated Sep. 23, 2022, 2 pages.
ANDROIDANDYUK,"Endomondo Android App Review", Available online at: https://www.youtube.com/watch?v=Wyjyrza-P1E, Jan. 9, 2013, 17 pages.
Applicant-Initiated Interview Summary received for U.S. Appl. No. 16/820,383, dated Aug. 12, 2022, 2 pages.
Applicant-Initiated Interview Summary received for U.S. Appl. No. 17/030,337, dated Jul. 27, 2022, 2 pages.
Applicant-Initiated Interview Summary received for U.S. Appl. No. 17/031,854, dated Jul. 27, 2022, 5 pages.
Applicant-Initiated Interview Summary received for U.S. Appl. No. 17/031,859, dated Jul. 28, 2022, 3 pages.
Applicant-Initiated Interview Summary received for U.S. Appl. No. 17/031,874, dated Jul. 27, 2022, 5 pages.
Applicant-Initiated Interview Summary received for U.S. Appl. No. 17/381,570, dated Aug. 24, 2022, 5 pages.
Applicant-Initiated Interview Summary received for U.S. Appl. No. 17/516,537, dated Jul. 5, 2022, 4 pages.
Applicant-Initiated Interview Summary received for U.S. Appl. No. 17/591,184, dated Sep. 23, 2022, 2 pages.
Communication of the Board of Appeal received for European Patent Application No. 13811085.3, dated Jul. 28, 2022, 13 pages.
Corrected Notice of Allowance received for U.S. Appl. No. 16/418,786, dated Jun. 23, 2022, 2 pages.
Corrected Notice of Allowance received for U.S. Appl. No. 17/030,321, dated Aug. 15, 2022, 3 pages.
Corrected Notice of Allowance received for U.S. Appl. No. 17/030,337, dated Aug. 31, 2022, 2 pages.
Corrected Notice of Allowance received for U.S. Appl. No. 17/030,337, dated Oct. 18, 2022, 2 pages.
Corrected Notice of Allowance received for U.S. Appl. No. 17/030,337, dated Sep. 21, 2022, 2 pages.
Corrected Notice of Allowance received for U.S. Appl. No. 17/031,543, dated Aug. 22, 2022, 2 pages.
Corrected Notice of Allowance received for U.S. Appl. No. 17/031,543, dated Jul. 18, 2022, 2 pages.
Corrected Notice of Allowance received for U.S. Appl. No. 17/197,628, dated Jul. 29, 2022, 2 pages.
Decision to Grant received for Danish Patent Application No. PA202070615, dated Jul. 29, 2022, 2 pages.
Examiner's Answer to Appeal Brief received for U.S. Patent Application No. 16/145,033, mailed on Aug. 4, 2022, 10 pages.
Extended European Search Report received for European Patent Application No. 22170561.9, dated Aug. 10, 2022, 11 pages.
Extended European Search Report received for European Patent Application No. 22173249.8, dated Aug. 19, 2022, 15 pages.

(56) References Cited

OTHER PUBLICATIONS

Final Office Action received for U.S. Appl. No. 16/820,383, dated Jun. 22, 2022, 21 pages.
Final Office Action received for U.S. Appl. No. 17/031,854, dated Jun. 10, 2022, 15 pages.
Final Office Action received for U.S. Appl. No. 17/031,859, dated Jun. 10, 2022, 13 pages.
Final Office Action received for U.S. Appl. No. 17/381,570, dated Jul. 20, 2022, 22 pages.
Final Office Action received for U.S. Appl. No. 17/516,537, dated Oct. 11, 2022, 9 pages.
Google, "Android User's Guide", Retrieved from the Internet: https://static.googleusercontent.com/media/www.google.com/en//help/hc/pdfs/mobile/AndroidUsersGuide-30-100.pdf, Feb. 23, 2011, 140 pages.
GPSCity, "Garmin Connect 2.0 Overview with GPS City", Available online at: https://www.youtube.com/watch?v=EJ6U10y_8y0, Feb. 28, 2014, 8 pages.
Heinrich Peter, "More Player Engagement Potential: GameCircle Now Rewards Player Experience across Games", Available online at: https://www.developer.amazon.com/es-mx/blogs/home/tag/badges, Apr. 11, 2014, 9 pages.
Intention to Grant received for Danish Patent Application No. PA202070614, dated Aug. 8, 2022, 2 pages.
Intention to Grant received for Danish Patent Application No. PA202070815, dated Sep. 13, 2022, 2 pages.
International Preliminary Report on Patentability received for PCT Patent Application No. PCT/US2021/017736, dated Aug. 25, 2022, 19 pages.
International Search Report and Written Opinion received for PCT Patent Application No. PCT/US2022/029297, dated Aug. 11, 2022, 13 pages.
Non-Final Office Action received for U.S. Appl. No. 16/389,722, dated Jul. 7, 2022, 16 pages.
Non-Final Office Action received for U.S. Appl. No. 16/418,786, dated Aug. 1, 2022, 18 pages.
Non-Final Office Action received for U.S. Appl. No. 17/030,318, dated Jun. 14, 2022, 9 pages.
Non-Final Office Action received for U.S. Appl. No. 17/030,337, dated Jun. 14, 2022, 13 pages.
Non-Final Office Action received for U.S. Appl. No. 17/030,340, dated Jun. 14, 2022, 15 pages.
Non-Final Office Action received for U.S. Appl. No. 17/031,854, dated Sep. 26, 2022, 17 pages.
Non-Final Office Action received for U.S. Appl. No. 17/031,859, dated Sep. 12, 2022, 17 pages.
Non-Final Office Action received for U.S. Appl. No. 17/031,874, dated Oct. 4, 2022, 20 pages.
Non-Final Office Action received for U.S. Appl. No. 17/381,570, dated Sep. 28, 2022, 20 pages.
Non-Final Office Action received for U.S. Appl. No. 17/591,184, dated Aug. 4, 2022, 18 pages.
Notice of Acceptance received for Australian Patent Application No. 2021203216, dated Jul. 26, 2022, 3 pages.
Notice of Acceptance received for Australian Patent Application No. 2021204422, dated Aug. 15, 2022, 3 pages.
Notice of Allowance received for Japanese Patent Application No. 2019-044107, dated Jul. 11, 2022, 31 pages (1 page of English Translation and 30 pages of Official Copy).
Notice of Allowance received for Japanese Patent Application No. 2020-160052, dated Jun. 3, 2022, 4 pages (1 page of English Translation and 3 pages of Official Copy).
Notice of Allowance received for Japanese Patent Application No. 2022-107902, dated Aug. 26, 2022, 4 pages (1 page of English Translation and 3 pages of Official Copy).
Notice of Allowance received for Korean Patent Application No. 10-2020-0123815, dated Aug. 26, 2022, 7 pages (2 pages of English Translation and 5 pages of Official Copy).
Notice of Allowance received for Korean Patent Application No. 10-2021-7026284, dated Jul. 28, 2022, 6 pages (2 pages of English Translation and 4 pages of Official Copy).
Notice of Allowance received for Korean Patent Application No. 10-2021-7036016, dated Sep. 28, 2022, 7 pages (2 pages of English Translation and 5 pages of Official Copy).
Notice of Allowance received for Korean Patent Application No. 10-2022-7017918, dated Jun. 13, 2022, 6 pages (2 pages of English Translation and 4 pages of Official Copy).
Notice of Allowance received for U.S. Appl. No. 16/388,493, dated Jun. 20, 2022, 5 pages.
Notice of Allowance received for U.S. Appl. No. 16/418,786, dated Jun. 14, 2022, 9 pages.
Notice of Allowance received for U.S. Appl. No. 16/679,967, dated Jun. 15, 2022, 7 pages.
Notice of Allowance received for U.S. Appl. No. 16/987,275, dated Jul. 27, 2022, 6 pages.
Notice of Allowance received for U.S. Appl. No. 17/030,337, dated Aug. 22, 2022, 10 pages.
Notice of Allowance received for U.S. Appl. No. 17/030,340, dated Sep. 28, 2022, 7 pages.
Notice of Allowance received for U.S. Appl. No. 17/030,343, dated Sep. 16, 2022, 11 pages.
Notice of Allowance received for U.S. Appl. No. 17/197,628, dated Jun. 24, 2022, 8 pages.
Office Action received for Australian Patent Application No. 2021218036, dated Jun. 21, 2022, 5 pages.
Office Action received for Chinese Patent Application No. 201911401161.0, dated Aug. 9, 2022, 17 pages (9 pages of English Translation and 8 pages of Official Copy).
Office Action received for Chinese Patent Application No. 202110363565.6, dated May 7, 2022, 12 pages (7 pages of English Translation and 5 pages of Official Copy).
Office Action received for Danish Patent Application No. PA202070612, dated Sep. 12, 2022, 3 pages.
Office Action received for Danish Patent Application No. PA202070613, dated Oct. 13, 2022, 7 pages.
Office Action received for Danish Patent Application No. PA202070815, dated Jun. 14, 2022, 3 pages.
Office Action received for Danish Patent Application No. PA202170113, dated Aug. 18, 2022, 2 pages.
Office Action received for Japanese Patent Application No. 2020-160053, dated Aug. 1, 2022, 8 pages (4 pages of English Translation and 4 pages of Official Copy).
Office Action received for Japanese Patent Application No. 2021-023661, dated on Oct. 3, 2022, 8 pages (4 pages of English Translation and 4 pages of Official Copy).
Office Action received for Japanese Patent Application No. 2021-131726, dated Aug. 22, 2022, 8 pages (4 pages of English Translation and 4 pages of Official Copy).
Office Action received for Japanese Patent Application No. 2021-163700, dated on Oct. 7, 2022, 4 pages (2 pages of English Translation and 2 pages of Official Copy).
Office Action received for Korean Patent Application No. 10-2020-0123815, dated May 31, 2022, 10 pages (5 pages of English Translation and 5 pages of Official Copy).
Office Action received for Korean Patent Application No. 10-2020-0123821, dated Sep. 20, 2022, 11 pages (5 pages of English Translation and 6 pages of Official Copy).
Office Action received for Korean Patent Application No. 10-2022-0061486, dated Aug. 29, 2022, 5 pages (2 pages of English Translation and 3 pages of Official Copy).
Programmatically download APK from google play store, retrieved from the Internet: https://stackoverflow.com/questions/13703982/prog ram maticallydownload-apk-from-google-play-store/13704021#13704021, Dec. 10, 2012, 2 pages.
Puryear Blake, "A modular framework for home healthcare monitoring", Online available at:—https://scholarworks.uark.edu/cgi/viewcontent.cgi?article=1009&context=csceuht, May 2012, 92 pages.
Summons to Attend Oral Proceedings received for European Patent Application No. 20203526.7, dated Jun. 23, 2022, 9 pages.
Supplemental Notice of Allowance received for U.S. Appl. No. 16/994,352, dated Jun. 20, 2022, 2 pages.

(56) References Cited

OTHER PUBLICATIONS

Supplemental Notice of Allowance received for U.S. Appl. No. 17/030,321, dated Jul. 27, 2022, 2 pages.
Supplemental Notice of Allowance received for U.S. Appl. No. 17/030,321, dated Jun. 10, 2022, 2 pages.
Supplemental Notice of Allowance received for U.S. Appl. No. 17/030,343, dated Oct. 5, 2022, 2 pages.
Supplemental Notice of Allowance received for U.S. Appl. No. 17/192,161, dated Jun. 13, 2022, 2 pages.
Venusivenus, "Nike Training Club", Available online at: https://www.youtube.com/watch?v=_pe6fqJPA04, Mar. 28, 2011, 6 pages.
Willem Jonker, "Secure Data Management", Online available at: http://ndl.ethernet.edu.et/bitstream/123456789/21649/1/291.pdf, Sep. 17, 2010, 177 pages.
Allen Ray, "Join the Nike Training Club and let your iPhone be your fitness instructor", Apr. 19, 2011, 26 pages.
Applicant-Initiated Interview Summary received for U.S. Appl. No. 17/892,534, dated Feb. 10, 2023, 2 pages.
Corrected Notice of Allowance received for U.S. Appl. No. 17/030,337, dated Feb. 10, 2023, 2 pages.
Corrected Notice of Allowance received for U.S. Appl. No. 17/030,337, dated Feb. 17, 2023, 2 pages.
Final Office Action received for U.S. Appl. No. 17/031,854, dated Feb. 23, 2023, 19 pages.
Final Office Action received for U.S. Appl. No. 17/031,859, dated Feb. 8, 2023, 15 pages.
Final Office Action received for U.S. Appl. No. 17/381,570, dated Feb. 10, 2023, 22 pages.
Intention to Grant received for European Patent Application No. 20203526.7, dated Feb. 10, 2023, 9 pages.
Non-Final Office Action received for U.S. Appl. No. 17/666,301, dated Feb. 16, 2023, 24 pages.
Non-Final Office Action received for U.S. Appl. No. 17/735,395, dated Feb. 10, 2023, 28 pages.
Notice of Acceptance received for Australian Patent Application No. 2020288139, dated Feb. 2, 2023, 3 pages.
Notice of Allowance received for Japanese Patent Application No. 2021-188824, dated Feb. 13, 2023, 4 pages (1 page of English Translation and 3 pages of Official Copy).
Notice of Allowance received for U.S. Appl. No. 17/591,184, dated Feb. 22, 2023, 5 pages.
Office Action received for Australian Patent Application No. 2020268150, dated Feb. 6, 2023, 5 pages.
Updated Notice of Allowance received for U.S. Appl. No. 17/030,318, dated Feb. 23, 2023, 3 pages.
Applicant-Initiated Interview Summary received for U.S. Appl. No. 17/381,570, dated Nov. 28, 2022, 5 pages.
Applicant-Initiated Interview Summary received for U.S. Appl. No. 17/516,537, dated Nov. 22, 2022, 2 pages.
Decision to Grant received for Danish Patent Application No. PA202070614, dated Nov. 10, 2022, 2 pages.
Final Office Action received for U.S. Appl. No. 17/030,318, dated Nov. 28, 2022, 13 pages.
Notice of Allowance received for U.S. Appl. No. 16/418,786, dated Nov. 22, 2022, 6 pages.
Notice of Allowance received for U.S. Appl. No. 16/820,383, dated Nov. 22, 2022, 16 pages.
Office Action received for Australian Patent Application No. 2021218036, dated Nov. 16, 2022, 4 pages.
Applicant-Initiated Interview Summary received for U.S. Appl. No. 16/389,722, dated Nov. 4, 2022, 4 pages.
Corrected Notice of Allowance received for U.S. Appl. No. 17/030,337, dated Nov. 3, 2022, 2 pages.
Corrected Notice of Allowance received for U.S. Appl. No. 17/030,337, dated Nov. 15, 2022, 2 pages.
Decision to Refuse received for European Patent Application No. 20721342.2, dated Nov. 10, 2022, 14 pages.
Garmin, "EDGE 520 Plus Owner's Manual", Online Available at: https://www8.garmin.com/manuals/webhelp/edge520plus/EN-US/Edge_520_Plus_OM_EN-US.pdf, 2018, 30 pages.
Intention to Grant received for European Patent Application No. 20182116.2, dated Nov. 11, 2022, 9 pages.
Minutes of Oral Proceedings received for European Patent Application No. 20721342.2, mailed on Nov. 8, 2022, 5 pages.
Office Action received for Australian Patent Application No. 2020268150, dated Nov. 3, 2022, 4 pages.
Office Action received for Australian Patent Application No. 2020288139, dated Oct. 31, 2022, 3 pages.
Office Action received for Australian Patent Application No. 2021266294, dated Nov. 11, 2022, 3 pages.
Supplemental Notice of Allowance received for U.S. Appl. No. 17/030,343, dated Nov. 9, 2022, 2 pages.
Updated Notice of Allowance received for U.S. Appl. No. 17/030,340, dated Nov. 10, 2022, 2 pages.
Advisory Action received for U.S. Appl. No. 16/389,722, dated Jun. 9, 2023, 4 pages.
Advisory Action received for U.S. Appl. No. 17/381,570, dated May 23, 2023, 5 pages.
Applicant-Initiated Interview Summary received for U.S. Appl. No. 16/389,722, dated May 31, 2023, 4 pages.
Applicant-Initiated Interview Summary received for U.S. Appl. No. 17/031,854, dated Apr. 6, 2023, 5 pages.
Applicant-Initiated Interview Summary received for U.S. Appl. No. 17/031,859, dated Aug. 1, 2023, 4 pages.
Applicant-Initiated Interview Summary received for U.S. Appl. No. 17/031,859, dated Mar. 3, 2023, 5 pages.
Applicant-Initiated Interview Summary received for U.S. Appl. No. 17/041,438, dated Jun. 23, 2023, 4 pages.
Applicant-Initiated Interview Summary received for U.S. Appl. No. 17/068,386, dated Apr. 24, 2023, 2 pages.
Applicant-Initiated Interview Summary received for U.S. Appl. No. 17/591,184, dated Feb. 27, 2023, 2 pages.
Applicant-Initiated Interview Summary received for U.S. Appl. No. 17/591,184, dated Jun. 28, 2023, 2 pages.
Applicant-Initiated Interview Summary received for U.S. Appl. No. 17/666,301, dated Mar. 28, 2023, 4 pages.
Applicant-Initiated Interview Summary received for U.S. Appl. No. 17/735,395, dated Apr. 28, 2023, 2 pages.
Applicant-Initiated Interview Summary received for U.S. Appl. No. 17/735,395, dated Aug. 1, 2023, 2 pages.
Applicant-Initiated Interview Summary received for U.S. Appl. No. 17/744,500, dated May 30, 2023, 4 pages.
Applicant-Initiated Interview Summary received for U.S. Appl. No. 17/862,097, dated Mar. 1, 2023, 4 pages.
Applicant-Initiated Interview Summary received for U.S. Appl. No. 17/862,097, dated May 18, 2023, 3 pages.
Applicant-Initiated Interview Summary received for U.S. Appl. No. 17/892,534, dated Aug. 3, 2023, 3 pages.
Applicant-Initiated Interview Summary received for U.S. Appl. No. 17/951,875, dated Feb. 28, 2023, 2 pages.
Applicant-Initiated Interview Summary received for U.S. Appl. No. 17/951,875, dated Jun. 27, 2023, 2 pages.
Applicant-Initiated Interview Summary received for U.S. Appl. No. 17/951,945, dated Apr. 28, 2023, 2 pages.
Applicant-Initiated Interview Summary received for U.S. Appl. No. 17/951,945, dated Aug. 1, 2023, 2 pages.
Applicant-Initiated Interview Summary received for U.S. Appl. No. 17/952,133, dated Jul. 3, 2023, 4 pages.
Applicant-Initiated Interview Summary received for U.S. Appl. No. 17/381,570, dated Apr. 6, 2023, 4 pages.
Brief Communication Regarding Oral Proceedings received for European Patent Application No. 18727543.3, dated Mar. 23, 2023, 1 page.
Corrected Notice of Allowance received for U.S. Appl. No. 16/145,033, dated Jun. 23, 2023, 3 pages.
Corrected Notice of Allowance received for U.S. Appl. No. 16/820,383, dated Apr. 28, 2023, 2 pages.
Corrected Notice of Allowance received for U.S. Appl. No. 17/030,318, dated Jun. 1, 2023, 3 pages.
Decision on Appeal received for U.S. Appl. No. 16/145,033, mailed on Apr. 4, 2023, 9 pages.
Decision to Grant received for European Patent Application No. 20182116.2, dated Mar. 23, 2023, 3 pages.

(56) References Cited

OTHER PUBLICATIONS

Decision to Grant received for European Patent Application No. 20203526.7, dated Jun. 22, 2023, 4 pages.
Dicristina John, "Fitness Monitoring Equipment Goes Wireless", Frontier Technology, China Academic journal Electronic Publishing House, Online Available at: http://www.cnki.net, Dec. 2012, pp. 44-45 (Official Copy Only). {See Communication Under 37 CFR § 1.98(a) (3)}.
Extended European Search Report received for European Patent Application No. 23150297.2, dated Mar. 28, 2023, 8 pages.
Extended European Search Report received for European Patent Application No. 23153898.4, dated May 4, 2023, 11 pages.
Extended European Search Report received for European Patent Application No. 23153899.2, dated May 4, 2023, 10 pages.
Extended European Search Report received for European Patent Application No. 23153900.8, dated May 4, 2023, 10 pages.
Final Office Action received for U.S. Appl. No. 16/389,722, dated Mar. 17, 2023, 14 pages.
Final Office Action received for U.S. Appl. No. 17/031,874, dated Mar. 17, 2023, 24 pages.
Final Office Action received for U.S. Appl. No. 17/068,386, dated May 8, 2023, 23 pages.
Final Office Action received for U.S. Appl. No. 17/735,395, dated May 17, 2023, 31 pages.
Final Office Action received for U.S. Appl. No. 17/862,097, dated Apr. 24, 2023, 17 pages.
Final Office Action received for U.S. Appl. No. 17/951,875, dated May 30, 2023, 12 pages.
Final Office Action received for U.S. Appl. No. 17/951,945, dated May 18, 2023, 18 pages.
GPSCity, "Garnnin Connect Mobile App iOS Overview with GPS City", Available on: https://www.youtube.com/watch?v=rD-KPOJpmOA, 2014, 9 pages.
Intention to Grant received for European Patent Application No. 16837432.0, dated Apr. 14, 2023, 8 pages.
Intention to Grant received for European Patent Application No. 18727543.3, dated Apr. 12, 2023, 9 pages.
Intention to Grant received for European Patent Application No. 19721883.7, dated May 11, 2023, 9 pages.
Nakasuji Yoshito, "Apple Watch", First Edition 1st Printing, Japan, Incorporated Company Technical Hyoronsha, Jun. 15, 2015, 4 pages (Official copy only). {See Communication Under 37 CFR § 1.98(a) (3)}.
Non-Final Office Action received for U.S. Appl. No. 17/031,859, dated Jul. 10, 2023, 15 pages.
Non-Final Office Action received for U.S. Appl. No. 17/041,438, dated May 25, 2023, 47 pages.
Non-Final Office Action received for U.S. Appl. No. 17/566,521, dated May 15, 2023, 12 pages.
Non-Final Office Action received for U.S. Appl. No. 17/591,184, dated Apr. 21, 2023, 15 pages.
Non-Final Office Action received for U.S. Appl. No. 17/744,500, dated Apr. 19, 2023, 30 pages.
Non-Final Office Action received for U.S. Appl. No. 17/892,534, dated May 10, 2023, 17 pages.
Non-Final Office Action received for U.S. Appl. No. 17/951,613, dated Aug. 2, 2023, 42 pages.
Non-Final Office Action received for U.S. Appl. No. 17/951,945, dated Mar. 24, 2023, 14 pages.
Non-Final Office Action received for U.S. Appl. No. 17/951,976, dated Aug. 3, 2023, 16 pages.
Non-Final Office Action received for U.S. Appl. No. 17/952,133, dated Jun. 2, 2023, 28 pages.
Non-Final Office Action received for U.S. Appl. No. 17/952,181, dated Aug. 7, 2023, 18 pages.
Notice of Acceptance received for Australian Patent Application No. 2021218036, dated May 9, 2023, 3 pages.
Notice of Acceptance received for Australian Patent Application No. 2021266294, dated Mar. 3, 2023, 3 pages.
Notice of Acceptance received for Australian Patent Application No. 2022200514, dated Apr. 17, 2023, 3 pages.
Notice of Acceptance received for Australian Patent Application No. 2022201761, dated Jun. 15, 2023, 3 pages.
Notice of Acceptance received for Australian Patent Application No. 2022209277, dated Apr. 28, 2023, 3 pages.
Notice of Acceptance received for Australian Patent Application No. 2022235614, dated Jul. 6, 2023, 3 pages.
Notice of Allowance received for Chinese Patent Application No. 201911396643.1, dated Jun. 15, 2023, 8 pages (4 pages of English Translation and 4 pages of Official Copy).
Notice of Allowance received for Chinese Patent Application No. 201911401161.0, dated Apr. 24, 2023, 11 pages (5 pages of English Translation and 6 pages of Official Copy).
Notice of Allowance received for Japanese Patent Application No. 2021-023661, dated Apr. 10, 2023, 4 pages (1 page of English Translation and 3 pages of Official Copy).
Notice of Allowance received for Japanese Patent Application No. 2021-131726, dated Mar. 17, 2023, 4 pages (1 page of English Translation and 3 pages of Official Copy).
Notice of Allowance received for Japanese Patent Application No. 2021-153558, dated Jun. 9, 2023, 4 pages (1 page of English Translation and 3 pages of Official Copy).
Notice of Allowance received for Japanese Patent Application No. 2021-571468, dated May 19, 2023, 4 pages (1 page of English Translation and 3 pages of Official Copy).
Notice of Allowance received for Japanese Patent Application No. 2022-076722, dated Jul. 28, 2023, 4 pages (1 page of English Translation and 3 pages of Official Copy).
Notice of Allowance received for Japanese Patent Application No. 2021-163700, dated Mar. 3, 2023, 4 pages (1 page of English Translation and 3 pages of Official Copy).
Notice of Allowance received for Korean Patent Application No. 10-2020-0123821, dated Mar. 28, 2023, 8 pages (2 pages of English Translation and 6 pages of Official Copy).
Notice of Allowance received for Korean Patent Application No. 10-2020-0123840, dated May 26, 2023, 9 pages (2 pages of English Translation and 7 pages of Official Copy).
Notice of Allowance received for Korean Patent Application No. 10-2022-7031866, dated May 1, 2023, 7 pages (2 pages of English Translation and 5 pages of Official Copy).
Notice of Allowance received for Korean Patent Application No. 10-2023-0023706, dated Mar. 27, 2023, 8 pages (2 pages of English Translation and 6 pages of Official Copy).
Notice of Allowance received for U.S. Appl. No. 16/145,033, dated May 3, 2023, 5 pages.
Notice of Allowance received for U.S. Appl. No. 16/820,383, dated Aug. 2, 2023, 14 pages.
Notice of Allowance received for U.S. Appl. No. 16/820,383, dated Mar. 8, 2023, 13 pages.
Notice of Allowance received for U.S. Appl. No. 17/030,318, dated May 16, 2023, 5 pages.
Notice of Allowance received for U.S. Appl. No. 17/381,570, dated Jul. 26, 2023, 14 pages.
Notice of Allowance received for U.S. Appl. No. 17/516,537, dated Apr. 17, 2023, 8 pages.
Notice of Allowance received for U.S. Appl. No. 17/666,301, dated May 4, 2023, 10 pages.
Notice of Allowance received for U.S. Appl. No. 17/852,020, dated Jul. 12, 2023, 9 pages.
Notice of Allowance received for U.S. Appl. No. 17/951,875, dated Jul. 26, 2023, 7 pages.
Office Action received for Australian Patent Application No. 2020268150, dated May 8, 2023, 4 pages.
Office Action received for Australian Patent Application No. 2021218036, dated Apr. 13, 2023, 3 pages.
Office Action received for Australian Patent Application No. 2022200514, dated Feb. 15, 2023, 2 pages.
Office Action received for Australian Patent Application No. 2022201761, dated Feb. 28, 2023, 5 pages.
Office Action received for Australian Patent Application No. 2022202977, dated Jul. 21, 2023, 3 pages.

(56) References Cited

OTHER PUBLICATIONS

Office Action received for Australian Patent Application No. 2022202977, dated May 2, 2023, 5 pages.
Office Action received for Australian Patent Application No. 2022203278, dated May 10, 2023, 4 pages.
Office Action received for Australian Patent Application No. 2022209277, dated Mar. 10, 2023, 6 pages.
Office Action received for Australian Patent Application No. 2022235614, dated May 9, 2023, 2 pages.
Office Action received for Australian Patent Application No. 2022235634, dated May 25, 2023, 4 pages.
Office Action received for Chinese Patent Application No. 201811303556.2, dated May 19, 2023, 6 pages (3 pages of English Translation and 3 pages of Official Copy).
Office Action received for Chinese Patent Application No. 201880032190.1, dated May 31, 2023, 20 pages (12 pages of English Translation and 8 pages of Official Copy).
Office Action received for Chinese Patent Application No. 201911396643.1, dated Apr. 6, 2023, 26 pages (15 pages of English Translation and 11 pages of official copy).
Office Action received for Chinese Patent Application No. 201911396744.9, dated Apr. 6, 2023, 19 pages (7 pages of English Translation and 12 pages of Official Copy).
Office Action received for Chinese Patent Application No. 201911396819.3, dated Apr. 6, 2023, 21 pages (10 pages of English Translation and 11 pages of Official copy).
Office Action received for Chinese Patent Application No. 201911401375.8, dated Apr. 7, 2023, 10 pages (5 pages of English Translation and 5 pages of Official Copy).
Office Action received for German Patent Application No. 112015007285.3, dated Mar. 7, 2023, 15 pages (5 pages of English Translation and 10 pages of Official Copy).
Office Action received for Japanese Patent Application No. 2021-565912, dated Jun. 26, 2023, 3 pages (1 page of English Translation and 2 pages of Official Copy).
Office Action received for Japanese Patent Application No. 2022-022159, dated Feb. 20, 2023, 10 pages (5 pages of English Translation and 5 pages of Official Copy).
Office Action received for Japanese Patent Application No. 2022-076722, dated Mar. 13, 2023, 6 pages (3 pages of English Translation and 3 pages of Official Copy).
Office Action received for Korean Patent Application No. 10-2022-7036278, dated Jun. 30, 2023, 10 pages (4 pages of English Translation and 6 pages of Official Copy).
Record of Oral Hearing received for U.S. Appl. No. 16/145,033, mailed on Apr. 19, 2023, 16 pages.
Result of Consultation received for European Patent Application No. 18727543.3, mailed on Mar. 15, 2023, 6 pages.
Summons to Attend Oral Proceedings received for European Patent Application No. 21165295.3, mailed on Jul. 25, 2023, 14 pages.
Summons to Attend Oral Proceedings received for European Patent Application No. 21168916.1, mailed on Jul. 14, 2023, 12 pages.
Supplemental Notice of Allowance received for U.S. Appl. No. 17/381,570, dated Aug. 11, 2023, 2 pages.
Supplemental Notice of Allowance received for U.S. Appl. No. 17/666,301, dated Jun. 5, 2023, 2 pages.
Supplemental Notice of Allowance received for U.S. Appl. No. 17/666,301, dated May 17, 2023, 2 pages.
Supplemental Notice of Allowance received for U.S. Appl. No. 17/852,020, dated Aug. 4, 2023, 2 pages.
Yuling et al., "Research on Motion Modeling of Virtual Gear Measuring Center", Tool Technology, vol. 43, No. 2, 2009, pp. 85-87 (Official Copy Only). {See Communication Under 37 CFR § 1.98(a) (3)}.
Advisory Action received for U.S. Patent Application No. 17/952,133, dated Oct. 20, 2023, 7 pages.
Applicant-Initiated Interview Summary received for U.S. Patent Application No. 17/591, 184, dated Oct. 30, 2023, 2 pages.
Applicant-Initiated Interview Summary received for U.S. Appl. No. 17/744,500, dated Oct. 17, 2023, 4 pages.
Applicant-Initiated Interview Summary received for U.S. Appl. No. 17/896,791, dated Oct. 12, 2023, 2 pages.
Applicant-Initiated Interview Summary received for U.S. Appl. No. 17/951,613, dated Sep. 8, 2023, 5 pages.
Applicant-Initiated Interview Summary received for U.S. Appl. No. 17/951,976, dated Aug. 23, 2023, 2 pages.
Applicant-Initiated Interview Summary received for U.S. Appl. No. 18/088,309, dated Oct. 27, 2023, 2 pages.
Chengcheng et al., "Platform of Development of Motion Control Systems Experimental Software", Experimental Technology and Management, vol. 30, No. 1, Jan. 2013, 3 pages (Official Copy Only). {See Communication Under Rule 37 CFR § 1.98(a) (3)}.
Corrected Notice of Allowance received for U.S. Appl. No. 17/041,438, dated Sep. 27, 2023, 3 pages.
Decision to Grant received for European Patent Application No. 18727543.3, dated Aug. 18, 2023, 2 pages.
To Grant received for European Patent Application No. 19721883.7, dated Aug. 31, 2023, 4 pages.
To Grant received for German Patent Application No. 112015007285.3, dated Jul. 25, 2023, 11 pages (1 page of English Translation and 10 pages of Official Copy).
Interview received for U.S. Appl. No. 17/896,791, dated Sep. 1, 2023, 2 pages.
Office Action received for U.S. Patent Application No. 17/591,184, dated Sep. 22, 2023, 19 pages.
Office Action received for U.S. Appl. No. 17/744,500, dated Sep. 19, 2023, 35 pages.
Office Action received for U.S. Patent Application No. 17/952,133, dated Sep. 26, 2023, 20 pages.
To Grant received for European Patent Application No. 16837432.0, dated Sep. 7, 2023, 9 pages.
To Grant received for European Patent Application No. 22173249.8, dated Oct. 2, 2023, 9 pages.
To Pay Search Fees received for European Patent Application No. 21714460.9, dated Aug. 8, 2023, 3 pages.
Office Action received for U.S. Appl. No. 17/031,854, dated Oct. 18, 2023, 22 pages.
Office Action received for U.S. Appl. No. 17/735,395, dated Sep. 20, 2023, 29 pages.
Office Action received for U.S. Appl. No. 17/896,791, dated Aug. 30, 2023, 11 pages.
Office Action received for U.S. Appl. No. 17/951,624, dated Sep. 19, 2023, 41 pages.
Office Action received for U.S. Appl. No. 17/951,945, dated Sep. 20, 2023, 19 pages.
Office Action received for U.S. Appl. No. 18/088,309, dated Sep. 21, 2023, 11 pages.
Notice of Acceptance received for Australian Patent Application No. 2022202977, dated Sep. 26, 2023, 3 pages.
Notice of Acceptance received for Australian Patent Application No. 2023203050, dated Oct. 24, 2023, 3 pages.
Notice of Allowance received for Chinese Patent Application No. 201811303556.2, dated Jul. 28, 2023, 2 pages (1 page of English Translation and 1 page of Official Copy).
Notice of Allowance received for Chinese Patent Application No. 201880032190.1, dated Oct. 7, 2023, 4 pages (1 page of English Translation and 3 pages of Official Copy).
Notice of Allowance received for Chinese Patent Application No. 201911396744.9, dated Aug. 3, 2023, 5 pages (1 page of English Translation and 4 pages of Official Copy).
Notice of Allowance received for Chinese Patent Application No. 201911396819.3, dated Aug. 3, 2023, 5 pages (1 page of English Translation and 4 pages of Official Copy).
Notice of Allowance received for Chinese Patent Application No. 201911396876.1, dated Sep. 6, 2023, 5 pages (1 page of English Translation and 4 pages of Official Copy).
Notice of Allowance received for Japanese Patent Application No. 2022-022159, dated Aug. 10, 2023, 4 pages (1 page of English Translation and 3 pages of Official Copy).
Notice of Allowance received for Japanese Patent Application No. 2022-107903, dated Sep. 1, 2023, 4 pages (1 page of English Translation and 3 pages of Official Copy).

(56) References Cited

OTHER PUBLICATIONS

Notice of Allowance received for U.S. Appl. No. 16/145,033, dated Aug. 17, 2023, 8 pages.
Notice of Allowance received for U.S. Appl. No. 17/041,438, dated Oct. 19, 2023, 2 pages.
Notice of Allowance received for U.S. Appl. No. 17/041,438, dated Sep. 20, 2023, 11 pages.
Notice of Allowance received for U.S. Appl. No. 17/951,875, dated Oct. 20, 2023, 8 pages.
Notice of Allowance received for U.S. Appl. No. 17/952, 181, dated Sep. 27, 2023, 9 pages.
Notice of Allowance received for U.S. Appl. No. 17/952, 185, dated Aug. 30, 2023, 12 pages.
Action received for Australian Patent Application No. 2020268150, dated Aug. 24, 2023, 5 pages.
Action received for Australian Patent Application No. 2022203278, dated Aug. 12, 2023, 5 pages.
Action received for Australian Patent Application No. 2023203050, dated Sep. 1, 2023, 3 pages.
Action received for Australian Patent Application No. 2023237090, dated Oct. 18, 2023, 3 pages.
Action received for Chinese Patent Application No. 201911396876. 1, dated Apr. 7, 2023, 16 pages (9 pages of English Translation and 7 pages of Official Copy).
Office Action received for Chinese Patent Application No. 201911401375.8, dated Sep. 26, 2023, 13 pages (6 pages of English Translation and 7 pages of Official Copy).
Office Action received for Chinese Patent Application No. 202211193170.7, dated un. 30, 2023, 19 pages (9 pages of English Translation and 10 pages of Official Copy).
Office Action received for European Patent Application No. 21714460. 9, dated Oct. 24, 2023, 13 pages.
Office Action received for Japanese Patent Application No. 2022-130087, dated Oct. 2, 2023, 12 pages (6 pages of English Translation and 6 pages of Official Copy).
Office Action received for Korean Patent Application No. 10-2021-7036242, dated Sep. 19, 2023, 13 pages (6 pages of English Translation and 7 pages of Official Copy).
Office Action received for Korean Patent Application No. 10-2022-7044515, dated Aug. 21, 2023, 11 pages (5 pages of English Translation and 6 pages of Official Copy).
Prasad et al., "Understanding Sharing Preferences and Behavior for Mhealth Devices", Proceedings of the 2012 ACM workshop on Privacy in the electronic society, Available online at: https://dl.acm.org/doi/10.1145/2381966.2381983, Oct. 15, 2012, pp. 117-128.
Supplemental Notice of Allowance received for U.S. Appl. No. 17/381,570, dated Sep. 13, 2023, 2 pages.
Supplemental Notice of Allowance received for U.S. Appl. No. 17/951,875, dated Aug. 25, 2023, 2 pages.
Supplemental Notice of Allowance received for U.S. Appl. No. 17/952, 181, dated Oct. 6, 2023, 2 pages.
Supplemental Notice of Allowance received for U.S. Appl. No. 17/952, 181, dated Oct. 27, 2023, 2 pages.
Supplemental Notice of Allowance received for U.S. Appl. No. 17/952, 185, dated Oct. 2, 2023, 2 pages.
Advisory Action received for U.S. Appl. No. 17/591,184, dated Nov. 14, 2023, 5 pages.
Advisory Action received for U.S. Appl. No. 17/744,500, dated Nov. 14, 2023, 5 pages.
Applicant-Initiated Interview Summary received for U.S. Appl. No. 17/735,395, dated Nov. 15, 2023, 2 pages.
Applicant-Initiated Interview Summary received for U.S. Appl. No. 17/951,624, dated Nov. 16, 2023, 3 pages.
Applicant-Initiated Interview Summary received for U.S. Appl. No. 17/951,945, dated Nov. 15, 2023, 2 pages.
Final Office Action received for U.S. Appl. No. 17/031,859, dated Nov. 13, 2023, 15 pages.
Final Office Action received for U.S. Appl. No. 17/892,534, dated Nov. 9, 2023, 17 pages.
Notice of Acceptance received for Australian Patent Application No. 2022235634, dated Nov. 2, 2023, 3 pages.
Notice of Allowance received for U.S. Appl. No. 17/951,976, dated Nov. 17, 2023, 9 pages.
Office Action received for Australian Patent Application No. 2023203776, dated Nov. 7, 2023, 2 pages.
Office Action received for Japanese Patent Application No. 2023-110196, dated Nov. 6, 2023, 4 pages (2 pages of English Translation and 2 pages of Official Copy).
Pre-Appeal Review Report received for Japanese Patent Application No. 2021-565912, dated Oct. 12, 2023, 5 pages (2 pages of English Translation and 3 pages of Official Copy).
Corrected Notice of Allowance received for U.S. Appl. No. 17/041,438, dated Dec. 1, 2023, 2 pages.
Extended European Search Report received for European Patent Application No. 23189089.8, dated Nov. 23, 2023, 11 pages.
International Preliminary Report on Patentability received for PCT Patent Application No. PCT/US2022/029297, dated Nov. 30, 2023, 10 pages.
Notice of Allowance received for Chinese Patent Application No. 201911401375.8, dated Nov. 26, 2023, 2 pages (1 page of English Translation and 1 page of Official Copy).
Supplemental Notice of Allowance received for U.S. Patent Application No. 17/952,185, dated Nov. 30, 2023, 2 pages.
Applicant-Initiated Interview Summary received for U.S. Appl. No. 17/952,233, dated May 24, 2023, 5 pages.
Applicant-Initiated Interview Summary received for U.S. Appl. No. 17/952,233, dated Sep. 7, 2023, 4 pages.
Applicant-Initiated Interview Summary received for U.S. Appl. No. 17/952,239, dated May 31, 2023, 2 pages.
Corrected Notice of Allowance received for U.S. Appl. No. 17/952,239, dated Jul. 12, 2023, 2 pages.
Corrected Notice of Allowance received for U.S. Appl. No. 17/952,239, dated Nov. 15, 2023, 2 pages.
Decision to Grant received for European Patent Application No. 22173249.8, dated Dec. 14, 2023, 2 pages.
Final Office Action received for U.S. Appl. No. 17/735,395, dated Dec. 7, 2023, 29 pages.
Final Office Action received for U.S. Appl. No. 17/951,945, dated Dec. 7, 2023, 20 pages.
Final Office Action received for U.S. Appl. No. 17/952,233, dated Jun. 26, 2023, 18 pages.
International Search Report and Written Opinion received for PCT Patent Application No. PCT/US2023/024104, dated Oct. 18, 2023, 18 pages.
International Search Report and Written Opinion received for PCT Patent Application No. PCT/US2023/024185, dated Sep. 18, 2023, 12 pages.
Non-Final Office Action received for U.S. Appl. No. 17/952,233, dated Apr. 28, 2023, 21 pages.
Non-Final Office Action received for U.S. Appl. No. 17/952,239, dated Apr. 4, 2023, 45 pages.
Non-Final Office Action received for U.S. Appl. No. 18/135,056, dated Dec. 7, 2023, 16 pages.
Notice of Acceptance received for Australian Patent Application No. 2022203278, dated Dec. 4, 2023, 3 pages.
Notice of Allowance received for U.S. Appl. No. 16/820,383, dated Dec. 7, 2023, 13 pages.
Notice of Allowance received for U.S. Appl. No. 17/068,386, dated Dec. 13, 2023, 12 pages.
Notice of Allowance received for U.S. Appl. No. 17/591, 184, dated Dec. 11, 2023, 9 pages.
Notice of Allowance received for U.S. Appl. No. 17/896,791, dated Dec. 15, 2023, 9 pages.
Notice of Allowance received for U.S. Appl. No. 17/951,613, dated Dec. 8, 2023, 13 pages.
Notice of Allowance received for U.S. Appl. No. 17/952, 185, dated Dec. 13, 2023, 9 pages.
Notice of Allowance received for U.S. Appl. No. 17/952,239, dated Jun. 23, 2023, 5 pages.
Notice of Allowance received for U.S. Appl. No. 17/952,239, dated Oct. 20, 2023, 5 pages.

(56) References Cited

OTHER PUBLICATIONS

Office Action received for European Patent Application No. 22152524.9, dated Dec. 5, 2023, 8 pages.
Result of consultation received for European Patent Application No. 21168916.1, dated Dec. 11, 2023, 25 pages.

* cited by examiner

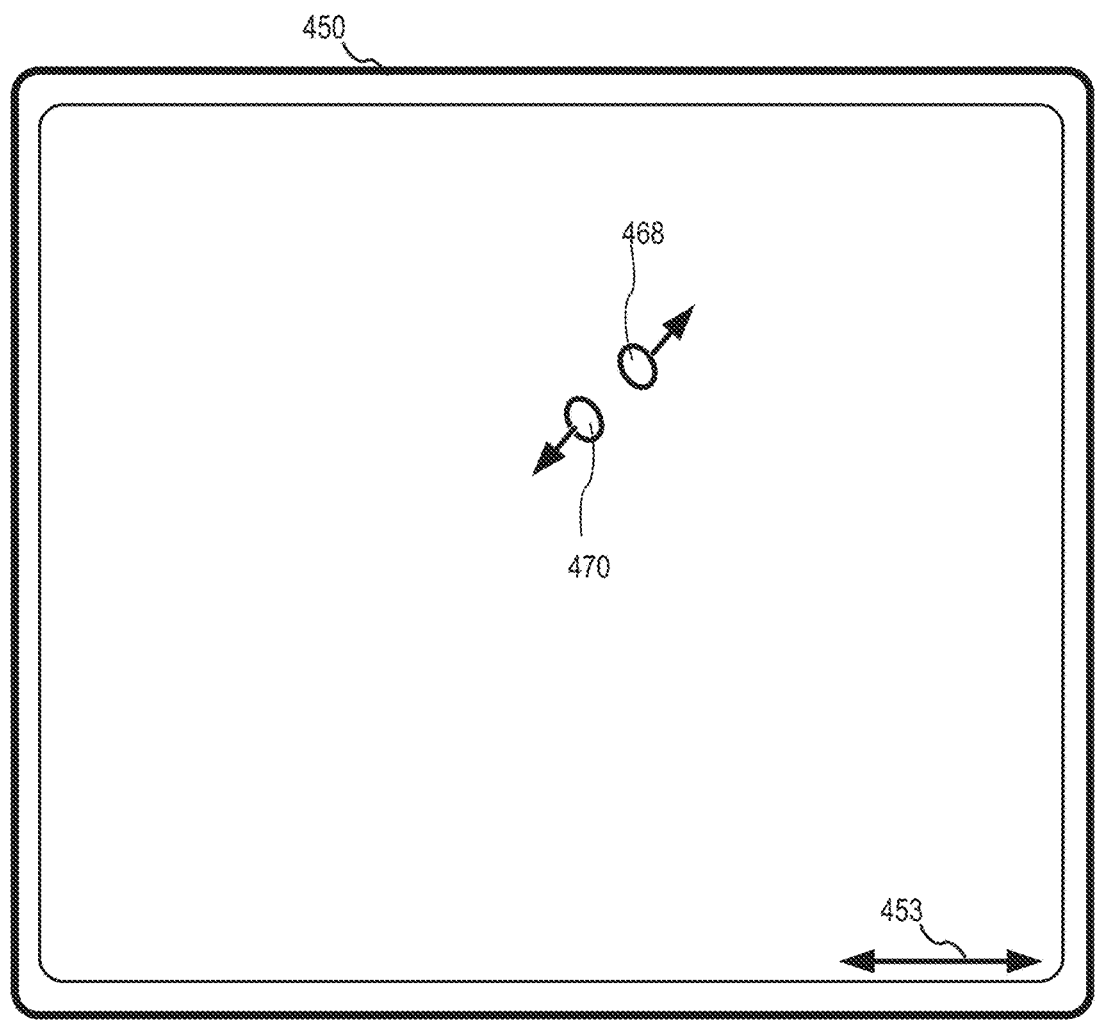
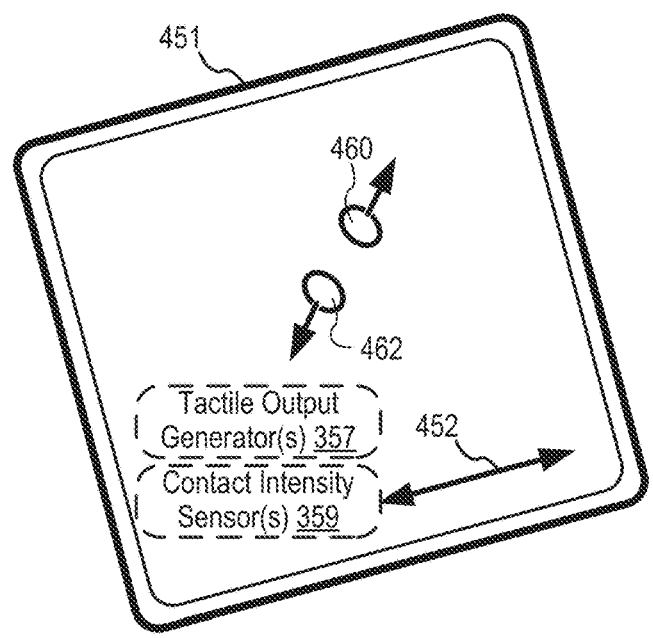
*FIG. 4B*

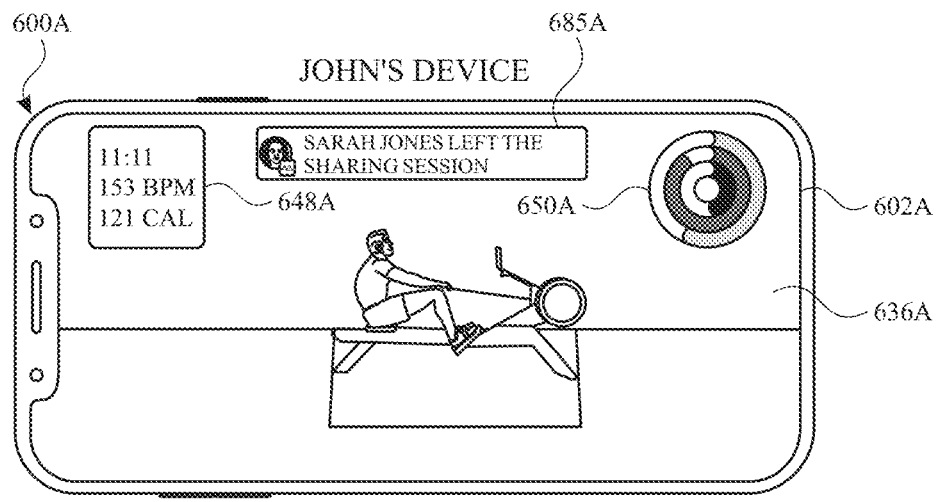
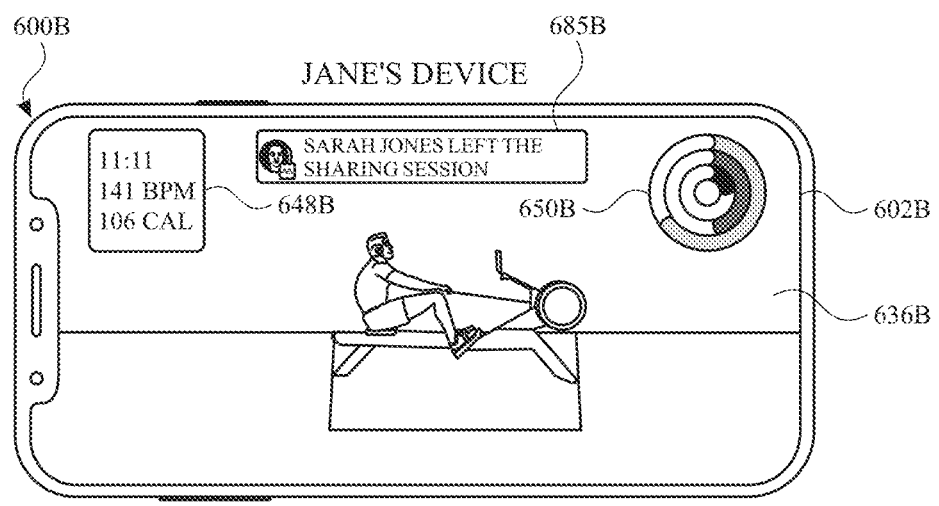
FIG. 6Q

750 ↘

752
While the computer system is participating in a communication session of a first type with one or more external computer systems including a first external computer system:

754
Receive an indication that the first external computer system has initiated a shared workout session.

756
In response to receiving the indication that the first external computer system has initiated the shared workout session:

758
Display, via the display generation component, a user interface object corresponding to the shared workout session.

760
While displaying the user interface object corresponding to the shared workout session:

762
Detect, via the one or more input devices, a user input.

764
In response to detecting the user input:

766
In accordance with a determination that the user input corresponds to a request to join the shared workout session, display, via the display generation component, content corresponding to the shared workout session, while maintaining the communication session of the first type, wherein display of the content corresponding to the shared workout session is initiated from a first playback position based on a playback position of corresponding content being displayed at the first external computer system.

768
In accordance with a determination that the user input does not to a request to join the shared workout session, forgo displaying the content corresponding to the shared workout session, while maintaining the communication session of the first type.

```
902
Detect, via the one or more input devices, a set of one or more user inputs corresponding to a
request to initiate a workout session, wherein initiating the workout session includes initiating
display of content corresponding to a workout
```

↓

```
904
In response to detecting the set of one or more user inputs:

906
    In accordance with a determination that the first external computer system satisfies one
    or more workout sharing criteria, wherein the one or more workout sharing criteria
    includes a first criterion that is met when the first external computer system is
    participating in a communication session of a first type with one or more external
    computer systems:

908
        Display, via the display generation component, a first user interface, wherein the
        first user interface includes: a first user interface object that is selectable to share
        content corresponding to the workout session to the one or more external
        computer systems in the communication session of the first type; and a second
        user interface object that is selectable to display, via the display generation
        component, content corresponding to the workout session without sharing the
        content corresponding to the workout session to the one or more computer
        systems in the communication session of the first type.

910
    In accordance with a determination that the first external computer system does not
    satisfy the one or more workout sharing criteria:

912
        Initiate the workout session, including displaying, via the display generation
        component, content corresponding to the workout, without displaying the first
        user interface.
```

1102
Display, via the display generation component, a user interface corresponding to a workout session, the user interface including one or more physical activity metrics corresponding to the workout session

1104
While displaying the user interface corresponding to the workout session, detect, via the one or more input devices, one or more user inputs

1106
In response to detecting the set of one or more user inputs:

1108
In accordance with a determination that the workout session is a shared workout session with one or more external computer systems, display, via the display generation component, a first set of one or more options, wherein the first set of one or more options includes a first option that, when selected, causes the one or more external computer systems participating in the shared workout session to display visual content corresponding to the first option.

*FIG. 11*

USER INTERFACES FOR GROUP WORKOUTS

CROSS-REFERENCE TO RELATED APPLICATIONS

This application is a continuation of U.S. Non-Provisional application Ser. No. 17/744,500, entitled "USER INTERFACES FOR GROUP WORKOUTS," filed on May 13, 2022, which claims priority from U.S. Provisional Patent Application Ser. No. 63/243,576, entitled "USER INTERFACES FOR GROUP WORKOUTS," filed on Sep. 13, 2021 and U.S. Provisional Patent Application Ser. No. 63/189,085, entitled "USER INTERFACES FOR GROUP WORKOUTS," filed on May 15, 2021. The content of these applications is hereby incorporated by reference in their entirety.

FIELD

The present disclosure relates generally to computer user interfaces, and more specifically to techniques for navigating and outputting workout content, including shared workout content.

BACKGROUND

As electronic devices, such as smartphones have become more widely used, their functions have grown beyond phone calls and text messaging. These functions can include providing workout (e.g., exercise programming) content. Providing an efficient method for using and implementing the various functions on these electronic devices can be complex and time-consuming.

BRIEF SUMMARY

Some techniques for navigating, displaying, and sharing workout content using electronic devices, such as audio and/or video content that guides a user to perform a physical activity, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices. As another example, some existing techniques for coordinating display of workout content among multiple devices are not intuitive and thus lead to erroneous inputs or require multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for navigating, displaying, and sharing workout content. Such methods and interfaces optionally complement or replace other methods for navigating, displaying, and sharing workout content. Such methods and interfaces reduce the cognitive burden on a user and produce a more efficient human-machine interface. For battery-operated computing devices, such methods and interfaces conserve power and increase the time between battery charges.

In accordance with some embodiments, a method is described. The method comprises: at a computer system that is in communication with a display generation component and one or more input devices: displaying, via the display generation component, a user interface including a first user interface object corresponding to a first workout; detecting, via the one or more input devices, a user input corresponding to selection of the first user interface object; and in response to detecting the user input: initiating a workout session corresponding to the first workout, including initiating a process for displaying, via the display generation component, content associated with the first workout; in accordance with a determination that the computer system is engaged in a communication session of a first type with one or more external computer systems including a first external computer system, causing display of a selectable user interface object at the first external computer system, wherein the selectable user interface object is selectable to display the content associated with the workout at the first external computer system; and in accordance with a determination that the computer system is not engaged in the communication session of the first type, forgoing causing the first external computer system to display the selectable user interface object.

In accordance with some embodiments, a non-transitory computer-readable storage medium is described. In some embodiments, the non-transitory computer-readable storage medium stores one or more programs configured to be executed by one or more processors of a computer system that is in communication with a display generation component and one or more input devices, the one or more programs including instructions for: displaying, via the display generation component, a user interface including a first user interface object corresponding to a first workout; detecting, via the one or more input devices, a user input corresponding to selection of the first user interface object; and in response to detecting the user input: initiating a workout session corresponding to the first workout, including initiating a process for displaying, via the display generation component, content associated with the first workout; in accordance with a determination that the computer system is engaged in a communication session of a first type with one or more external computer systems including a first external computer system, causing display of a selectable user interface object at the first external computer system, wherein the selectable user interface object is selectable to display the content associated with the workout at the first external computer system; and in accordance with a determination that the computer system is not engaged in the communication session of the first type, forgoing causing the first external computer system to display the selectable user interface object.

In accordance with some embodiments, a transitory computer-readable storage medium is described. In some embodiments, the transitory computer-readable storage medium stores one or more programs configured to be executed by one or more processors of a computer system that is in communication with a display generation component and one or more input devices, the one or more programs including instructions for: displaying, via the display generation component, a user interface including a first user interface object corresponding to a first workout; detecting, via the one or more input devices, a user input corresponding to selection of the first user interface object; and in response to detecting the user input: initiating a workout session corresponding to the first workout, including initiating a process for displaying, via the display generation component, content associated with the first workout; in accordance with a determination that the computer system is engaged in a communication session of a first type with one or more external computer systems including a first external computer system, causing display of a selectable user interface object at the first external computer system, wherein the selectable user interface object is selectable to display the content associated with the workout at the first external computer system; and in accordance with a determination that the computer system is not engaged in the communication session of the first type, forgoing causing the first external computer system to display the selectable user interface object.

In accordance with some embodiments, a computer system is described. In some embodiments, the computer system is in communication with a display generation component and one or more input devices, and comprises: one or more processors; and memory storing one or more programs configured to be executed by the one or more processors, the one or more programs including instructions for: displaying, via the display generation component, a user interface including a first user interface object corresponding to a first workout; detecting, via the one or more input devices, a user input corresponding to selection of the first user interface object; and in response to detecting the user input: initiating a workout session corresponding to the first workout, including initiating a process for displaying, via the display generation component, content associated with the first workout; in accordance with a determination that the computer system is engaged in a communication session of a first type with one or more external computer systems including a first external computer system, causing display of a selectable user interface object at the first external computer system, wherein the selectable user interface object is selectable to display the content associated with the workout at the first external computer system; and in accordance with a determination that the computer system is not engaged in the communication session of the first type, forgoing causing the first external computer system to display the selectable user interface object.

In accordance with some embodiments, a computer system is described. In some embodiments, the computer system is in communication with a display generation component and one or more input devices, and comprises: means for displaying, via the display generation component, a user interface including a first user interface object corresponding to a first workout; means for detecting, via the one or more input devices, a user input corresponding to selection of the first user interface object; and means for, in response to detecting the user input: initiating a workout session corresponding to the first workout, including initiating a process for displaying, via the display generation component, content associated with the first workout; in accordance with a determination that the computer system is engaged in a communication session of a first type with one or more external computer systems including a first external computer system, causing display of a selectable user interface object at the first external computer system, wherein the selectable user interface object is selectable to display the content associated with the workout at the first external computer system; and in accordance with a determination that the computer system is not engaged in the communication session of the first type, forgoing causing the first external computer system to display the selectable user interface object.

In accordance with some embodiments, a computer program product is described. In some embodiments, the computer program product comprises one or more programs configured to be executed by one or more processors of a computer system that is in communication with a display generation component and one or more input devices, the one or more programs including instructions for: displaying, via the display generation component, a user interface including a first user interface object corresponding to a first workout; detecting, via the one or more input devices, a user input corresponding to selection of the first user interface object; and in response to detecting the user input: initiating a workout session corresponding to the first workout, including initiating a process for displaying, via the display generation component, content associated with the first workout; in accordance with a determination that the computer system is engaged in a communication session of a first type with one or more external computer systems including a first external computer system, causing display of a selectable user interface object at the first external computer system, wherein the selectable user interface object is selectable to display the content associated with the workout at the first external computer system; and in accordance with a determination that the computer system is not engaged in the communication session of the first type, forgoing causing the first external computer system to display the selectable user interface object.

In accordance with some embodiments, a method is described. The method comprises: at a computer system that is in communication with a display generation component and one or more input devices: while the computer system is participating in a communication session of a first type with one or more external computer systems including a first external computer system: receiving an indication that the first external computer system has initiated a shared workout session; in response to receiving the indication that the first external computer system has initiated the shared workout session, displaying, via the display generation component, a user interface object corresponding to the shared workout session; while displaying the user interface object corresponding to the shared workout session, detecting, via the one or more input devices, a user input; and in response to detecting the user input: in accordance with a determination that the user input corresponds to a request to join the shared workout session, displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and in accordance with a determination that the user input does not correspond to a request to join the shared workout session, forgo displaying the content corresponding to the shared workout session, while maintaining the communication session of the first type.

In accordance with some embodiments, a non-transitory computer-readable storage medium is described. In some embodiments, the non-transitory computer-readable storage medium stores one or more programs configured to be executed by one or more processors of a computer system that is in communication with a display generation component and one or more input devices, the one or more programs including instructions for: while the computer system is participating in a communication session of a first type with one or more external computer systems including a first external computer system: receiving an indication that the first external computer system has initiated a shared workout session; in response to receiving the indication that the first external computer system has initiated the shared workout session, displaying, via the display generation component, a user interface object corresponding to the shared workout session; while displaying the user interface object corresponding to the shared workout session, detecting, via the one or more input devices, a user input; and in response to detecting the user input: in accordance with a determination that the user input corresponds to a request to join the shared workout session, displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and in accordance with a determination that the user input does not correspond to a request to join the shared workout session, forgo displaying the content corresponding to the shared workout session, while maintaining the communication session of the first type.

In accordance with some embodiments, a transitory computer-readable storage medium is described. In some embodiments, the transitory computer-readable storage medium stores one or more programs configured to be executed by one or more processors of a computer system that is in communication with a display generation component and one or more input devices, the one or more programs including instructions for: while the computer system is participating in a communication session of a first type with one or more external computer systems including a first external computer system: receiving an indication that the first external computer system has initiated a shared workout session; in response to receiving the indication that the first external computer system has initiated the shared workout session, displaying, via the display generation component, a user interface object corresponding to the shared workout session; while displaying the user interface object corresponding to the shared workout session, detecting, via the one or more input devices, a user input; and in response to detecting the user input: in accordance with a determination that the user input corresponds to a request to join the shared workout session, displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and in accordance with a determination that the user input does not correspond to a request to join the shared workout session, forgo displaying the content corresponding to the shared workout session, while maintaining the communication session of the first type.

In accordance with some embodiments, a computer system is described. In some embodiments, the computer system is in communication with a display generation component and one or more input devices, and comprises: one or more processors; and memory storing one or more programs configured to be executed by the one or more processors, the one or more programs including instructions for: while the computer system is participating in a communication session of a first type with one or more external computer systems including a first external computer system: receiving an indication that the first external computer system has initiated a shared workout session; in response to receiving the indication that the first external computer system has initiated the shared workout session, displaying, via the display generation component, a user interface object corresponding to the shared workout session; while displaying the user interface object corresponding to the shared workout session, detecting, via the one or more input devices, a user input; and in response to detecting the user input: in accordance with a determination that the user input corresponds to a request to join the shared workout session, displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and in accordance with a determination that the user input does not correspond to a request to join the shared workout session, forgo displaying the content corresponding to the shared workout session, while maintaining the communication session of the first type.

In accordance with some embodiments, a computer system is described. In some embodiments, the computer system is in communication with a display generation component and one or more input devices, and comprises: while the computer system is participating in a communication session of a first type with one or more external computer systems including a first external computer system: means for receiving an indication that the first external computer system has initiated a shared workout session; means for, in response to receiving the indication that the first external computer system has initiated the shared workout session, displaying, via the display generation component, a user interface object corresponding to the shared workout session; means for, while displaying the user interface object corresponding to the shared workout session, detecting, via the one or more input devices, a user input; and means for, in response to detecting the user input: in accordance with a determination that the user input corresponds to a request to join the shared workout session, displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and in accordance with a determination that the user input does not correspond to a request to join the shared workout session, forgo displaying the content corresponding to the shared workout session, while maintaining the communication session of the first type.

In accordance with some embodiments, a computer program product is described. In some embodiments, the computer program product comprises one or more programs configured to be executed by one or more processors of a computer system that is in communication with a display generation component and one or more input devices, the one or more programs including instructions for: while the computer system is participating in a communication session of a first type with one or more external computer systems including a first external computer system: receiving an indication that the first external computer system has initiated a shared workout session; in response to receiving the indication that the first external computer system has initiated the shared workout session, displaying, via the display generation component, a user interface object corresponding to the shared workout session; while displaying the user interface object corresponding to the shared workout session, detecting, via the one or more input devices, a user input; and in response to detecting the user input: in accordance with a determination that the user input corresponds to a request to join the shared workout session, displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and in accordance with a determination that the user input does not correspond to a request to join the shared workout session, forgo displaying the content corresponding to the shared workout session, while maintaining the communication session of the first type.

In accordance with some embodiments, a method is described. The method comprises: at a computer system that is in communication with a display generation component, one or more input devices, and a first external computer system: detecting, via the one or more input devices, a set of one or more user inputs corresponding to a request to initiate a workout session, wherein initiating the workout session includes initiating display of content corresponding to a workout; and in response to detecting the set of one or more user inputs: in accordance with a determination that the first external computer system satisfies one or more workout sharing criteria, wherein the one or more workout sharing criteria includes a first criterion that is met when the first external computer system is participating in a communication session of a first type with one or more external computer systems: displaying, via the display generation component, a first user interface, wherein the first user interface includes: a first user interface object that is selectable to share content corresponding to the workout session to the one or more external computer systems in the communication session of the first type, and a second user interface object that is selectable to display, via the display generation component, content corresponding to the workout session without sharing the content corresponding to the workout session to the one or more computer systems in the communication session of the first type; and in accordance with a determination that the first external computer system does not satisfy the one or more workout sharing criteria: initiating the workout session, including displaying, via the display generation component, content corresponding to the workout, without displaying the first user interface.

In accordance with some embodiments, a non-transitory computer-readable storage medium is described. In some embodiments, the non-transitory computer-readable storage medium stores one or more programs configured to be executed by one or more processors of a computer system that is in communication with a display generation component, one or more input devices, and a first external computer system, the one or more programs including instructions for: detecting, via the one or more input devices, a set of one or more user inputs corresponding to a request to initiate a workout session, wherein initiating the workout session includes initiating display of content corresponding to a workout; and in response to detecting the set of one or more user inputs: in accordance with a determination that the first external computer system satisfies one or more workout sharing criteria, wherein the one or more workout sharing criteria includes a first criterion that is met when the first external computer system is participating in a communication session of a first type with one or more external computer systems: displaying, via the display generation component, a first user interface, wherein the first user interface includes: a first user interface object that is selectable to share content corresponding to the workout session to the one or more external computer systems in the communication session of the first type, and a second user interface object that is selectable to display, via the display generation component, content corresponding to the workout session without sharing the content corresponding to the workout session to the one or more computer systems in the communication session of the first type; and in accordance with a determination that the first external computer system does not satisfy the one or more workout sharing criteria: initiating the workout session, including displaying, via the display generation component, content corresponding to the workout, without displaying the first user interface.

In accordance with some embodiments, a transitory computer-readable storage medium is described. In some embodiments, the transitory computer-readable storage medium stores one or more programs configured to be executed by one or more processors of a computer system that is in communication with a display generation component, one or more input devices, and a first external computer system, the one or more programs including instructions for: detecting, via the one or more input devices, a set of one or more user inputs corresponding to a request to initiate a workout session, wherein initiating the workout session includes initiating display of content corresponding to a workout; and in response to detecting the set of one or more user inputs: in accordance with a determination that the first external computer system satisfies one or more workout sharing criteria, wherein the one or more workout sharing criteria includes a first criterion that is met when the first external computer system is participating in a communication session of a first type with one or more external computer systems: displaying, via the display generation component, a first user interface, wherein the first user interface includes: a first user interface object that is selectable to share content corresponding to the workout session to the one or more external computer systems in the communication session of the first type, and a second user interface object that is selectable to display, via the display generation component, content corresponding to the workout session without sharing the content corresponding to the workout session to the one or more computer systems in the communication session of the first type; and in accordance with a determination that the first external computer system does not satisfy the one or more workout sharing criteria: initiating the workout session, including displaying, via the display generation component, content corresponding to the workout, without displaying the first user interface.

In accordance with some embodiments, a computer system is described. In some embodiments, the computer system is in communication with a display generation component, one or more input devices, and a first external computer system, and comprises: one or more processors; and memory storing one or more programs configured to be executed by the one or more processors, the one or more programs including instructions for: detecting, via the one or more input devices, a set of one or more user inputs corresponding to a request to initiate a workout session, wherein initiating the workout session includes initiating display of content corresponding to a workout; and in response to detecting the set of one or more user inputs: in accordance with a determination that the first external computer system satisfies one or more workout sharing criteria, wherein the one or more workout sharing criteria includes a first criterion that is met when the first external computer system is participating in a communication session of a first type with one or more external computer systems: displaying, via the display generation component, a first user interface, wherein the first user interface includes: a first user interface object that is selectable to share content corresponding to the workout session to the one or more external computer systems in the communication session of the first type, and a second user interface object that is selectable to display, via the display generation component, content corresponding to the workout session without sharing the content corresponding to the workout session to the one or more computer systems in the communication session of the first type; and in accordance with a determination that the first external computer system does not satisfy the one or more workout sharing criteria: initiating the workout session, including displaying, via the display generation component, content corresponding to the workout, without displaying the first user interface.

In accordance with some embodiments, a computer system is described. In some embodiments, the computer system is in communication with a display generation component, one or more input devices, and a first external computer system, and comprises: means for detecting, via the one or more input devices, a set of one or more user inputs corresponding to a request to initiate a workout session, wherein initiating the workout session includes initiating display of content corresponding to a workout; and means for, in response to detecting the set of one or more user inputs: in accordance with a determination that the first external computer system satisfies one or more workout sharing criteria, wherein the one or more workout sharing criteria includes a first criterion that is met when the first external computer system is participating in a communication session of a first type with one or more external computer systems: displaying, via the display generation component, a first user interface, wherein the first user interface includes: a first user interface object that is selectable to share content corresponding to the workout session to the one or more external computer systems in the communication session of the first type, and a second user interface object that is selectable to display, via the display generation component, content corresponding to the workout session without sharing the content corresponding to the workout session to the one or more computer systems in the communication session of the first type; and in accordance with a determination that the first external computer system does not satisfy the one or more workout sharing criteria: initiating the workout session, including displaying, via the display generation component, content corresponding to the workout, without displaying the first user interface.

In accordance with some embodiments, a computer program product is described. In some embodiments, the computer program product comprises one or more programs configured to be executed by one or more processors of a computer system that is in communication with a display generation component, one or more input devices, and a first external computer system, the one or more programs including instructions for: detecting, via the one or more input devices, a set of one or more user inputs corresponding to a request to initiate a workout session, wherein initiating the workout session includes initiating display of content corresponding to a workout; and in response to detecting the set of one or more user inputs: in accordance with a determination that the first external computer system satisfies one or more workout sharing criteria, wherein the one or more workout sharing criteria includes a first criterion that is met when the first external computer system is participating in a communication session of a first type with one or more external computer systems: displaying, via the display generation component, a first user interface, wherein the first user interface includes: a first user interface object that is selectable to share content corresponding to the workout session to the one or more external computer systems in the communication session of the first type, and a second user interface object that is selectable to display, via the display generation component, content corresponding to the workout session without sharing the content corresponding to the workout session to the one or more computer systems in the communication session of the first type; and in accordance with a determination that the first external computer system does not satisfy the one or more workout sharing criteria: initiating the workout session, including displaying, via the display generation component, content corresponding to the workout, without displaying the first user interface.

In accordance with some embodiments, a method is described. The method comprises: at a computer system that is in communication with a display generation component and one or more input devices: displaying, via the display generation component, a user interface corresponding to a workout session, the user interface including one or more physical activity metrics corresponding to the workout session; while displaying the user interface corresponding to the workout session, detecting, via the one or more input devices, one or more user inputs; and in response to detecting the one or more user inputs: in accordance with a determination that the workout session is a shared workout session with one or more external computer systems, displaying, via the display generation component, a first set of one or more options, wherein the first set of one or more options includes a first option that, when selected, causes the one or more external computer systems participating in the shared workout session to display visual content corresponding to the first option.

In accordance with some embodiments, a non-transitory computer-readable storage medium is described. In some embodiments, the non-transitory computer-readable storage medium stores one or more programs configured to be executed by one or more processors of a computer system that is in communication with a display generation component and one or more input devices, the one or more programs including instructions for: displaying, via the display generation component, a user interface corresponding to a workout session, the user interface including one or more physical activity metrics corresponding to the workout session; while displaying the user interface corresponding to the workout session, detecting, via the one or more input devices, one or more user inputs; and in response to detecting the one or more user inputs: in accordance with a determination that the workout session is a shared workout session with one or more external computer systems, displaying, via the display generation component, a first set of one or more options, wherein the first set of one or more options includes a first option that, when selected, causes the one or more external computer systems participating in the shared workout session to display visual content corresponding to the first option.

In accordance with some embodiments, a transitory computer-readable storage medium is described. In some embodiments, the transitory computer-readable storage medium stores one or more programs configured to be executed by one or more processors of a computer system that is in communication with a display generation component and one or more input devices, the one or more programs including instructions for: displaying, via the display generation component, a user interface corresponding to a workout session, the user interface including one or more physical activity metrics corresponding to the workout session; while displaying the user interface corresponding to the workout session, detecting, via the one or more input devices, one or more user inputs; and in response to detecting the one or more user inputs: in accordance with a determination that the workout session is a shared workout session with one or more external computer systems, displaying, via the display generation component, a first set of one or more options, wherein the first set of one or more options includes a first option that, when selected, causes the one or more external computer systems participating in the shared workout session to display visual content corresponding to the first option.

In accordance with some embodiments, a computer system is described. In some embodiments, the computer system is in communication with a display generation component and one or more input devices, and comprises: one or more processors; and memory storing one or more programs configured to be executed by the one or more processors, the one or more programs including instructions for: displaying, via the display generation component, a user interface corresponding to a workout session, the user interface including one or more physical activity metrics corresponding to the workout session; while displaying the user interface corresponding to the workout session, detecting, via the one or more input devices, one or more user inputs; and in response to detecting the one or more user inputs: in accordance with a determination that the workout session is a shared workout session with one or more external computer systems, displaying, via the display generation component, a first set of one or more options, wherein the first set of one or more options includes a first option that, when selected, causes the one or more external computer systems participating in the shared workout session to display visual content corresponding to the first option.

In accordance with some embodiments, a computer system is described. In some embodiments, the computer system is in communication with a display generation component and one or more input devices, and comprises: means for displaying, via the display generation component, a user interface corresponding to a workout session, the user interface including one or more physical activity metrics corresponding to the workout session; means for, while displaying the user interface corresponding to the workout session, detecting, via the one or more input devices, one or more user inputs; and means for, in response to detecting the one or more user inputs: in accordance with a determination that the workout session is a shared workout session with one or more external computer systems, displaying, via the display generation component, a first set of one or more options, wherein the first set of one or more options includes a first option that, when selected, causes the one or more external computer systems participating in the shared workout session to display visual content corresponding to the first option.

In accordance with some embodiments, a computer program product is described. In some embodiments, the computer program product comprises one or more programs configured to be executed by one or more processors of a computer system that is in communication with a display generation component and one or more input devices, the one or more programs including instructions for: displaying, via the display generation component, a user interface corresponding to a workout session, the user interface including one or more physical activity metrics corresponding to the workout session; while displaying the user interface corresponding to the workout session, detecting, via the one or more input devices, one or more user inputs; and in response to detecting the one or more user inputs: in accordance with a determination that the workout session is a shared workout session with one or more external computer systems, displaying, via the display generation component, a first set of one or more options, wherein the first set of one or more options includes a first option that, when selected, causes the one or more external computer systems participating in the shared workout session to display visual content corresponding to the first option.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for navigating and outputting workout content, thereby increasing the effectiveness, efficiency, and user satisfaction with such devices. Such methods and interfaces may complement or replace other methods for navigating and outputting workout content.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIG. 7B is a flow diagram illustrating an exemplary process for displaying group workout content, in accordance with some embodiments.

FIG. 9 is a flow diagram illustrating an exemplary process for displaying group workout content, in accordance with some embodiments.

FIG. 11 is a flow diagram illustrating an exemplary process for displaying group workout content, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for navigating and outputting workout content, including sharing group workout content. For example, a user would benefit from being able to share synchronized workout content with one or more other users on separate and/or remote computing devices. Such techniques can reduce the cognitive burden on a user who accesses workout content, thereby enhancing productivity. Further, such techniques can reduce processor and battery power otherwise wasted on redundant user inputs.

Figure 6A:
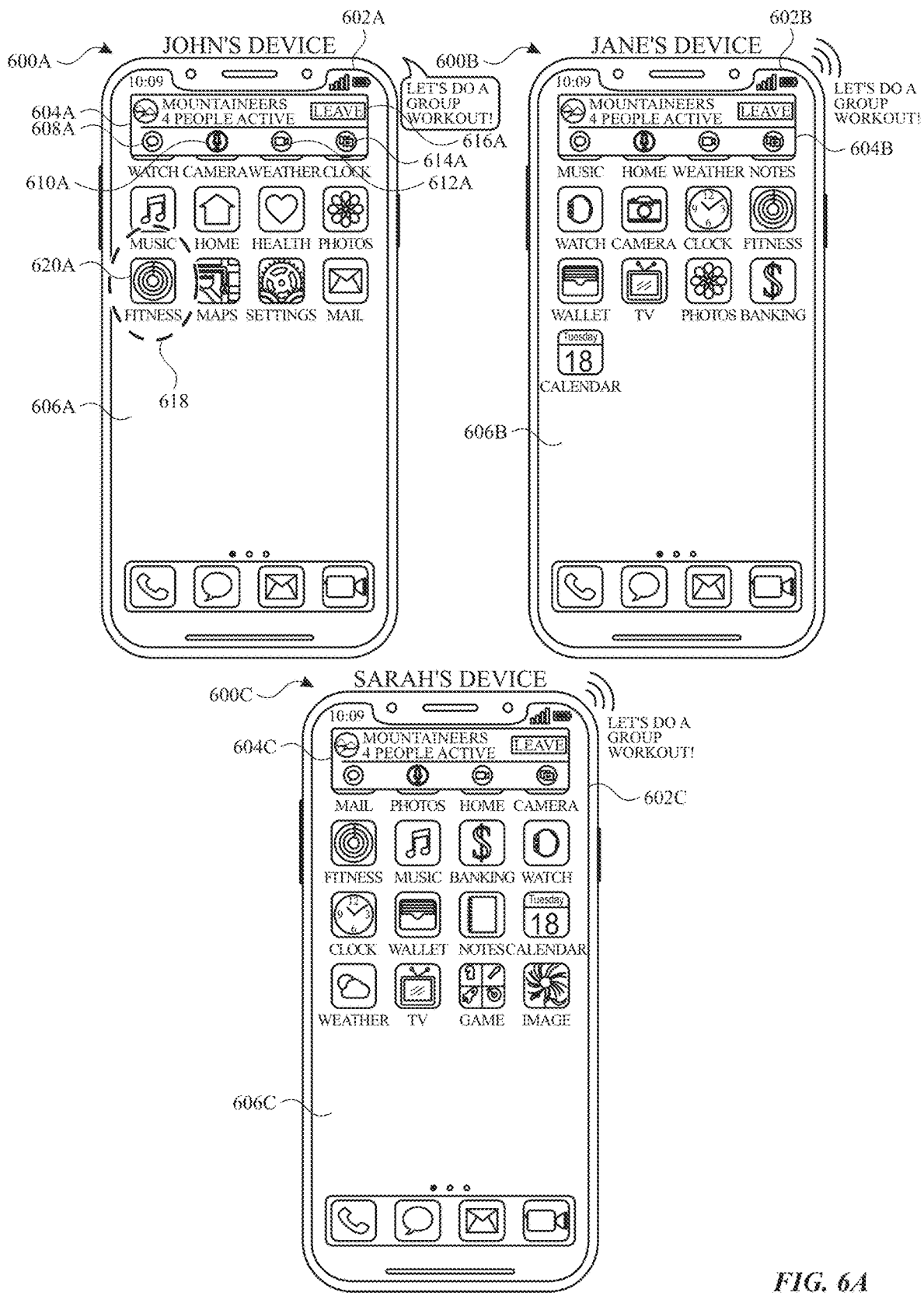
FIGS. 6A-6X illustrate exemplary user interfaces for displaying and sharing group workout content, in accordance with some embodiments.
Figures 1, 6P:
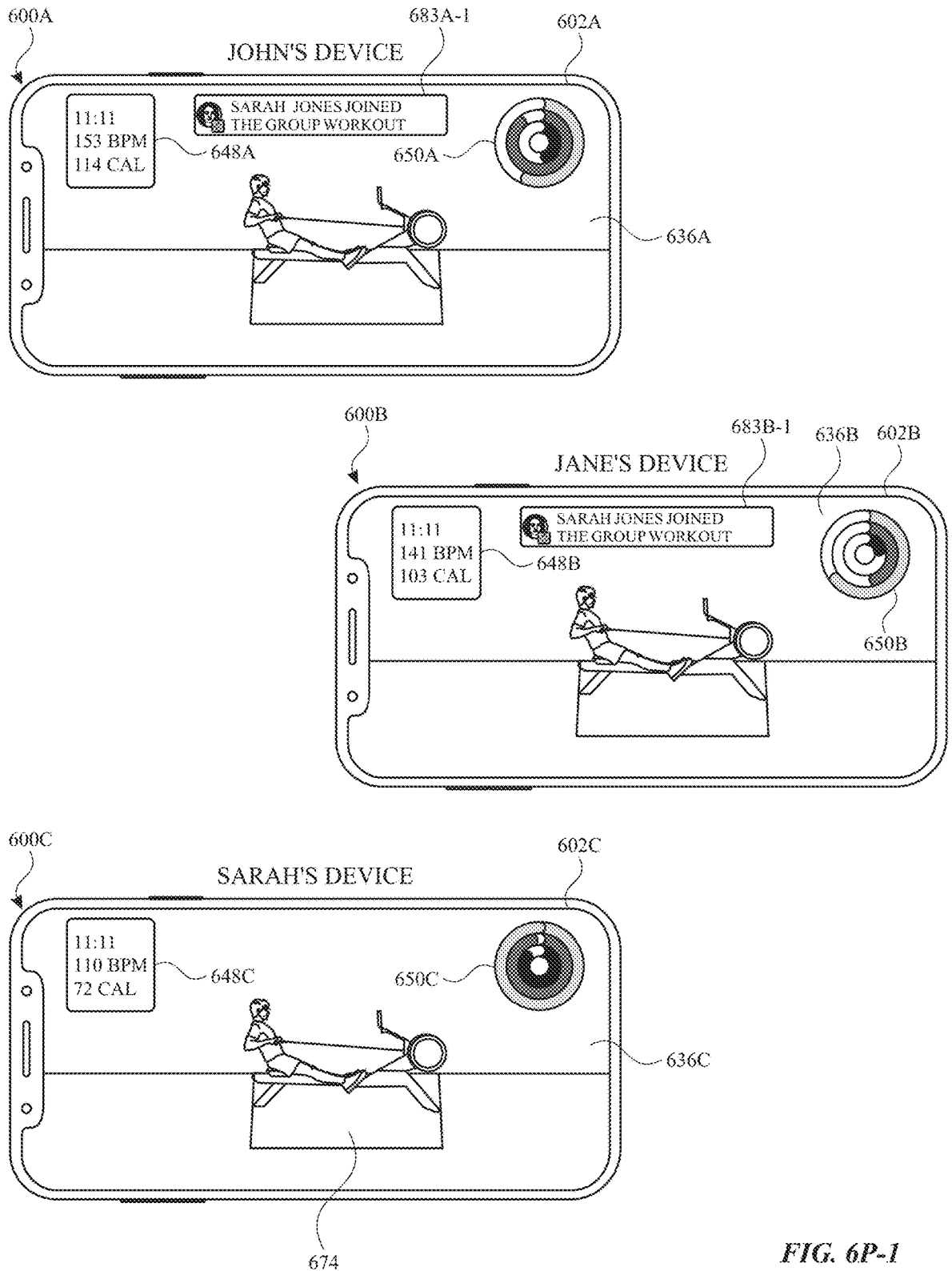
FIGS. 8A-1-8I illustrate exemplary user interfaces for displaying group workout content, in accordance with some embodiments.
Figure 6X:
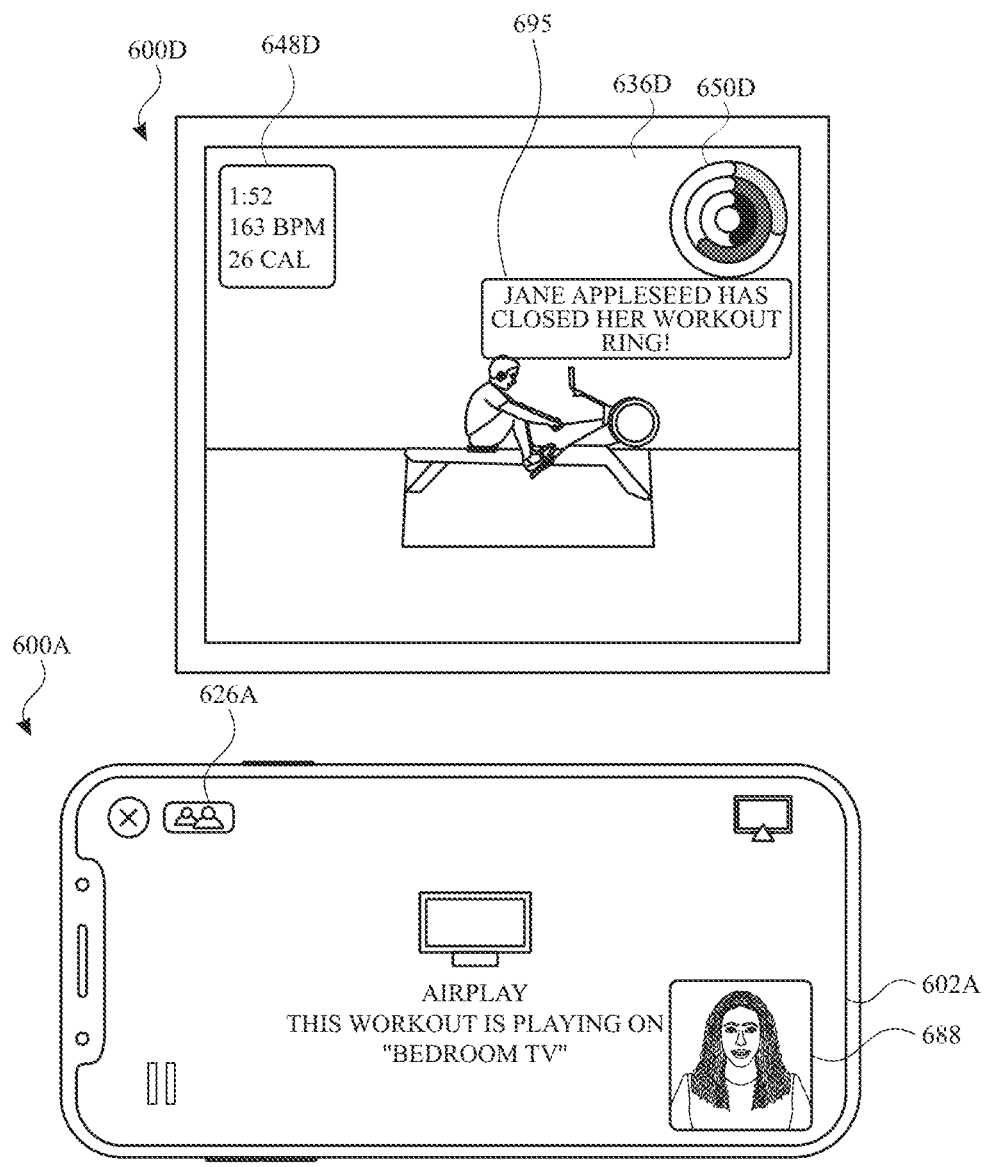
Figure 7A:
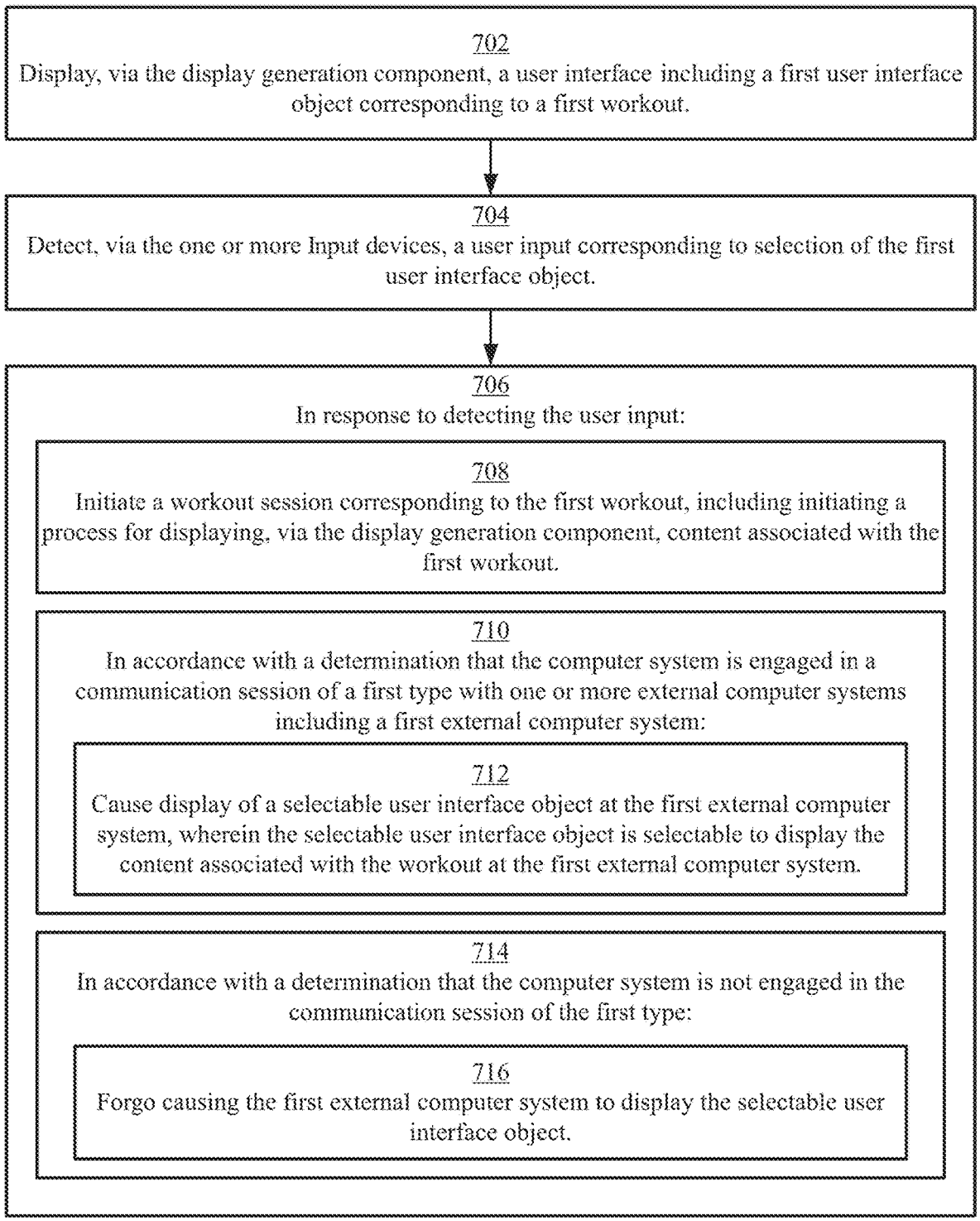
FIG. 7A is a flow diagram illustrating an exemplary process for displaying group workout content, in accordance with some embodiments.
Figures 1, 8A:
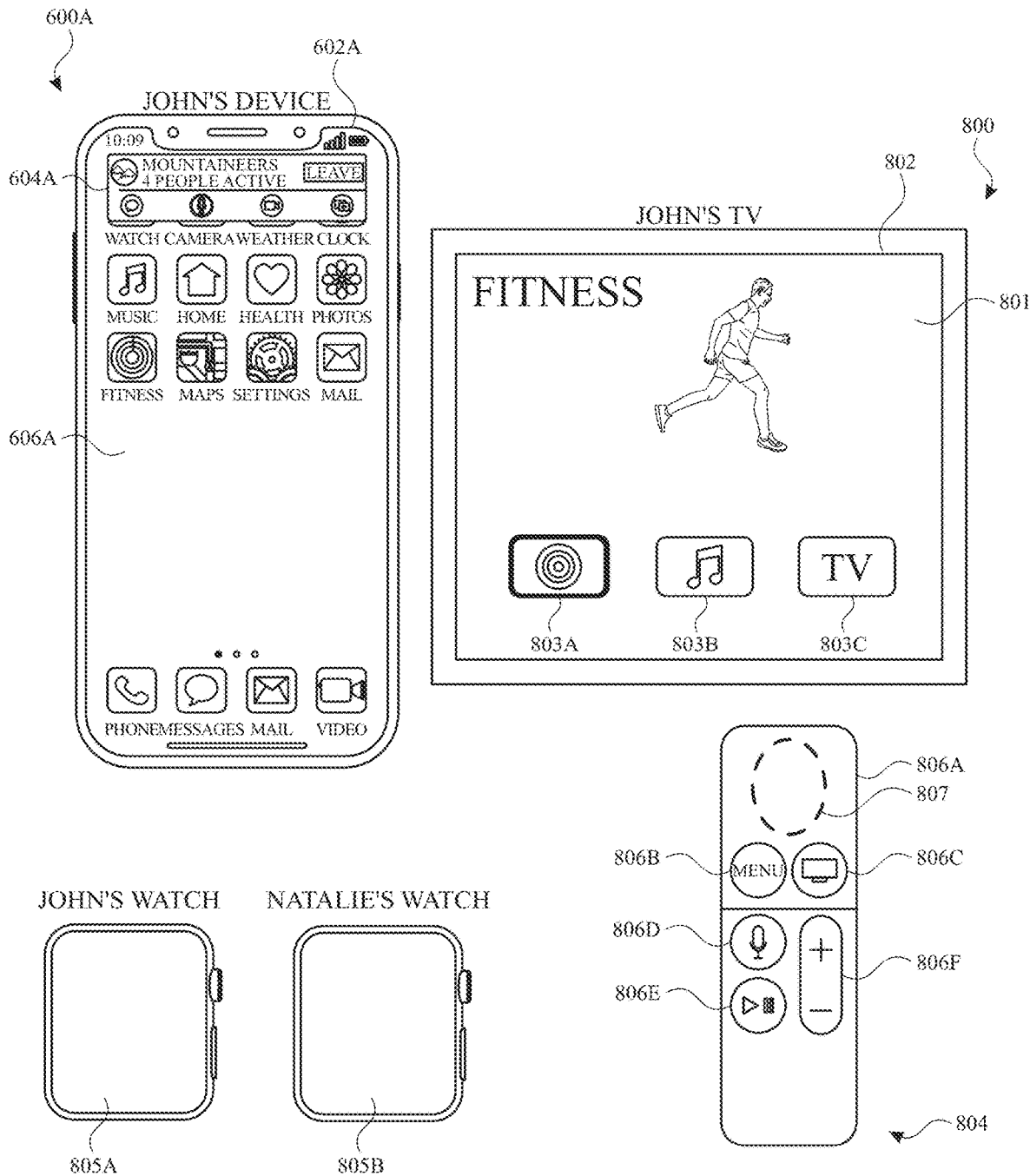
Figures 2, 8A:
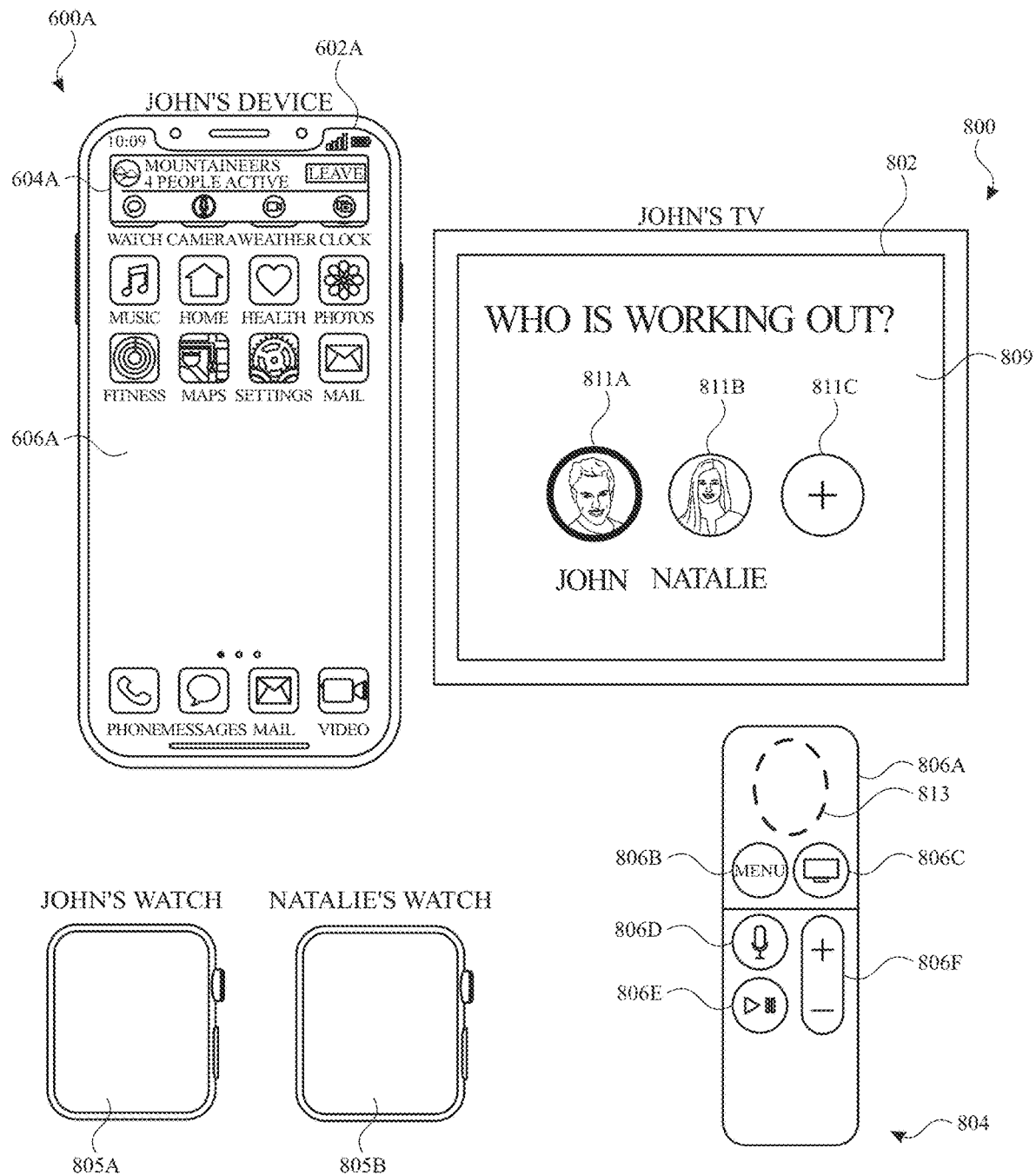
Figures 3, 8A:
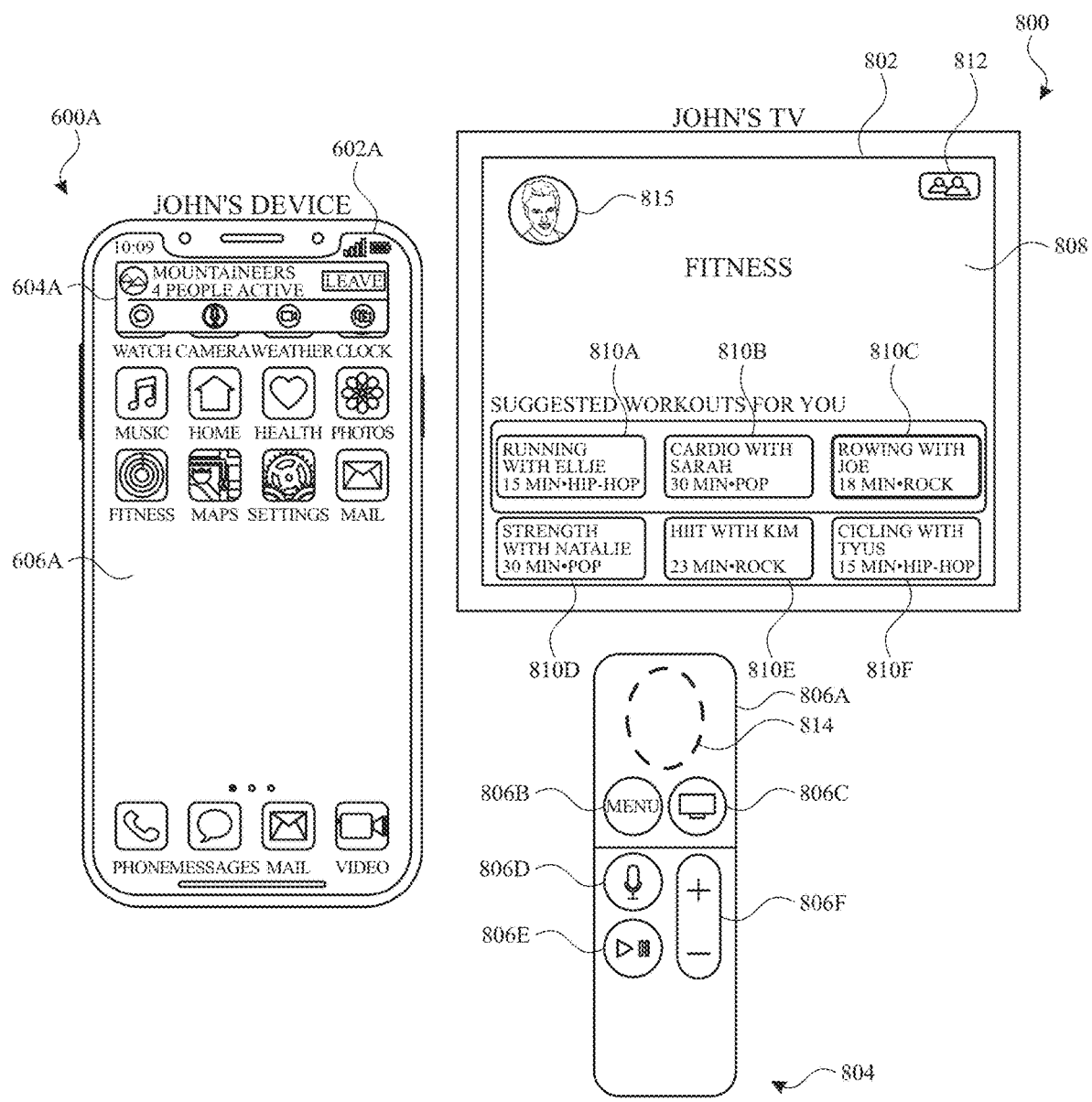
Figure 10A:
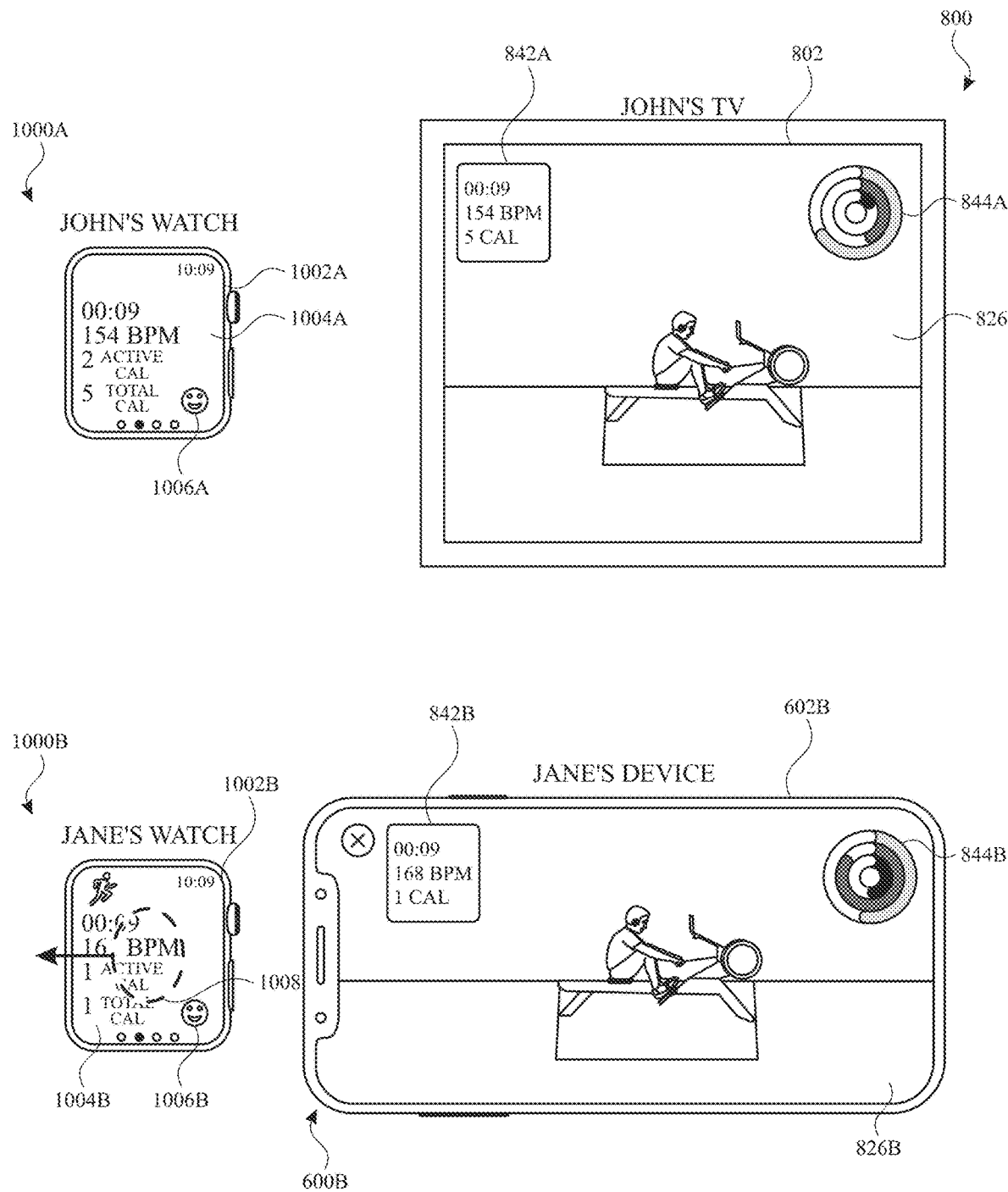
FIGS. 10A-10K illustrate exemplary user interfaces for displaying group workout content, in accordance with some embodiments.

Below, FIGS. 1A-1B, 2, 3, 4A-4B, and 5A-5B provide a description of exemplary devices for performing the techniques for displaying and sharing workout content. FIGS. 6A-6X illustrate exemplary user interfaces for displaying and sharing group workout content. FIG. 7A is a flow diagram illustrating methods of displaying and sharing group workout content in accordance with some embodiments. FIG. 7B is a flow diagram illustrating methods of accessing and displaying group workout content, in accordance with some embodiments. The user interfaces in FIGS. 6A-6X are used to illustrate the processes described below, including the processes in FIGS. 7A and 7B. FIGS. 8A-1-8I illustrate exemplary user interfaces for displaying and sharing group workout content. FIG. 9 is a flow diagram illustrating methods of displaying and sharing group workout content in accordance with some embodiments. The user interfaces in FIGS. 8A-1-8I are used to illustrate the processes described below, including the processes in FIG. 9. FIGS. 10A-10K illustrate exemplary user interfaces for displaying and sharing group workout content. FIG. 11 is a flow diagram illustrating methods of displaying and sharing group workout content in accordance with some embodiments. The user interfaces in FIGS. 10A-1K are used to illustrate the processes described below, including the processes in FIG. 11.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
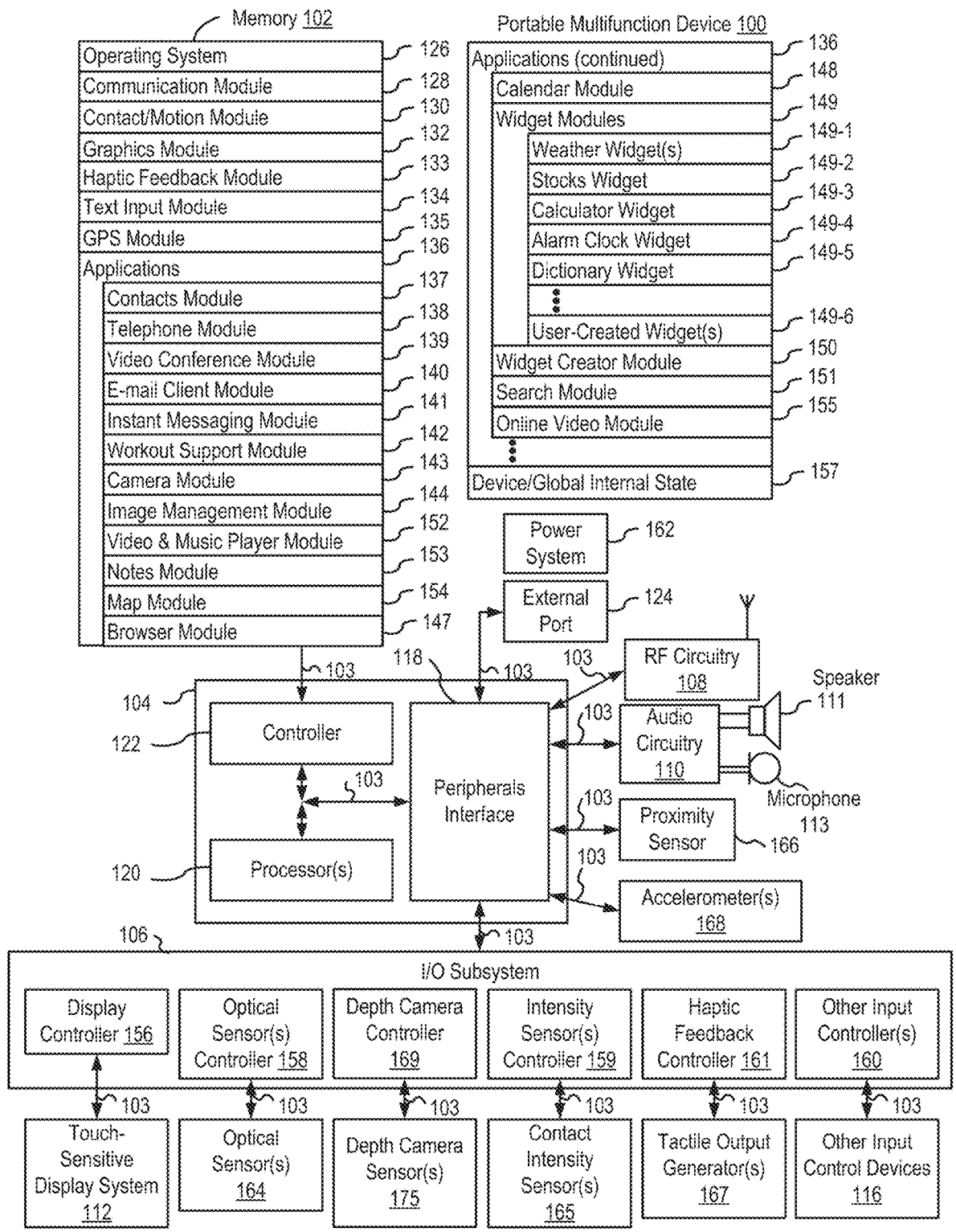
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
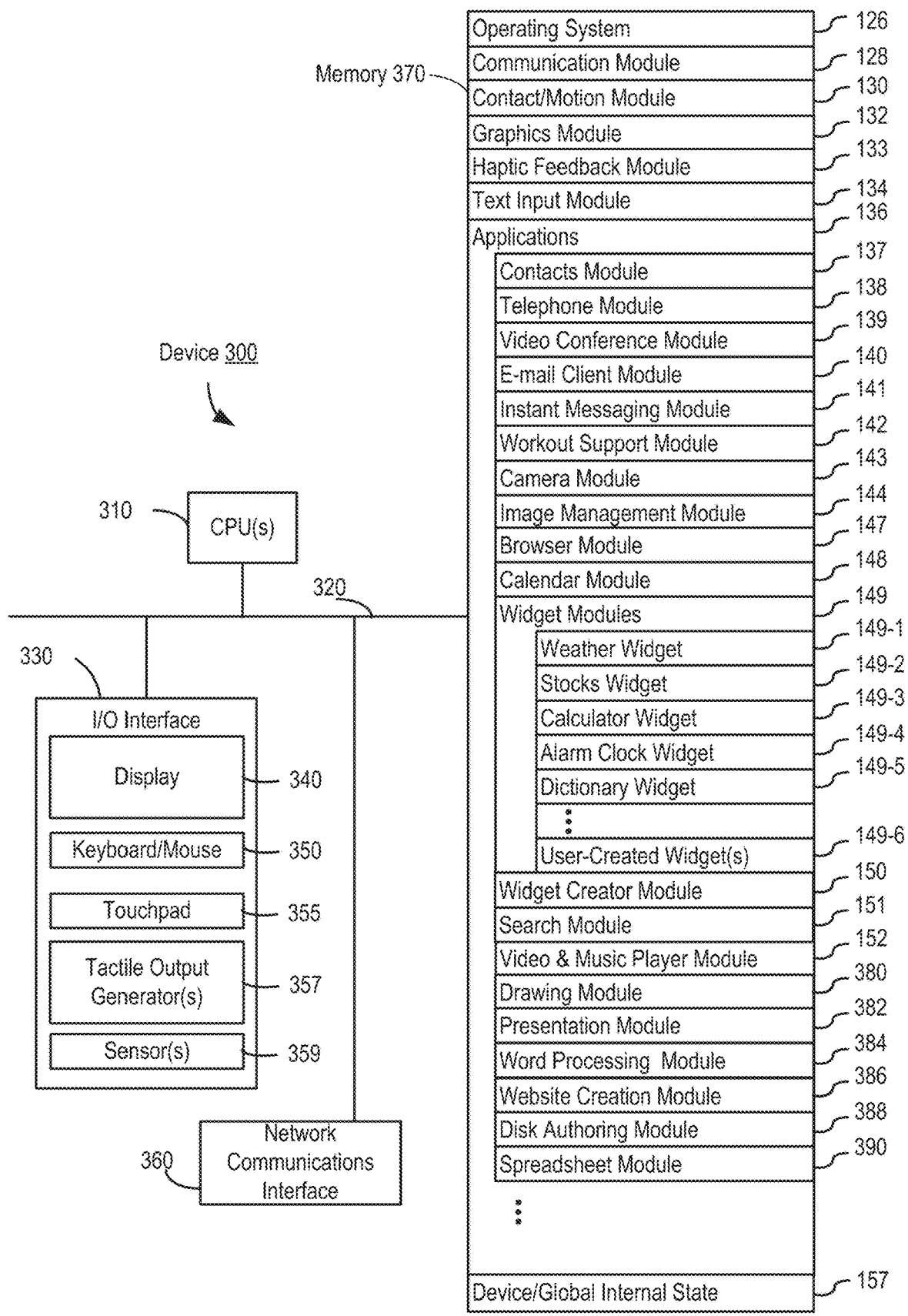
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
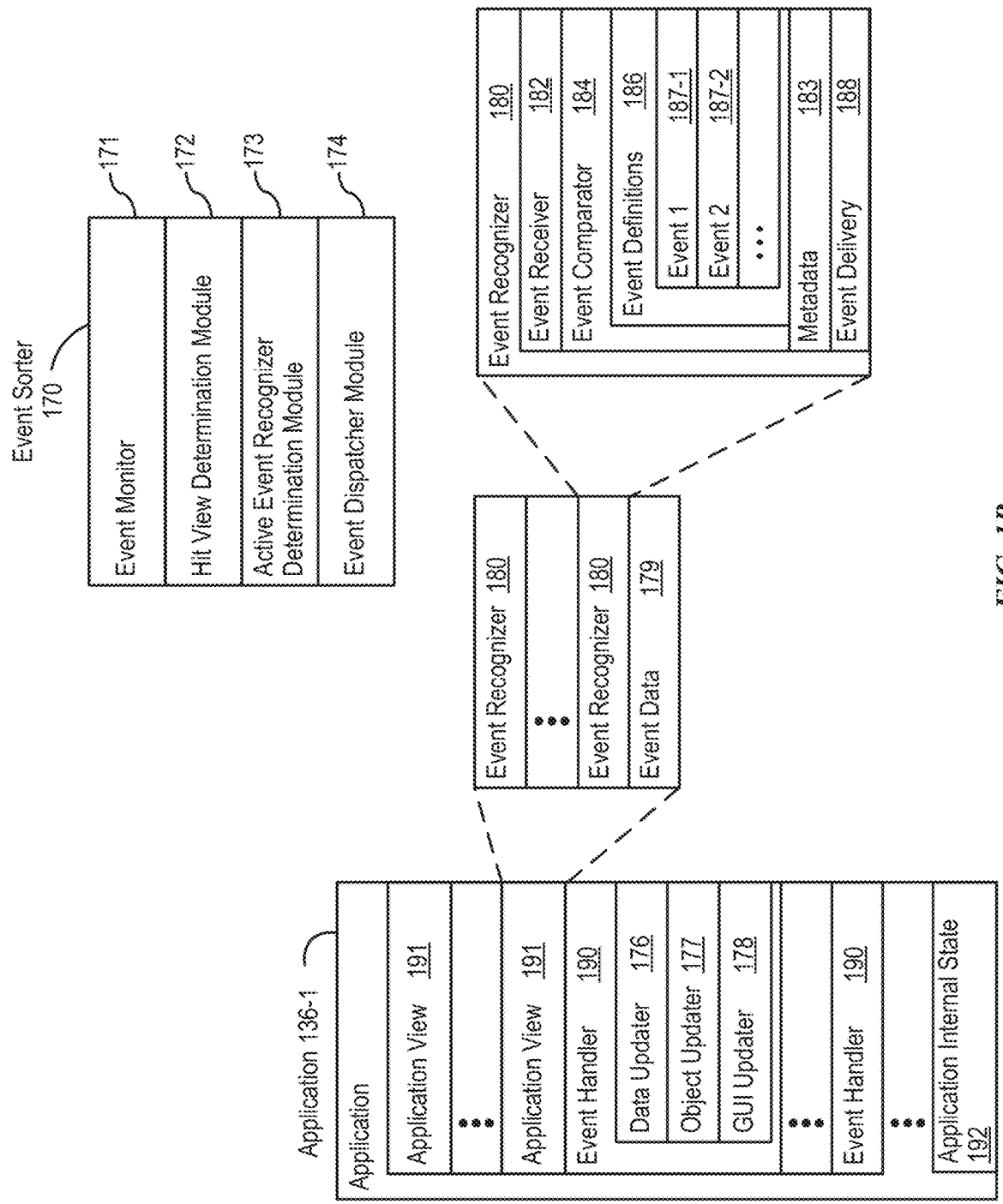
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
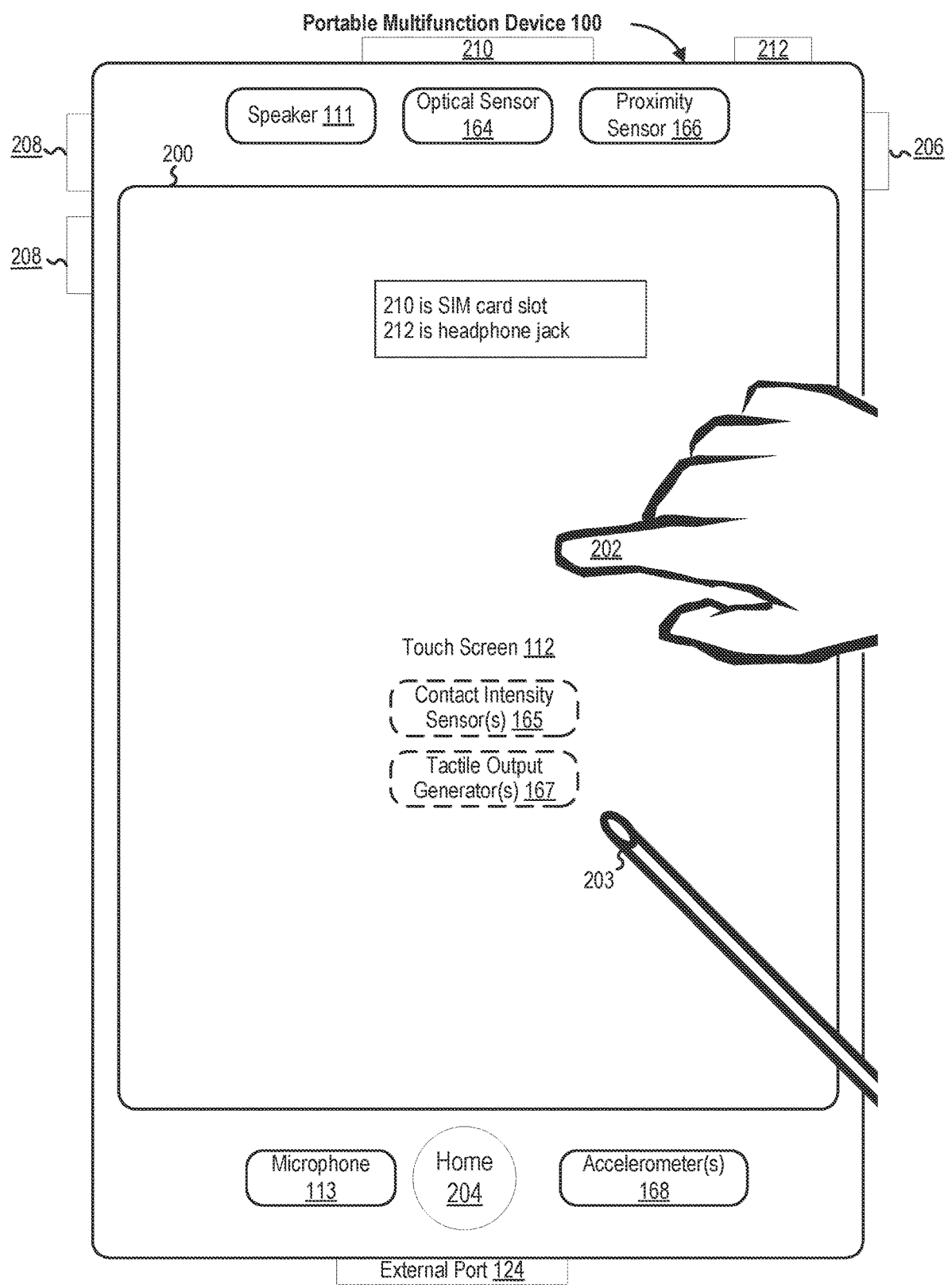
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
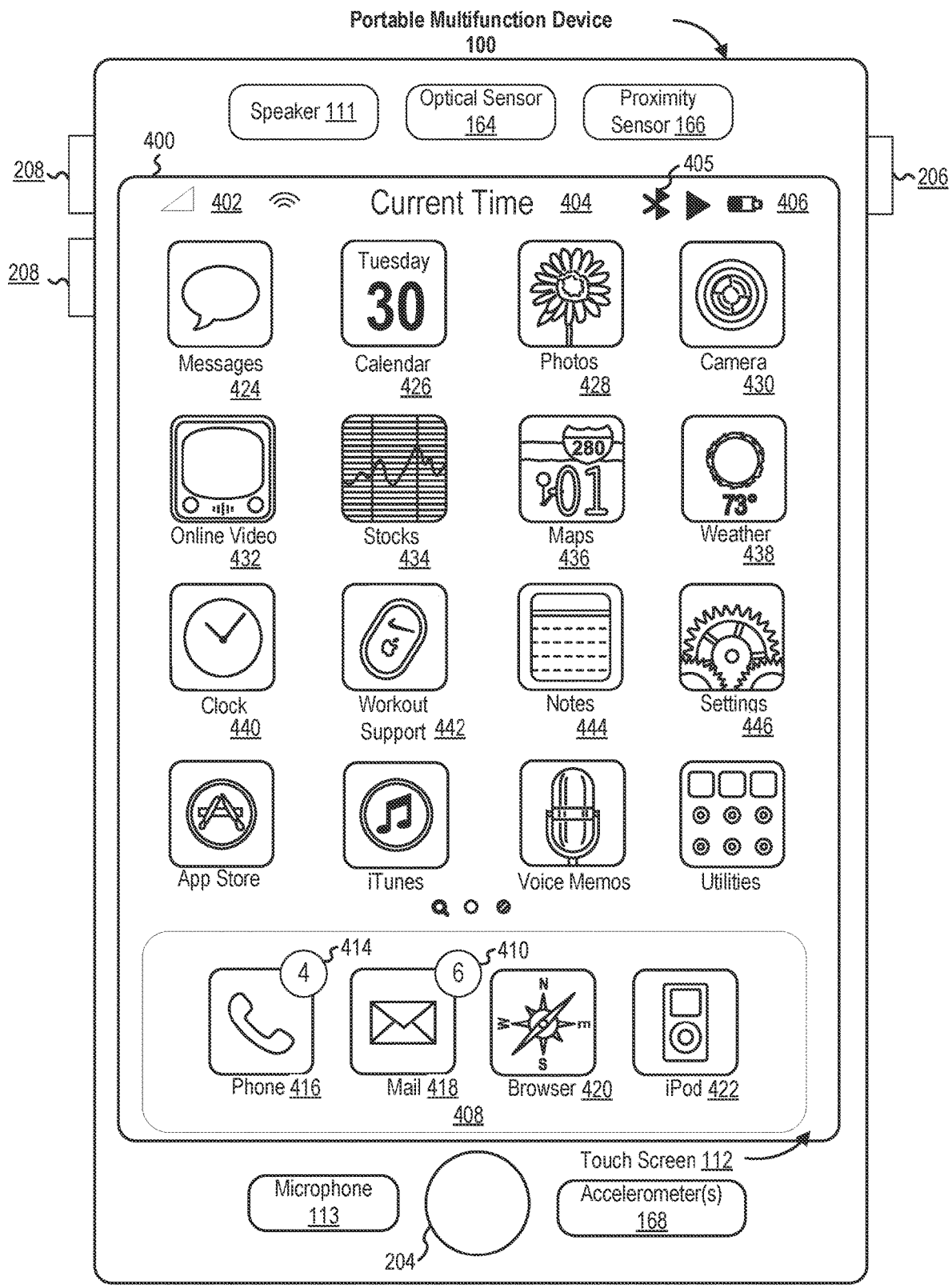
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
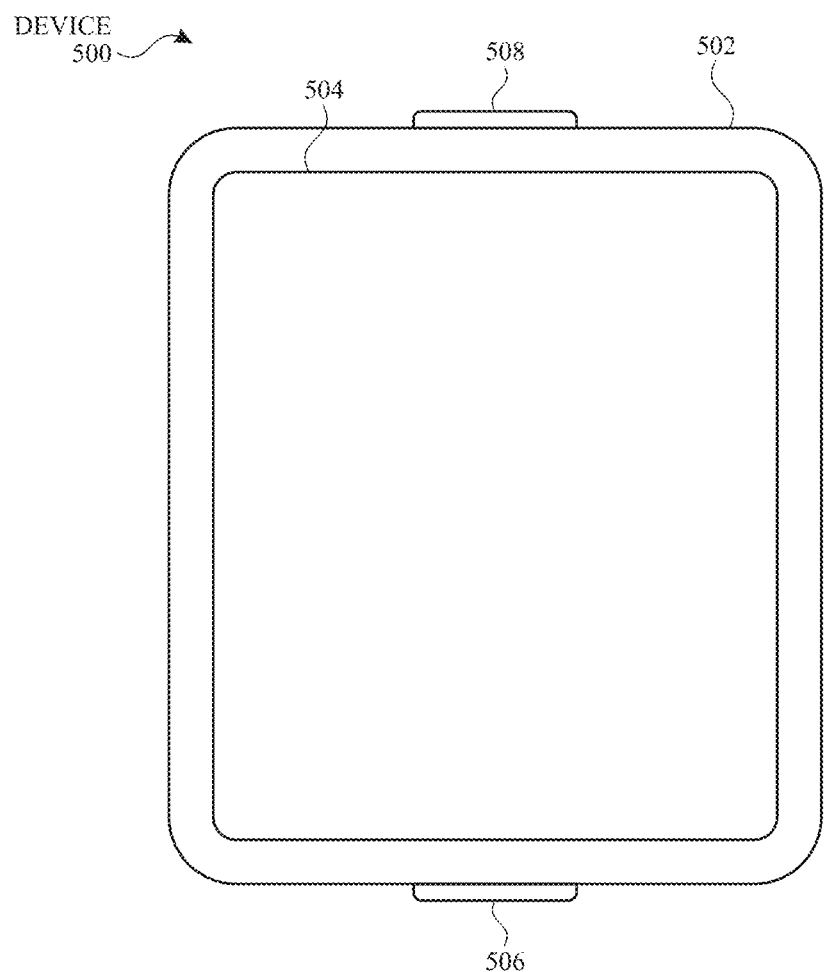
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
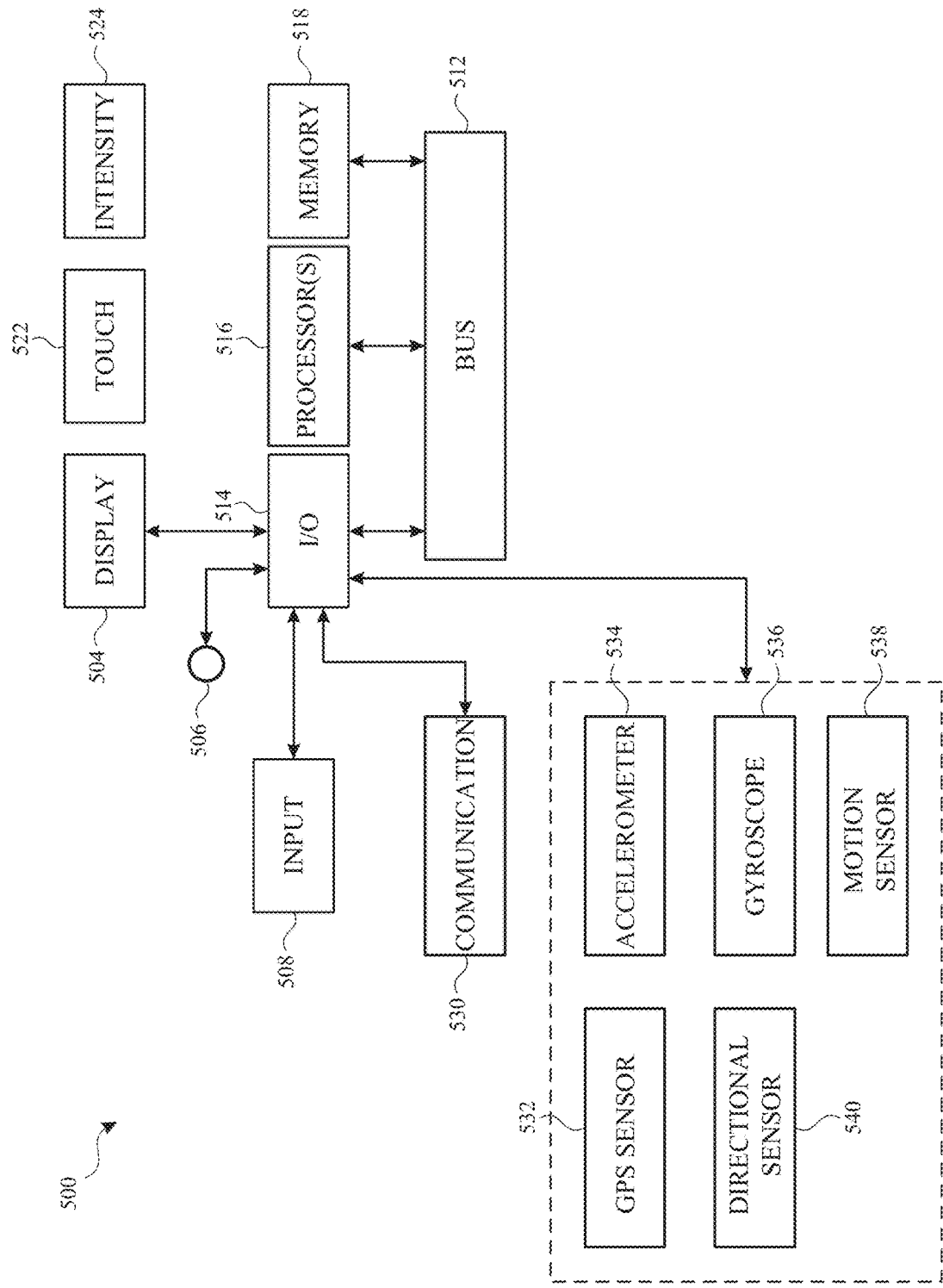
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 750, and 900 (FIGS. 7A, 7B, and 9). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;

a background application (or background processes), which is not currently displayed, but one or more processes for the application are being processed by one or more processors; and a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6X illustrate exemplary user interfaces for displaying and sharing group workout (e.g., exercise programming) content, in accordance with some embodiments. The user interfaces in these figures are used to illustrate the processes described below, including the processes in FIG. 7A and FIG. 7B.

FIG. 6A depicts electronic device 600A, which is a smartphone with display 602A, electronic device 600B, a smartphone with display 602B, and electronic device 600C, a smartphone with display 602C. Electronic device 600A displays communication session overlay 604A overlaid on home user interface 606A. Communication session overlay 604A indicates that electronic device 600A is participating in a communication session (e.g., a communication that is currently active, a synchronized media and communication session) with three other devices (e.g., a communication session facilitated by a communication application). Electronic device 600B is also participating in the communication session with electronic device 600A. Accordingly, electronic device 600B displays communication session overlay 604B overlaid on home user interface 606B. Electronic device 600C is also participating in the communication session with electronic devices 600A and 600B. Accordingly, electronic device 600C displays communication session overlay 604C overlaid on home user interface 606C. The fourth device participating in the communication session with electronic devices 600A, 600B, 600C is not depicted in the figures. In the depicted scenario, electronic device 600A corresponds to a user named John (e.g., John is logged into electronic device 600A), electronic device 600B corresponds to a user named Jane (e.g., Jane is logged into electronic device 600B), and electronic device 600C corresponds to a user named Sarah (e.g., Sarah is logged into electronic device 600C).

In the depicted embodiment, the communication session connects electronic devices 600A, 600B, 600C, and enables communication between electronic devices via various communication mediums. For example, communication session overlay 604A includes messaging option 608A that is selectable to exchange text-based communications within the communication session, audio communication option 610A that is selectable to exchange audio-based communications within the communication session (e.g., voice communications), video communication option 612A that is selectable to exchange video-based communications within the communication session (e.g., live video communication), and synchronized content (e.g., media content) sharing option 614A that is selectable to exchange synchronized content within the communication session. For example, synchronized content sharing option 614A enables a user to share video content to the communication session, and users in the communication session can view the video content in a synchronized manner (e.g., playback of the video content is synchronized across all of the electronic devices participating in the communication session and viewing the video content). In this way, the communication session allows for communication between multiple electronic devices via various communication mediums. Communication session overlay 604A also includes leave option 616A that is selectable to cause electronic device 600A to leave (e.g., disconnect from) the communication session. Communication session overlays 604B and 604C are identical to communication session overlay 604A.

In FIG. 6A, the user of electronic device 600A, John, says "Let's do a group workout." Electronic device 600A receives the audio input, and transmits the audio input to electronic devices 600B, 600C via the communication session. Electronic devices 600B and 600C output a corresponding audio output to their respective users, Jane and Sarah. In FIG. 6A, electronic device 600A detects user input 618 (e.g., a tap input) corresponding to selection of a fitness application option 620A.

Figure 6B:
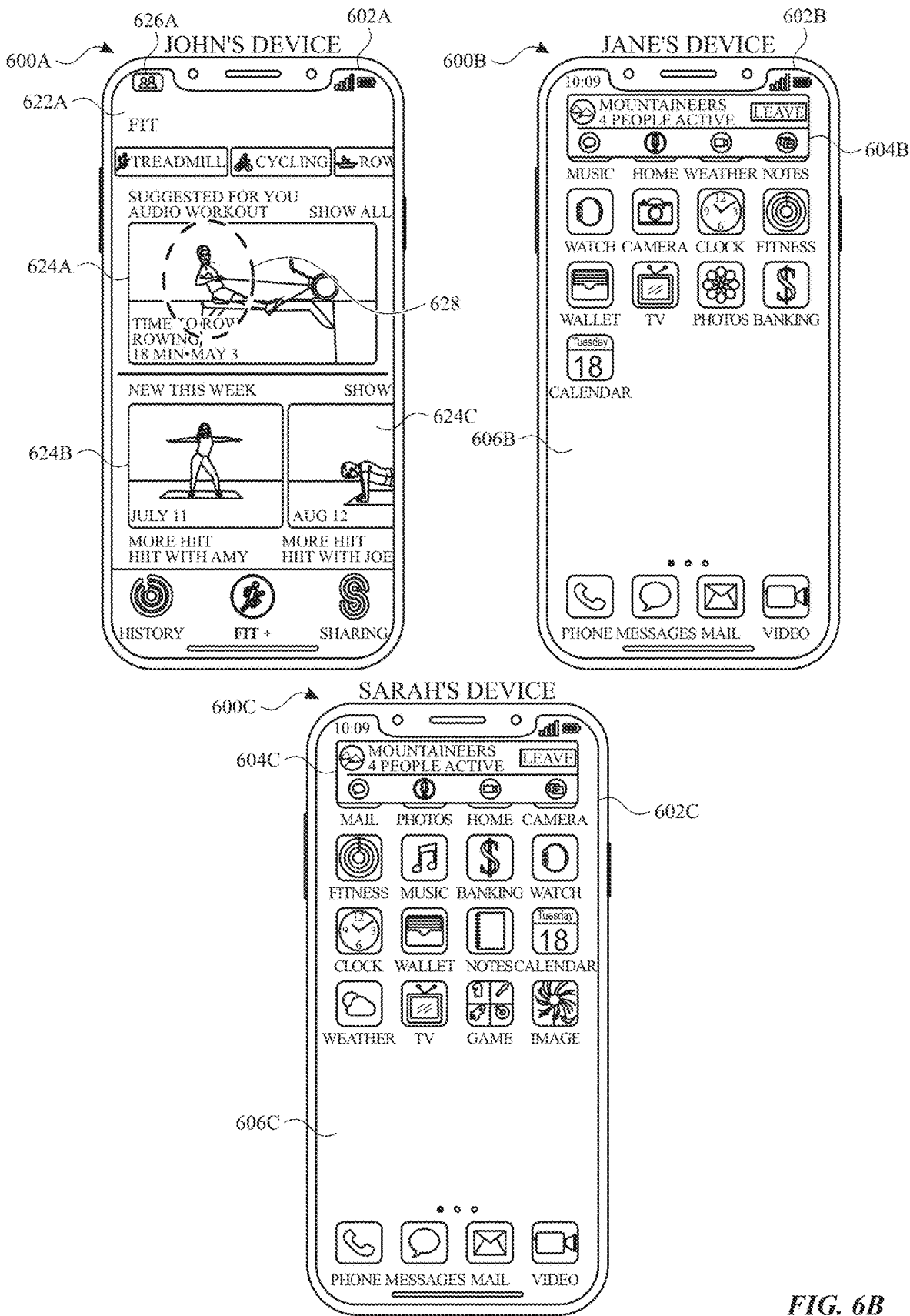

In FIG. 6B, in response to detecting user input 618, electronic device 600A displays workout suggestion user interface 622A generated by the fitness application, which includes a plurality of workout suggestions 624A-624C that are selectable by a user to initiate a process for playing a particular workout (e.g., initiate a process to play audio and/or video content corresponding to the selected workout). Electronic device 600A also displays active communication session indication 626A indicating that electronic device 600A is currently participating in a communication session. In some embodiments, electronic device 600A ceases displaying communication session overlay 604A and displays active communication session indication 626A in response to a determination that a threshold duration of time has passed since the user has interacted with communication session overlay 604A and/or in response to a predetermined user gesture (e.g., a swipe up on communication session overlay 604A). In FIG. 6B, electronic device 600A detects user input 628 (e.g., a tap input) corresponding to selection of workout suggestion 624A, which corresponds to a rowing workout.

Figure 6C:
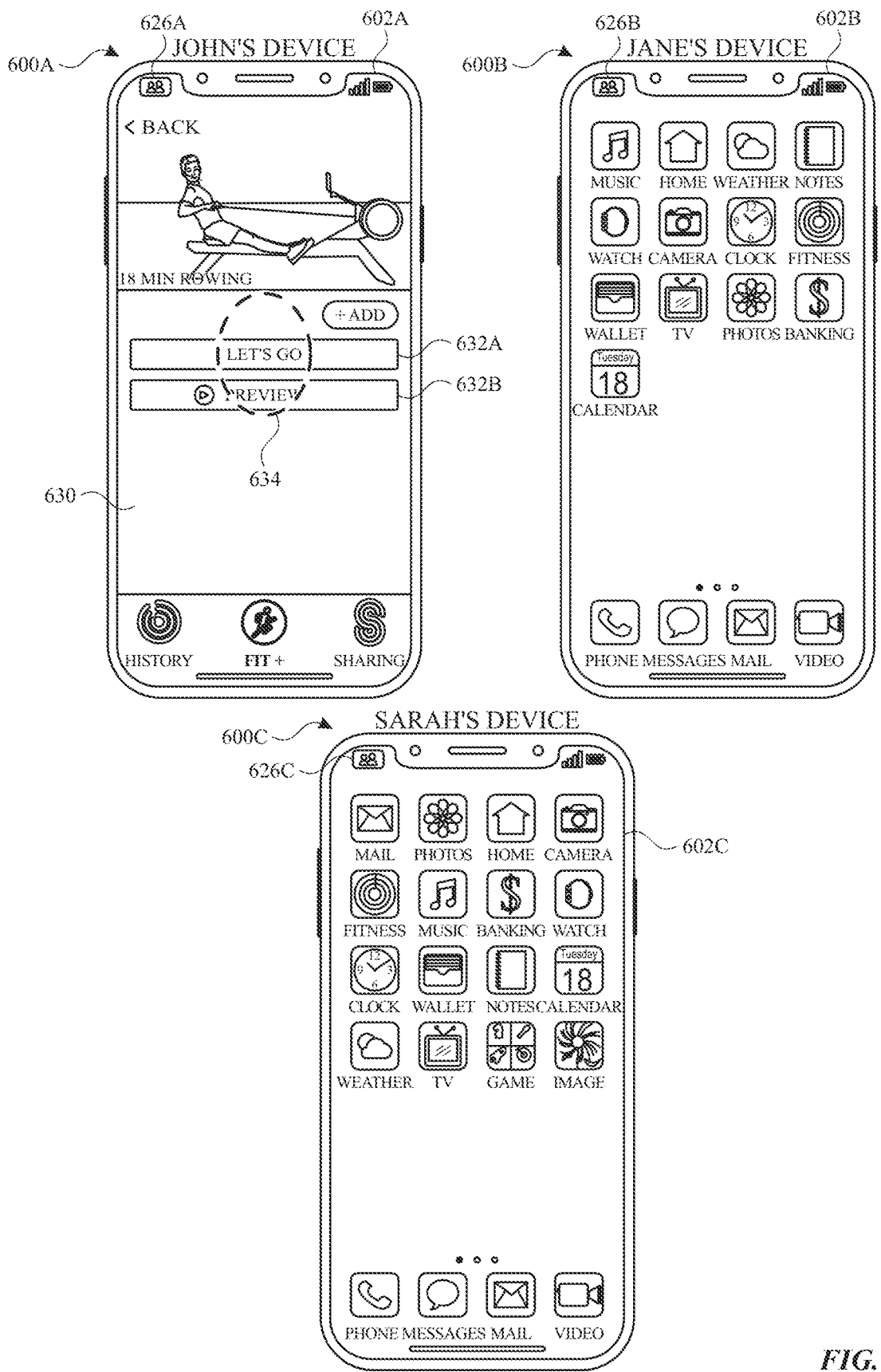

In FIG. 6C, in response to detecting user input 628, electronic device 600A displays workout start user interface 630. Workout start user interface 630 includes a first option 632A that is selectable to initiate playing the selected workout (e.g., begin playing audio and/or video content corresponding to the selected workout), and a second option 632B that is selectable to view a preview of the selected workout (e.g., begin playing preview audio and/or preview video content corresponding to the selected workout). In FIG. 6C, electronic device 600A detects user input 634 (e.g., a tap input) corresponding to selection of option 632A.

Figure 6D:
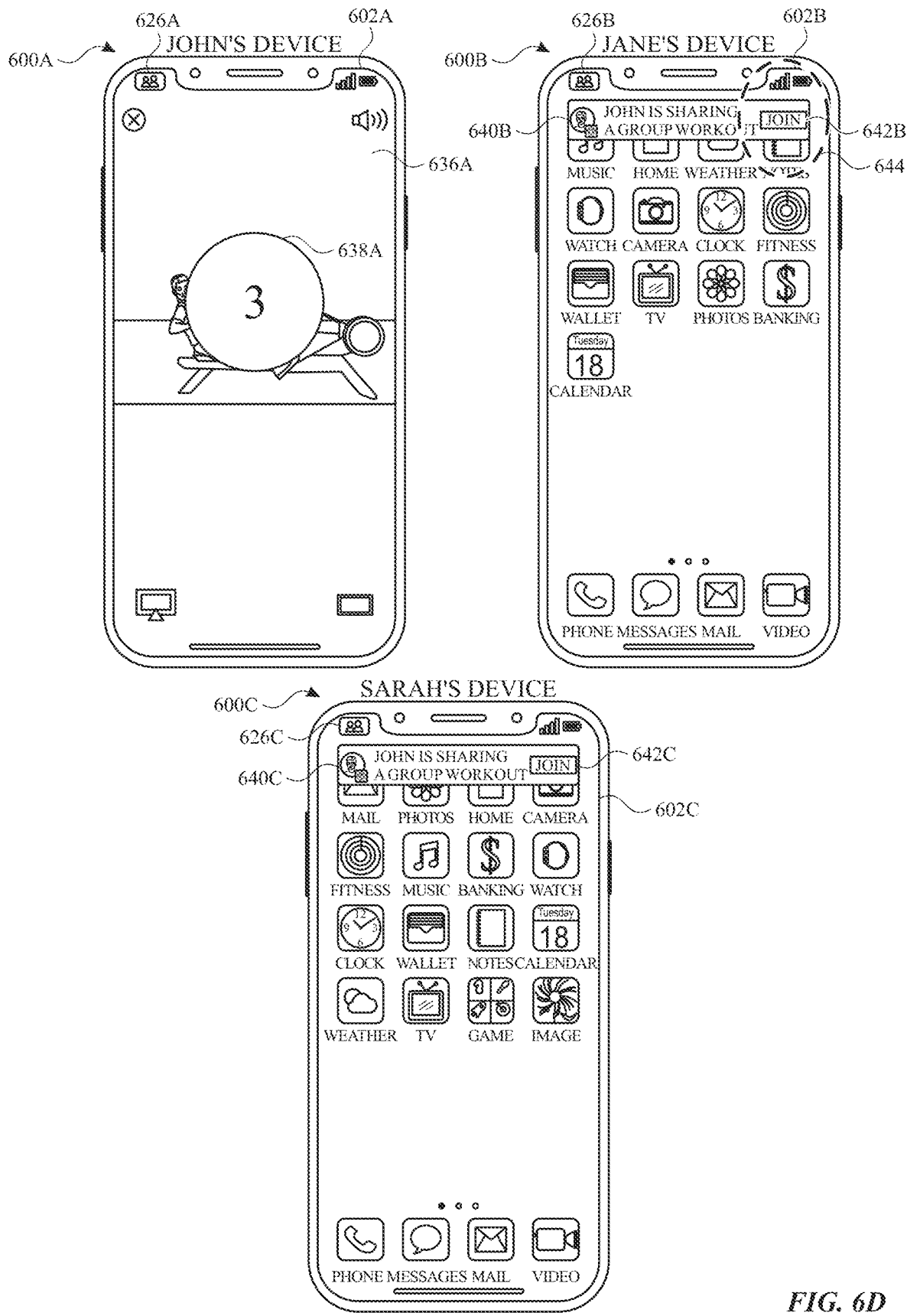

In FIG. 6D, in response to detecting user input 634, electronic device 600A displays workout user interface 636A. Workout user interface 636A displays video content (e.g., audio-visual content) corresponding to the selected workout (e.g., plays audio and/or video of the selected workout that provides the user with instructions and/or demonstrations of the selected workout). In FIG. 6D, workout user interface 636A displays timer 638A indicating that the workout will begin playing in three seconds.

In FIG. 6D, in response to electronic device 600A detecting user input 634 to begin a workout, and based on electronic device 600A participating in the communication session with electronic device 600B, electronic device 600B displays notification 640B indicating that electronic device 600A has initiated a group workout (e.g., has initiated a workout while participating in the communication session with electronic device 600B). Notification 640B includes join option 642B that is selectable to cause electronic device 600B to join the group workout. Similarly, in response to electronic device 600A detecting user input 634 to begin a workout, and based on electronic device 600A participating in the communication session with electronic device 600C, electronic device 600C displays notification 640C indicating that electronic device has initiated a group workout (e.g., has initiated a workout while participating in the communication session with electronic device 600C). Notification 640C includes join option 642C that is selectable to cause electronic device 600C to join the group workout. In some embodiments, in response to detecting user input 634, electronic device 600A transmits to electronic devices 600B and 600C (e.g., via the communication session) and/or causes to be transmitted to electronic device 600B and 600C an indication that electronic device 600A has received a user input corresponding to a request to initiate a group workout. In FIG. 6D, electronic device 600B detects user input 644 (e.g., a tap input) corresponding to selection of join option 642B.

Figure 6E:
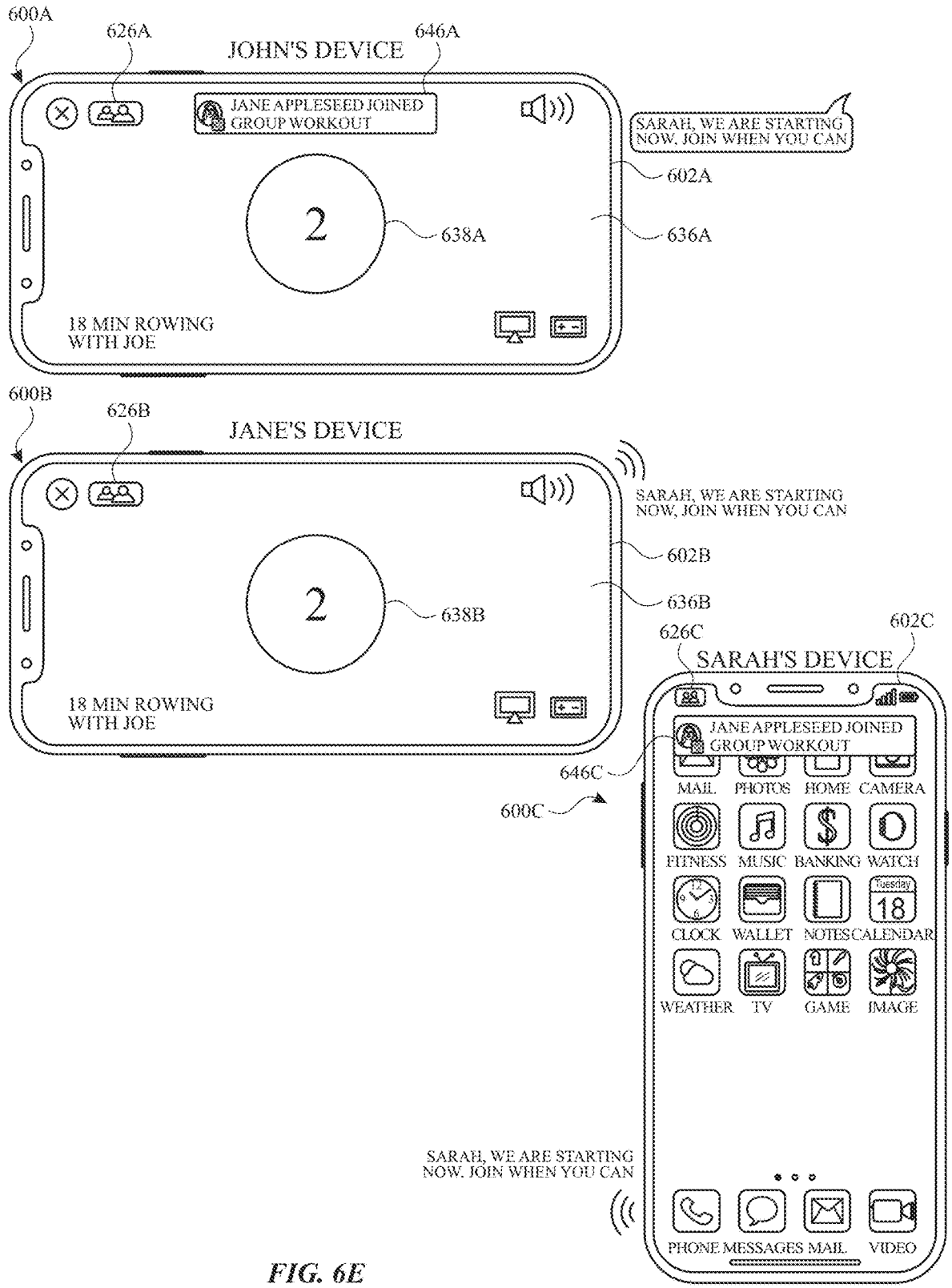

In FIG. 6E, in response to detecting user input 644, electronic device 600B joins the group workout, and displays workout user interface 636B. Workout user interface 636B corresponds to workout user interface 636A, and displays synchronized video content with workout user interface 636A (e.g., playback of video content in workout user interface 636B is synchronized with playback of video content in workout user interface 636A). For example, workout user interface 636B displays timer 638B indicating that the workout will begin in two seconds at the same time that workout user interface 636A displays timer 638A, which also indicates that the workout will begin in two seconds. Furthermore, in response to electronic device 600B joining the group workout, electronic device 600A displays notification 646A indicating that electronic device 600B has joined the group workout, and electronic device 600C displays notification 646C indicating that electronic device 600B has joined the group workout. In some embodiments, electronic device 600B transmits to electronic devices 600A and 600C (e.g., via the communication session) and/or causes to be transmitted to electronic devices 600A and 600C an indication that electronic device 600B has detected user input 644 corresponding to a request to join the group workout, and electronic devices 600A and 600C display notifications 646A, 646C in response to receiving the indication.

In FIG. 6E, electronic device 600A receives an audio input of user John saying "Sarah, we are starting now. Join when you can." Electronic device 600A transmit the audio input to electronic devices 600B and 600C (e.g., via the communication session), which causes electronic devices 600B and 600C to output corresponding audio output.

Figure 6F:
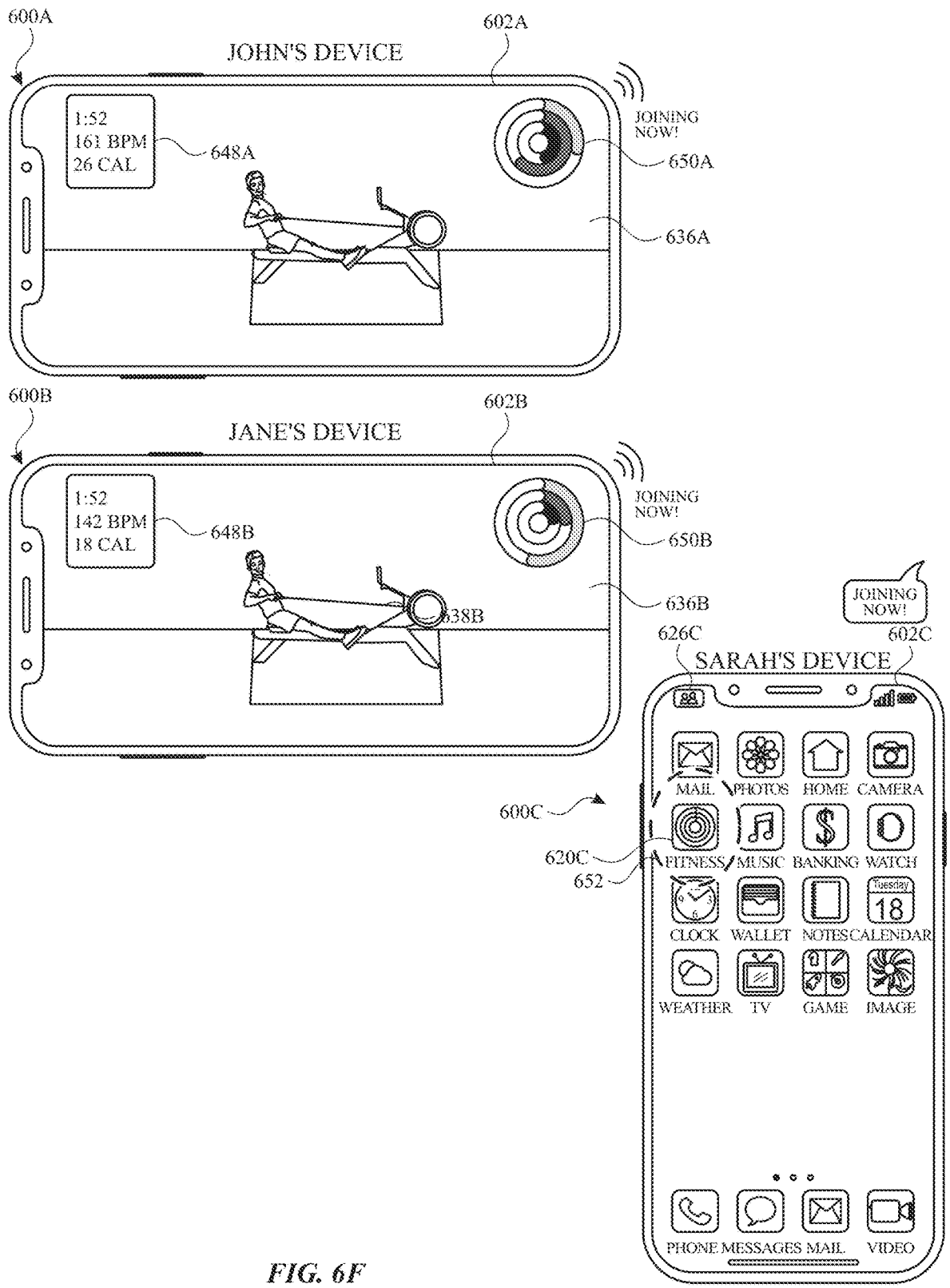

In FIG. 6F, the group workout has progressed for 1 minute and 52 seconds. Electronic device 600A continues to display workout user interface 636A which displays video content corresponding to the workout (e.g., video content demonstrating the workout). Workout user interface 636A also includes workout physical activity metrics 648A indicative of (e.g., corresponding to) physical activity of a user of electronic device 600A (e.g., "John"). Workout physical activity metrics 648A display John's heartrate (e.g., 161 BPM), and the number of calories John has burned during the workout (e.g., 26 calories). Workout user interface 636A also includes daily physical activity metrics 650A. Daily physical activity metrics 650A include physical activity metrics for John for the current day, including time outside of the current workout. For example, in some embodiments, the outer ring of daily physical activity metrics 650A indicates the number of calories John has burned in the current day (e.g., indicates John's progress towards a daily calorie goal), the middle ring of daily physical activity metrics 650A indicates the number of minutes John has exercised in the current day (e.g., indicates John's progress towards a daily exercise minutes goal), and the innermost ring of daily physical activity metrics 650A indicates the number hours in the current day that John has stood for a threshold amount of time (e.g., how many hours John has stood for at least 3 minutes) (e.g., indicates John's progress towards a daily stand goal).

Similarly, electronic device 600B displays workout user interface 636B, which also displays video content corresponding to the workout. The video content displayed in workout user interface 636B is synchronized with video content displayed in workout user interface 636A. Workout user interface 636B also displays workout physical activity metrics 648B indicative of physical activity of a user of electronic device 600B (e.g., "Jane") during the workout. Workout user interface 636B also displays daily physical activity metrics 650B that are indicative of Jane's physical activity in the current day, as described above with reference to daily physical activity metrics 650A.

In FIG. 6F, electronic device 600C receives audio input of user Sarah stating, "Joining now!" Electronic device 600C transmits the received audio input to electronic devices 600A and 600B (e.g., via the communication session), and electronic devices 600A and 600B output corresponding audio output. In FIG. 6F, electronic device 600C detects user input 652 (e.g., a tap input) corresponding to selection of fitness application option 620C.

Figure 6G:
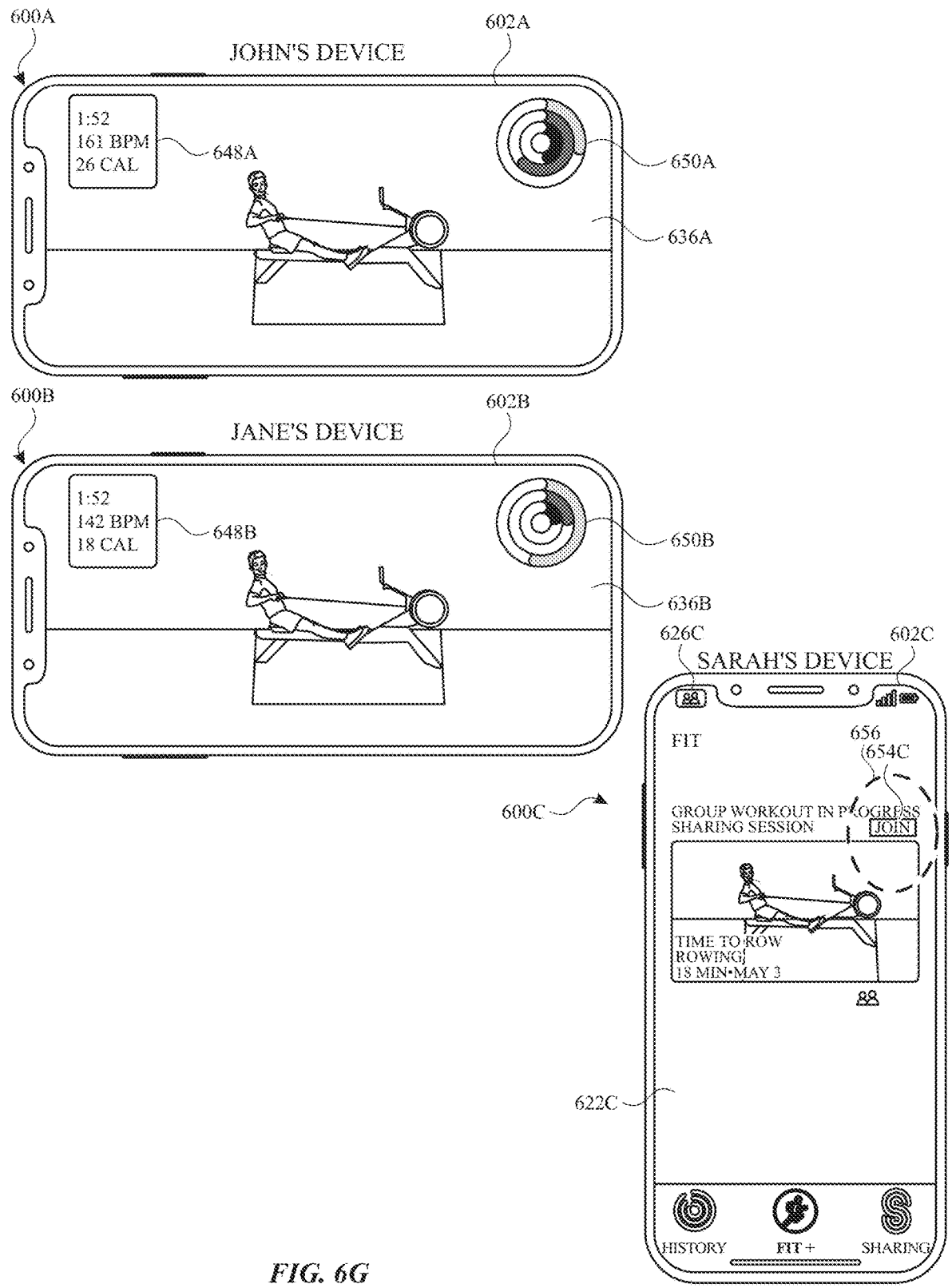

In FIG. 6G, in response to detecting user input 652, electronic device 600C displays workout suggestion user interface 622C. Whereas workout suggestion user interface 622C would typically display a plurality of workout suggestions for Sarah (e.g., similar to workout suggestion user interface 622A of FIG. 6B), because electronic device 600C is participating in a communication session in which a group workout is currently taking place, workout suggestion user interface 622C in FIG. 6G includes only option 654C to join the group workout that is in progress. In the depicted embodiment, in order to take other actions within the fitness application, Sarah would have to leave the communication session, or the group workout taking place in the communication session would have to be terminated. In FIG. 6G, while displaying option 654C, electronic device 600C detects user input 656 (e.g., a tap input) corresponding to selection of option 654C.

Figure 6H:
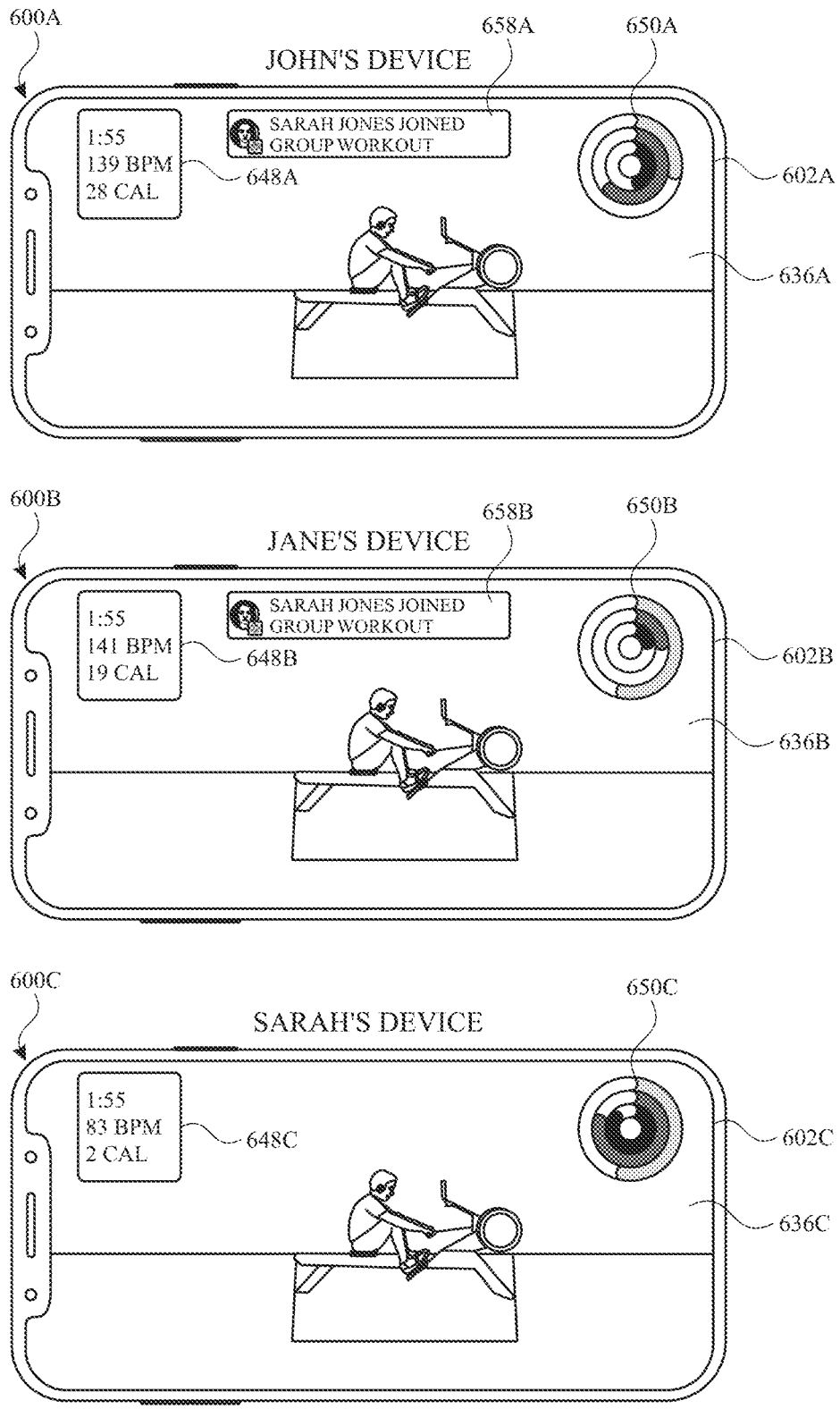

In FIG. 6H, in response to detecting user input 656, electronic device 600C joins the group workout and displays workout user interface 636C. Workout user interface 636C displays video content corresponding to the group workout. The video content displayed in workout user interface 636C is synchronized with video content displayed in workout user interfaces 636A and 636B (e.g., the timer shows 1 minute and 55 seconds have elapsed in the workout). Workout interface 636C displays workout physical activity metrics 648C indicative of (e.g., corresponding to) physical activity of a user of electronic device 600C (e.g., "Sarah") during the workout. Workout user interface 636C also displays daily physical activity metrics 650C that are indicative of (e.g., correspond to) Sarah's physical activity in the current day, as described above with reference to daily physical activity metrics 650A.

Furthermore, in FIG. 6H, in response to electronic device 600C detecting user input 656 and joining the group workout, electronic device 600A displays notification 658A indicating that electronic device 600C has joined the group workout, and electronic device 600B displays notification 658B indicating that electronic device 600C has joined the group workout. In some embodiments, in response to detecting user input 656, electronic device 600C transmits (e.g., via the communication session) to electronic devices 600A, 600B and/or causes to be transmitted to electronic devices 600A, 600B an indication that electronic device 600C has detected a user input corresponding to a request to join the group workout.

Figure 6I:
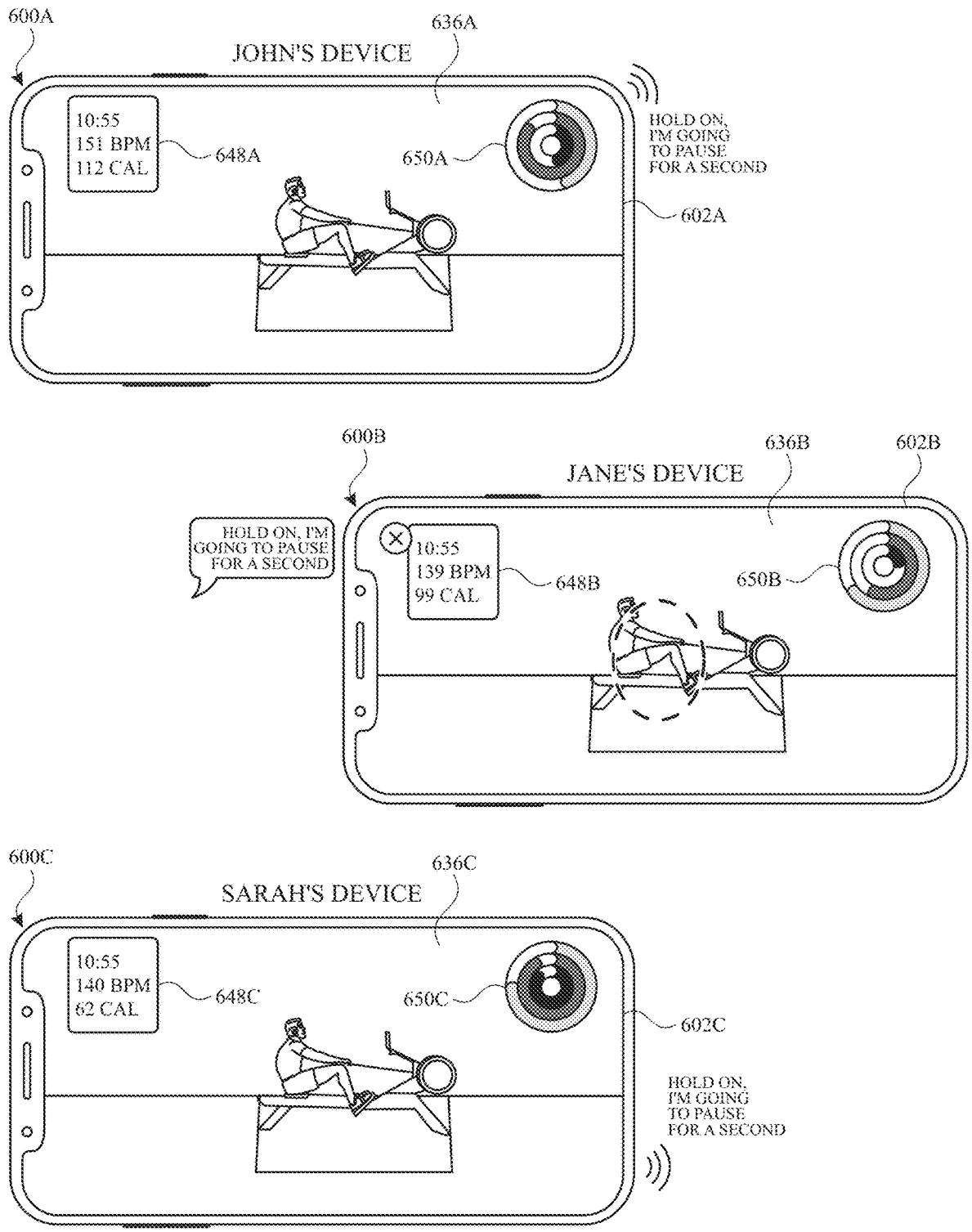

In FIG. 6I, the group workout has progressed to the 10 minute 55 second mark. In FIG. 6I, electronic device 600B receives an audio input of user Jane stating, "Hold on, I'm going to pause for a second." Electronic device 600B transmits the received audio input to electronic devices 600A and 600C via the active communication session, and electronic devices 600A and 600C output corresponding audio outputs. In FIG. 6I, electronic device 600B detects user input 660 (e.g., a tap input).

Figure 6J:
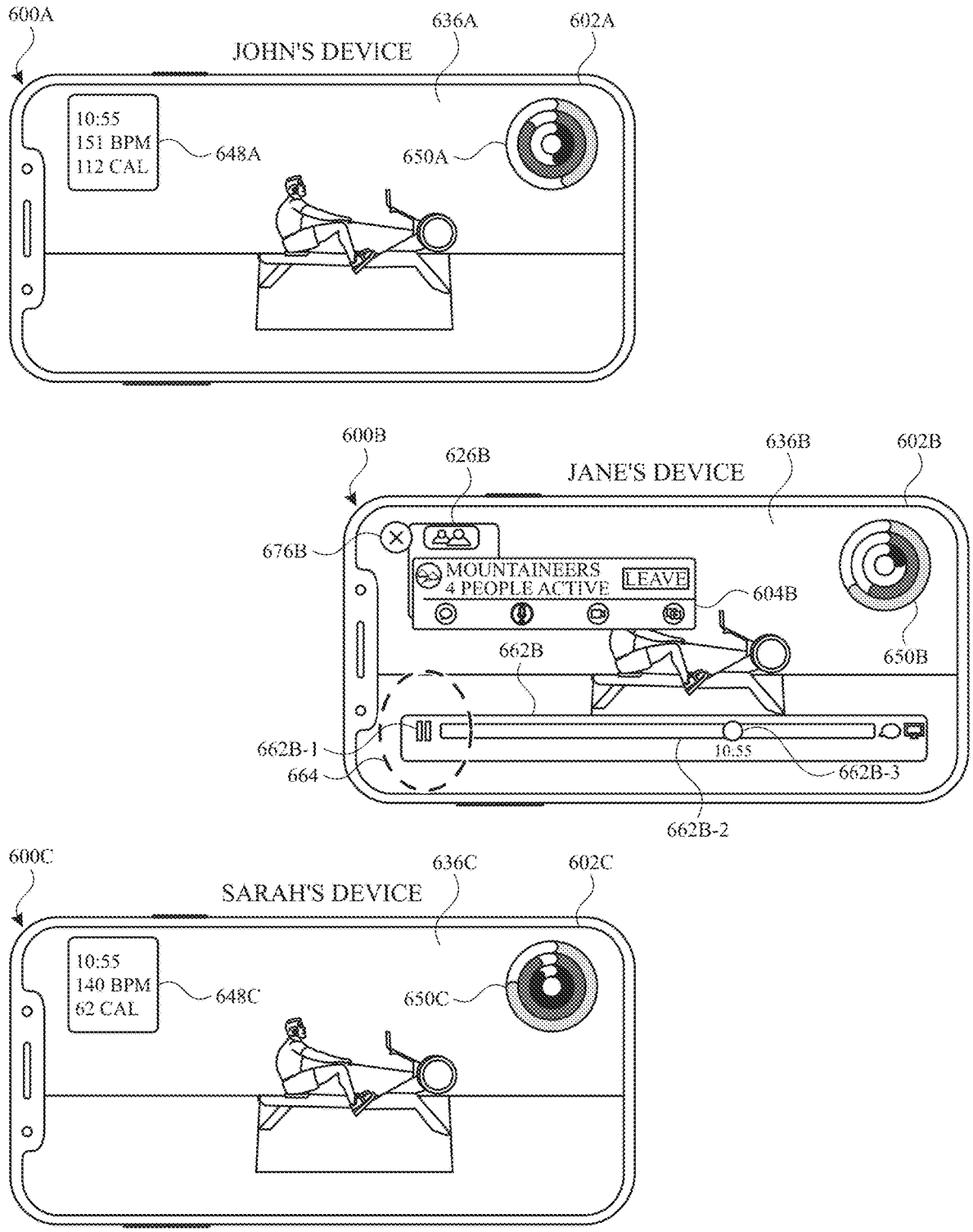

In FIG. 6J, in response to detecting user input 660, electronic device 600B displays active communication session indication 626B, communication session overlay 604B, and playback controls 662B. Playback controls 662B include pause option 662B-1, playback progress indication 662B-2, and scrubber 662B-3. In FIG. 6J, electronic device 600B detects user input 664 (e.g., a tap input) corresponding to selection of pause option 662B-1.

Figure 6K:
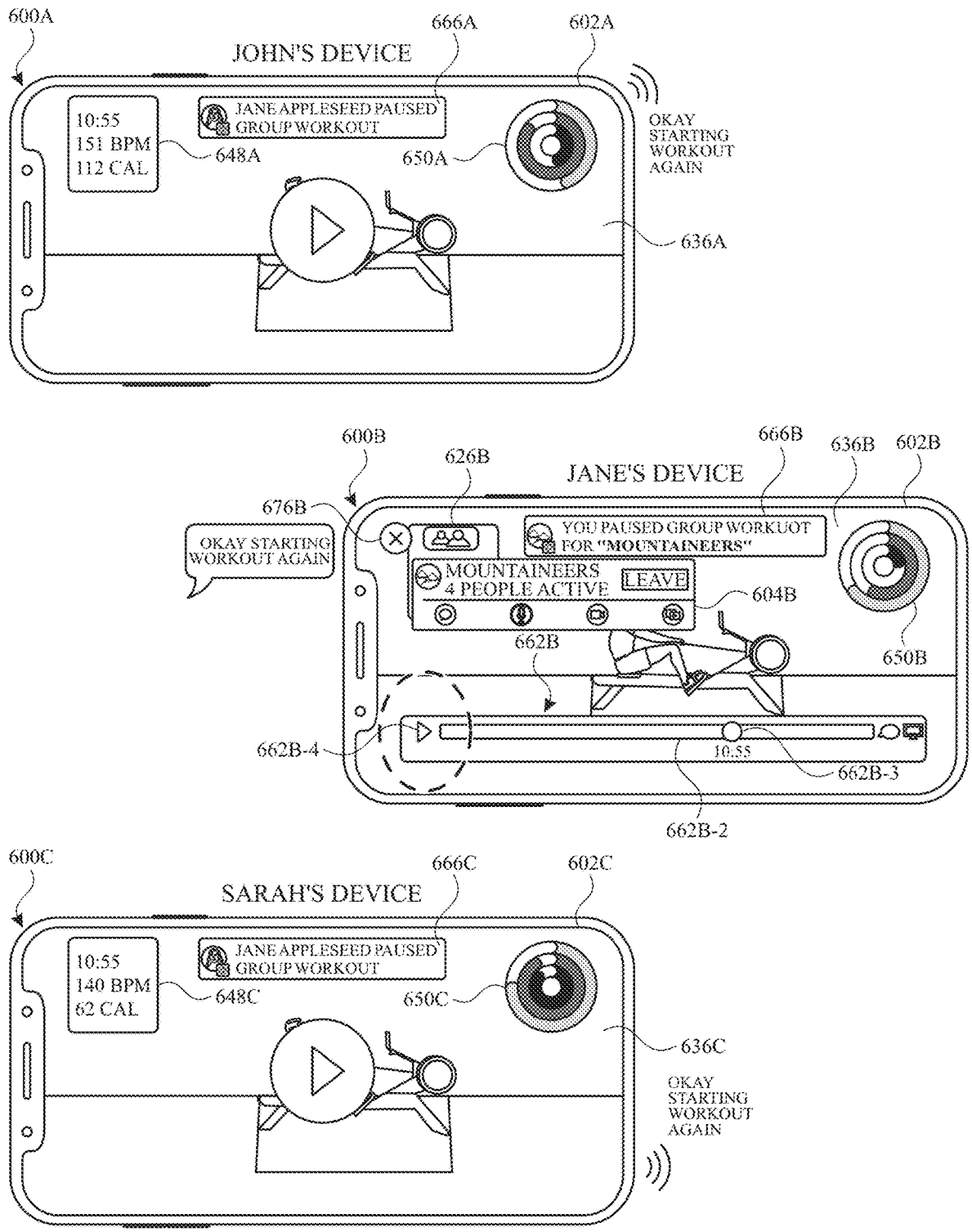

In FIG. 6K in response to detecting input 664, electronic device 600B pauses playback of video content corresponding to the group workout. As noted previously, video playback of group workout content is synchronized across devices 600A, 600B, 600C. Accordingly, user input 664 also causes pausing of playback of video content corresponding to the group workout on electronic devices 600A and 600C as well. For example, in some embodiments, electronic device 600B transmits (e.g., via the active communication session) an indication to electronic devices 600A and 600C and/or causes to be transmitted to electronic devices 600A and 600C an indication that a pause input has been received at electronic device 600B, and electronic devices 600A and 600C pause playback of the video content in response to receiving the indication of the pause input received at electronic device 600B. Furthermore, in response to pause input 664 (e.g., in response to receiving an indication of pause input 664), electronic device 600A displays notification 666A, electronic device 600B displays notification 666B, and electronic device 600C displays notification 666C indicating that electronic device 600B has paused the group workout.

In FIG. 6K, in response to input 664, electronic device 600B replaces pause option 662B-1 with play option 662B-4. At FIG. 6K, electronic device 600B receives audio input from a user stating "Okay, starting the workout again," and transmits the audio input to electronic devices 600A and 600C via the active communication session. Electronic devices 600A and 600C output corresponding audio output.

Electronic device 600B also detects user input 668 (e.g., a tap input) corresponding to selection of play option 662B-4.

Figure 6L:
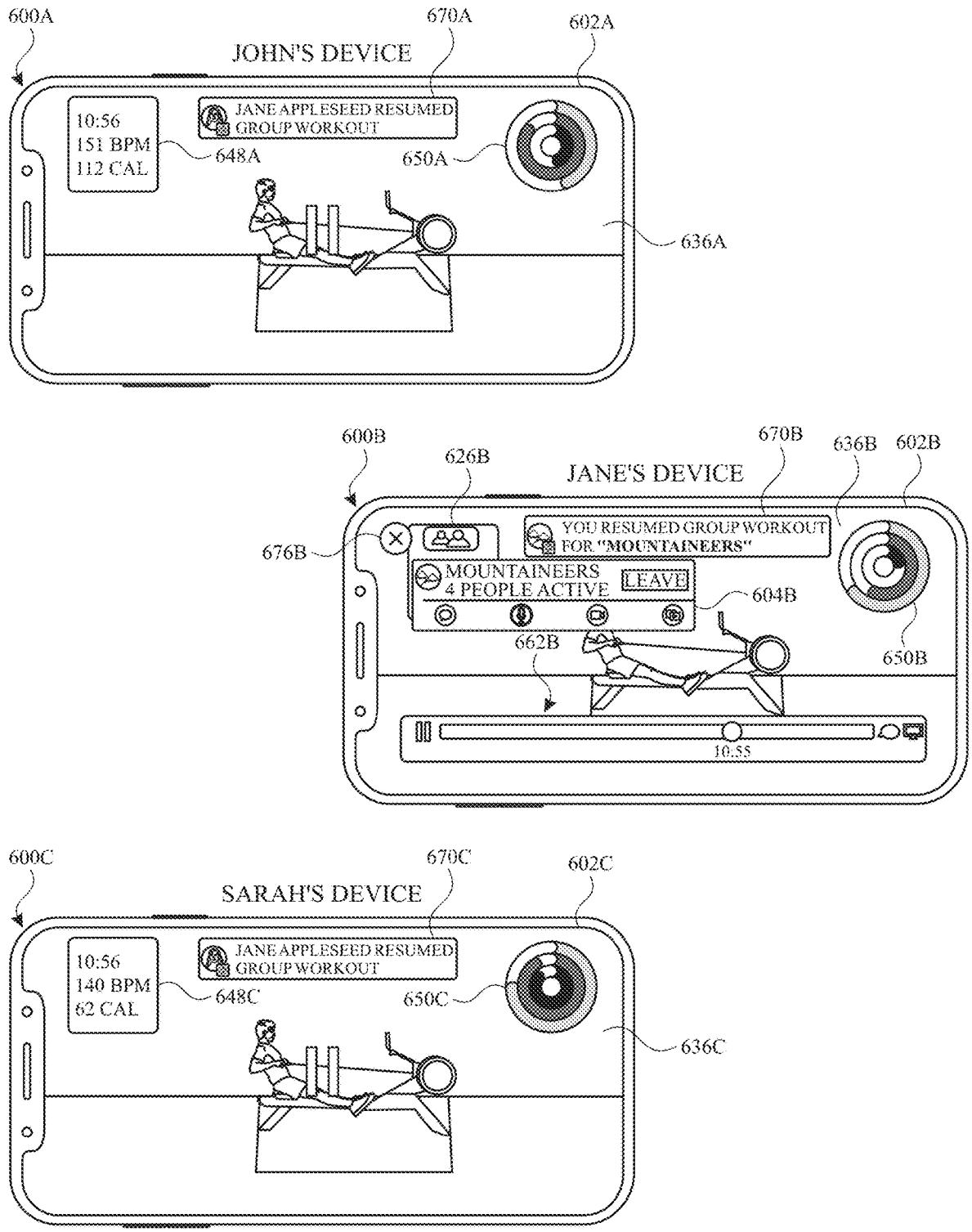

In FIG. 6L, in response to detecting user input 664, electronic device 600B resumes playing video content corresponding to the group workout. Electronic device 600B also transmits an indication to electronic devices 600A and 600C (e.g., via the active communication session) and/or causes an indication to be transmitted to electronic devices 600A, 600C that electronic device 600B has detected a user input corresponding to a request to resume playback of the group workout. In response to receiving this indication, electronic devices 600A and 600C also resume playback of video content corresponding to the group workout, and display notifications 670A, 670C indicating that electronic device 600B has resumed playback of the group workout.

Figure 6M:
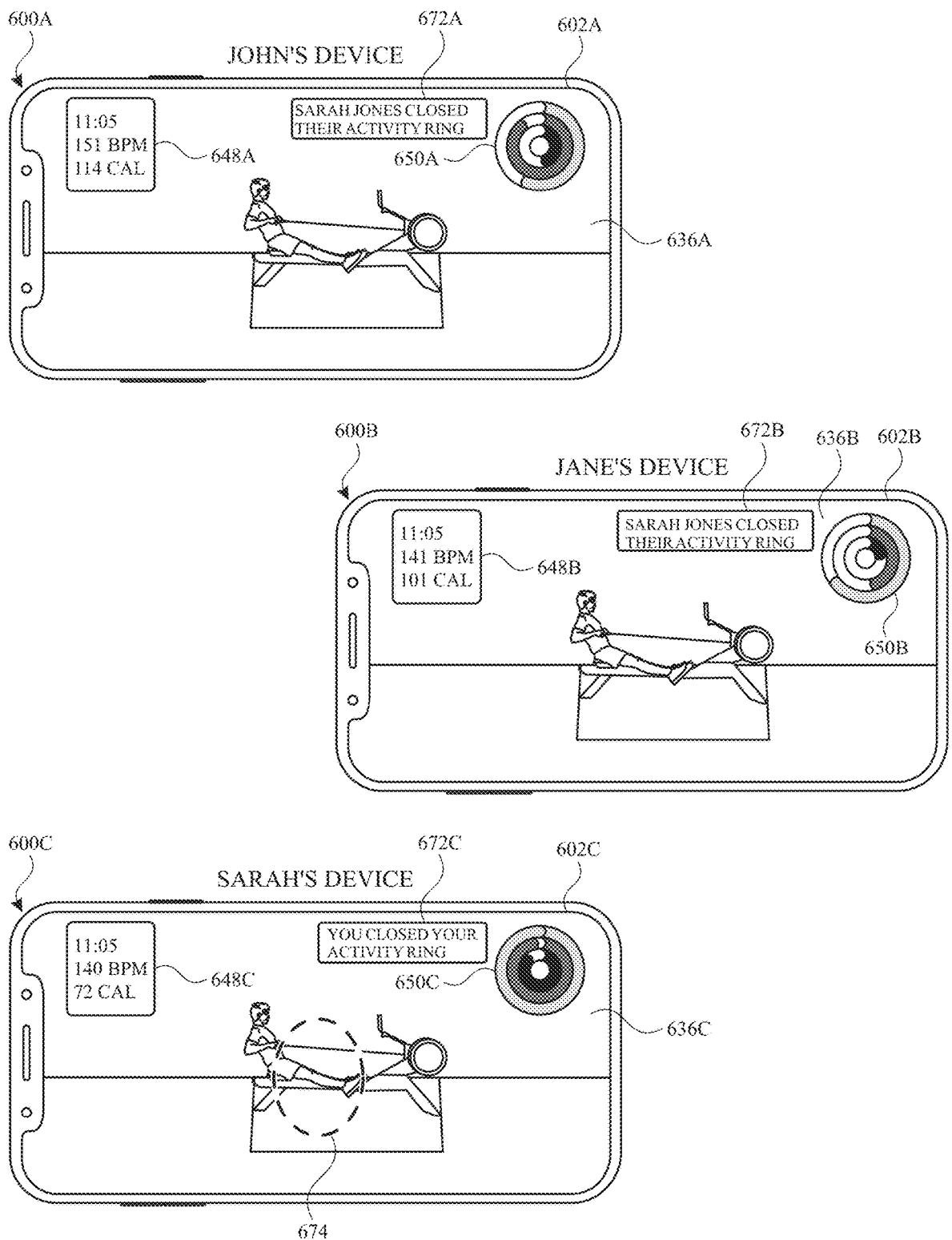

In FIG. 6M, the group workout has progressed to the 11 minute 5 second mark. In FIG. 6M, electronic device 600C determines and/or detects that the user corresponding to electronic device 600C (e.g., "Sarah") has accomplished a physical activity goal (e.g., has accomplished their daily activity goal), as indicated by the closed outermost circle in daily physical activity metrics 650C. In response to this determination, electronic device 600C displays fitness notification 672C. Furthermore, electronic device 600C transmits (e.g., via the active communication session) and/or causes to be transmitted an indication to electronic devices 600A and 600B that Sarah has accomplished the physical activity goal. In response to receiving this indication, electronic devices 600A and 600B display fitness notifications 672A, 672B indicating that Sarah has accomplished her physical activity goal.

It can be seen in FIG. 6M, as well as earlier FIGS. 6H and 6K, that notifications pertaining to the fitness application (e.g., notifications generated by the fitness application) (e.g., FIG. 6M), are displayed in a first display region (e.g., an upper right hand corner of the display region), while notifications pertaining to the communication session (e.g., notifications generated by a communication application) (e.g., FIGS. 6H and 6K), are displayed in a second, different display region (e.g., an upper center region). In some embodiments, fitness application notifications include notifications pertaining to users achieving one or more physical activity goals and/or one or more physical activity achievements by users during the group workout, while active communication session notifications include notifications pertaining to one or more users joining and/or leaving the group workout, one or more users joining and/or leaving the communication session, and/or one or more users pausing and/or resuming playing video content of the group workout.

At FIG. 6M, electronic device 600C detects user input 674 (e.g., a tap input).

Figure 6N:
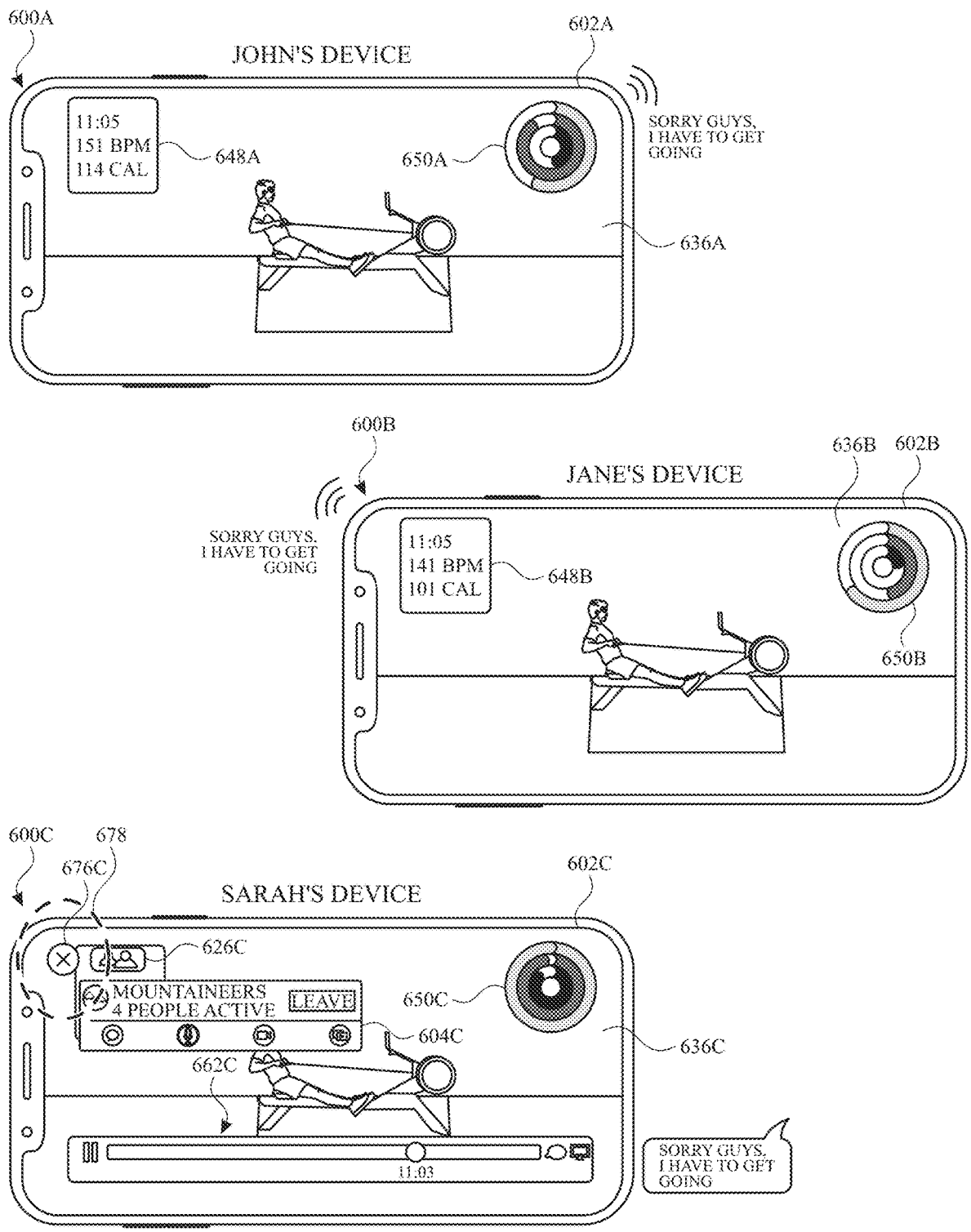

In FIG. 6N, in response to detecting user input 674, electronic device 600C displays playback controls 662C, active communication session indication 626C, communication session overlay 604C, and exit option 676C. Exit option 676C is selectable by a user to leave the group workout, and cease displaying video content corresponding to the group workout (e.g., cease displaying workout user interface 636C). In FIG. 6N, electronic device 600C detects user input 678 (e.g., a tap input) corresponding to selection of exit option 676C.

Figure 6O:
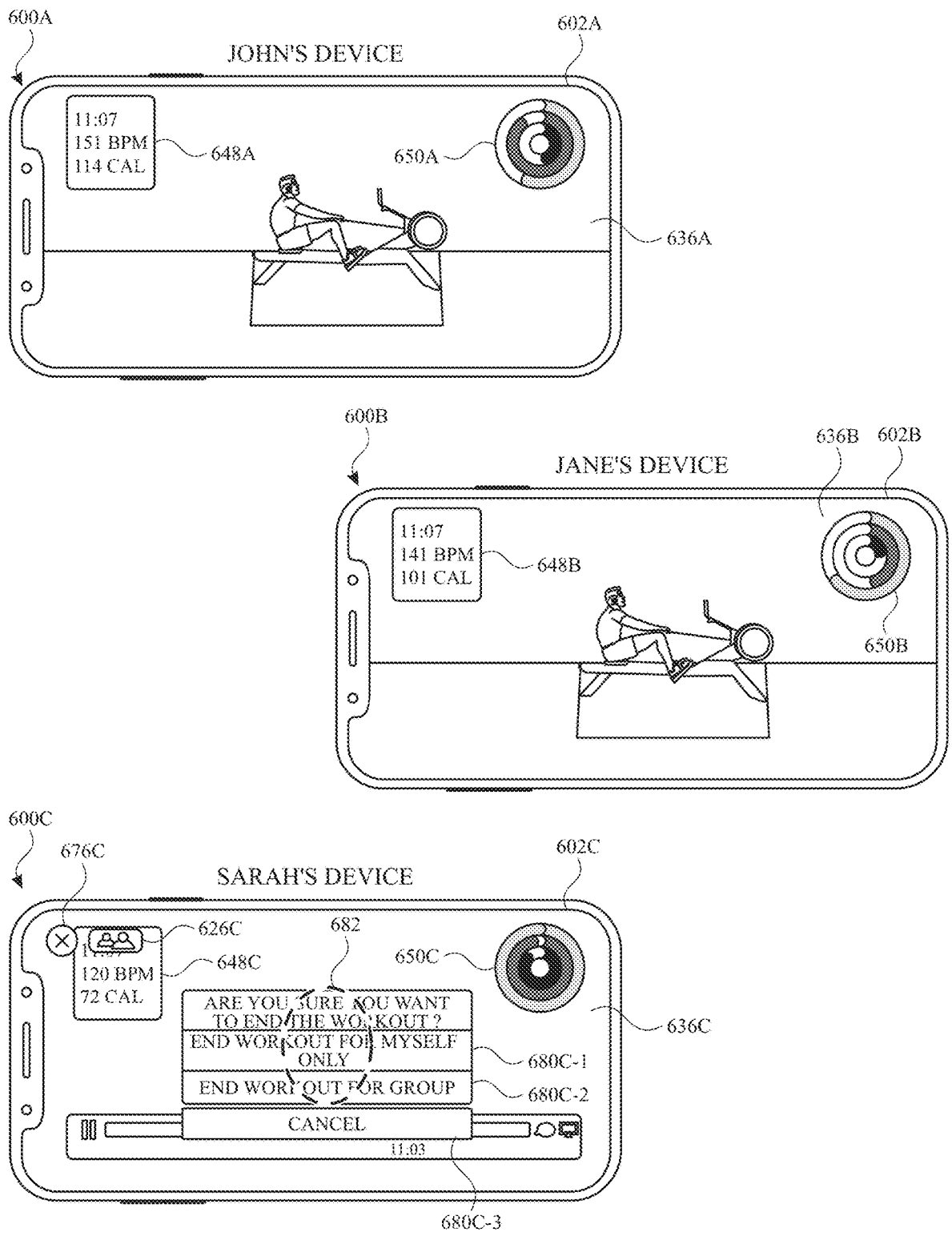

In FIG. 6O, in response to detecting user input 678, electronic device 600C displays options 680C-1, 680C-2, and 680C-3. Option 680C-1 is selectable by a user to end the group workout for that user and that device only (e.g., only device 600C). Option 680C-2 is selectable by a user to end the group workout for all users participating in the group workout (e.g., electronic devices 600A, 600B, and 600C). Option 680C-3 is selectable to cease displaying options 680C-1, 680C-2, 680C-3, and return to the group workout. In FIG. 6O, electronic device 600C detects user input 682 (e.g., a tap input) corresponding to selection of option 680C-1.

Figure 6P:
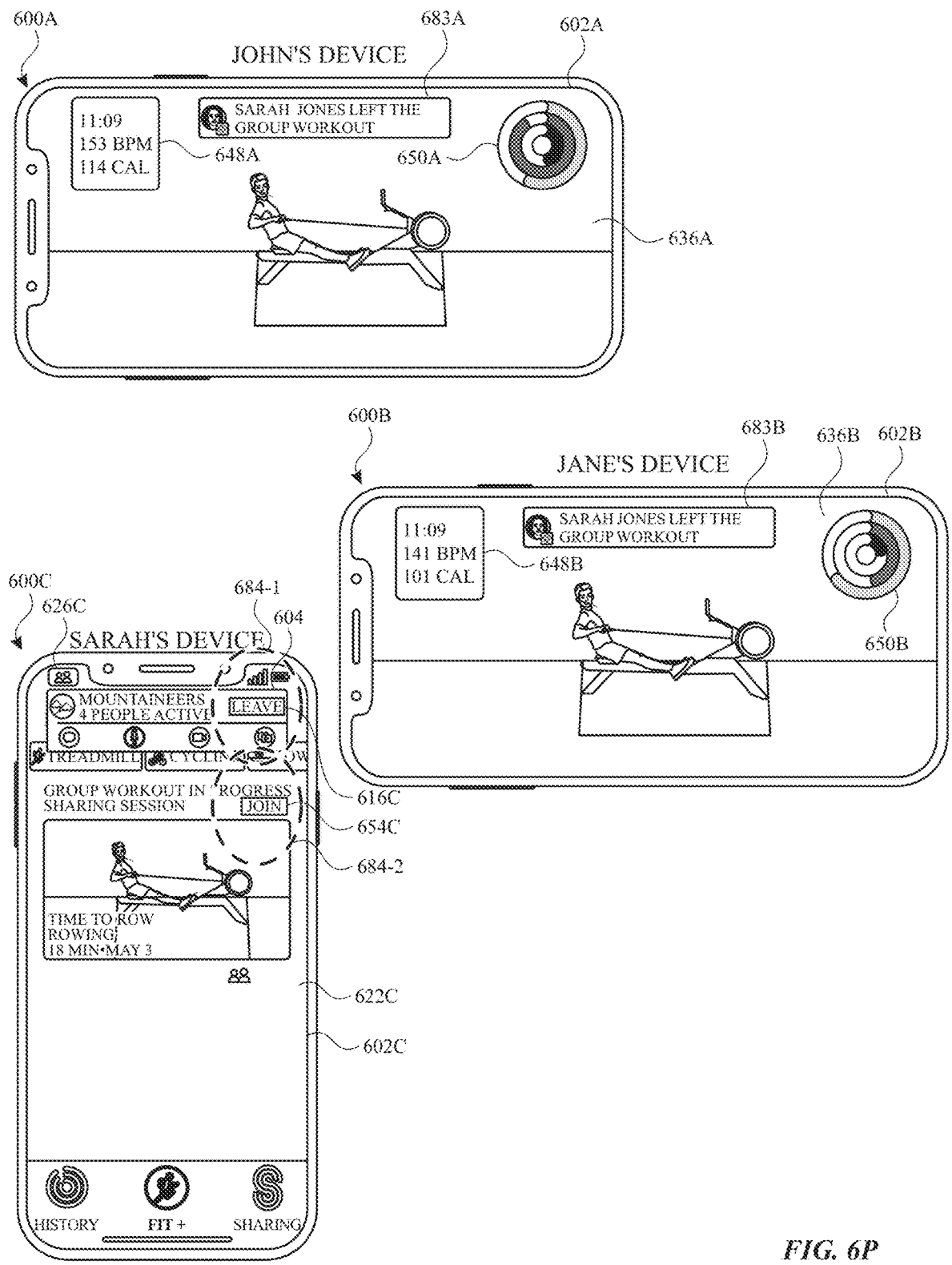

In FIG. 6P, in response to detecting user input 682, electronic device 600C ceases display of workout user interface 636C, and displays workout suggestion user interface 622C overlaid by communication session overlay 604C. Additionally, in response to user input 682, electronic device 600C transmits an indication to electronic devices 600A and 600B (e.g., via the communication session) and/or causes an indication to be transmitted to electronic devices 600A and 600B indicating that electronic device 600C has left the group workout. In response to receiving this indication, electronic devices 600A and 600B display notifications 683A, 683B, respectively, indicating that electronic device 600C has left the group workout.

As discussed above, communication session overlay 604C includes leave option 616C that is selectable to cause electronic device 600C to leave the communication session (e.g., disconnect from the communication session). Workout suggestion user interface 622C also includes join option 654C that is selectable to re-join the group workout. At FIG. 6P, electronic device 600C detects user input 684-1 corresponding to selection of the leave option 616C and user input 684-2 corresponding to selection of join option 654C.

FIG. 6P-1 depicts an example scenario in which, in response to detecting user input 684-2, electronic device 600C re-displays workout user interface 636C. As discussed above, workout content displayed in workout user interface 636C is synchronized with workout content displayed in workout user interfaces 636A, 636B on electronic device 600A and 600B, respectively. Accordingly, in response to detecting user input 684-2, electronic device 600C re-joins the group workout at the 11 minute and 11 second mark.

Alternatively, FIG. 6Q depicts an example scenario in which, in response to detecting user input 684-1 in FIG. 6P (e.g., rather than detecting user input 684-2, as was described in FIG. 6P-1), electronic device 600C has left (e.g., disconnected from) the communication session. Additionally, in response to user input 684-1 and prior to leaving the communication session, electronic device 600C transmits (e.g., via the communication session) to electronic devices 600A and 600B and/or causes to be transmitted to electronic devices 600A and 600B an indication that electronic device 600C has left (e.g., is leaving) the communication session. In response to receiving this indication, electronic devices 600A and 600B display notifications 685A, 685B indicating that electronic device 600C has left the communication session.

Figure 6R:
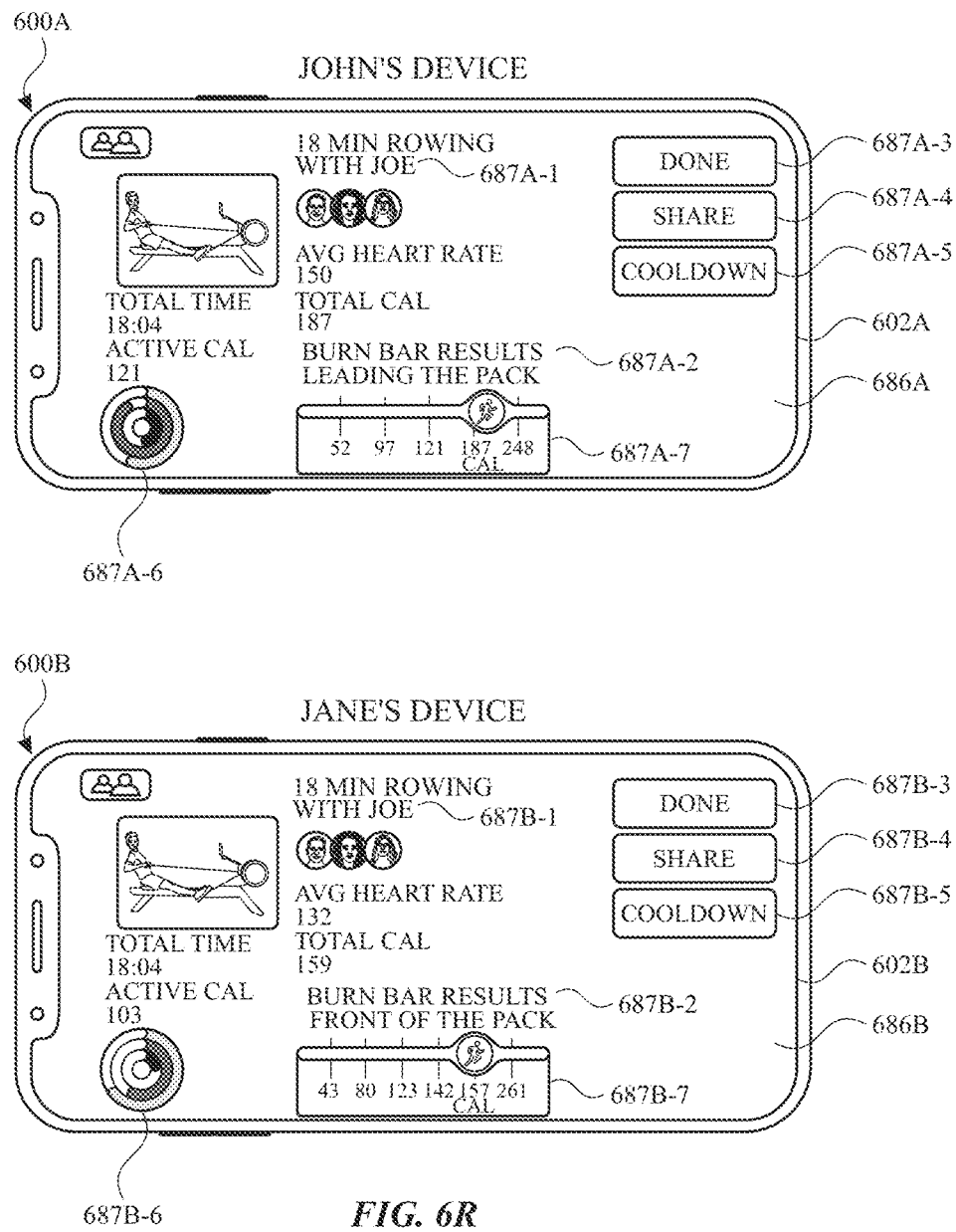

In FIG. 6R, the group workout has completed (e.g., the video content corresponding to the group workout has played to completion and/or a user has ended the group workout for all users). In response to detecting that the group workout has completed, electronic device 600A displays workout summary user interface 686A. Workout summary user interface 686A includes workout physical activity metrics 687A-2 for the user corresponding to electronic device 600A ("John"), including a workout performance bar 687A-7 indicative of John's performance relative to other users that performed the same workout. Workout summary user interface 686A also includes daily physical activity metrics 687A-6 for John, as discussed above. Workout summary user interface 686A also includes an indication 687A-1 of users that participated in the group workout session. In the example scenario depicted, the indication 687A-1 includes representations of John, Jane, and Sarah. Workout summary user interface 686A also includes done option 687A-3, that is selectable to close (e.g., cease display of) workout summary user interface 686A, share option 687A-4 that is selectable to share workout summary information with one or more other users, and cooldown option 687A-5 that is selectable to initiate playback of a cooldown workout. In some embodiments, the cooldown workout is a shared workout (e.g., shared via the communication session). In some embodiments, the cooldown workout is not shared, even if device 600A remains in the communication session.

Similar to electronic device 600A, electronic device 600B displays workout summary user interface 686B. Workout summary user interface 686B is substantially identical to workout summary user interface 686A, except that workout summary user interface 686B includes workout physical activity metrics 687B-2, workout performance bar 687B-7, and daily physical activity metrics 687B-6 that correspond to the user associated with electronic device 600B ("Jane").

Figure 6S:
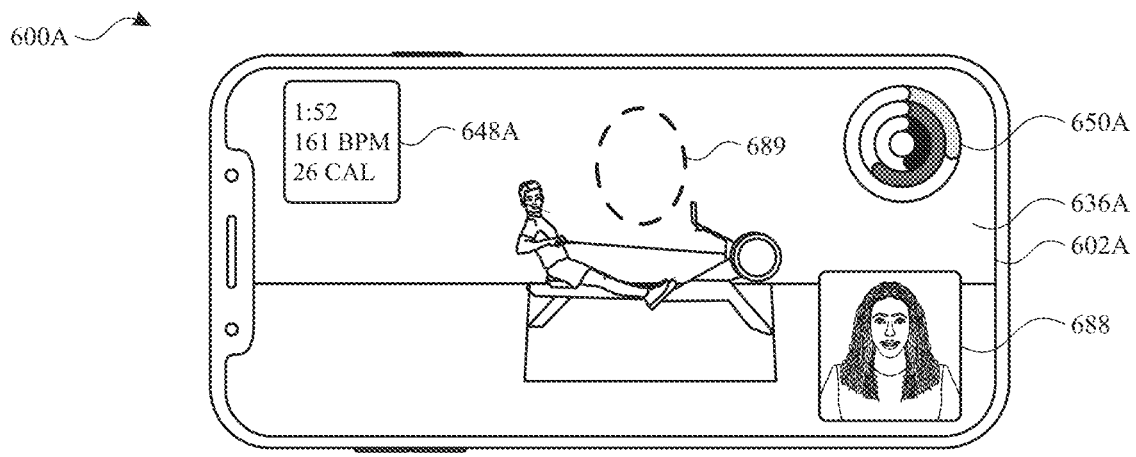

FIG. 6S depicts an example scenario in which electronic device 600A is participating in video communication with another electronic device within the communication session (e.g., electronic device 600A is participating in video communication with electronic device 600B within the communication session). In FIG. 6S, while displaying workout user interface 636A, electronic device 600A displays video communication object 688 in the corner of the display overlaid on workout user interface 636A. In the example scenario discussed above with reference to FIGS. 6A-6R, various examples were demonstrated in which audio communication via the communication session was enabled and audio communications were transmitted between electronic devices while electronic devices participated in (e.g., displayed) the group workout. Similarly, in the example scenario shown in FIG. 6S, electronic devices can maintain video communication with one another (e.g., audio-visual communication, video and audio communication) via the communication session while the group workout takes place. At FIG. 6S, electronic device 600A detects user input 689 (e.g., a tap input).

Figure 6T:
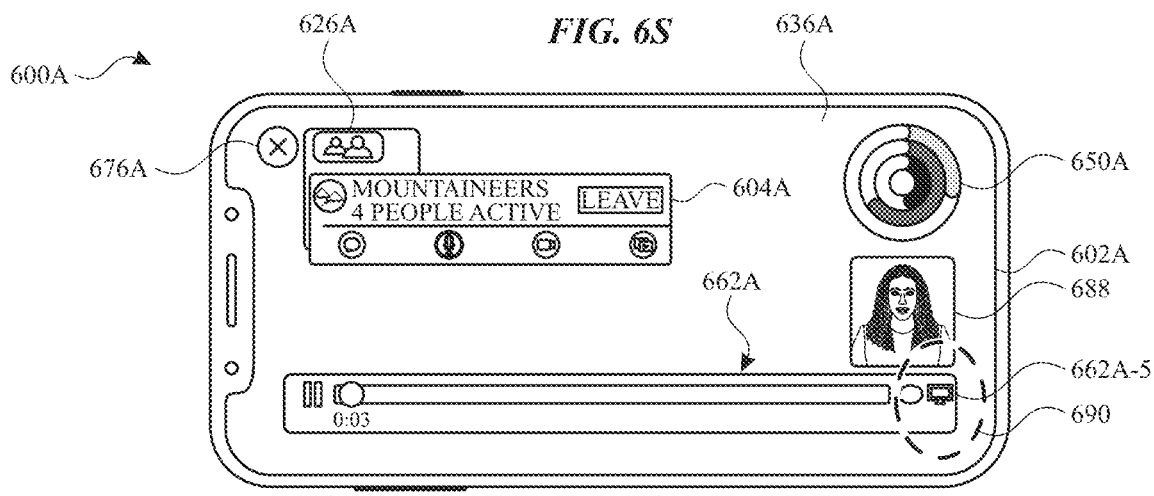

In FIG. 6T, in response to detecting user input 689, electronic device 600A displays communication session overlay 604A, exit option 676A, active communication session indication 626A, and playback controls 662A. The playback controls 662A include display selection option 662A-5 that is selectable to initiate a process to display video content on a different display (e.g., a display different from display 602A). At FIG. 6T, electronic device 600A detects user input 690 corresponding to selection of display selection option 662A-5.

Figure 6U:
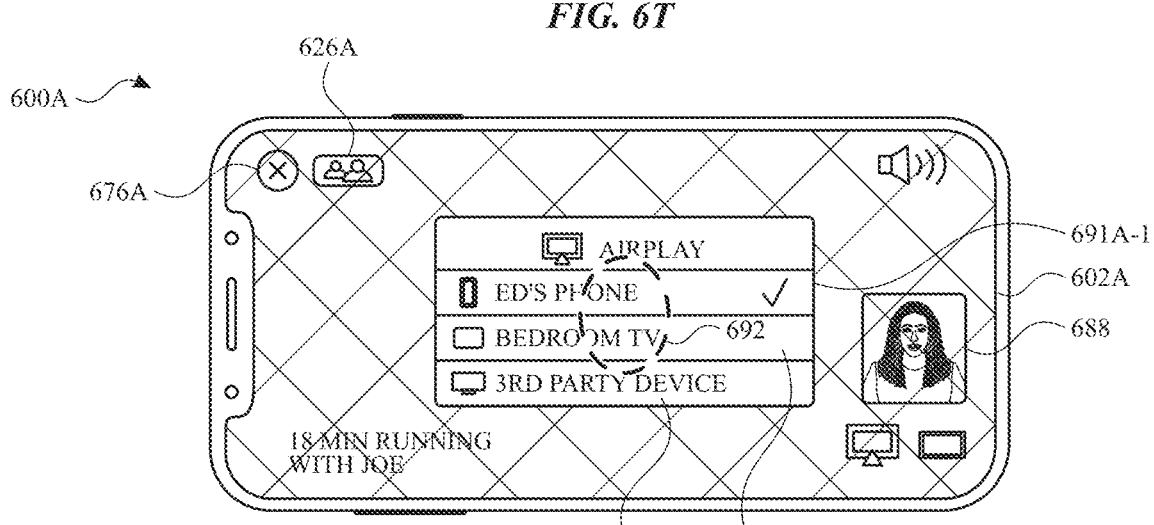

In FIG. 6U, in response to detecting user input 690, electronic device 600A displays options 691A-1, 691A-2, and 691A-3 corresponding to three different display devices. Option 691A-1 corresponds to display 602A, option 691A-2 corresponds to a television display device, and option 691A-3 corresponds to a third display device. At FIG. 6U, electronic device 600A detects user input 692 corresponding to selection of option 691A-2.

Figure 6V:
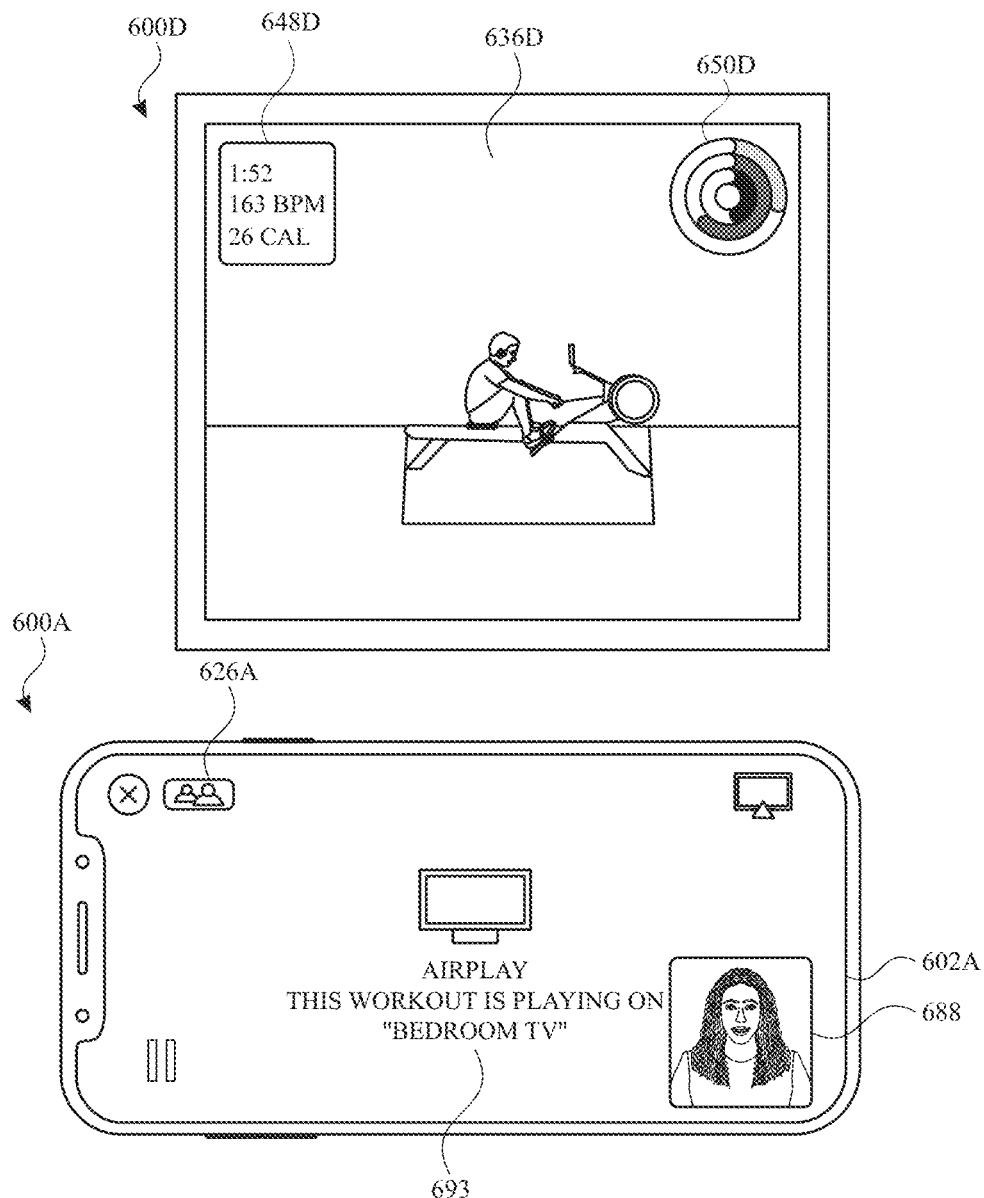

In FIG. 6V, in response to detecting user input 692, electronic device 600A causes television display device 600D to display workout user interface 636D. Additionally, in response to detecting user input 692, electronic device 600A displays user interface 693 indicating that workout video content (e.g., workout user interface 636D) is being displayed on a different display device. In FIG. 6V, while workout user interface 636D is displayed on television display device 600D, video communication object 688 continues to be displayed on device 600A via display 602A. In some embodiments, display components pertaining to the fitness application (e.g., display components generated by the fitness application) (e.g., workout user interface 636D) are displayed via television display device 600D, while display components pertaining to the communication session (e.g., display components generated by the communication application) (e.g., video communication object 688) are displayed via display 602A on electronic device 600A.

Figure 6W:
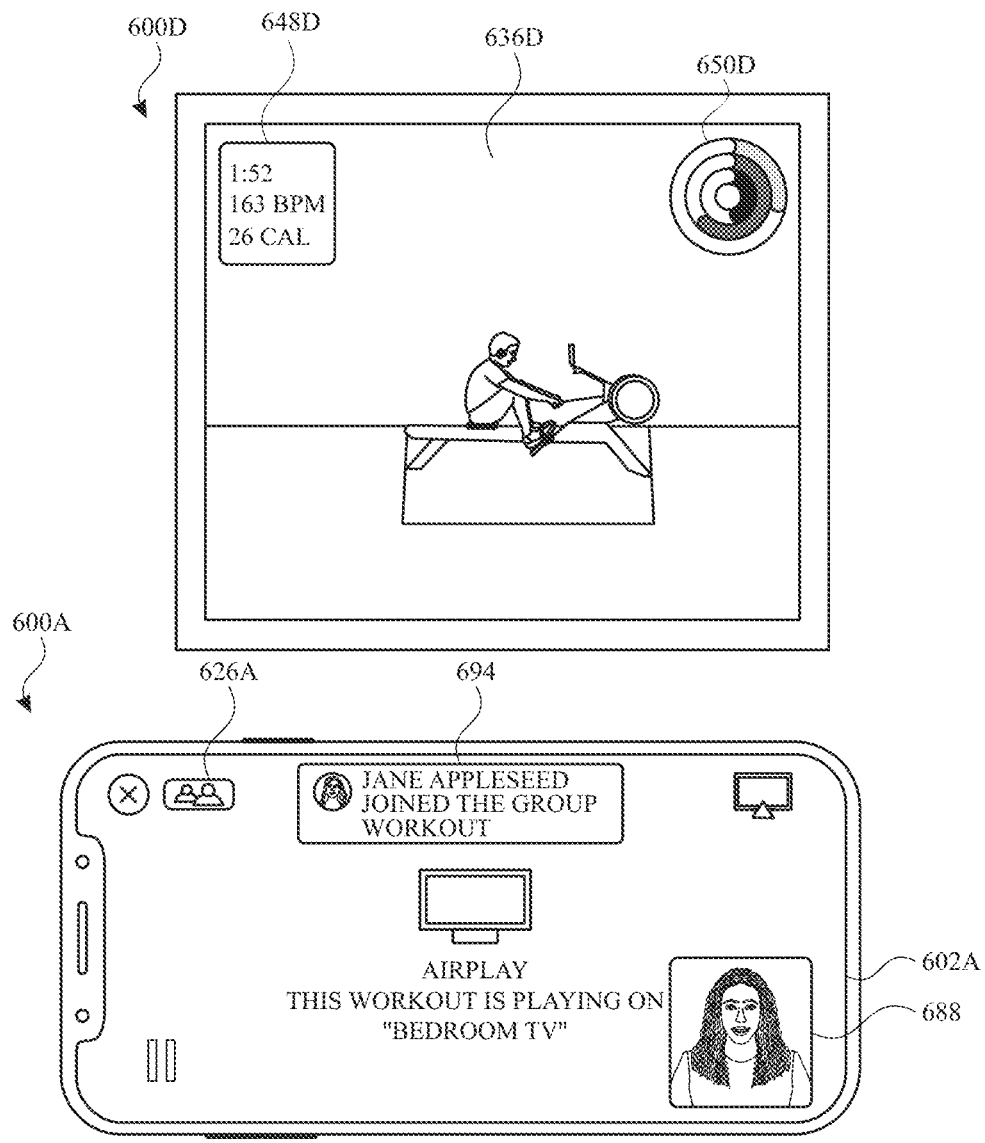

In FIG. 6W, electronic device 600A receives an indication that another electronic device associated with a user Jane Appleseed (e.g., electronic device 600B) has joined the group workout. Based on a determination that the indication pertains to the communication session (e.g., an indication that a user has joined the group workout via the communication session), electronic device 600A displays notification 694 indicating that Jane Appleseed has joined the group workout.

In FIG. 6X, electronic device 600A receives an indication that a user participating in the group workout has achieved a physical activity goal. In response to receiving this indication, and based on a determination that the indication pertains to the fitness application, electronic device 600A causes television display device 600D to display notification 695 indicating that Jane Appleseed has achieved a physical activity goal.

FIG. 7A is a flow diagram illustrating a method for displaying and sharing group workout content using a computer system in accordance with some embodiments. Method 700 is performed at a computer system (e.g., 100, 300, 500) that is in communication with a display generation component and one or more input devices. Some operations in method 700 are, optionally, combined, the orders of some operations are, optionally, changed, and some operations are, optionally, omitted.

As described below, method 700 provides an intuitive way for displaying and sharing group workout content. The method reduces the cognitive burden on a user for displaying and sharing group workout content, thereby creating a more efficient human-machine interface. For battery-operated computing devices, enabling a user to display and share group workout content faster and more efficiently conserves power and increases the time between battery charges.

A computer system (e.g., a smart phone, a smart watch, a tablet, a digital media player, a computer set top entertainment box; a smart TV; a computer system controlling an external display) (e.g., 600A, 600B, 600C) that is in communication with a display generation component (e.g., 602A, 602B, 602C) (e.g., a display controller; a touch-sensitive display system; and/or a display (e.g., integrated and/or connected)) and one or more input devices (e.g., a touch-sensitive surface (e.g., a touch-sensitive display); a mouse; a keyboard; and/or a remote control) displays (702), via the display generation component, a user interface (e.g., a fitness application workout user interface) (e.g., 622A) including a first user interface object (e.g., 624A) corresponding to a first workout.

The computer system detects (704), via the one or more input devices, a user input (e.g., a tap input and/or a non-tap input) (e.g., 628) corresponding to selection of the first user interface object.

In response to detecting the user input (706), the computer system initiates (708) a workout session (in some embodiments, initiating the workout session includes initiating a user physical activity tracking function) corresponding to the first workout, including initiating a process for displaying, via the display generation component, content (e.g., video content, instructions, tutorials) associated with the first workout (e.g., initiate playback of video content associated with the workout) (e.g., video content demonstrating the workout). In some embodiments, initiating the workout session also includes initiating recording of one or more physical activity metrics (e.g., heartrate and/or calories burned) for the workout session.

In accordance with a determination that the computer system is engaged in a communication session of a first type with one or more external computer systems including a first external computer system (e.g., 600B, 600C) (710) (e.g., is engaged in the communication session of the first type at the time the user input is detected), the computer system causes display (712) of a selectable user interface object (e.g., 640B, 642B, 640C, 642C) at the first external computer system (e.g., 600B, 600C) (e.g., causes display of a selectable user interface object at the one or more external computer systems), wherein the selectable user interface object is selectable to display the content associated with the workout at the first external computer system (e.g., selectable to initiate playback of the video content associated with the workout at the first external computer system) (e.g., a selectable user interface object that is selectable to cause the first external computer system to join the workout session). In some embodiments, display of the video content associated with the workout at the first external computer system is synced with display of the video content associated with the workout at the computer system. In some embodiments, the communication session of the first type includes audio communication, video communication, and/or text-based communication. In some embodiments, the communication session is a synchronized media and communication session. In some embodiments, the communication session of the first type enables the computer system to output respective content (e.g., synchronized content (e.g., audio and/or video data for which output is synchronized at the computer system and an external computer system (e.g., the one or more external computer systems)) and/or screen-share content (e.g., image data generated by a device (e.g., a computer system in the communication session of the first type) that provides a real-time representation of an image or video content that is currently displayed at the device)) while the respective content is being output by the first external computer system. In some embodiments, during the communication session of the first type, respective content is concurrently output at both the computer system and the one or more external computer systems. In some embodiments, the respective content is screen-share content from the computer system (e.g., content displayed on the display of the computer system) that is transmitted to the one or more external computer systems so that the computer system and the one or more external computer systems are concurrently outputting the screen-share content from the computer system. In some embodiments, the respective content is screen-share content from the first external computer system (e.g., content displayed on the display of the first external computer system) that is transmitted to the computer system so that the computer system and the one or more external computer systems, including the first external computer system, are concurrently outputting the screen-share content from the first external computer system. In some embodiments, the respective content is synchronized content that is output at the computer system and the one or more external computer systems. In some embodiments, the computer system and the one or more external computer systems each separately access the respective content (e.g., a video; a movie; a TV show; a song) from a remote server and are synchronized in their respective output of the respective content such that the content is output (e.g., via an application local to the respective computer system) at the computer system and the one or more external computer systems while each computer system separately accesses the respective content from the remote server(s). In some embodiments, the computer system and one or more external computer systems separately access the respective content (e.g., synchronized content) in response to a selection that is received at the computer system or at one of the one or more external computer systems for requesting output of the respective content. Performing multiple operations in response to a single user input, including displaying workout content at a computer system in response to the user input, and also automatically causing display of a selectable user interface object at an external computer system that is selectable to display content associated with the workout at the external computer system in response to the same user input, enables a user to quickly share workout content with an external computer system, thereby reducing the number of inputs needed for sharing workout content with an external computer system. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In accordance with a determination that the computer system is not engaged in the communication session of the first type (714) (e.g., is not engaged in the communication of the first type at the time the user input is detected), the computer system forgoes causing (716) the first external computer system to display the selectable user interface object. In some embodiments, the computer system forgoes causing any external computer system to display the selectable user interface object.

In some embodiments, while displaying the content associated with the first workout and while the computer system is engaged in the communication session of the first type with one or more external computer systems, the computer system (e.g., 600A) is configured to communicate with (e.g., transmit to or receive from) the one or more external computer systems (e.g., 600B, 600C) via a communication modality of the communication session of the first type selected from the group consisting of: audio communication (e.g., speech audio), video communication (e.g., using one or more cameras in communication with the computer system), text communication, screen content sharing communication, and a combination thereof (e.g., FIGS. 6E, 6F, 6I, 6J, 6N (participating in audio communication while displaying the content associated with the first workout), and/or FIG. 6W (participating in video communication while displaying the content associated with the first workout)). Configuring the computer system to communicate with one or more external computer systems via a communication modality of the communication session of the first type while displaying the content associated with the first workout enables a user to quickly and easily communicate with other users while viewing workout content, thereby reducing the number of inputs needed for communicating with other users while viewing workout content. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content associated with the first workout and while the computer system is engaged in the communication session of the first type with one or more external computer systems including the first external computer system (in some embodiments, and while the first external computer system is displaying the content associated with the first workout), the computer system receives (e.g., from an external device; from an application executing on the computer system) notification data. In response to receiving the notification data, in accordance with a determination that the notification data is associated with the communication session of the first type (e.g., the notification data is received from the one or more external computer systems; the notification relates to a communication from one of the participants), the computer system displays a first notification (e.g., 646A, 658A, 658B, 666A, 666C, 670A, 670C, 683A, 683B, 685A, 685B) (e.g., a communication from the one or more external computer systems) at a first location of the display generation component (e.g., FIG. 6E, FIG. 6H, FIG. 6K, FIG. 6L, FIG. 6P, FIG. 6Q); and in accordance with a determination that the notification data is associated with the first workout (e.g., is associated with a workout application managing the first workout), the computer system displays a second notification (e.g., 672A, 672B) (e.g., a workout-related notification) at a second location of the display generation component (e.g., FIG. 6M), different than the first location. In some embodiments, the first and second locations are non-overlapping. Displaying notifications associated with the communication session of the first type at a first display location, and displaying notifications associated with the first workout at a second display location, provides the user with feedback about the current state of the device (e.g., whether a particular notification pertains to the communication session of the first type or to the first workout). These notifications also quickly and easily provide a user with information about other users' actions either in a communication session or in the workout session. By providing different types of notifications in different areas of a screen, an electronic device can enhance glanceability for users and allow them to understand the current state of other user devices without additional user input. Providing improved feedback to the user further enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first notification indicates that a second external computer system is, via the communication session of the first type (e.g., via one or more communication protocols of the communication session of the first type), beginning to display the content associated with the first workout (e.g., 646A, 658A, 658B) or ceasing to display the content associated with the first workout (e.g., 683A, 683B). Displaying a notification that a second external computer system is beginning to display the content associated with the first workout or ceasing to display the content associated with the first workout provides the user with feedback about the current state of the device (e.g., that the device has detected and/or received information about the second external computer system beginning to display and/or ceasing to display the content associated with the first workout). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first notification (e.g., a communication session status notification) indicates that a third external computer system is joining (in some embodiments, has joined) the communication session of the first type or leaving (in some embodiments, has left) the communication session of the first type (e.g., 685A, 685B). Displaying a notification that a third external computer system is joining the communication session of the first type or leaving the communication session of the first type provides the user with feedback about the current state of the device (e.g., that the device has detected and/or received information about the third external computer system joining and/or leaving the communication session of the first type). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second notification is a notification that includes first information related to the first workout for the computer system or for one or more external computer systems that are in the communication session of the first type and that are displaying the content associated with the first workout (e.g., notifications 672A, 672B, 672C in FIG. 6M). In some embodiments, the second notification can be a workout-related notification from any user in the communication session of the first type that is participating in the first workout). Displaying notifications pertaining to the first workout for the computer system or for one or more external computer systems provides the user with feedback about the current state of the device (e.g., that the device has detected and/or received first information related to the first workout). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first information is an indication that a user of a fourth external computer system that is in the communication session of the first type and that is displaying the content associated with the first workout has achieved a predetermined physical activity goal (e.g., met a calorie target, met activity intensity level target) or has achieved a change in status relative to one or more other participants in the first workout (e.g., the user has achieved a level of physical activity that places the user within a predetermined segment of participants in the first workout) (e.g., notifications 672A, 672B, 672C in FIG. 6M). Displaying a notification indicating that a user of the fourth external computer system has achieved a predetermined physical activity goal or has achieved a change in status relative to one or more other participants in the first workout provides the user with feedback about the current state of the device (e.g., that the device has detected and/or received information indicating that the user of the fourth external computer system has achieved a predetermined physical activity goal or has achieved a change in status relative to one or more other participants in the first workout). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content associated with the first workout and while the computer system is engaged in the communication session of the first type with one or more external computer systems, the computer system receives a user input (e.g., 678) corresponding to a request to initiate a process for ending the workout session corresponding to the first workout. In response to receiving the user input corresponding to the request to initiate the process for ending the workout session corresponding to the first workout, the computer system displays: a first end option (e.g., 680C-1) that, when selected, causes the computer system to cease displaying the content associated with the first workout (e.g., user interface 636C) (e.g., end the workout session associated with the first workout), without causing at least one external computer system that is in the communication session of the first type and that is displaying the content associated with the first workout to cease displaying (in some embodiments, and to end a workout at the external computer system that is associated with the first workout) the content associated with the first workout; and a second end option (e.g., 680C-2) that, when selected, causes the computer system to cease displaying the content associated with the first workout and causes at least one external computer system that is in the communication session of the first type and that is displaying the content associated with the first workout to cease displaying (in some embodiments, and to end a workout at the external computer system that is associated with the first workout) the content associated with the first workout. Concurrently displaying a first end option that is selectable to cause the computer system to cease displaying the content associated with the first workout and a second end option that is selectable to cause multiple computer systems to cease displaying the content associated with the first workout provides the user with the ability to end the workout for only themselves, or to end the workout for multiple computer systems. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system receives a user input (e.g., 682) corresponding to the first end option (e.g., 680C-1). In response to receiving the user input corresponding to the first end option, the computer system ceases to display, via the display generation component in communication with the computer system, the content associated with the first workout (e.g., end the workout session associated with the first workout), wherein the content associated with the first workout continues to be displayed by a display generation component that is in communication with at least one external computer system in the communication session of the first type after the display generation component in communication with the computer system ceases to display the content associated with the first workout (e.g., FIG. 6P, device 600C ceases to display the workout, while devices 600A and 600B continue to display the workout). In some embodiments, selection of the first end option causes only the computer system to cease displaying the content associated with the first workout, without causing any external computer system to cease displaying the content associated with the first workout. Concurrently displaying a first end option that is selectable to cause the computer system to cease displaying the content associated with the first workout and a second end option that is selectable to cause multiple computer systems to cease displaying the content associated with the first workout provides the user with the ability to end the workout for only themselves, or to end the workout for multiple computer systems. Providing additional control of the device enhances the operability of the device and makes the user-device interface more efficient (e.g., by helping the user to provide proper inputs and reducing user mistakes when operating/ interacting with the device) which, additionally, reduces power usage and improves battery life of the device by enabling the user to use the device more quickly and efficiently.

In some embodiments, the computer system receives a user input corresponding to the second end option (e.g., 680C-2). In response to receiving the user input corresponding to the second end option: the computer system ceases to display, via the display generation component in communication with the computer system, the content associated with the first workout (e.g., workout user interface 636C) (e.g., end the workout session associated with the first workout); and causes at least one external computer system (e.g., device 600A and/or 600B) in the communication session of the first type and displaying the content associated with the first workout to, via a display generation component that is in communication with the at least one external computer system, cease displaying (in some embodiments, and to end a workout at the external computer system that is associated with the first workout) the content associated with the first workout. Concurrently displaying a first end option that is selectable to cause the computer system to cease displaying the content associated with the first workout and a second end option that is selectable to cause multiple computer systems to cease displaying the content associated with the first workout provides the user with the ability to end the workout for only themselves, or to end the workout for multiple computer systems. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content associated with the first workout (e.g., device 600B in FIG. 6J) and while the computer system is engaged in the communication session of the first type with one or more external computer systems that includes a fifth external computer system (e.g., devices 600A and 600C in FIG. 6J) that is displaying the content associated with the first workout, the computer system receives a user input (e.g., 664) corresponding to a request pause the workout session corresponding to the first workout (e.g., pausing display of the content associated with the first workout session). In response to receiving the user input corresponding to the request to pause the workout session corresponding to the first workout: the computer system pauses the workout session corresponding to the first workout (e.g., pausing display of the content associated with the first workout at the display generation component (e.g., without ending the workout session)) (e.g., FIG. 6K); and causes the fifth external computer system (e.g., devices 600A, 600C) to pause display of the content associated with the first workout (e.g., FIG. 6K). In some embodiments, after pausing the workout, the computer system receives a user input corresponding to a request to resume the workout, and in response, resumes the workout at the computer system and at the fifth external computer system. Pausing display of the content associated with the workout on multiple computer systems in response to a user input on the computer system provides the user with the capability to pause the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content associated with the first workout and while the computer system is engaged in the communication session of the first type with one or more external computer systems including a sixth external computer system that is displaying the content associated with the first workout, the computer system receives a request from the sixth external computer system to end the workout session associated with the first workout and to cease displaying the content associated with the first workout (e.g., a request initiated by selection of an "end for all" option at the sixth external computer system) (e.g., if device 600C receives a selection of option 680C-2 in FIG. 6O, devices 600A and/or 600B receive a request from device 600C to end the workout session). In response to receiving the request from the sixth external computer system, the computer system ends the workout session on the computer system. In some embodiments, ending the workout session includes ceasing to display the workout session and/or ceasing to display the content associated with the first workout on the computer system. Ending the workout session automatically in response to a received request from the sixth external computer system provides a user with the capability to end the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content associated with the first workout and while the computer system is engaged in the communication session of the first type with one or more external computer systems including a seventh external computer system that is displaying the content associated with the first workout, the computer system receives a request from the seventh external computer system to pause displaying the content associated with the first workout (e.g., a request initiated by selection of an "pause" option at the seventh external computer system) (e.g., device 600B receives selection of pause option 662B-1 in FIG. 6J, and devices 600A and/or 600C receive a request from device 600B to pause displaying the content associated with the workout). In response to receiving the request from the seventh external computer system, the computer system pauses display of the content associated with the first workout on the computer system (e.g., FIG. 6K) (e.g., without ending the workout session). In some embodiments, after pausing display of the content, the computer system receives an indication that an external computer system in the communication session of the first type has resumed display of the content, and in response to that indication, the computer system resumes displaying of the content associated with the first workout. Pausing display of the content associated with the workout in response to a received request from the seventh external computer system provides a user with the capability to pause the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after completing the workout session associated with the first workout, the computer system displays, via the display generation component, a workout summary user interface (e.g., 686A, 686B) that includes: physical activity data (e.g., calories burned data; heart rate data) collected by the computer system for a user of the computer system (e.g., 687A-2, 687B-2); and an indication of one or more external computer systems (e.g., an indication of users of the external computer systems) that were in the communication session of the first type with the computer system and that participated in (e.g., displayed) the workout session associated with the first workout (e.g., that participated in the shared workout) (e.g., 687A-1, 687B-1). Displaying a workout summary user interface that includes physical activity data and an indication of one or more external computer systems that were in the communication session of the first type and displayed content associated with the first workout provides the user with feedback about the current state of the device (e.g., that the workout session has ended) as well as feedback about the state of the one or more external computer systems (e.g., which computer systems were in the communication session of the first type and displayed content associated with the first workout). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the workout summary user interface also includes: one or more indications that a user of an external computer system achieved a predetermined physical activity goal (e.g., met a calorie target, met activity intensity level target) (e.g., 687A-6, 687B-6) (e.g., an indication similar to notifications 672A, 672B, 672C). Displaying a workout summary user interface that includes one or more indications that a user of an external computer system achieved a predetermined physical activity goal provides the user with feedback about the current state of the device (e.g., that the computer system received and/or detected information that a user of an external computer system achieved a predetermined physical activity goal) as well as feedback about the state of the one or more external computer systems (e.g., that an external computer system received and/or detected that the user of the external computer system achieved the predetermined physical activity goal). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying, via the display generation component, the content associated with the first workout, the computer system receives a request (e.g., inputs 690, 692) to cause a second display generation component (e.g., 600D) (e.g., a smart television; a digital media player that is connected to a television or monitor) that is in communication with the computer system to display the content associated with the first workout. In response to the request to cause a second display generation component that is in communication with the computer system to display the content associated with the first workout, the computer system causes the second display generation component to display the content associated with the first workout (e.g., FIG. 6V). In some embodiments, the computer system also ceases to display the content via the display generation component). Causing a second display generation component to display content associated with the first workout in response to a request provides the user with the ability to display the content associated with the first workout on a second display generation component. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while causing display of the content associated with the first workout at the second display generation component, the computer system receives second notification data. In response to the second notification data: in accordance with a determination that the second notification data is associated with the communication session of the first type (e.g., the second notification data is received from the one or more external computer systems), the computer system displays a third notification (e.g., 694) (e.g., a communication from the one or more external computer systems) via the display generation component; and in accordance with a determination that the second notification data is associated with the first workout (e.g., is associated with a workout application managing the first workout), the computer system causes display of a fourth notification (e.g., 695) (e.g., a workout-related notification) at the second display generation component. In some embodiments, notifications are displayed at different displays depending on the type of notification. Displaying notifications associated with the communication session of the first type on the display generation component, and displaying notifications associated with the first workout at the second display generation component, provides the user with feedback about the current state of the device (e.g., whether a particular notification pertains to the communication session of the first type or to the first workout). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after completing the workout session associated with the first workout, the computer system causes the second display generation component to cease displaying the content associated with the first workout and displaying a workout summary user interface via the display generation component.

Note that details of the processes described above with respect to method 700 (e.g., FIG. 7A) are also applicable in an analogous manner to the methods described below. For example, methods 750, 900, and 1100 optionally include one or more of the characteristics of the various methods described above with reference to method 700. For example, the communication session of the first type recited in methods 700, 750, 900, and 1100 are, in some embodiments, the same communication session in all three methods. In another example, the workout initiated via method 700 can, in some embodiments, result in the indication of method 750. For brevity, these details are not repeated below.

FIG. 7B is a flow diagram illustrating a method for accessing and displaying group workout content using a computer system in accordance with some embodiments. Method 750 is performed at a computer system (e.g., 100, 300, 500) that is in communication with a display generation component and one or more input devices. Some operations in method 750 are, optionally, combined, the orders of some operations are, optionally, changed, and some operations are, optionally, omitted.

As described below, method 750 provides an intuitive way for accessing and displaying group workout content. The method reduces the cognitive burden on a user for accessing and displaying group workout content, thereby creating a more efficient human-machine interface. For battery-operated computing devices, enabling a user to access and display group workout content faster and more efficiently conserves power and increases the time between battery charges.

In some embodiments, a computer system (e.g., a smart phone, a smart watch, a tablet, a digital media player, a computer set top entertainment box; a smart TV; a computer system controlling an external display) that is in communication with a display generation component (e.g., a display controller; a touch-sensitive display system; and/or a display (e.g., integrated and/or connected)) and one or more input devices (e.g., a touch-sensitive surface (e.g., a touch-sensitive display); a mouse; a keyboard; and/or a remote control), while the computer system is participating in a communication session of a first type with one or more external computer systems including a first external computer system (752), receives (754) (e.g., via a communication protocol associated with the communication session of the first type) an indication that the first external computer system has initiated a shared workout session.

In some embodiments, the communication session is a synchronized media and communication session. In some embodiments, the communication session of the first type includes audio communication, video communication, and/ or text-based communication. In some embodiments, the communication session of the first type enables the computer system to output respective content (e.g., synchronized content (e.g., audio and/or video data for which output is synchronized at the computer system and an external computer system (e.g., the one or more external computer systems)) and/or screen-share content (e.g., image data generated by a device (e.g., a computer system in the communication session of the first type) that provides a real-time representation of an image or video content that is currently displayed at the device)) while the respective content is being output by the first external computer system. In some embodiments, during the communication session of the first type, respective content is concurrently output at both the computer system and the one or more external computer systems. In some embodiments, the respective content is screen-share content from the computer system (e.g., content displayed on the display of the computer system) that is transmitted to the one or more external computer systems so that the computer system and the one or more external computer systems are concurrently outputting the screen-share content from the computer system. In some embodiments, the respective content is screen-share content from the first external computer system (e.g., content displayed on the display of the first external computer system) that is transmitted to the computer system so that the computer system and the one or more external computer systems, including the first external computer system, are concurrently outputting the screen-share content from the first external computer system. In some embodiments, the respective content is synchronized content that is output at the computer system and the one or more external computer systems. In some embodiments, the computer system and the one or more external computer systems each separately access the respective content (e.g., a video; a movie; a TV show; a song) from a remote server and are synchronized in their respective output of the respective content such that the content is output (e.g., via an application local to the respective computer system) at the computer system and the one or more external computer systems while each computer system separately accesses the respective content from the remote server(s). In some embodiments, the computer system and one or more external computer systems separately access the respective content (e.g., synchronized content) in response to a selection that is received at the computer system or at one of the one or more external computer systems for requesting output of the respective content).

In response to receiving the indication that the first external computer system has initiated the shared workout session (756), the computer system displays (758), via the display generation component, a user interface object (e.g., a notification and/or a selectable user interface object) (e.g., 640B, 642B, 640C, 642C) corresponding to the shared workout session. While displaying the user interface object corresponding to the shared workout session (760), the computer system detects (762), via the one or more input devices, a user input (e.g., a tap input and/or a non-tap input). Displaying a user interface object corresponding to a shared workout session in response to receiving an indication that a first external computer system has initiated a shared workout session, provides the user with feedback about the current state of the device (e.g., that the computer system has received an indication that the first external computer system has initiated a shared workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In response to detecting the user input (764), and in accordance with a determination that the user input corresponds to a request to join the shared workout session (766) (e.g., 644) (e.g., in accordance with a determination that the user input corresponds to selection of the user interface object), the computer system displays (e.g., playing and/or initiating playback of), via the display generation component, content (e.g., video content, instructions, tutorials) corresponding to the shared workout session, while maintaining the communication session of the first type, wherein display of the content corresponding to the shared workout session is initiated from a first playback position based on a playback position of corresponding content being displayed at the first external computer system (e.g., device 600B in FIG. 6E). In some embodiments, playback of the video content on the computer system is synced to playback of the video content on the first external computer system. In some embodiments, further in accordance with the determination that the user input corresponds to a request to join the shared workout session, the computer system initiates a user physical activity tracking function.

In response to detecting the user input (764), and in accordance with a determination that the user input does not correspond to a request to join the shared workout session (768) (e.g., in accordance with a determination that the user input does not correspond to selection of the user interface object), the computer system forgoes displaying (e.g., forgo playing, and/or forgo initiating playback of) the content corresponding to the shared workout session, while maintaining the communication session of the first type (e.g., device 600C in FIG. 6E) (e.g., maintain audio, video, and/or text-based communication session without displaying the video content corresponding to the workout session). In some embodiments, even if the computer system forgoes displaying the video content corresponding to the workout session, the first external computer system (e.g., device 600A) continues to display (e.g., play) the video content corresponding to the workout session.

In some embodiments, after forgoing displaying the content corresponding to the shared workout session (e.g., after the user input is determined to not correspond to a request to the shared workout session) and while the computer system continues to participate in the communication session of the first type with one or more external computer systems, the computer system receives a first set of one or more inputs (e.g., 652) corresponding to a request to display a user interface of a workout application. In some embodiments, the workout application is the same application that causes/manages display of the content corresponding to the shared workout session when the user input is determined to be a request to join the shared workout session. In response to the first set of one or more inputs, the computer system displays the user interface of the workout application (e.g., 622C), wherein the user interface of the workout application includes a second user interface object (e.g., 654C) corresponding to the shared workout session that, when selected, causes display, via the display generation component, of the content corresponding to the shared workout. In some embodiments, the computer system displays the user interface of the workout application while maintaining the communication session of the first type. In some embodiments, display of the content corresponding to the shared workout session is initiated from a playback position based on a playback position of corresponding content being displayed at the first external computer system. In some embodiments, the user interface of the workout application does not include one or more user interface objects (e.g., affordances to start a new workout or select a new workout) that would be included when displaying the user interface of the workout application when the computer system is not in a communication session of the first type with an external computer that has initiated a shared workout session. In some embodiments, the second user interface object corresponding to the shared workout session, when selected, causes display, via the display generation component, of the content corresponding to the shared workout from a playback position (e.g., a playback time) that corresponds to a current playback position of the shared workout at the time the input selecting the second user interface object is received (e.g., when the second user interface object is selected, the shared workout starts playing from the current playback position of the shared workout as seen by other participants in the shared workout (e.g., rather than from the beginning)). Displaying a second user interface object corresponding to the shared workout session provides the user with feedback about the current state of the device (e.g., that the computer system has detected that a participant in the communication session of the first type is sharing a workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content associated with the shared workout session and while the computer system is participating in the communication session of the first type with one or more external computer systems, the computer system (e.g., 600B, 600C) is configured to communicate with (e.g., transmit to or receive from) the one or more external computer systems (e.g., 600A, 600B, 600C) via a communication modality of the communication session of the first type selected from the group consisting of: audio communication (e.g., speech audio), video communication (e.g., using one or more cameras in communication with the computer system), text communication, screen content sharing communication, and a combination thereof (e.g., FIGS. 6E, 6F, 6I, 6J, 6N (participating in audio communication while displaying the content associated with the first workout), and/or FIG. 6W (participating in video communication while displaying the content associated with the first workout)). Configuring the computer system to communicate with one or more external computer systems via a communication modality of the communication session of the first type while displaying the content corresponding to the shared workout session enables a user to quickly and easily communicate with other users while viewing workout content, thereby reducing the number of inputs needed for communicating with other users while viewing workout content. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content corresponding to the shared workout session and while the computer system is participating in the communication session of the first type with one or more external computer systems, the computer system receives (e.g., from an external device; from an application executing on the computer system) notification data. In response to receiving the notification data: in accordance with a determination that the notification data is associated with the communication session of the first type (e.g., the notification data is received from the one or more external computer systems; the notification relates to a communication from one of the participants), the computer system displays a first notification (e.g., 646A, 658A, 658B, 666A, 666C, 670A, 670C, 683A, 683B, 685A, 685B) (e.g., a communication from the one or more external computer systems) at a first location of the display generation component (e.g., FIG. 6E, FIG. 6H, FIG. 6K, FIG. 6L, FIG. 6P, FIG. 6Q); and in accordance with a determination that the notification data is associated with the shared workout session (e.g., is associated with a workout application managing the shared workout), the computer system displays a second notification (e.g., 672A, 672B) (e.g., a workout-related notification) at a second location of the display generation component (e.g., FIG. 6M), different than the first location. In some embodiments, the first and second locations are non-overlapping. Displaying notifications associated with the communication session of the first type at a first display location, and displaying notifications associated with the shared workout session at a second display location, provides the user with feedback about the current state of the device (e.g., whether a particular notification pertains to the communication session of the first type or to the shared workout session). These notifications also quickly and easily provide a user with information about other users' actions either in a communication session or in the workout session. By providing different types of notifications in different areas of a screen, an electronic device can enhance glanceability for users and allow them to understand the current state of other user devices without additional user input. Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first notification indicates that a second external computer system is, via the communication session of the first type (e.g., via one or more communication protocols of the communication session of the first type), joining the shared workout session (e.g., 646A, 658A, 658B) or leaving the shared workout session (e.g., 683A, 683B). Displaying a notification that a second external computer system is joining the shared workout session or leaving the shared workout session provides the user with feedback about the current state of the device (e.g., that the device has detected and/or received information about the second external computer system joining or leaving the shared workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first notification (e.g., a communication session status notification) indicates that a third external computer system is joining (in some embodiments, has joined) the communication session of the first type or leaving (in some embodiments, has left) the communication session of the first type (e.g., 685A, 685B). Displaying a notification that a third external computer system is joining the communication session of the first type or leaving the communication session of the first type provides the user with feedback about the current state of the device (e.g., that the device has detected and/or received information about the third external computer system joining and/or leaving the communication session of the first type). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second notification is a notification that includes first information related to the shared workout session for the computer system or for one or more external computer systems that are participating in the shared workout session (e.g., notifications 672A, 672B, 672C in FIG. 6M). In some embodiments, the second notification can be a workout-related notification from any user in the communication session of the first type that is participating in the shared workout session. Displaying notifications pertaining to the shared workout session for the computer system or for one or more external computer systems provides the user with feedback about the current state of the device (e.g., that the device has detected and/or received first information related to the shared workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first information is an indication that a user of a fourth external computer system that is in the communication session of the first type and that is participating in the shared workout session has achieved a predetermined physical activity goal (e.g., met a calorie target, met activity intensity level target) or has achieved a change in status relative to one or more other participants for a first workout that corresponds to the shared workout session (e.g., notifications 672A, 672B, 672C in FIG. 6M) (e.g., the user has achieved a level of physical activity that places the user within a predetermined segment of participants (e.g., participants in the shared workout session; participants who are not in the shared workout session but have also participated in the first workout)). Displaying a notification indicating that a user of the fourth external computer system has achieved a predetermined physical activity goal or has achieved a change in status relative to one or more other participants in the first workout provides the user with feedback about the current state of the device (e.g., that the device has detected and/or received information indicating that the user of the fourth external computer system has achieved a predetermined physical activity goal or has achieved a change in status relative to one or more other participants in the first workout). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content corresponding to the shared workout session and while the computer system is engaged in the communication session of the first type with one or more external computer systems, the computer system receives a user input (e.g., 678) corresponding to a request to initiate a process for ending the display of content corresponding to the shared workout session. In response to receiving the user input corresponding to a request to initiate a process for ending the display of content corresponding to the shared workout session, the computer system displays: a first end option (e.g., 680C-1) that, when selected, causes the computer system to cease displaying the content corresponding to the shared workout session (e.g., user interface 636C) (e.g., leave the shared workout session for just the user of the computer system), without causing at least one external computer system that is in the communication session of the first type and that is displaying the content corresponding to the shared workout session to cease displaying (in some embodiments, and to end a workout at the external computer system that is associated with the shared workout session) the content corresponding to the shared workout session; and a second end option (e.g., 680C-2) that, when selected, causes the computer system to cease displaying the content corresponding to the shared workout session and causes at least one external computer system (in some embodiments, all computer systems participating in the shared workout session (e.g., end the shared workout session for all participants)) that is in the communication session of the first type and that is displaying the content corresponding to the shared workout session to cease displaying (in some embodiments, and to end the shared workout session at the external computer system) the content corresponding to the shared workout session. Concurrently displaying a first end option that is selectable to cause the computer system to cease displaying the content corresponding to the shared workout session and a second end option that is selectable to cause multiple computer systems to cease displaying the content corresponding to the shared workout session provides the user with the ability to end the workout for only themselves, or to end the workout for multiple computer systems. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system receives a user input (e.g., 682) corresponding to the first end option (e.g., 680C-1). In response to receiving the user input corresponding to the first end option, the computer system ceases to display, via the display generation component in communication with the computer system, the content corresponding to the shared workout session (e.g., leave the shared workout session for just the user of the computer system), wherein the content corresponding to the shared workout session continues to be displayed via a display generation component that is in communication with at least one external computer system that is in the communication session of the first type after the computer system ceases to display the content corresponding to the shared workout session (e.g., FIG. 6P, device 600C ceases to display the workout, while devices 600A and 600B continue to display the workout). In some embodiments, selection of the first end option causes only the computer system to leave the shared workout session, without causing any external computer system to cease displaying the content corresponding to the shared workout session (e.g., to leave the shared workout session). Concurrently displaying a first end option that is selectable to cause the computer system to cease displaying the content corresponding to the shared workout session and a second end option that is selectable to cause multiple computer systems to cease displaying the content corresponding to the shared workout session provides the user with the ability to end the workout for only themselves, or to end the workout for multiple computer systems. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, subsequent to ceasing to display the content corresponding to the shared workout session via the display generation component in communication with the computer system, the computer system receives a first set of user inputs (e.g., one or more tap inputs and/or one or more non-tap inputs) (e.g., 684-2) corresponding to a request to re-join the shared workout session (e.g., receiving a first set of user inputs corresponding to selection of a displayed option to re-join the shared workout session) (e.g., 654C). In response to receiving the first set of user inputs, the computer system displays, via the display generation component in communication with the computer system, content corresponding to the shared workout session (e.g., device 600C in FIG. 6P-1), wherein the content corresponding to the shared workout session that is displayed via the display generation component (e.g., 602C) in communication with the computer system (e.g., 600C) is synchronized with content corresponding to the shared workout session (e.g., 636A, 636B) that is displayed via the display generation component that is in communication with the at least one external computer system (e.g., 600A, 600B) that is in the communication session of the first type. In some embodiments, the content corresponding to the shared workout session that is displayed via the display generation component that is in communication with the computer system is displayed from a particular playback position based on the playback position of the content corresponding to the shared workout session being played at and/or by the at least one external computer system (e.g., the playback position of the content displayed at and/or by the computer system is synchronized to (e.g., matches) the playback position of the content displayed at and/or by the at least one external computer system). Allowing a user to re-join a shared workout session provides the user with the ability to temporarily leave a shared workout session, and then to re-join the shared workout session in a synchronized manner with at least one external computer system. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system receives a user input corresponding to the second end option (e.g., 680C-2). In response to receiving the user input corresponding to the second end option: the computer system ceases to display, via the display generation component, the content corresponding to the shared workout session (e.g., workout user interface 636C) (e.g., leave the shared workout session); and causes at least one external computer system (e.g., device 600A and/or 600B) that is in the communication session of the first type and that is displaying the content corresponding to the shared workout session to cease displaying the content corresponding to the shared workout session. Concurrently displaying a first end option that is selectable to cause the computer system to cease displaying the content corresponding to the shared workout session and a second end option that is selectable to cause multiple computer systems to cease displaying the content corresponding to the shared workout session provides the user with the ability to end the workout for only themselves, or to end the workout for multiple computer systems. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content corresponding to the shared workout session (e.g., device 600B in FIG. 6J) and while the computer system is engaged in the communication session of the first type with one or more external computer systems that includes a fifth external computer system (e.g., devices 600A and 600C in FIG. 6J) that is displaying the content corresponding to the shared workout session, the computer system receives a user input (e.g., 664) corresponding to a request pause the shared workout session (e.g., pausing display of the content corresponding to the shared workout session). In response to receiving the user input corresponding to the request to pause the shared workout session: the computer system pauses the shared workout session (e.g., pausing display of the content corresponding to the shared workout session at the display generation component (e.g., without ending the shared workout session)) (e.g., FIG. 6K); and causes the fifth external computer system (e.g., devices 600A, 600C) to pause display of the content corresponding to the shared workout session (e.g., FIG. 6K). In some embodiments, after pausing the workout, the computer system receives a user input corresponding to a request to resume the workout, and in response, resumes the workout at the computer system and at the fifth external computer system. Pausing display of the content associated with the workout on multiple computer systems in response to a user input on the computer system provides the user with the capability to pause the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content corresponding to the shared workout session and while the computer system is engaged in the communication session of the first type with one or more external computer systems including a sixth external computer system that is displaying the content corresponding to the shared workout session, the computer system receives a request from the sixth external computer system to end the shared workout session and to cease displaying the content corresponding to the shared workout session (e.g., a request initiated by selection of an "end for all" option at the sixth external computer system) e.g., if device 600C receives a selection of option 680C-2 in FIG. 6O, devices 600A and/or 600B receive a request from device 600C to end the workout session). In response to receiving the request from the sixth external computer system, the computer system ends the workout session on the computer system. In some embodiments, ending the workout session includes ceasing to display the content corresponding to the shared workout session on the computer system. Ending the workout session automatically in response to a received request from the sixth external computer system provides a user with the capability to end the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the content corresponding to the shared workout session and while the computer system is engaged in the communication session of the first type with one or more external computer systems including a seventh external computer system that is displaying the content corresponding to the shared workout session, the computer system receives a request from the seventh external computer system to pause displaying the content corresponding to the shared workout session (e.g., a request initiated by selection of an "pause" option at the seventh external computer system) (e.g., device 600B receives selection of pause option 662B-1 in FIG. 6J, and devices 600A and/or 600C receive a request from device 600B to pause displaying the content associated with the workout). In response to receiving the request from the seventh external computer system, the computer system pauses display of the content corresponding to the shared workout session (e.g., FIG. 6K) (e.g., without ending the shared workout session). In some embodiments, after pausing display of the content, the computer system receives an indication that an external computer system in the communication session of the first type has resumed display of the content, and in response to that indication, resumes displaying of the content corresponding to the shared workout session. Pausing display of the content associated with the workout in response to a received request from the seventh external computer system provides a user with the capability to pause the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after completing the shared workout session, the computer system displays, via the display generation component, a workout summary user interface (e.g., 686A, 686B) that includes: physical activity data (e.g., calories burned data; heart rate data) collected by the computer system for a user of the computer system (e.g., 687A-2, 687B-2); and an indication of one or more external computer systems (e.g., an indication of users of the external computer systems) that were in the communication session of the first type with the computer system and participated in the shared workout session (e.g., 687A-1, 687B-1) (e.g., that was displaying the content corresponding to the shared workout session). Displaying a workout summary user interface that includes physical activity data and an indication of one or more external computer systems that were in the communication session of the first type and participated in the shared workout session provides the user with feedback about the current state of the device (e.g., that the shared workout session has ended) as well as feedback about the state of the one or more external computer systems (e.g., which computer systems were in the communication session of the first type and participated in the shared workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying, via the display generation component, the content corresponding to the shared workout session, the computer system receives a request (e.g., inputs 690, 692) to cause a second display generation component (e.g., 600D) (e.g., a smart television; a digital media player that is connected to a television or monitor) that is in communication with the computer system to display the content corresponding to the shared workout session. In response to the request to cause a second display generation component that is in communication with the computer system to display the content corresponding to the shared workout session, the computer system causes the second display generation component to display the content corresponding to the shared workout session (e.g., FIG. 6V). In some embodiments, the computer system also ceases to display the content via the display generation component. Causing a second display generation component to display content corresponding to the shared workout session in response to a request provides the user with the ability to display the content corresponding to the shared workout session on a second display generation component. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while causing display of the content corresponding to the shared workout session at the second display generation component, the computer system receives second notification data. In response to the second notification data: in accordance with a determination that the second notification data is associated with the communication session of the first type (e.g., the second notification data is received from the one or more external computer systems), the computer system displays a third notification (e.g., 694) (e.g., a communication from the one or more external computer systems) via the display generation component; and in accordance with a determination that the second notification data is associated with the shared workout session (e.g., is associated with a workout application managing the shared workout session), the computer system causes display of a fourth notification (e.g., 695) (e.g., a workout-related notification) at the second display generation component. In some embodiments, notifications are displayed at different displays depending on the type of notification. Displaying notifications associated with the communication session of the first type on the display generation component, and displaying notifications associated with the shared workout session at the second display generation component, provides the user with feedback about the current state of the device (e.g., whether a particular notification pertains to the communication session of the first type or to the shared workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 750 (e.g., FIG. 7B) are also applicable in an analogous manner to the methods described below and/or above. For example, methods 700, 900, and 1100 optionally include one or more of the characteristics of the various methods described above with reference to method 750. For example, the communication session of the first type recited in methods 700, 750, 900, and 1100 are, in some embodiments, the same communication session in all three methods. For example, the indication received in method 750 is, in some embodiments, corresponds to a workout shared via method 900. For brevity, these details are not repeated below.

FIGS. 8A-1-8I illustrate exemplary user interfaces for displaying and sharing group workout content, in accordance with some embodiments. The user interfaces in these figures are used to illustrate the processes described below, including the process in FIG. 9.

FIGS. 8A-1-8I illustrate exemplary devices and user interfaces. At FIG. 8A-1, electronic device 800 (e.g., device 100, 300, 500) is displaying media home user interface 801 on display 802 (e.g., a smart television (e.g., a computer system with dedicated media playback functionality) (e.g., a device having one or more features of device 100, 300, or 500)), a television connected to a digital media player (e.g., a computer system with dedicated media playback functionality (e.g., a device having one or more features of device 100, 300, or 500))). In some embodiments, display 802 is an integrated part of electronic device 800. In some embodiments, electronic device 800 is a separate digital media player that is in communication (e.g., wirelessly, wired) with display 802. Media home user interface 801 includes a plurality of options 803A, 803B, 803C corresponding to different applications (e.g., different media applications). Option 803A corresponds to a fitness application, option 803B corresponds to a music application, and option 803C corresponds to a television application.

FIG. 8A-1 also illustrates remote control 804, which is configured to transmit data (e.g., via RF communication, via Bluetooth, via infrared) to electronic device 800 based on user input that is detected at remote control 804. Remote control 804 includes a selection region 806A, which includes a touch-sensitive surface for detecting tap, press, and swipe gestures, a menu button 806B, a television button 806C, a microphone button 806D, a play/pause button 806E, and volume control buttons 806F.

FIG. 8A-1 also illustrates electronic device 600A, which is a smartphone with display 602A. In the depicted embodiment, electronic device 600A and electronic device 800 are associated with (e.g., correspond uniquely to) the same user, John. In some embodiments, electronic device 600A and electronic device 800 are both logged into the same user account corresponding to the same user. In some embodiments, electronic device 600A is associated with one or more user accounts (e.g., one or more user accounts are logged into and/or have previously logged into electronic device 600A), electronic device 800 is associated with one or more user accounts (e.g., one or more user accounts are logged into and/or have previously logged into electronic device 800), and the one or more user accounts associated with electronic device 600A overlap with the one or more user accounts associated with electronic device 800, such that both electronic device 600A and electronic device 800 are associated with the user John. Electronic device 600A displays communication session overlay 604A overlaid on home user interface 606A. Communication session overlay 604A indicates that electronic device 600A is participating in a communication session with three other devices. In some embodiments, the communication session is a synchronized media communication session. As discussed above with reference to FIG. 6A, the communication session enables communication between electronic devices via multiple communication mediums, including text-based communication, audio-based communication, video-based communication, and synchronized content sharing.

FIG. 8A-1 also depicts two electronic devices 805A, 805B (e.g., wearable electronic devices and/or smart watches). In the depicted embodiments, electronic devices 805A, 805B are smart watches. Electronic device 805A corresponds to a first user, John (e.g., is logged into a user account corresponding to the first user), and electronic device 805B corresponds to a second user, Natalie (e.g., is logged into a user account corresponding to the second user). In some embodiments, electronic devices 805A, 805B satisfy proximity criteria relative to electronic device 800 (e.g., are within a threshold distance of electronic device 800 and/or satisfy signal strength criteria relative to electronic device 800).

While electronic device 800 causes display of media home user interface 801 with a focus on option 803A, remote control 804 detects activation of selection region 806A via button press input 807 corresponding to selection of option 803A, and transmits an indication of the input to electronic device 800. Electronic device 800 receives, from remote control 804, the indication of input 807 corresponding to selection of option 803A.

At FIG. 8A-2, in response to detecting (e.g., receiving the indication of) input 807, and, in some embodiments, in accordance with a determination that there are a plurality of electronic devices of a particular type (e.g., a plurality of wearable devices, a plurality of smart watches) that satisfy proximity criteria, electronic device 800 causes display 802 to display disambiguation user interface 809 that includes options 811A, 811B, 811C. Option 811A corresponds to electronic device 805A and option 811B corresponds to electronic device 805B. Option 811A is selectable to indicate that the user associated with electronic device 805A ("John") is the user that will be performing a workout, and option 811B is selectable to indicate that the user associated with electronic device 805B ("Natalie") is the user that will be performing a workout. Option 811C is selectable to add a new user and/or device (e.g., to indicate that neither John nor Natalie is the user that will be performing the workout).

While electronic device 800 causes display of disambiguation user interface 809 with a focus on option 811A, remote control 804 detects activation of selection region 806A via button press input 813 corresponding to selection of option 811A, and transmits an indication of the input to electronic device 800. Electronic device 800 receives, from remote control 804, the indication of input 813 corresponding to selection of option 811A.

At FIG. 8A-3, in response to detecting (e.g., receiving the indication of) input 813, electronic device 800 displays workout suggestion user interface 808. Workout suggestion user interface 808 includes a plurality of workout suggestions 810A-810F that are selectable to initiate a process for playing content (e.g., video content, audio-visual content, and/or audio content) corresponding to the selected workout suggestion.

Furthermore, workout suggestion user interface 808 includes indication 815 that indicates that the user John is the active user in the workout session (e.g., based on the selection of option 811A in FIG. 8A-2). In some embodiments, electronic device 800 receives user information (e.g., user-specific physical activity metrics (e.g., daily physical activity metrics), user name, user alias, and/or user profile picture) from electronic device 805A in response to user input 813. Alternatively, in some embodiments, if the user had selected option 811B in FIG. 8A-2, electronic device 800 would have received user information from electronic device 805B, and indication 815 would have displayed a profile picture corresponding to the user Natalie rather than the user John. In some embodiments, if electronic device 800 detected only a single electronic device of a particular type (e.g., only a single smart watch) that satisfied proximity criteria, electronic device 800 would have pulled user information from the single electronic device and, in some embodiments, would not have displayed disambiguation user interface 809 (e.g., would have displayed workout suggestion user interface 808 instead of disambiguation user interface 809).

In FIG. 8A-3, electronic device 800 displays indication 812. Indication 812 is displayed based on a determination that one or more electronic devices (e.g., electronic device 600A) satisfy one or more criteria relative to electronic device 800. In some embodiments, the one or more criteria include one or more proximity criteria that are satisfied if an electronic device is within a threshold proximity of the electronic device 800 (e.g., electronic device 600A is within a threshold distance and/or proximity of electronic device 800 (e.g., based on signal strength information of wireless signals transmitted between electronic device 600A and electronic device 800)). In some embodiments, the one or more criteria includes a criterion that is satisfied when an electronic device satisfies the one or more proximity criteria and is participating in a communication session (e.g., a synchronized media communication session). In some embodiments, the one or more criteria includes user account criteria that is satisfied when an electronic device satisfies the one or more proximity criteria, is participating in a communication session, and is associated with a common user account with electronic device 800. In FIG. 8A-3, electronic device 600A satisfies the one or more criteria and, accordingly, electronic device 800 causes display 802 to display indication 812.

While electronic device 800 causes display of workout suggestion user interface 808 with a focus on workout suggestion 810C, remote control 804 detects activation of selection region 806A via button press input 814 corresponding to selection of workout suggestion 810C, and transmits an indication of the input to electronic device 800. Electronic device 800 receives, from remote control 804, the indication of input 814 corresponding to selection of workout suggestion 810C.

Figure 8B:
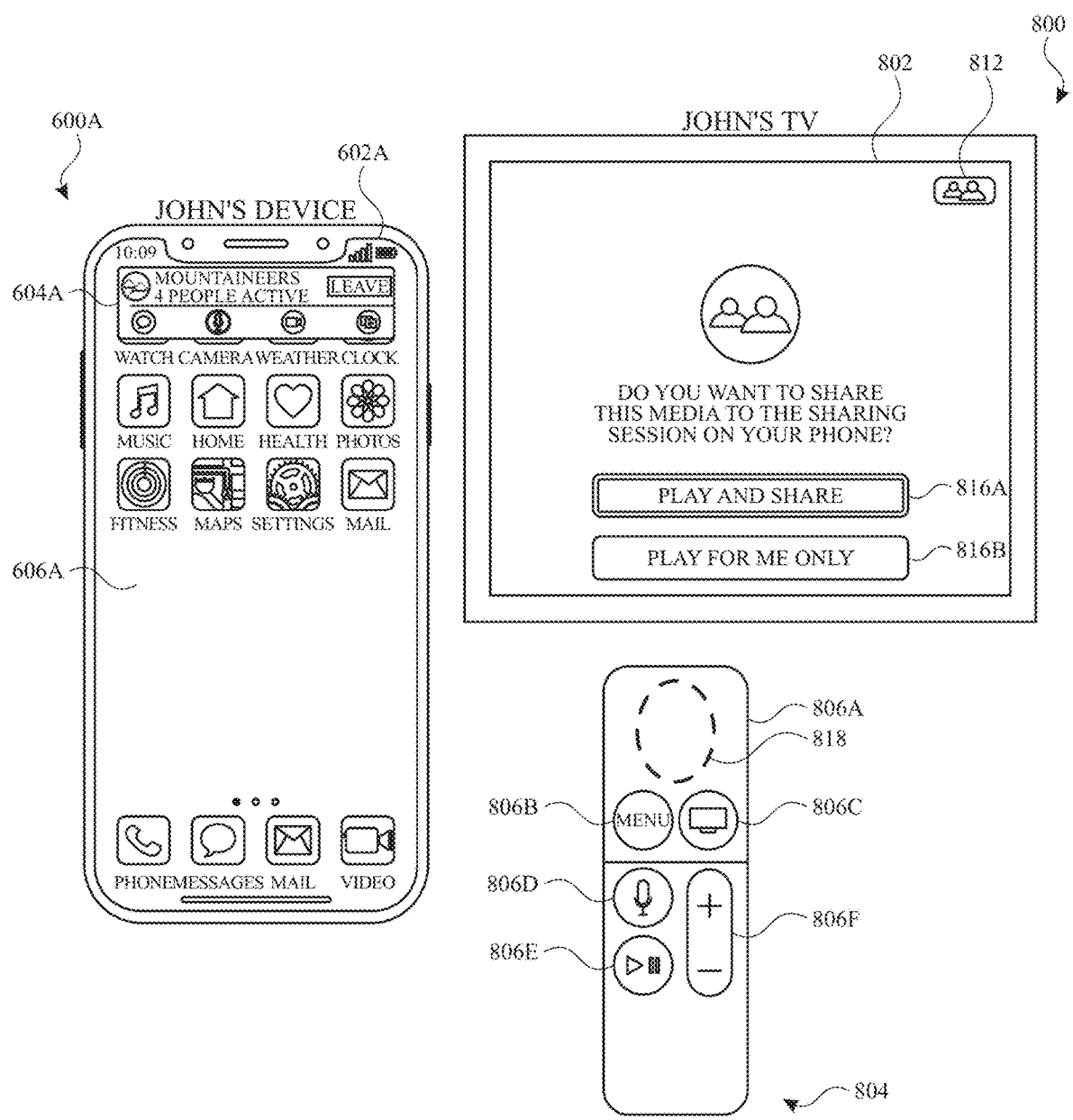

In FIG. 8B, in response to detecting (e.g., receiving the indication of) input 814, and in accordance with a determination that one or more electronic devices satisfy the one or more criteria (e.g., in accordance with a determination that electronic device 600A satisfies the one or more criteria), electronic device 800 causes display 802 to display options 816A, 816B. Option 816A is selectable to initiate a process for sharing workout content corresponding to the selected workout suggestion 810C to one or more external electronic devices (e.g., via the communication session), while option 816B is selectable to cause electronic device 800 and/or display 802 to display workout content corresponding to the selected workout suggestion 810C on display 802 only (e.g., without displaying and/or sharing the workout content to any other electronic devices). At FIG. 8B, while electronic device 800 causes display of options 816A, 816B with a focus on option 816A, remote control 804 detects activation of selection region 806A via button press input 818 corresponding to selection of option 816A, and transmits an indication of the input to electronic device 800. Electronic device 800 receives, from remote control 804, the indication of input 818 corresponding to selection of option 816A.

Figure 8C:
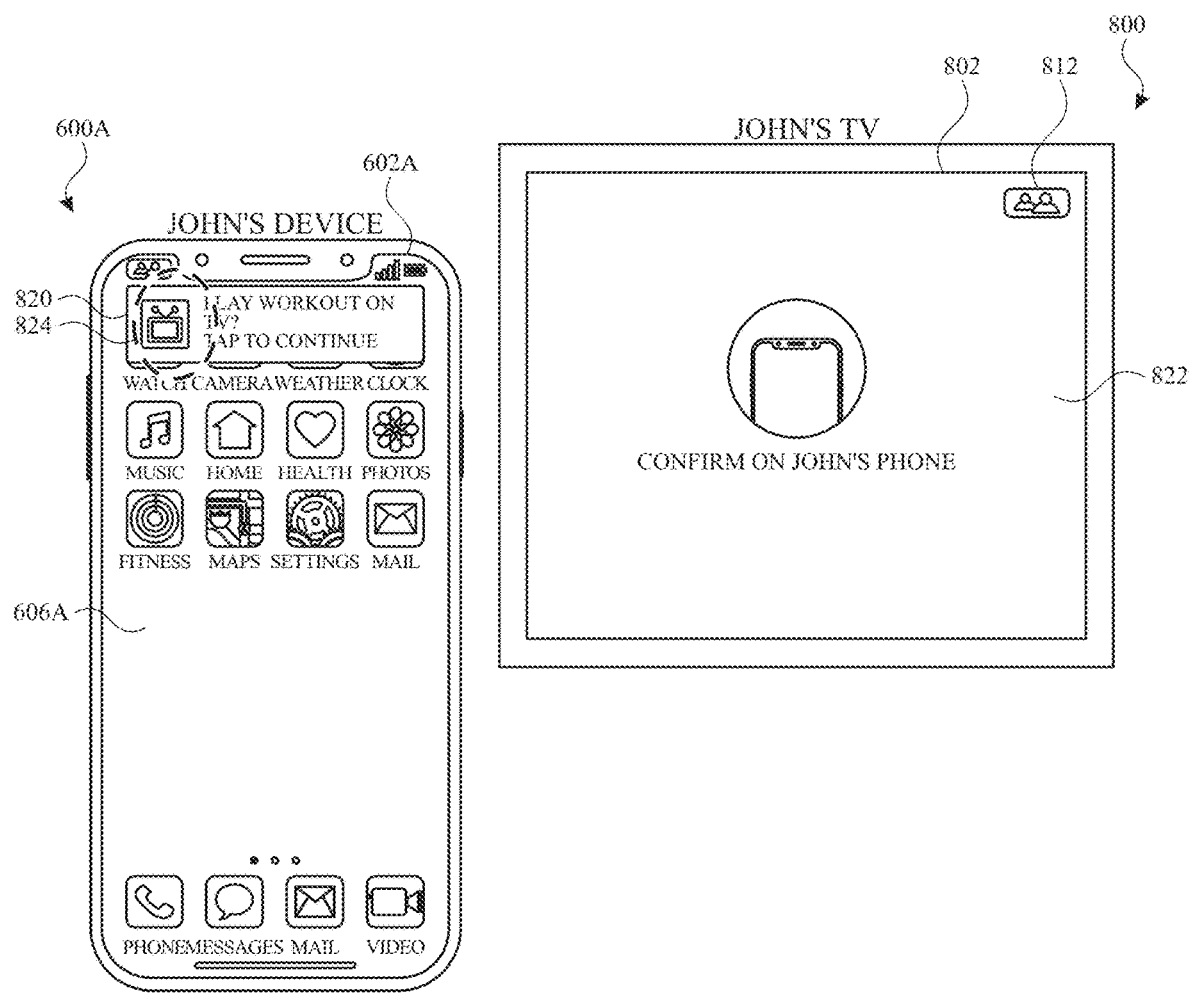

In FIG. 8C, in response to detecting (e.g., receiving the indication of) input 818, electronic device 800 causes display 802 to display user interface 822. User interface 822 instructs a user to confirm, using electronic device 600A, that the user wishes to share workout content from electronic device 800 to the communication session. Furthermore, in response to detecting (e.g., receiving the indication of) input 818, electronic device 800 causes electronic device 600A to display notification 820 that is selectable by a user to confirm the user's intent to share workout content from electronic device 800 to the communication session. While displaying notification 820, electronic device 600A detects user input 824 (e.g., a tap input) corresponding to selection of notification 820.

Figure 8D:
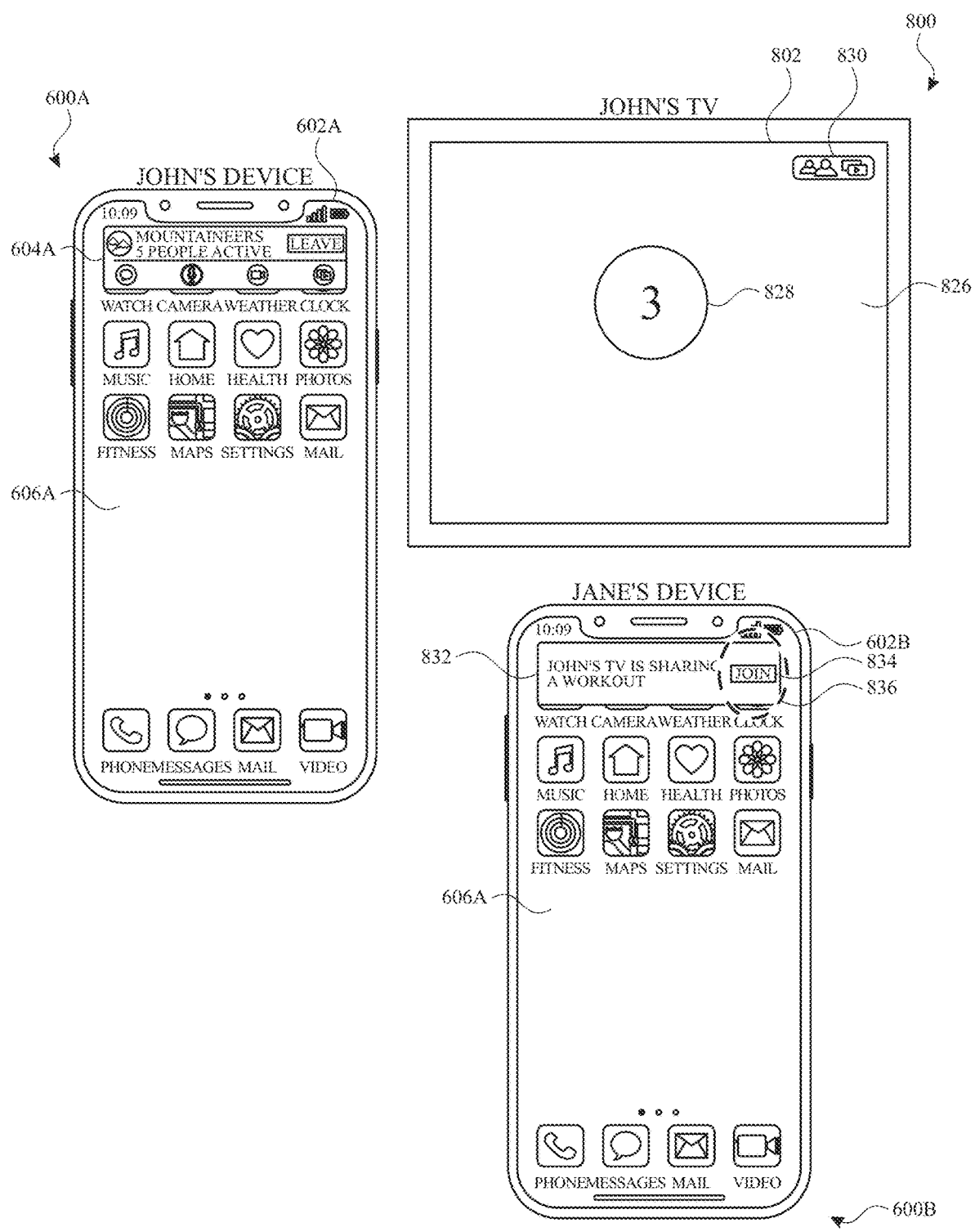

In FIG. 8D, in response to detecting user input 824, electronic device 600A transmits and/or causes to be transmitted to electronic device 800A an indication that electronic device 600A has detected user input 824 corresponding to selection of notification 820. In response to receiving this indication, electronic device 800 joins the communication session, and displays workout user interface 826, which includes timer 828 indicating that the workout will start in three seconds. Communication session overlay 604A on device 600A now indicates that there are five devices participating in the communication session, as electronic device 800 has been added as a participating device in the communication session. Furthermore, in response to electronic device 800 being added to the communication session, electronic device 800 causes display 802 to display indication 830 indicating that electronic device 800 is participating in the communication session. In response to electronic device 800 being added to the communication session, and sharing workout content to the communication session, the other devices participating in the communication session, including electronic device 600B, display notifications (e.g., notification 832) indicating that electronic device 800 is sharing a group workout in the communication session. Notification 832 includes join option 834 that is selectable to cause electronic device 600B to join the group workout. At FIG. 8D, electronic device 600B detects user input 836 (e.g., a tap input) corresponding to selection of the join option 834.

Figure 8E:
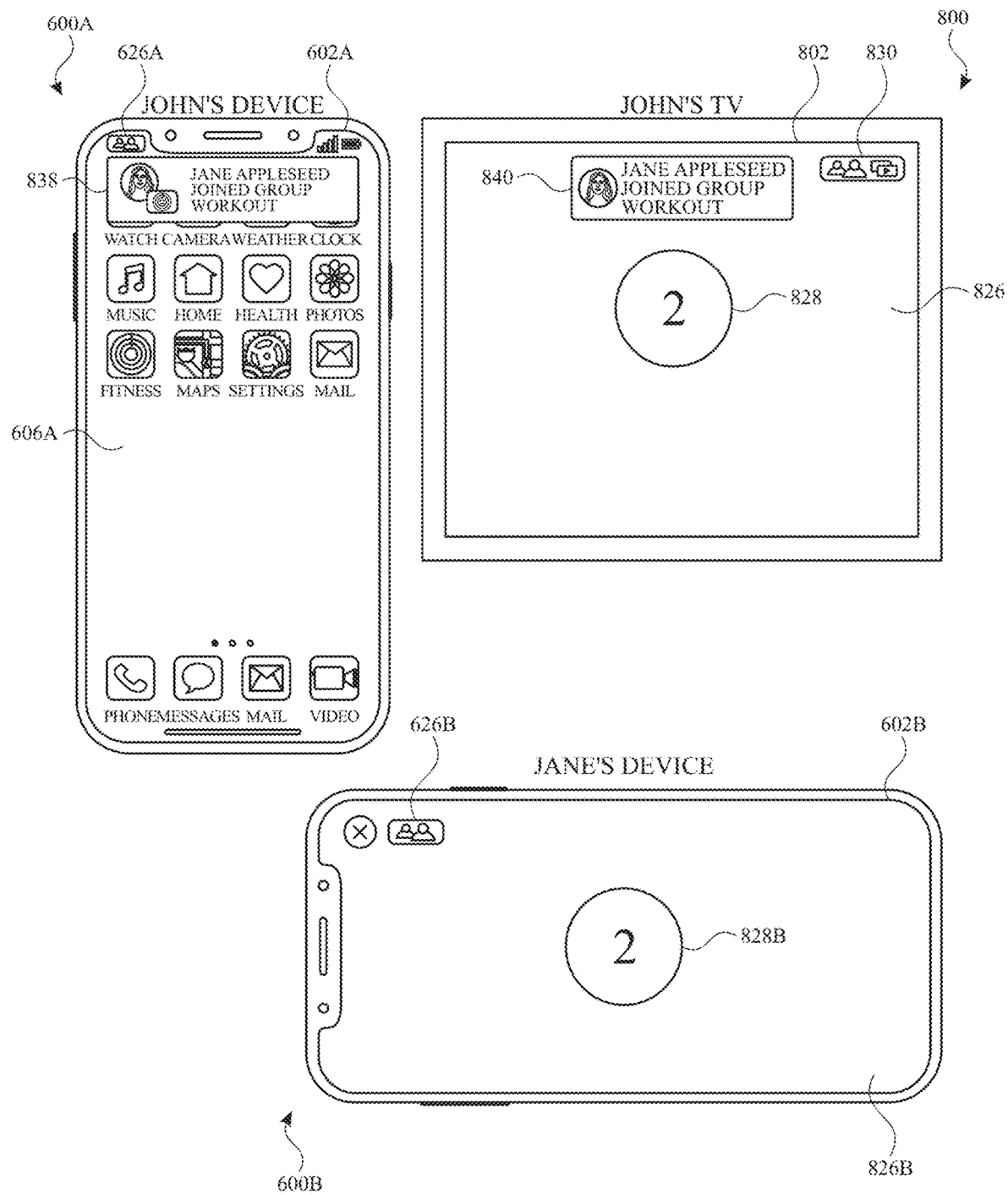

In FIG. 8E, in response to detecting user input 836, electronic device 600B joins the group workout, and displays workout user interface 826B. Workout user interface 826B corresponds to workout user interface 826, and displays synchronized video content with workout user interface 826 (e.g., playback of video content in workout user interface 826B is synchronized with playback of video content in workout user interface 826). For example, workout user interface 826B displays timer 828B indicating that the workout will begin in two seconds at the same time that workout user interface 826 displays timer 828, which also indicates that the workout will begin in two seconds. Furthermore, in response to electronic device 600B joining the group workout, electronic device 600A displays notification 838, and electronic device 800 displays notification 840 indicating that electronic device 600B has joined the group workout. In some embodiments, electronic device 600B transmits to electronic devices 600A and 800 (e.g., via the communication session) and/or causes to be transmitted to electronic device 600A and 800 an indication that electronic device 600B has detected user input 836 corresponding to a request to join the group workout, and electronic devices 600A and 800 display notifications 838 and 840 in response to receiving the indication.

Figure 8F:
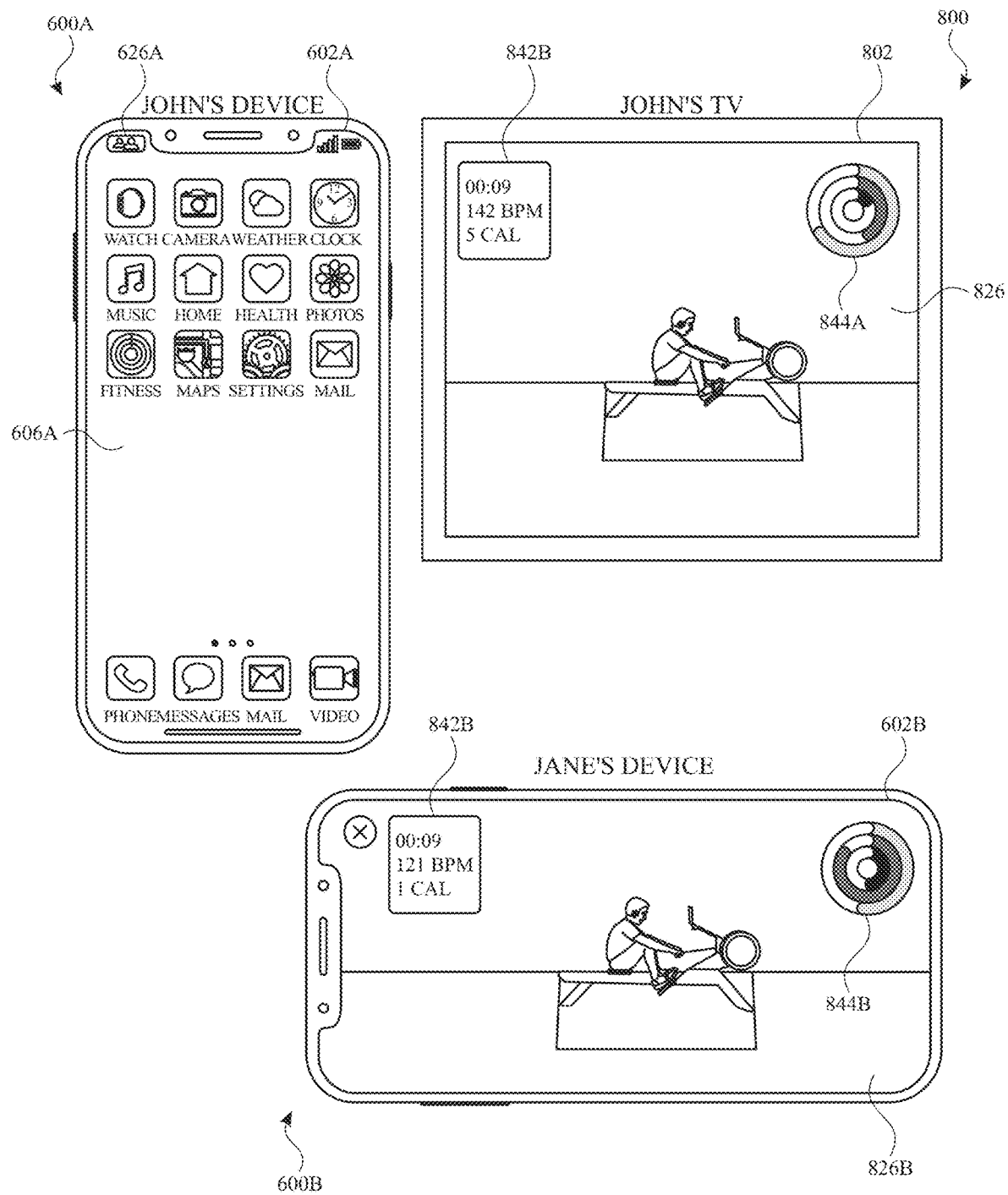

In FIG. 8F, the group workout has progressed for nine seconds. Electronic device 800 continues to display workout user interface 826, which displays video content corresponding to the workout (e.g., video content demonstrating the workout). Workout user interface 826 also includes workout physical activity metrics 842A indicative of (e.g., corresponding to) physical activity of a user of electronic device 800 (e.g., "John"). Workout physical activity metrics 842A display John's heartrate (e.g., 142 BPM), and the number of calories John has burned during the workout (e.g., 5 calories). Workout user interface 826 also includes daily physical activity metrics 844A for John for the current day, including time outside of the current workout. For example, as discussed above with reference to daily physical activity metrics 650A, the outer ring of daily physical activity metrics 844A indicates the number of calories John has burned in the current day (e.g., indicates John's progress towards a daily calorie goal), the middle ring of daily physical activity metrics 844A indicates the number of minutes John has exercised in the current day (e.g., indicates John's progress towards a daily exercise minutes goal), and the innermost ring of daily physical activity metrics 844A indicates the number hours in the current day that John has stood for a threshold amount of time (e.g., how many hours John has stood for at least 3 minutes) (e.g., indicates John's progress towards a daily stand goal).

Similarly, electronic device 600B displays workout user interface 826B, which also displays video content corresponding to the workout. The video content displayed in workout user interface 826B is synchronized with video content displayed in workout user interface 826. Workout user interface 826B also displays workout physical activity metrics 842B indicative of physical activity of a user of electronic device 600B (e.g., "Jane") during the workout. Workout user interface 826B also displays daily physical activity metrics 844B that are indicative of Jane's physical activity in the current day, as described above with reference to daily physical activity metrics 844A.

Figure 8G:
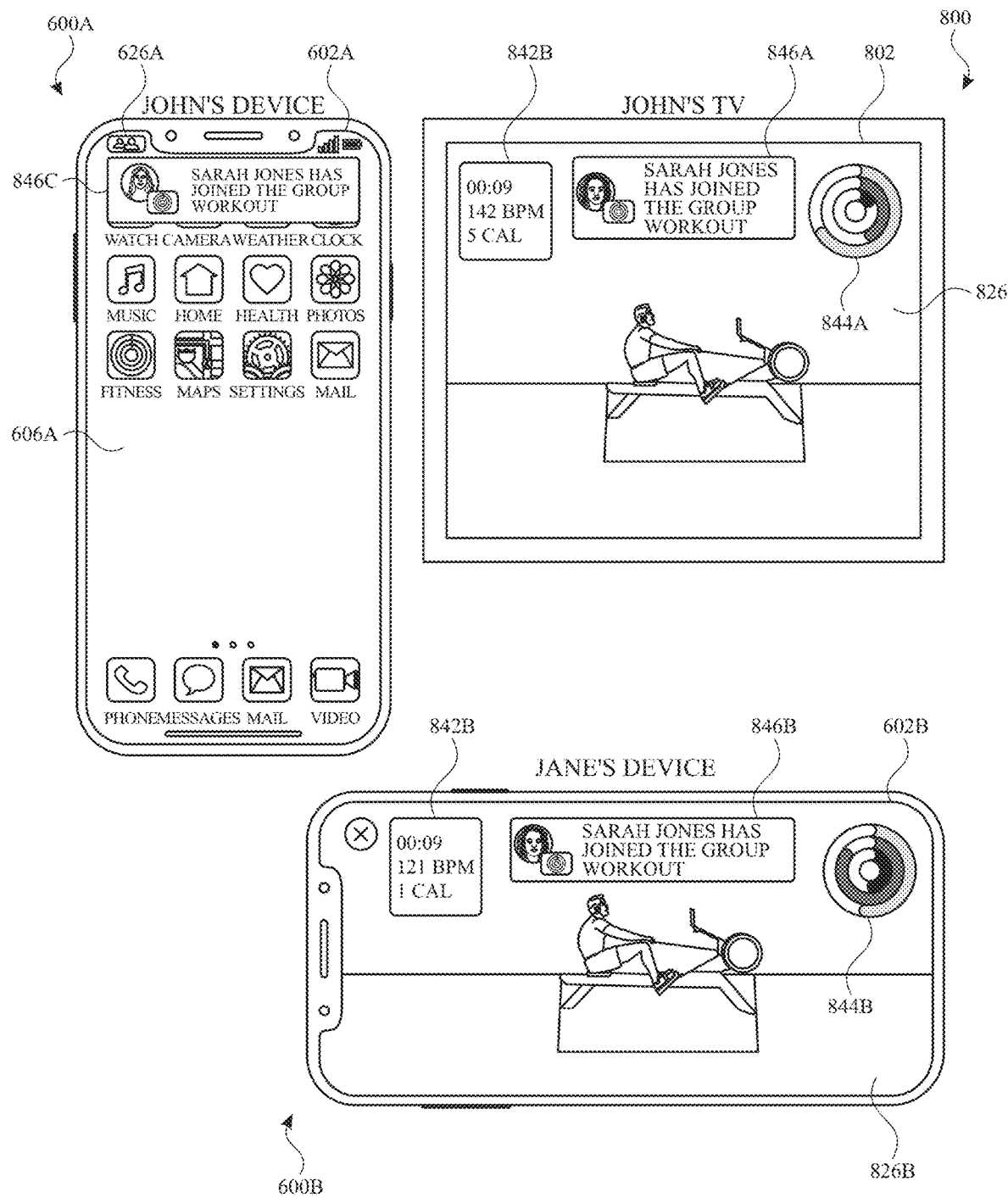

In FIG. 8G, electronic devices participating in the communication session (e.g., all electronic devices participating in the communication session), including electronic devices 600A, 800, and 600B, receive an indication that a new electronic device that is participating in the communication has joined the group workout (e.g., an electronic device corresponding to a user Sarah Jones). In response to receiving this indication, electronic device 600A displays notification 846C, electronic device 800 causes display 802 to display notification 846A, and electronic device 600B displays notification 846B indicating that a new electronic device has joined the group workout.

Figure 8H:
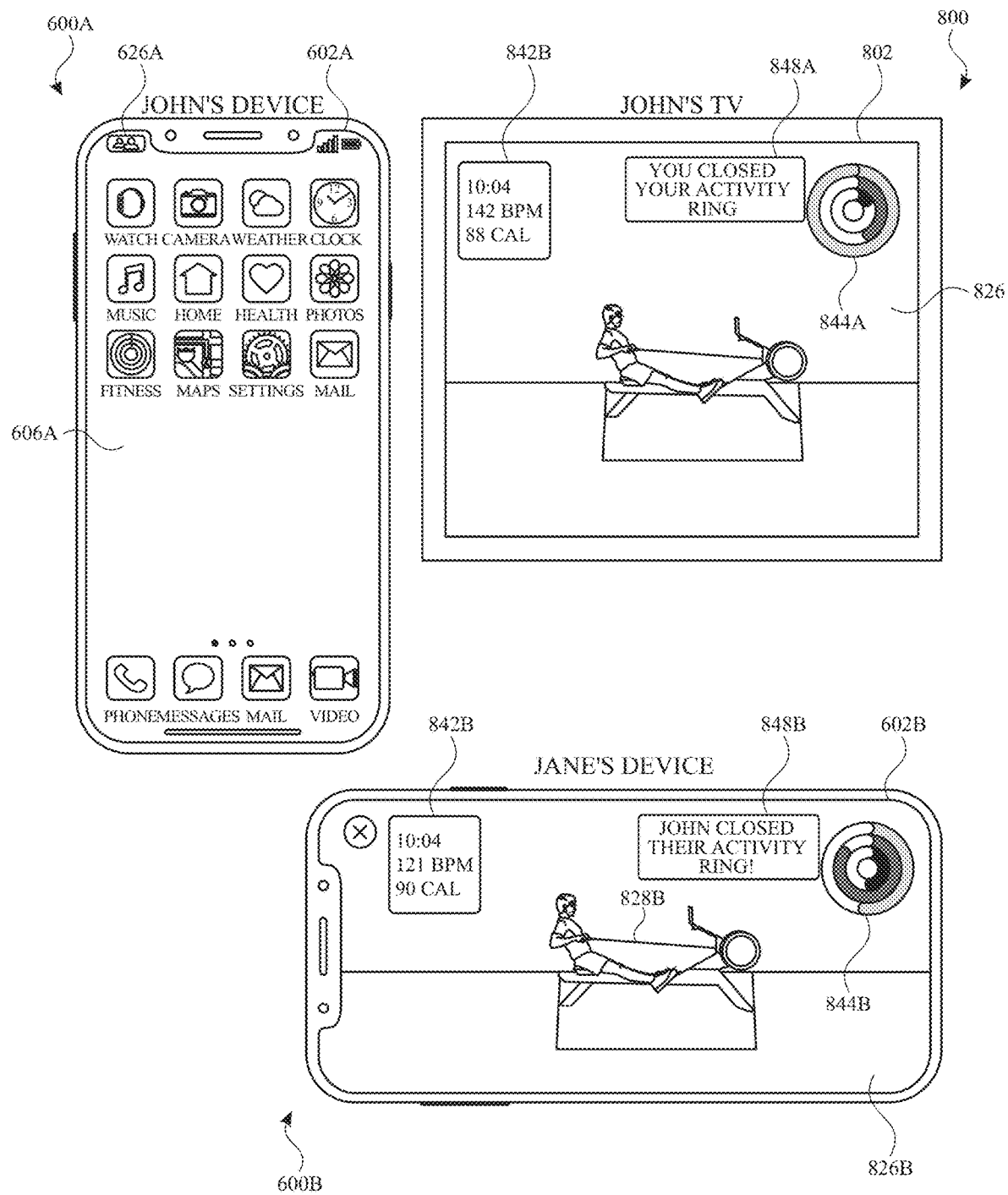
Figure 8I:
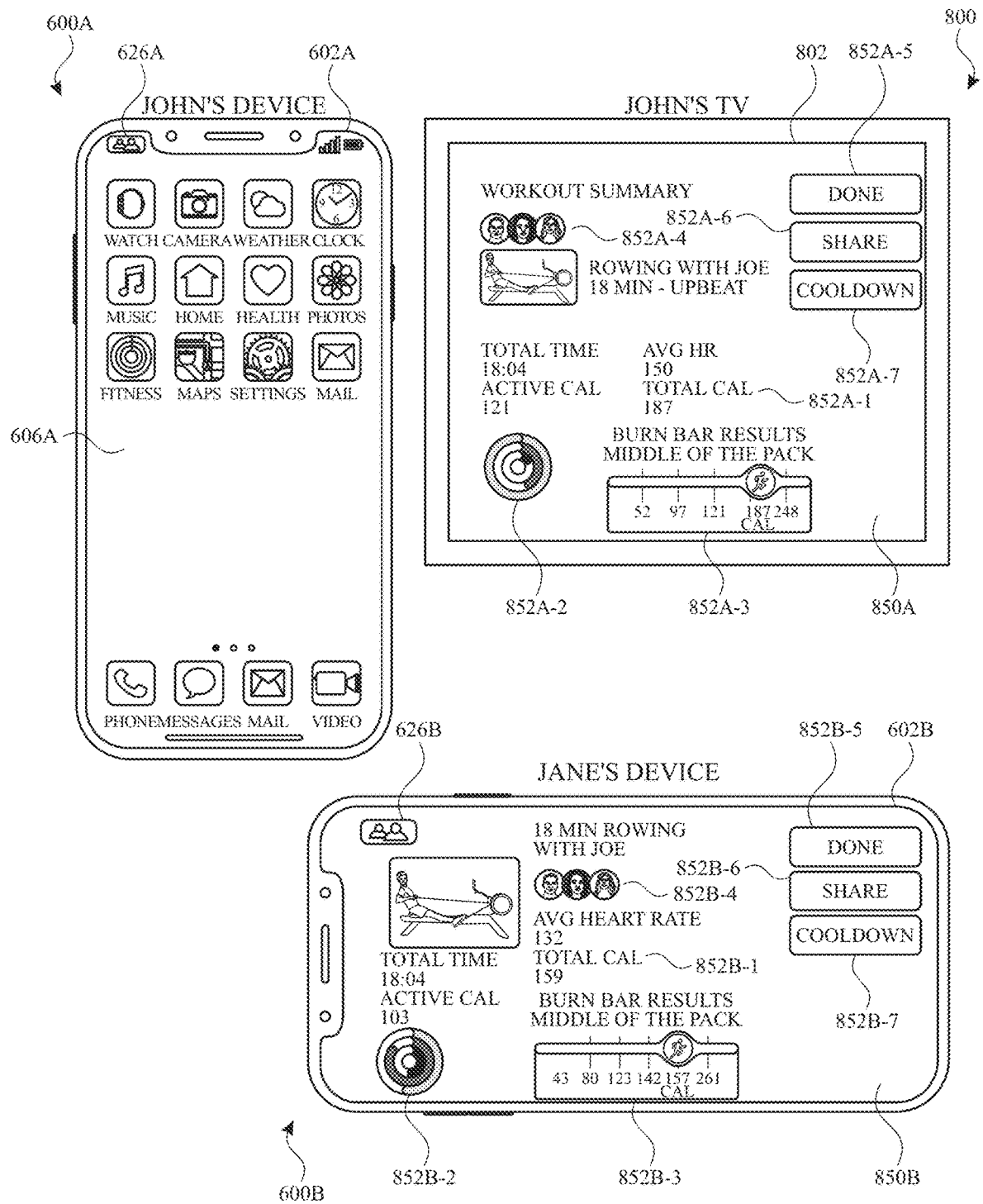

In FIG. 8H, electronic device 800 detects and/or determines that its user, John, has accomplished a physical activity goal (e.g., has accomplished their daily calorie goal), as indicated by the closed outermost circle in daily physical activity metrics 844A. In response to this determination, electronic device 800 displays, via display 802, fitness notification 848A. Furthermore, electronic device 800 transmits (e.g., via the active communication session) and/or causes to be transmitted to electronic devices participating in the group workout, including electronic device 600B, an indication that John has accomplished the physical activity goal. In response to receiving this indication, electronic device 600B displays fitness notification 848B indicating that John has accomplished his physical activity goal. In some embodiments, electronic devices that are participating in the communication session but are not participating in the group workout, such as electronic device 600A, do not receive the indication that John achieved the physical activity goal and/or do not display a notification that John achieved the physical activity goal.

It can be seen in FIGS. 8G and 8H that notifications pertaining to the fitness application (e.g., notifications generated by the fitness application) (e.g., FIG. 8H), are displayed in a first display region (e.g., an upper right hand corner of the display region), while notifications pertaining to the communication session (e.g., notifications generated by a communication application) (e.g., FIG. 8G), are displayed in a second, different display region (e.g., an upper center region). In some embodiments, fitness application notifications include notifications pertaining to users achieving one or more physical activity goals and/or one or more physical activity achievements by users during the group workout, while active communication session notifications include notifications pertaining to one or more users joining and/or leaving the group workout, one or more users joining and/or leaving the communication session, and/or one or more users pausing and/or resuming playing video content of the group workout.

In FIG. 8I, the group workout has completed (e.g., the video content corresponding to the group workout has played to completion and/or a user has ended the group workout for all users). In response to detecting that the group workout has completed, electronic device 800 displays workout summary user interface 850A. Workout summary user interface 850A includes workout physical activity metrics 852A-1 for the user corresponding to electronic device 800 ("John"), including a workout performance bar 852A-3 indicative of John's performance relative to other users that performed the same workout. Workout summary user interface 850A also includes daily physical activity metrics 852A-2 for John, as discussed above. Workout summary user interface 850A also includes an indication 852A-4 of users that participated in the group workout session. In the example scenario depicted, the indication 852A-4 includes representations of John, Jane, and Sarah. Workout summary user interface 850A also includes done option 852A-5, that is selectable to close (e.g., cease display of) workout summary user interface 850A, share option 852A-6 that is selectable to share workout summary information with one or more other users, and cooldown option 852A-7 that is selectable to initiate playback of a cooldown workout.

Similar to electronic device 800, electronic device 600B displays workout summary user interface 850B. Workout summary user interface 850B is substantially identical to workout summary user interface 850A, except that workout summary user interface 850B includes workout physical activity metrics 852B-1, workout performance bar 852B-3, and daily physical activity metrics 852B-2 that correspond to the user associated with electronic device 600B ("Jane").

While certain example features have been depicted in FIGS. 8A-1-8I, it should be understood that any of the features disclosed above with reference to FIGS. 6A-6X can be applied to the example embodiments depicted in FIGS. 8A-1-8I. For example, in some embodiments, in FIGS. 8A-1-8I, if the group workout is paused on one electronic device, the group workout is also paused on all electronic devices participating in the group workout. In another example, in some embodiments, in FIGS. 8A-1-8I, if a user attempts to exit the group workout on his or her electronic device, the user is presented with options to end the group workout for only the user (e.g., only on that electronic device), and/or for all users participating in the group workout (e.g., for all electronic devices participating in the group workout).

FIGS. 6V-6X above depicted an example scenario in which workout content was displayed on a television device 600D. In some embodiments, the example scenario depicted in FIGS. 6V-6X differs from the example scenario depicted in FIGS. 8A-1-8I in that in FIGS. 6V-6X, device 600D simply acts as a display for device 600A, and device 600D is not added as a separate device to the communication session. In contrast, in some embodiments, in the example scenario depicted in FIGS. 8A-1-8I, electronic device 800 is added to the communication session separately from electronic device 600A, and is independently sharing workout content to the communication session separately from electronic device 600A.

FIG. 9 is a flow diagram illustrating a method for displaying and sharing group workout content using a computer system in accordance with some embodiments. Method 900 is performed at a computer system (e.g., 100, 300, 500) that is in communication with a display generation component, one or more input devices, and a first external computer system. Some operations in method 900 are, optionally, combined, the orders of some operations are, optionally, changed, and some operations are, optionally, omitted.

As described below, method 900 provides an intuitive way for displaying and sharing group workout content. The method reduces the cognitive burden on a user for displaying and sharing group workout content, thereby creating a more efficient human-machine interface. For battery-operated computing devices, enabling a user to display and share group workout content faster and more efficiently conserves power and increases the time between battery charges.

In some embodiments, a computer system (e.g., a digital media player; a computer set top entertainment box; a smart TV; a computer system controlling an external display) (e.g., 800) that is in communication with a display generation component (e.g., 802) (e.g., a display controller; a touch-sensitive display system; and/or a display (e.g., integrated and/or connected)), one or more input devices (e.g., a touch-sensitive surface (e.g., a touch-sensitive display); a mouse; a keyboard; and/or a remote control), and a first external computer system (e.g., 600A) (e.g., a smart phone, a tablet; a smart watch) (e.g., a first external computer system different from the computer system) detects (902), via the one or more input devices, a set of one or more user inputs (e.g., 814) (e.g., a single input (e.g., a tap input, a non-tap input, a remote control input, and/or a touch-sensitive display input)) corresponding to a request to initiate a workout session (e.g., a user input selecting a workout option from a plurality of workout options), wherein initiating the workout session includes initiating display of (e.g., initiating playback of) content (e.g., video content, instructions, tutorials) corresponding to a workout.

In response to detecting the set of one or more user inputs (904), and in accordance with a determination that the first external computer system (e.g., 600A) satisfies one or more workout sharing criteria (906) (e.g., satisfies one or more workout sharing criteria with respect to the computer system), wherein the one or more workout sharing criteria includes a first criterion that is met when the first external computer system is participating in a communication session of a first type with one or more external computer systems (e.g., that do not include the computer system), the computer system displays (908), via the display generation component, a first user interface (e.g., device 800 in FIG. 8B). The first user interface includes: a first user interface object (e.g., 816A) that is selectable to share content corresponding to the workout session to the one or more external computer systems in the communication session of the first type (in some embodiments, the first user interface object is selectable to also add the computer system to the communication session of the first type) (in some embodiments, selection of the first user interface object causes one or more external computer systems participating in the communication session of the first type to display a user interface object (e.g., a notification) corresponding to (e.g., indicative of) the workout session), and a second user interface object (e.g., 816B) that is selectable to display, via the display generation component, content corresponding to the workout session (e.g., selectable to initiate playback of video content corresponding to the workout session) without sharing the content corresponding to the workout session to the one or more computer systems in the communication session of the first type (e.g., and, optionally, without adding the computer system to the communication session of the first type).

In response to detecting the set of one or more user inputs (904), and in accordance with a determination that the first external computer system does not satisfy the one or more workout sharing criteria (910) (e.g., in accordance with a determination that the one or more workout sharing criteria are not satisfied by any external computer system with respect to the computer system), the computer system initiates (912) the workout session (in some embodiments, initiating the workout session includes initiating a user physical activity tracking function), including displaying, via the display generation component, content corresponding to the workout (e.g., initiating playback of video content corresponding to the workout), without displaying the first user interface (e.g., without sharing the video content corresponding to the workout session to a communication session of the first type).

In some embodiments, the one or more workout sharing criteria includes a second criterion that is met when the first external computer system satisfies one or more proximity criteria with respect to the computer system (e.g., when the first external computer system is within a threshold distance of the computer system (e.g., as indicated by signal strength information)). In some embodiments, the one or more workout sharing criteria includes a third criterion that is met when the first external computer system and the computer system are associated with the same user account (e.g., the same user account is logged into both the first external computer system and the computer system, and/or the same user account has previously logged into both the first external computer system and the computer system). In some embodiments, the communication session is a synchronized media and communication session. In some embodiments, the communication session of the first type enables the first external computer system to output respective content (e.g., synchronized content (e.g., audio and/or video data for which output is synchronized at the first external computer system and an external computer system (e.g., the one or more external computer systems)) and/or screen-share content (e.g., image data generated by a device (e.g., a computer system in the communication session of the first type) that provides a real-time representation of an image or video content that is currently displayed at the device)) while the respective content is being output by an external computer system of the one or more external computer systems. In some embodiments, during the communication session of the first type, respective content is concurrently output at both the first external computer system and the one or more external computer systems. In some embodiments, the respective content is screen-share content from the first external computer system (e.g., content displayed on the display of the first external computer system) that is transmitted to the one or more external computer systems so that the first external computer system and the one or more external computer systems are concurrently outputting the screen-share content from the first external computer system. In some embodiments, the respective content is screen-share content from a second external computer system of the one or more external computer systems (e.g., content displayed on the display of the second external computer system) that is transmitted to the first external computer system so that the first external computer system and the one or more external computer systems, including the second external computer system, are concurrently outputting the screen-share content from the second external computer system. In some embodiments, the respective content is synchronized content that is output at the first external computer system and the one or more external computer systems. In some embodiments, the first external computer system and the one or more external computer systems each separately access the respective content (e.g., a video; a movie; a TV show; a song) from a remote server and are synchronized in their respective output of the respective content such that the content is output (e.g., via an application local to the respective computer system) at the first external computer system and the one or more external computer systems while each computer system separately accesses the respective content from the remote server(s). In some embodiments, the first external computer system and one or more external computer systems separately access the respective content (e.g., synchronized content) in response to a selection that is received at the first external computer system or at one of the one or more external computer systems for requesting output of the respective content).

Displaying the first user interface in accordance with a determination that a first external computer system satisfies one or more workout sharing criteria provides the user with feedback about the current state of the device (e.g., that the computer system has detected a first external computer system that satisfies the one or more workout sharing criteria). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Concurrently displaying the first user interface object that is selectable to share content corresponding to the workout session and the second user interface object that is selectable to display content corresponding to the workout session without sharing the content provides the user with the ability to choose whether or not to share workout content. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the one or more workout sharing criteria includes a criterion that is satisfied when the first external computer system (e.g., 600A) is signed into a user account that is associated with the computer system (e.g., 800) (e.g., the computer system is also signed into the same user account; the computer system is associated with (e.g., signed into) multiple user accounts that includes the user account that the first external computer system is signed into). Displaying the option to share content corresponding to the workout session in accordance with a determination that the first external computer system is signed into a user account that is associated with the computer system enhances security by preventing unauthorized devices from sharing workout content. Providing improved security enhances the operability of the device and makes the user-device interface more efficient (e.g., by restricting unauthorized access) which, additionally, reduces power usage and improves battery life of the device by limiting the performance of restricted operations.

In some embodiments, the one or more workout sharing criteria includes a criterion that is satisfied when the first external computer system satisfies a proximity criteria relative to the computer system (e.g., device 600A satisfies proximity criteria relative to device 800D) (e.g., the first external computer system is determined to be within a predetermined distance of the computer system). Displaying the option to share content corresponding to the workout session in accordance with a determination that the first external computer system satisfies proximity criteria relative to the computer system enhances security by preventing unauthorized devices from sharing workout content. Providing improved security enhances the operability of the device and makes the user-device interface more efficient (e.g., by restricting unauthorized access) which, additionally, reduces power usage and improves battery life of the device by limiting the performance of restricted operations.

In some embodiments, in accordance with a determination that the first external computer system (e.g., 600A) (in some embodiments, any external computer system) satisfies the one or more workout sharing criteria, the computer system displays (in some embodiments, before detecting the set of one or more user inputs; after detecting the set of one or more user inputs), via the display generation component (e.g., 802), a first indicator (e.g., 812) that indicates that the one or more workout sharing criteria are currently satisfied; and in accordance with a determination that the one or more workout sharing criteria are not satisfied (e.g., not satisfied by the first external computer system), forgo displaying the first indicator. Displaying the first indicator in accordance with a determination that the first external computer system satisfies the one or more workout sharing criteria provides the user with feedback about the current state of the device (e.g., that the device has detected an external computer system that satisfies the one or more workout sharing criteria). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in accordance with a determination that the computer system has joined (e.g., has been added to; is now participating in) the communication session of the first type with the one or more external computers (in some embodiments, and while displaying the first visual indicator), the computer system displays, via the display generation component, a second indicator (e.g., 830) (e.g., that is different than the first indicator) that indicates that the computer system has joined the communication session of the first type with the one or more external computers. In some embodiments, the second visual indicator replaces the first visual indicator. Displaying the second indicator in accordance with a determination that the computer system has joined the communication session of the first type with the one or more external computers provides the user with feedback about the current state of the device (e.g., that the computer system has joined the communication session of the first type with the one or more external computers). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system detects, via the one or more input devices, a user input (e.g., 818) corresponding to the first user interface object (e.g., 816A). In response to detecting the user input corresponding to the first user interface object, the computer system causes the first external computer system (e.g., 600A) to display a request (e.g., 820) (e.g., as part of a notification) to confirm that the computer system should be added to the communication session of the first type with the one or more external computer systems. In some embodiments, the request includes a selectable user interface object that, when selected, causes the computer system to be added to the communication session of the first type. Causing the first external computer system to display a request to confirm that the computer system should be added to the communication session of the first type enhances security by preventing unauthorized devices from joining the communication session of the first type. Providing improved security enhances the operability of the device and makes the user-device interface more efficient (e.g., by restricting unauthorized access) which, additionally, reduces power usage and improves battery life of the device by limiting the performance of restricted operations.

In some embodiments, after completing the workout session, the computer system displays, via the display generation component, a workout summary user interface (e.g., 850A). In some embodiments, the workout summary user interface includes: physical activity data (e.g., calories burned data; heart rate data) collected by the computer system for a user of the computer system. In some embodiments, the workout summary user interface includes an indication of one or more external computer systems (e.g., an indication of users of the external computer systems) that were in the communication session of the first type with the computer system and that also participated in the workout session (e.g., a shared workout session). In some embodiments, the workout summary user interface is not displayed at the external computer system. Displaying a workout summary user interface provides the user with feedback about the current state of the device (e.g., that the workout session has ended). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while sharing content corresponding to the workout session to the one or more external computer system in the communication session of the first type, the computer system receives (e.g., from an external device; from an application executing on the computer system) notification data. In response to receiving the notification data: in accordance with a determination that the notification data is associated with the communication session of the first type (e.g., the notification data is received from the one or more external computer systems; the notification relates to a communication from one of the participants in the communication session), the computer system displays a first notification (e.g., 840, 846A) (e.g., a communication from the one or more external computer systems) at a first location of the display generation component (e.g., FIGS. 8E, 8G); and in accordance with a determination that the notification data is associated with the workout session (e.g., is associated with a workout application managing the workout session), the computer system displays a second notification (e.g., 848A) (e.g., a workout-related notification) at a second location on the display, different than the first location (e.g., FIG. 8H). In some embodiments, the first and second locations are non-overlapping. Displaying notifications associated with the communication session of the first type at a first display location, and displaying notifications associated with the workout session at a second display location, provides the user with feedback about the current state of the device (e.g., whether a particular notification pertains to the communication session of the first type or to the workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first notification indicates that a second external computer system is, via the communication session of the first type (e.g., via one or more communication protocols of the communication session of the first type), beginning to display the content corresponding to the workout session or ceasing to display the content corresponding to the workout session (e.g., 840, 846A) (e.g., is joining or leaving the workout session, which is a shared workout session). Displaying a notification that a second external computer system is beginning to display the content corresponding to the workout session or ceasing to display the content corresponding to the workout session provides the user with feedback about the current state of the device (e.g., that the device has detected and/or received information about the second external computer system beginning to display and/or ceasing to display the content corresponding to the workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first notification (e.g., a communication session status notification) indicates that a third external computer system is joining (in some embodiments, has joined) the communication session of the first type or leaving (in some embodiments, has left) the communication session of the first type (e.g., 685A, 685B). Displaying a notification that a third external computer system is joining the communication session of the first type or leaving the communication session of the first type provides the user with feedback about the current state of the device (e.g., that the device has detected and/or received information about the third external computer system joining and/or leaving the communication session of the first type). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second notification is a notification that includes first information related to the workout session for the computer system or for one or more external computer systems that are in the communication session of the first type and that are displaying the content corresponding to the workout session (e.g., notifications 672A, 672B, 672C in FIG. 6M and/or notifications 848A, 848B in FIG. 8H). In some embodiments, the second notification can be a workout-related notification from any user in the communication session of the first type that is participating in the workout session. Displaying notifications pertaining to the workout session for the computer system or for one or more external computer systems provides the user with feedback about the current state of the device (e.g., that the device has detected and/or received first information related to the workout session). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first information is an indication that a user of a fourth external computer system that is in the communication session of the first type and that is displaying the content the content corresponding to the workout session has achieved a predetermined physical activity goal (e.g., met a calorie target, met activity intensity level target) or has achieved a change in status relative to one or more other participants for a first workout that corresponds to the workout session (e.g., the user has achieved a level of physical activity that places the user within a predetermined segment of participants (e.g., participants in the shared workout session; participants who are not in the shared workout session but have also participated in the first workout)) (e.g., 848A, 848B). Displaying a notification indicating that a user of the fourth external computer system has achieved a predetermined physical activity goal or has achieved a change in status relative to one or more other participants in the first workout provides the user with feedback about the current state of the device (e.g., that the device has detected and/or received information indicating that the user of the fourth external computer system has achieved a predetermined physical activity goal or has achieved a change in status relative to one or more other participants in the first workout). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while sharing the content corresponding to the workout session, the computer system receives a user input (e.g., 678) corresponding to a request to initiate a process for ending the display of content corresponding to the workout session. In response to receiving the user input corresponding to a request to initiate a process for ending the display of content corresponding to the workout session, the computer system displays: a first end option (e.g., 680C-1) that, when selected, causes the computer system to cease displaying the content corresponding to the workout session (e.g., leave the shared workout session for just the user of the computer system), without causing at least one external computer system that is in the communication session of the first type and that is displaying the content corresponding to the workout session to cease displaying (in some embodiments, and to end a workout at the external computer system that is associated with the workout session) the content corresponding to the workout session; and a second end option (e.g., 680C-2) that, when selected, causes the computer system to cease sharing the content corresponding to the workout session (in some embodiments, cease displaying the content corresponding to the workout session) and causes at least one external computer system (in some embodiments, all computer systems participating in the workout session (e.g., end the workout session for all participants)) that is in the communication session of the first type and that is displaying the content corresponding to the workout session to cease displaying (in some embodiments, and to end the workout session at the external computer system) the content corresponding to the workout session. Concurrently displaying a first end option that is selectable to cause the computer system to cease displaying the content corresponding to the workout session and a second end option that is selectable to cause multiple computer systems to cease displaying the content corresponding to the workout session provides the user with the ability to end the workout for only themselves, or to end the workout for multiple computer systems. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while sharing the content corresponding to the workout session and while there is a fifth external computer system that is participating in the communication session of the first type and that is displaying the content corresponding to the workout session, the computer system receives a user input (e.g., 664) corresponding to a request pause the workout session (e.g., pausing display of the content corresponding to the workout session; pause sharing of the content). In response to receiving the user input corresponding to the request to pause the workout session: the computer system pauses the workout session (e.g., pausing display of the content corresponding to the workout session at the display generation component (e.g., without ending the workout session)) (e.g., FIG. 6K); and causes the fifth external computer system to pause display of the content corresponding to the workout session (e.g., FIG. 6K). In some embodiments, after pausing the workout, the computer system receives a user input corresponding to a request to resume the workout, and in response, resumes the workout at the computer system and at the fifth external computer system. Pausing display of content corresponding to the workout session on multiple computer systems in response to a user input on the computer system provides the user with the capability to pause the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while sharing the content corresponding to the workout session and while there is a sixth external computer system that is participating in the communication session of the first type and that is displaying the content corresponding to the workout session, the computer system receives a request from the sixth external computer system to end the workout session (e.g., a request initiated by selection of an "end for all" option at the sixth external computer system). In response to receiving the request from the sixth external computer system, the computer system ends the workout session (e.g., ceasing to share and/or ceasing to display the content corresponding to the workout session). Ending the workout session automatically in response to a received request from the sixth external computer system provides a user with the capability to end the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while sharing the content corresponding to the workout session and while there is a seventh external computer system that is participating in the communication session of the first type and that is displaying the content corresponding to the workout session, the computer system receives a request from the seventh external computer system to pause the content (in some embodiments, to pause sharing of and/or display of the content) corresponding to the workout session (e.g., a request initiated by selection of an "pause" option at the seventh external computer system). In response to receiving the request from the seventh external computer system, the computer system pauses sharing of the content corresponding to the workout session (e.g., FIG. 6K) (e.g., without ending the shared workout session). In some embodiments, after pausing display of the content, receiving an indication that an external computer system in the communication session of the first type has resumed display of the content, and in response to that indication, resuming sharing of the content corresponding to the shared workout session. Pausing display of the content corresponding to the workout session in response to a received request from the seventh external computer system provides a user with the capability to pause the workout content on multiple computer systems without requiring further inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while displaying the first user interface, the computer system detects, via the one or more input devices, a first set of selection inputs (e.g., one or more user inputs received via a remote control) (e.g., one or more tap inputs and/or one or more non-tap inputs) (e.g., 818) corresponding to selection of the first user interface object (e.g., 816A). In response to detecting the first set of selection inputs, the computer system receives (in some embodiments, requesting and receiving), from a second external computer system (e.g., a smart phone, a tablet, a smart watch) (e.g., 805A, 805B) different from the first external computer system (e.g., 600A) and the computer system (e.g., 800), user identification information corresponding to a user (e.g., user physical activity metrics, a user name, a user alias, and/or a user identification photo and/or image) (e.g., 844A). In some embodiments, the user corresponds to the second external computer system (e.g., 805A, 805B) (e.g., is registered on the second external computer system as a user of the second external computer system). Automatically receiving user identification information corresponding to a user in response to one or more selection inputs corresponding to selection of the first user interface object allows the computer system to receive user identification information without requiring additional user inputs. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, subsequent to receiving the user identification information from the second external computer system: the computer system (e.g., 800) displays, via the display generation component (e.g., 802), the user identification information (e.g., 815, 844A) concurrently with content corresponding to the workout session (e.g., 826)

(e.g., video content corresponding to the workout session (e.g., an instructional video demonstrating a workout for the workout session) (e.g., video content that is synchronized across the plurality of computer systems participating in the communication session of the first type (e.g., participating in the shared workout session))). The computer system causes the one or more external computer systems (e.g., 600B) in the communication session of the first type to display the user identification information (e.g., 848B) concurrently with content corresponding to the workout session (e.g., 826B). Displaying the user identification information concurrently with content corresponding to the workout session provides the user with feedback about the current state of the device (e.g., that the device has received user identification information). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the user identification information corresponding to the user is received from the second external computer system (e.g., 805A, 805B) in accordance with a determination that a second set of selection inputs (e.g., 813) received at the computer system (e.g., one or more user inputs received via a remote control) (e.g., one or more tap inputs and/or one or more non-tap inputs) corresponds to (e.g., are indicative of) selection of the second external computer system (e.g., by a user) from a plurality of external computer systems (e.g., a plurality of external computer systems in communication with and/or detected by the computer system) (e.g., FIG. 8A-2). Providing a user with options to select the second external computer system from a plurality of external computer systems provides the user with the ability to select the appropriate external computer system from which the computer system should receive user identification information. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 900 (e.g., FIG. 9) are also applicable in an analogous manner to the methods described above and/or below. For example, methods 700, 750, and 1100 optionally include one or more of the characteristics of the various methods described above with reference to method 900. For example, the communication session of the first type recited in methods 700, 750, 900, and 1100 are the same communication session in all three methods. For brevity, these details are not repeated above.

FIGS. 10A-10K illustrate exemplary user interfaces for displaying and sharing group workout content, in accordance with some embodiments. The user interfaces in these figures are used to illustrate the processes described below, including the process in FIG. 11.

FIGS. 10A-10K illustrate exemplary devices and user interfaces. At FIG. 10A, electronic device 800 is displaying workout user interface 826 on display 802. Workout interface 826 includes workout physical activity metrics 842A and daily physical activity metrics 844A that correspond to a first user ("John"), as described above, for example, with reference to FIG. 8F.

Similarly, electronic device 600B displays, via display 602B, workout user interface 826B that includes workout physical activity metrics 842B and daily physical activity metrics 844B that correspond to a second user ("Jane"), as described above, for example, with reference to FIG. 8F. As also described above, electronic device 800 and electronic device 600B are participating in a communication session of a first type, and workout user interfaces 826, 826B correspond to a group workout session such that workout content that is displayed on device 800 is synchronized with workout content that is displayed on device 600B.

In FIG. 10A, electronic device 800 is connected to (e.g., wirelessly connected to) electronic device 1000A which, in the depicted embodiment, is a smart watch with display 1002A. For example, in some embodiments, electronic device 800 is connected to electronic device 1000A via a short range communication medium (e.g., near field communications and/or Bluetooth). In some embodiments, electronic device 1000A includes one or more sensors that measure physical activity metrics (e.g., heart rate sensor, blood oxygen level sensor, gyroscope, and/or accelerometer) for a user, and transmits measured physical activity metrics to electronic device 800. Similarly, electronic device 600B is connected to (e.g., wirelessly connected to) electronic device 1000B, which is a smart watch with display 1002B, and electronic device 1000B includes one or more sensors that measure physical activity metrics for a user, and transmits measured physical activity metrics to electronic device 600B.

In FIG. 10A, electronic device 1000A displays physical activity metrics user interface 1004A, which displays one or more physical activity metrics for a user of electronic device 1000A (e.g., a heartrate of 154 beats per minute, 2 active calories burned during the current group workout session, and 5 total calories burned during the current group workout session). Physical activity metrics user interface 1004A also includes quick send option 1006A, which is selectable to cause one or more electronic devices participating in the group workout session to display visual content corresponding to quick send option 1006A, as will be described in greater detail below. In some embodiments, physical activity metrics user interface 1004A includes quick send option 1006A in accordance with a determination that electronic device 1000A is participating in a group workout session (in some embodiments, in accordance with a determination that electronic device 800, which is connected to electronic device 1000A, is participating in a group workout session). In some embodiments, if electronic device 1000A was not participating in a group workout session (e.g., was displaying physical activity metrics for an individual workout session), physical activity metrics user interface 1004A would not include quick send option 1006A. Similarly, electronic device 1000B displays physical activity metrics user interface 1004B which displays one or more physical activity metrics for the user of electronic device 1000B. Physical activity metrics user interface 1004B also includes quick send option 1006B, which will be described in greater detail below.

At FIG. 10A, while displaying physical activity metrics user interface 1004B, electronic device 1000B detects user input 1008, which is a swipe left gesture on touch-screen display 1002B.

Figure 10B:
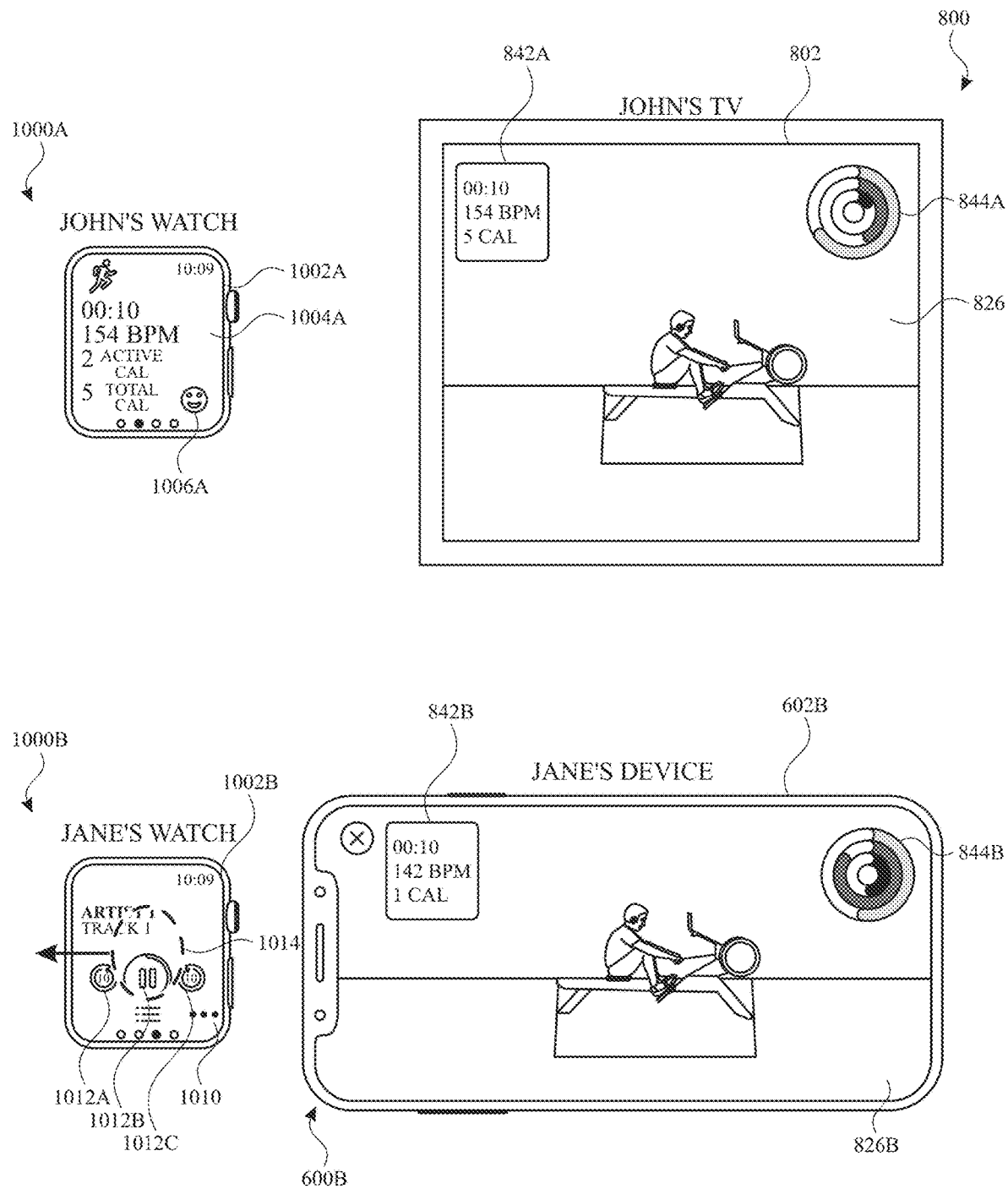

At FIG. 10B, in response to user input 1008, electronic device 1000B replaces display of physical activity metrics user interface 1004B with music user interface 1010. Music user interface 1010 includes information pertaining to an audio track that is currently playing (e.g., "ARTIST 1" and "TRACK 1"), and also includes playback options 1012A-1012C that are selectable to modify playback of the audio track (e.g., skip forward or backward 10 seconds, pause playback).

At FIG. 10B, while displaying music user interface 1010, electronic device 1000B detects user input 1014, which is a swipe left gesture on touch-screen display 1002B.

Figure 10C:
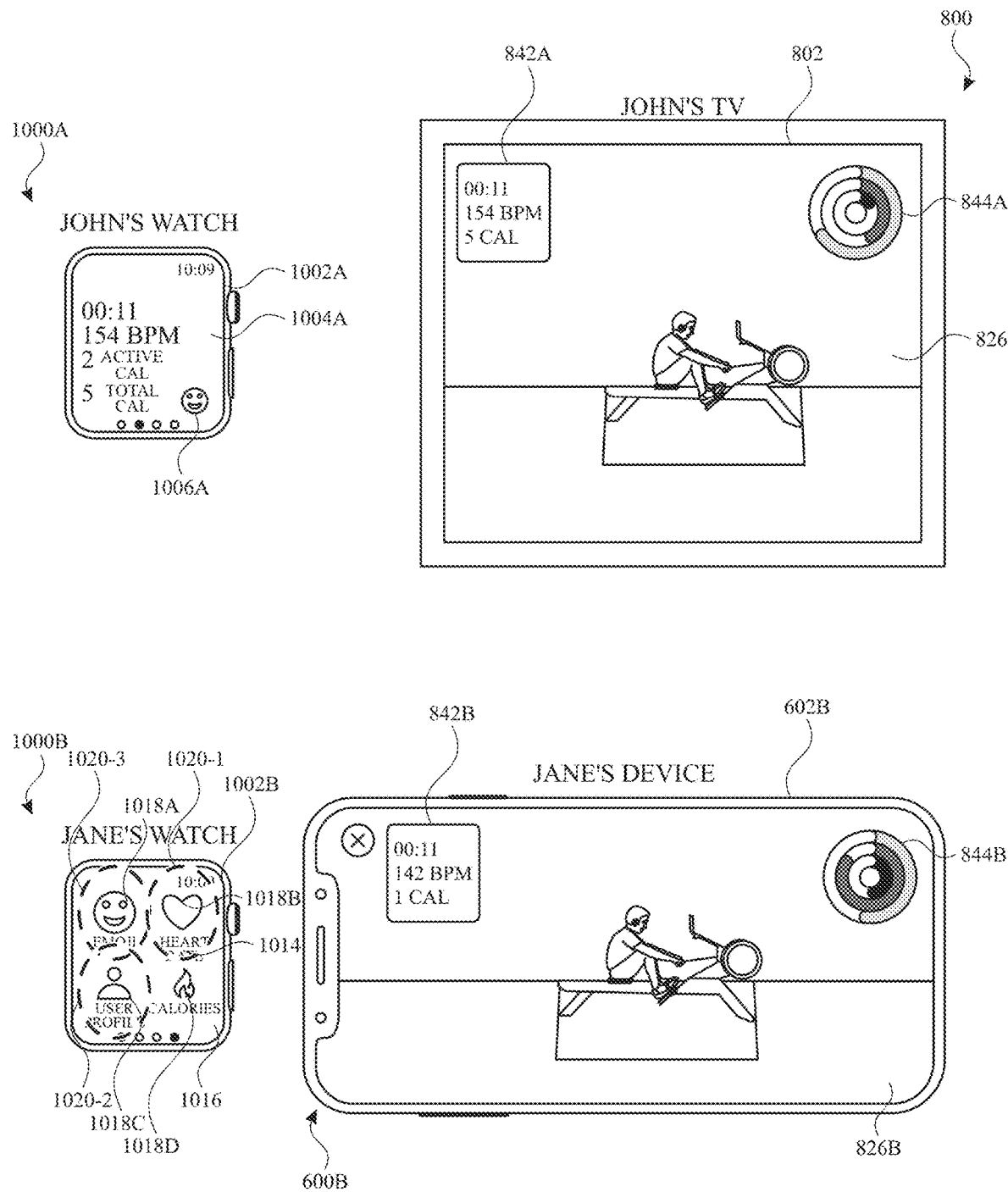

At FIG. 10C, in response to user input 1014, electronic device 1000B replaces display of music user interface 1010 with shout out user interface 1016. In some embodiments, shout out user interface 1016 is only accessible and/or available in accordance with a determination that electronic device 1000B is participating in a group workout session (e.g., in accordance with a determination that electronic device 600B, which is connected to electronic device 1000B, is participating in a group workout session). For example, in some embodiments, if electronic device 1000B was displaying physical activity metrics corresponding to an individual workout session, rather than a group workout session, shout out user interface 1016 would not be accessible, and user input 1014 would result in electronic device 1000B continuing to display music user interface 1010. Shout out user interface 1016 includes various options that are selectable to cause electronic devices participating in the group workout session to display visual effects corresponding to the selected option (e.g., in addition to displaying visual content of the group workout session (e.g., video content demonstrating the group workout, workout physical activity metrics, and/or daily physical activity metrics)), as will be demonstrated in greater detail below in later figures. Shout out user interface 1016 includes emoji option 1018A that is selectable to access an emoji user interface (e.g., FIG. 10F), heart rate option 1018B that is selectable to cause electronic devices participating in the group workout session to display a visual effect that includes a current heart rate of the user of electronic device 1000B, user profile option 1018C that is selectable to cause electronic devices participating in the group workout session to display a visual effect that includes a user profile image of the user of electronic device 1000B, and calories option 1018D that is selectable to cause electronic devices participating in the group workout session to display a visual effect that includes the current number of calories burned (e.g., within the group workout session) by the user of electronic device 1000B.

At FIG. 10C, electronic device 1000B detects user input 1020-1 (e.g., a tap input) corresponding to selection of option 1018B, user input 1020-2 (e.g., a tap input) corresponding to selection of option 1018C, and user input 1020-3 (e.g., a tap input) corresponding to selection of option 1018A. Each of these scenarios and user inputs will be described in turn below.

Figure 10D:
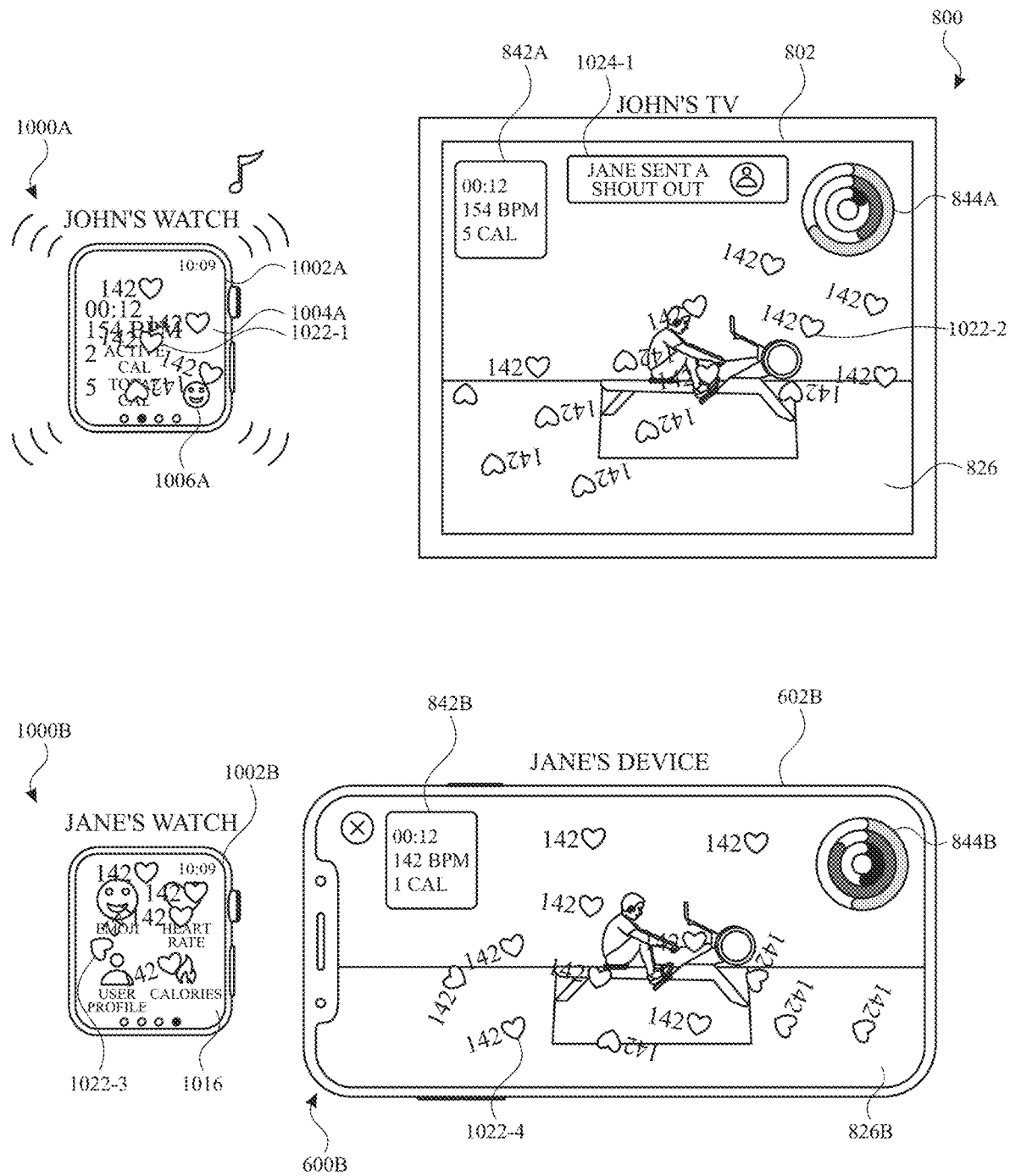

At FIG. 10D, in response to detecting user input 1020-1 corresponding to selection of heart rate option 1018B, electronic device 1000B displays visual effect 1022-3 that includes displaying a current heart rate for the user of electronic device 1000B (142 beats per minute). Furthermore, electronic device 1000B transmits to electronic device 600B an indication of user input 1020-1. In response to receiving the indication of user input 1020-1, electronic device 600B displays visual effect 1022-4 corresponding to heart rate option 1018B. Electronic device 600B also transmits (e.g., via the communication session of the first type) to electronic device 800 an indication of user input 1020-1. In response to receiving the indication of user input 1020-1, electronic device 800 displays visual effect 1022-2 corresponding to heart rate option 1018B, and also displays notification 1024-1 indicating that the user of electronic device 1000B has shared a shout out to the group workout session. In response to receiving the indication of user input 1020-1, electronic device 800 also transmits to electronic device 1000A an indication of user input 1020-1. In response to receiving the indication of user input 1020-1, electronic device 1000A displays visual effect 1022-1, and outputs a haptic output (e.g., a vibration) and an audio output (e.g., a chime or noise) indicating that a shout out has been received within the group workout session. In this way, user input 1020-1 corresponding to selection of heart rate option 1018B causes a plurality of devices participating in the group workout session (in some embodiments, all devices participating in the group workout session and/or some devices participating in the group workout session) to display a visual effect corresponding to selected option 1018B, and also causes at least a subset of the devices (e.g., wearable devices (e.g., smart watches)) to output haptic and/or audio output.

Figure 10E:
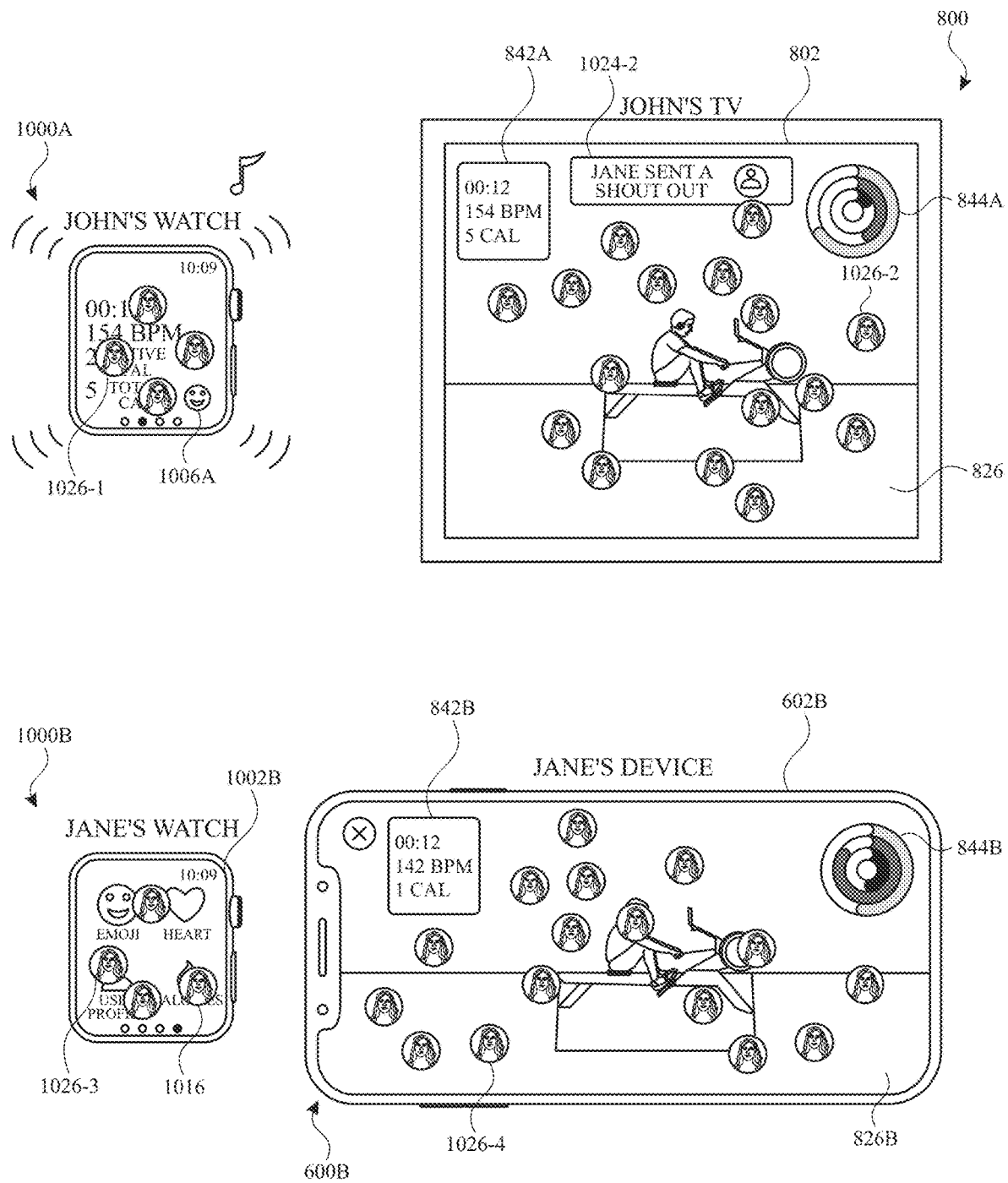

At FIG. 10E, similar to what was described above with reference to FIG. 10D, user input 1020-2 corresponding to selection of user profile option 1018C causes electronic devices 1000A, 800, 1000B, and 600B to display visual effects 1026-1, 1026-2, 1026-3, and 1026-4, respectively, which correspond to user profile option 1018C. In the depicted embodiment, visual effects 1026-1, 1026-2, 1026-3, and 1026-4 include display of a user profile picture corresponding to the user of electronic device 1000B. Furthermore, as described above with reference to FIG. 10D, user input 1020-2 causes electronic device 1000A to output a haptic output and an audio output.

Figure 10F:
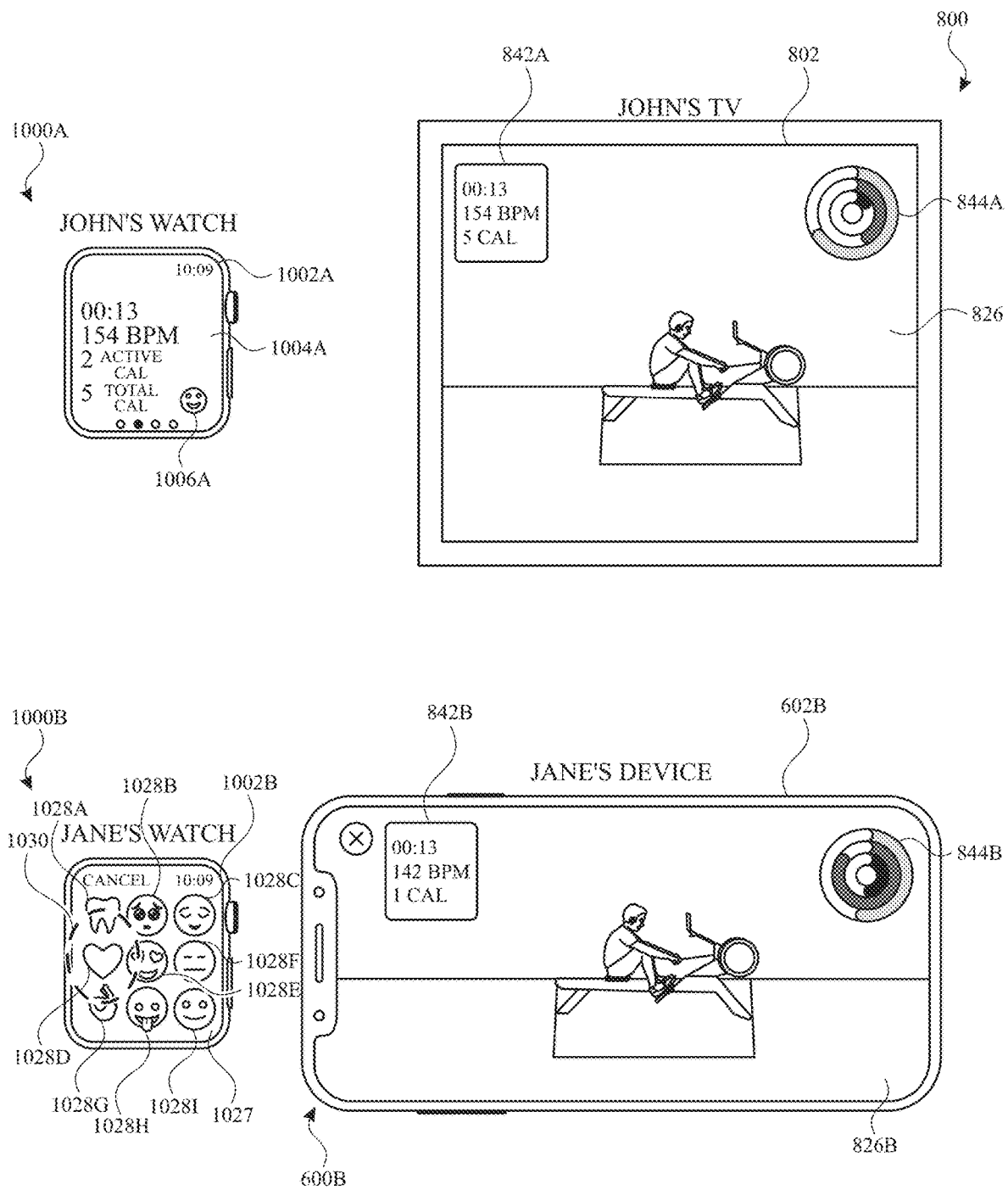
Figure 10G:
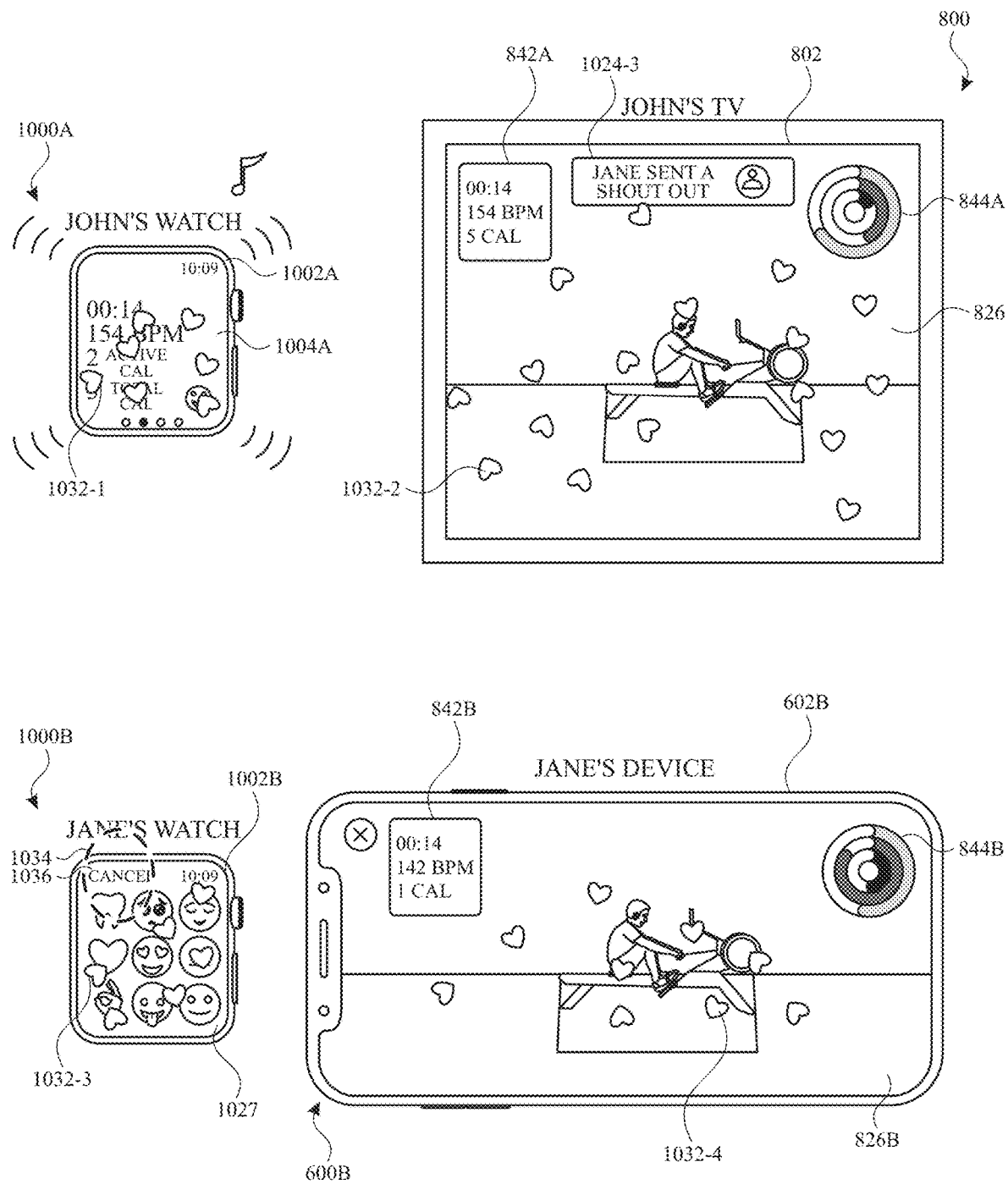

At FIG. 10F, in response to user input 1020-3 corresponding to selection of emoji option 1018A, electronic device 1000B replaces display of shout out user interface 1016 with emoji user interface 1027. Emoji user interface 1027 includes a plurality of selectable options 1028A-1028I. Each selectable option 1028A-1028I corresponds to a respective emoji, and selection of a respective option 1028A-1028I causes electronic devices participating in the group workout to display a visual effect corresponding to the respective option (e.g., displaying the respective emoji corresponding to the respective option). For example, in FIG. 10F, electronic device 1000B detects user input 1030 (e.g., a tap input) corresponding to selection of heart emoji option 1028D. In FIG. 10G, in response to user input 1030, electronic devices 1000A, 800, 100B, 600B display visual effects 1032-1, 1032-2, 1032-3, and 1032-4, respectively, which correspond to heart emoji option 1028D. Furthermore, in response to user input 1030, electronic device 1000A outputs a haptic output and an audio output.

At FIG. 10G, while display emoji user interface 1027, electronic device 1000B detects user input 1036 (e.g., a tap input) corresponding to selection of cancel option 1034. At FIG. 10H, in response to user input 1036, electronic device 1000B replaces display of emoji user interface 1027 with shout out user interface 1016.

Figure 10H:
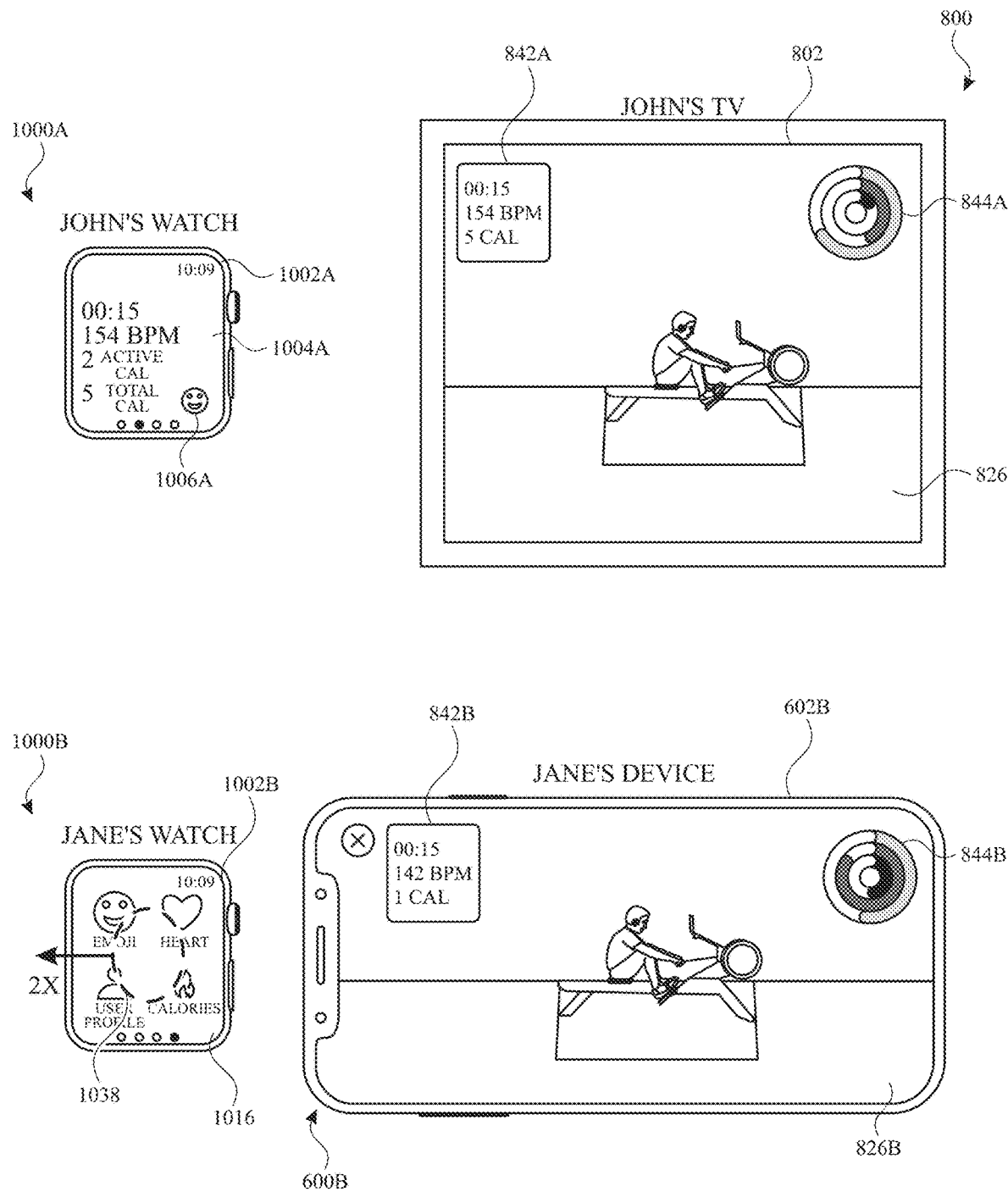

At FIG. 10H, electronic device 1000B detects two swipe right user inputs 1038. At FIG. 10I, in response to user input 1038, electronic device 1000B displays physical activity metrics user interface 1004B.

As previously discussed above with reference to FIG. 10A, physical activity metrics user interface 1004B includes quick send option 1006B. In FIG. 10A, quick send option 1006B was a smiley face emoji such that selection of quick send option 1006B would have caused electronic devices participating in the group workout session to display the smiley face emoji. However, in FIG. 10I, based on a determination that the most recent shout out transmitted from electronic device 1000B was the heart emoji (e.g., in FIG. 10G) (e.g., in response to user input 1030), quick send option 1006B has been updated to display the most recently selected shout out option (e.g., the heart emoji). As such, in some embodiments, quick send option 1006B is updated based on a most recently selected (e.g., most recently transmitted) shout out option to allow the user to re-transmit the most recently selected shout out option. In contrast to electronic device 1000B, physical activity metrics user interface 1004A on electronic device 1000A continues to display a default smiley face emoji as quick send option 1006A because the user of electronic device 1000A has not yet transmitted any shout outs during the current group workout session.

Figure 10I:
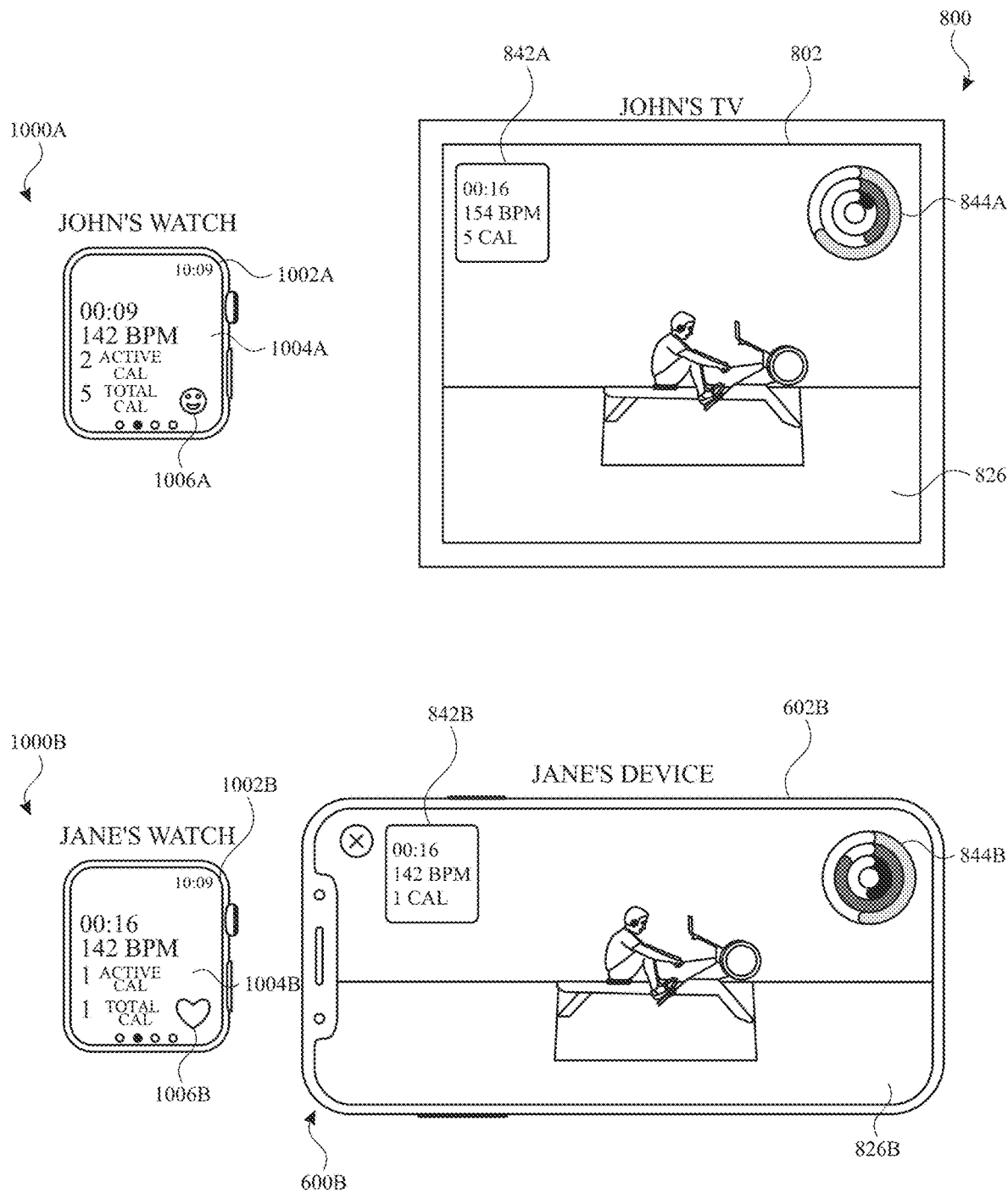
Figure 10J:
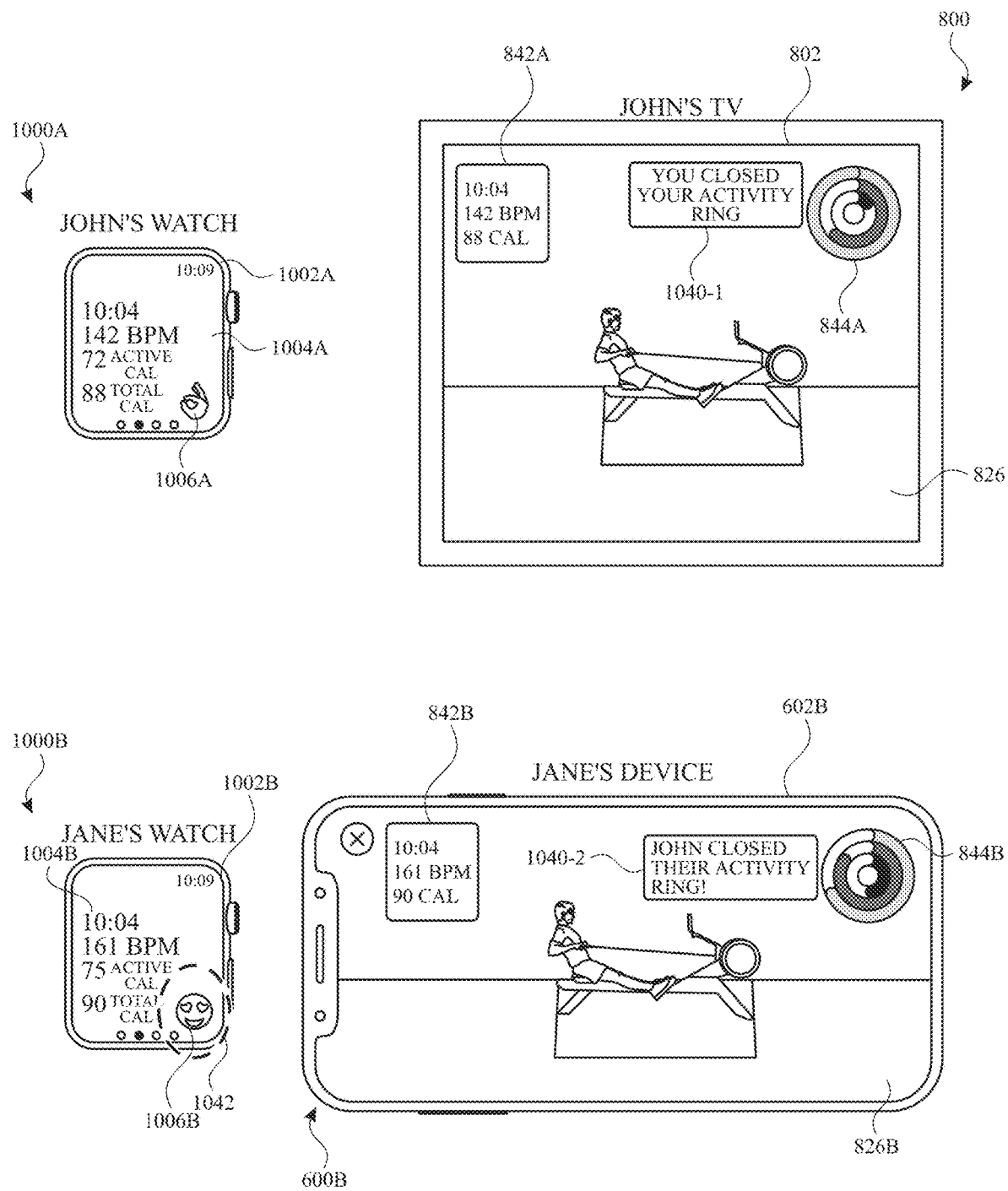
Figure 10K:
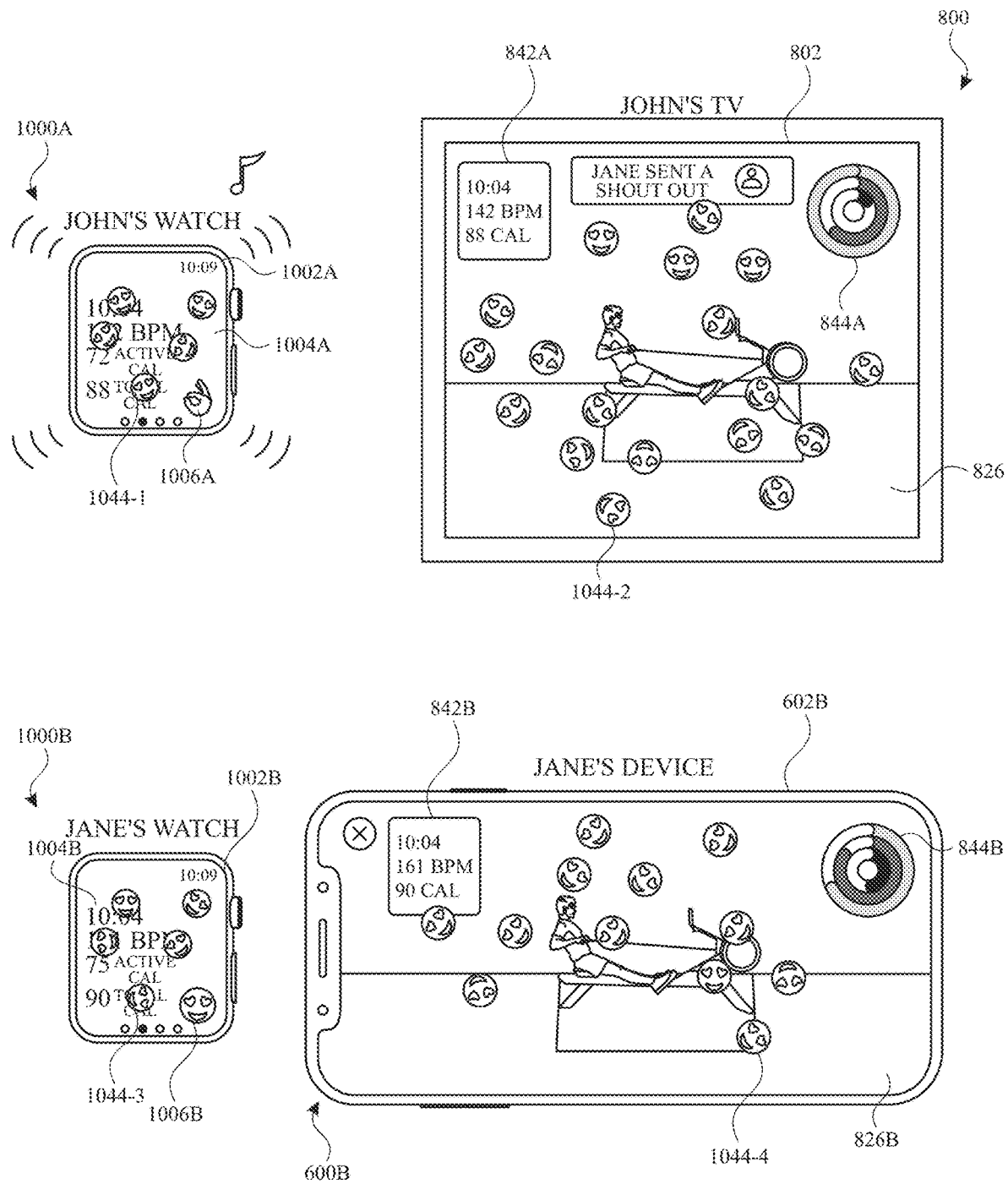

At FIG. 10J, electronic device 800 and/or electronic device 1000A determines that the user of electronic device 800 and/or 1000A has accomplished a goal (e.g., a physical activity goal (e.g., a daily physical activity goal)). In response to this determination, electronic device 800 displays notification 1040-1, and transmits an indication to electronic device 600B that the user of electronic device 800 has accomplished the goal. In response to receiving this indication, electronic device 600B also displays notification 1040-2. Furthermore, in response to the determination that the user of electronic device 800 has accomplished the goal, quick send option 1006A is updated to a "OK" emoji, and quick send option 1006B is updated to a heart eyes emoji. Accordingly, in some embodiments, quick send options 1006A, 1006B are updated based on one or more events that are detected within the group workout session. Although the depicted examples show primarily images and/or emojis as the shout out options (including the quick send option), other types of visual content can be used, such as a message of encouragement and/or a message of competition (e.g., trash talking).

At FIG. 10J, electronic device 1000B detects user input 1042 (e.g., a tap input) corresponding to selection of quick send option 1006B. At FIG. 10K, in response to user input 1042, electronic devices 1000A, 800, 1000B, and 600B display visual effects 1044-1, 1044-2, 1044-3, and 1044-4, respectively, corresponding to quick send option 1006B (e.g., heart eyes emojis).

In some embodiments, users participating in a group workout session are provided with the option to forego displaying shout out visual effects. In some embodiments, if a user opts to forego displaying shout out visual effects, the user's electronic device does not display visual content corresponding to a selected shout out option.

FIG. 11 is a flow diagram illustrating a method for displaying and sharing group workout content using a computer system in accordance with some embodiments. Method 1100 is performed at a computer system (e.g., 100, 300, 500) that is in communication with a display generation component, one or more input devices, and a first external computer system. Some operations in method 1100 are, optionally, combined, the orders of some operations are, optionally, changed, and some operations are, optionally, omitted.

As described below, method 1100 provides an intuitive way for displaying and sharing group workout content. The method reduces the cognitive burden on a user for displaying and sharing group workout content, thereby creating a more efficient human-machine interface. For battery-operated computing devices, enabling a user to display and share group workout content faster and more efficiently conserves power and increases the time between battery charges.

A computer system (e.g., a wearable device, a smart watch, a smart phone, a tablet, a digital media player) (e.g., 1000A, 1000B) that is in communication with a display generation component (e.g., 1002A, 1002B) (e.g., a display controller; a touch-sensitive display system; and/or a display (e.g., integrated and/or connected)) and one or more input devices (e.g., 1002A, 1002B) (e.g., a touch-sensitive surface (e.g., a touch-sensitive display); a mouse; a keyboard; and/or a remote control), displays (1102), via the display generation component, a user interface (e.g., 1004A, 1004B) (e.g., a fitness application workout user interface) corresponding to a workout session. In some embodiments, a workout session includes display of visual content (e.g., video content) (e.g., visual content demonstrating the workout) via a display generation component (in some embodiments, a second display generation component separate from the display generation component (in some embodiments, a second display generation component in communication with an external computer system different from the computer system)). In some embodiments, initiating the workout session includes initiating recording of one or more physical activity metrics (e.g., heartrate and/or calories burned) for the workout session (e.g., via one or more sensors in communication with the computer system). In some embodiments, initiating the workout session includes recording one or more physical activity metrics at a greater frequency than prior to initiation of the workout session.

The user interface (e.g., 1004A, 1004B) includes one or more physical activity metrics (e.g., elapsed time of workout session, heartrate, and/or calories burned) corresponding to the workout session (e.g., one or more physical activity metrics measured and/or recorded during the workout session). While displaying the user interface corresponding to the workout session, the computer system detects (1104), via the one or more input devices, one or more user inputs (e.g., 1008, 1014) (e.g., one or more touch inputs, one or more tap inputs, one or more non-touch inputs, and/or one or more non-tap inputs) (e.g., detecting at least a first user input of a sequence of user inputs (e.g., a single user input and/or a plurality of user inputs) while displaying the user interface corresponding to the workout session). In some embodiments, the one or more user inputs is a sequence of a plurality of user inputs, and at least one user input of the sequence of user inputs is detected while displaying the user interface corresponding to the workout session and at least one user input of the sequence of user inputs is detected subsequent to displaying the user interface (e.g., while the user interface is not displayed and/or while a different user interface is displayed).

In response to detecting the one or more user inputs (1106) and in accordance with a determination that the workout session is a shared workout session with one or more external computer systems (e.g., 800, 1000A) (e.g., one or more remote computer systems) (e.g., one or more external computer systems participating in a communication session of a first type with the computer system) (e.g., in accordance with a determination that the workout session is a shared workout session in which a plurality of computer systems, including the one or more external computer systems, are displaying workout content in a synchronized manner), the computer displays (1108), via the display generation component, a first set of one or more options (e.g., 1018A-1018D), wherein the first set of one or more options includes a first option (e.g., 1018A-1018D) (e.g., an affordance; a user-selectable graphical element) that, when selected, causes the one or more external computer systems (e.g., 800, 1000A) (in some embodiments, an instruction is transmitted (e.g., directly or indirectly) to the one or more external computer systems) participating in the shared workout session to display visual content corresponding to the first option (e.g., 1022-1-1022-4, 1026-1-1026-4, FIGS. 10D, 10E). In some embodiments, the first set of one or more options includes a second option (e.g., 1018A-1018D) different from the first option that, when selected, causes the one or more external computer systems (e.g., 800, 1000A) participating in the shared workout session to display visual content corresponding to the second option (e.g., 1022-1-1022-4, 1026-1-1026-4, FIGS. 10D, 10E), wherein the visual content corresponding to the second option is different from the visual content corresponding to the first option. In some embodiments, the first option is selectable to cause the one or more external computer systems participating in the shared workout session to display visual content corresponding to the first option while concurrently displaying video content corresponding to the shared workout session (e.g., 826, 826B) (e.g., video content separate from the visual content corresponding to the first option). In some embodiments, the video content corresponding to the shared workout session is displayed at each of the one or more external computer systems in a synchronized manner.

In some embodiments, the one or more external computer systems are participating in a communication session of a first type with the computer system (e.g., participating in the shared workout session includes participating in the communication session of the first type). In some embodiments, the communication session of the first type includes audio communication, video communication, and/or text-based communication. In some embodiments, the communication session is a synchronized media and communication session. In some embodiments, the communication session of the first type enables the computer system to output respective content (e.g., synchronized content (e.g., audio and/or video data for which output is synchronized at the computer system and an external computer system (e.g., the one or more external computer systems)) and/or screen-share content (e.g., image data generated by a device (e.g., a computer system in the communication session of the first type) that provides a real-time representation of an image or video content that is currently displayed at the device)) while the respective content is being output by the first external computer system. In some embodiments, during the communication session of the first type, respective content is concurrently output at both the computer system and the one or more external computer systems. In some embodiments, the respective content is screen-share content from the computer system (e.g., content displayed on the display of the computer system) that is transmitted to the one or more external computer systems so that the computer system and the one or more external computer systems are concurrently outputting the screen-share content from the computer system. In some embodiments, the respective content is screen-share content from the first external computer system (e.g., content displayed on the display of the first external computer system) that is transmitted to the computer system so that the computer system and the one or more external computer systems, including the first external computer system, are concurrently outputting the screen-share content from the first external computer system. In some embodiments, the respective content is synchronized content that is output at the computer system and the one or more external computer systems. In some embodiments, the computer system and the one or more external computer systems each separately access the respective content (e.g., a video; a movie; a TV show; a song) from a remote server and are synchronized in their respective output of the respective content such that the content is output (e.g., via an application local to the respective computer system) at the computer system and the one or more external computer systems while each computer system separately accesses the respective content from the remote server(s). In some embodiments, the computer system and one or more external computer systems separately access the respective content (e.g., synchronized content) in response to a selection that is received at the computer system or at one of the one or more external computer systems for requesting output of the respective content.

In some embodiments, in response to detecting the one or more user inputs: in accordance with a determination that the workout session is not a shared workout session (e.g., is an individual workout session and/or is a workout session that includes only one user) (e.g., is a workout session that is not shared amongst a plurality of computer systems that are participating in a communication session of a first type) (e.g., is a workout session that is not displayed at a plurality of computer systems in a synchronized manner), the computer system forgoes displaying the first set of one or more options (e.g., displaying a second user interface that does not include the first set of one or more options). In some embodiments, the method further comprises: in response to detecting the one or more user inputs, in accordance with a determination that the workout session is not a shared workout session, the computer system displays a second user interface that does not include the one or more options (e.g., does not include the first option).

In some embodiments, the computer system (e.g., 1000B) is in communication with a first external computer system (e.g., 600B) (e.g., a smart phone, a tablet; a digital media player; a computer set top entertainment box; a smart TV; a computer system controlling an external display) (e.g., a first external computer system different from the computer system). In some embodiments, the computer system is in communication with the first external computer system using a local communication modality (e.g., Bluetooth, near-field communications, and/or a local network), and while the computer system displays the user interface corresponding to the workout session (e.g., 1004B), the first external computer system displays video content corresponding to the workout session (e.g., 826B). In some embodiments, the computer system and the first external computer system correspond to a first user. Displaying the first set of one or more options that are selectable to cause one or more external computer systems participating in the shared workout session to display visual content corresponding to the selected option provides the user with the ability to cause the one or more external computer systems to display visual content selected by the user. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system (e.g., 1000B) is in communication with a first external electronic device (e.g., 600B) (e.g., a smart phone, a tablet; a digital media player; a computer set top entertainment box; a smart TV; a computer system controlling an external display) (e.g., a first external computer system different from the computer system) (in some embodiments, the computer system is in communication with the first external computer system using a local communication modality (e.g., Bluetooth, near-field communications, and/or a local network). While the computer system displays the user interface corresponding to the workout session (e.g., 1004B), the first external electronic device displays (in some embodiments, the computer system causes the first external electronic device to display the content) video content corresponding to the workout session (e.g., an instructional video demonstrating a workout) (e.g., 826B). In some embodiments, the computer system and the first external electronic device correspond to a first user (e.g., are both associated with a user account of the first user). Causing an external electronic device to display video content corresponding to the workout session while the computer system displays physical activity metrics of the user allows a user to simultaneously view different sets of information on different devices without additional user input. Increasing the amount of information visible to a user while minimizing the number of user inputs required enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to detecting the one or more user inputs and in accordance with a determination that the workout session is not a shared workout session (e.g., is an individual workout session and/or is a workout session that includes only one user) (e.g., is a workout session that is not shared amongst a plurality of computer systems that are participating in a communication session of a first type) (e.g., is a workout session that is not displayed at a plurality of computer systems in a synchronized manner), the computer system forgoes displaying the first set of one or more options (e.g., 1018A-1018D) (e.g., displays a second user interface that does not include the first set of one or more options). In some embodiments, in response to detecting the one or more user inputs, and in accordance with a determination that the workout session is not a shared workout session, the computer system displays a second user interface that does not include the one or more options (e.g., does not include the first option) (e.g., 1010). Automatically forgoing displaying the first set of one or more options in accordance with a determination that the workout session is not a shared workout session ensures that a user will not inadvertently provide undesirable user inputs (e.g., ensuring that the user does not select options that pertain to shared workout sessions when the user is not in a shared workout session). Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the user interface corresponding to the workout session (e.g., 1004B) comprises: in accordance with a determination that the workout session is a shared workout session with one or more external computer systems, the computer system displays, via the display generation component and within the user interface corresponding to the workout session, a quick send option (e.g., 1006A, 1006B) (e.g., an affordance; a user-selectable graphical element) that, when selected, causes the one or more external computer systems participating in the shared workout session to display visual content corresponding to the quick send option; and in accordance with a determination that the workout session is not a shared workout session (e.g., is an individual workout session and/or is a workout session that includes only one user) (e.g., is a workout session that is not shared amongst a plurality of computer systems that are participating in a communication session of a first type) (e.g., is a workout session that is not displayed at a plurality of computer systems in a synchronized manner), the computer system displays, via the display generation component, the user interface corresponding to the workout session (e.g., 1004A, 1004B) without displaying the quick send option (e.g., 1006A, 1006B) (e.g., forgoes displaying the first quick send option). In some embodiments, the quick send option is selectable to cause the one or more external computer systems participating in the shared workout session to display visual content corresponding to the quick send option while concurrently displaying video content corresponding to the shared workout session (e.g., video content separate from the visual content corresponding to the first option). Displaying a quick send option in the user interface corresponding to the workout session when the user is participating in a shared workout session provides the user with the ability to cause one or more external computer systems participating in the shared workout session to display particular visual content with minimal user input. Reducing the numbers of inputs required to perform an action, and providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the quick send option (e.g., 1006A, 1006B) within the user interface corresponding to the workout session (e.g., 1004A, 1004B) further comprises: displaying, at a first time, the quick send option with a first set of characteristics, wherein, at the first time: the quick send option is displayed in a first manner (e.g., is displayed with a first set of visual characteristics); and the quick send option is selectable to cause the one or more external computer systems participating in the shared workout session to display a first set of visual content (e.g., FIG. 10A, quick send option 1006B displayed at smiley face emoji); and displaying, at a second time subsequent to the first time, the quick send option with a second set of characteristics different from the first set of characteristics, wherein: the quick send option is transitioned from being displayed with the first set of characteristics to being displayed with the second of characteristics in response to detecting one or more user inputs (e.g., one or more touch inputs and/or one or more non-touch inputs) (e.g., 1030) corresponding to selection of a second option (e.g., 1028D) of the first set of one or more options (in some embodiments, the one or more user inputs corresponding to selection of the second option of the first set of one or more options causes the one or more external computer systems participating in the shared workout session to display visual content corresponding to the second option of the first set of one or more options); and, at the second time, the quick send option is displayed in a second manner that corresponds to the second option (e.g., with a second set of visual characteristics that correspond to the second option); and the quick send option is selectable to cause the one or more external computer systems participating in the shared workout session to display a second set of visual content that corresponds to the second option and is different from the first set of visual content (e.g., FIG. 10I, quick send option 1006B is transitioned to the heart emoji). In some embodiments, the quick send option is selectable to cause the one or more external computer systems participating in the shared workout session to display the same visual content that would be displayed if the user selected the second option of the first set of one or more options. Automatically updating the appearance and function of the quick send option in response to a most recent option selected by the user provides the user with the ability to re-send visual content to other computer systems with reduced user inputs. Performing an operation when a set of conditions has been met without requiring further user input and/or reducing the number of inputs required to perform an action enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the quick send option (e.g., 1006A, 1006B) further comprises: in accordance with a determination that a user has not selected an option from the first set of one or more options in the shared workout session: the quick send option is displayed with a first set of visual characteristics that correspond to the first option of the first set of one or more options (e.g., a predefined default option of the first set of one or more options) (e.g., 1006A, 1006B in FIG. 10A). The quick send option is selectable to cause the one or more external computer systems participating in the shared workout session to display a first set of visual content that corresponds to the first option. In some embodiments, the quick send option is selectable to cause the one or more external computer systems participating in the shared workout session to display the same visual content that would be displayed if the user selected the first option of the first set of one or more options. In some embodiments, the first option is a default option. Automatically applying a default set of characteristics to the quick send option provides the user with the ability to send visual content to other computer systems without further user input. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the quick send option (e.g., 1006A, 1006B) within the user interface corresponding to the workout session (e.g., 1004A, 1004B) further comprises: displaying, at a first time, the quick send option with a first set of characteristics, wherein, at the first time: the quick send option is displayed in a first manner (e.g., is displayed with a first set of visual characteristics); the quick send option is selectable to cause the one or more external computer systems participating in the shared workout session to display a first set of visual content (e.g., quick send options 1006A, 1006B in FIG. 10A); and displaying, at a second time subsequent to the first time, the quick send option with a second set of characteristics different from the first set of characteristics, wherein: the quick send option is transitioned from being displayed with the first set of characteristics to being displayed with the second set of characteristics in response to detecting a first event within the shared workout session (e.g., based on physical activity metrics for the plurality of computer systems participating in the shared workout session) (e.g., a goal accomplishment event) (e.g., based on a determination that a user of the computer system and/or a user of an external computer system participating in the shared workout session has satisfied one or more achievement criteria), wherein, at the second time, the quick send option is displayed in a second manner that corresponds to the first event (e.g., with a second set of visual characteristics that correspond to the first event (e.g., are determined based on the first event)); and the quick send option is selectable to cause the one or more external computer systems participating in the shared workout session to display a second set of visual content that corresponds to the first event (e.g., is determined based on the first event and/or is responsive to the first event) and is different from the first set of visual content (e.g., quick send options 1006A, 1006B in FIG. 10J). Automatically updating the appearance and function of the quick send option in response to an event that is detected in the shared workout session provides the user with the ability to send visual content to other computer systems that is responsive to the detected event with reduced user inputs. Performing an operation when a set of conditions has been met without requiring further user input and/or reducing the number of inputs required to perform an action enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the quick send option (e.g., 1006A, 1006B) within the user interface corresponding to the workout session (e.g., 1004A, 1004B) further comprises: displaying, at a first time, the quick send option with a first set of characteristics, wherein, at the first time: the quick send option is displayed in a first manner (e.g., is displayed with a first set of visual characteristics); and the quick send option is selectable to cause the one or more external computer systems participating in the shared workout session to display a first set of visual content (e.g., quick send option 1006A in FIG. 10A); and displaying, at a second time subsequent to the first time, the quick send option with a second set of characteristics different from the first set of characteristics, wherein the quick send option is transitioned from being displayed with the first set of characteristics to being displayed with the second set of characteristics in response to a determination that a first set of conditions has been satisfied at the computer system (e.g., in response to detecting a first achievement of a user of the computer system) (e.g., a first achievement of a plurality of predefined achievements) (e.g., based on physical activity metrics for the user of the computer system) (e.g., based on a determination that a user of the computer system has satisfied one or more achievement criteria and/or physical activity metric criteria) (e.g., based on a determination that the user has burned a target number of calories and/or has achieved a target heartrate and/or has exercised for a target number of minutes), wherein, at the second time, the quick send option is displayed in a second manner that corresponds to the first set of conditions (e.g., corresponds to a first achievement of the user of the computer system) (e.g., with a second set of visual characteristics that correspond to the first achievement of the user of the computer system (e.g., are determined based on the first achievement of the user of the computer system)); and the quick send option is selectable to cause the one or more external computer systems participating in the shared workout session to display a second set of visual content that corresponds to the first set of conditions (e.g., corresponds to the first achievement of the user of the computer system) (e.g., is determined based on the first achievement and/or is responsive to the first achievement) and is different from the first set of visual content (e.g., quick send option 1006A in FIG. 10J). Automatically updating the appearance and function of the quick send option in response to a first set of conditions being satisfied (e.g., in response to an achievement by the user of the computer system) provides the user with the ability to send visual content to other computer systems that is responsive to the first set of conditions with reduced user inputs. Performing an operation when a set of conditions has been met without requiring further user input and/or reducing the number of inputs required to perform an action enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, displaying the quick send option (e.g., 1006A, 1006B) within the user interface corresponding to the workout session (e.g., 1004A, 1004B) further comprises: displaying, at a first time, the quick send option with a first set of characteristics, wherein, at the first time: the quick send option is displayed in a first manner (e.g., is displayed with a first set of visual characteristics); and the quick send option is selectable to cause the one or more external computer systems participating in the shared workout session to display a first set of visual content (e.g., quick send option 1006B in FIG. 10A); and displaying, at a second time subsequent to the first time, the quick send option with a second set of characteristics different from the first set of characteristics, wherein: the quick send option is transitioned from being displayed with the first set of characteristics to being displayed with the second of characteristics in response to a determination that a second set of conditions has been satisfied at a first external computer system participating in the shared workout session (e.g., in response to detecting a first achievement of a user of a first external computer system participating in the shared workout session) (e.g., a first achievement of a plurality of pre-defined achievements) (e.g., based on physical activity metrics for the user of the first external computer system) (e.g., based on a determination that a user of the first external computer system has satisfied one or more achievement criteria and/or physical activity metric criteria) (e.g., based on a determination that the user of the first external computer system has burned a target number of calories and/or has achieved a target heartrate and/or has exercised for a target number of minutes), wherein, at the second time: the quick send option is displayed in a second manner that corresponds to the second set of conditions (e.g., corresponds to the first achievement of the user of the first external computer system) (e.g., with a second set of visual characteristics that correspond to the first achievement of the user of the first external computer system (e.g., are determined based on the first achievement of the user of the first external computer system)); and the quick send option is selectable to cause the one or more external computer systems participating in the shared workout session (e.g., including the first external computer system) (e.g., including a second external computer system different from the first external computer system) to display a second set of visual content that corresponds to the second set of conditions (e.g., corresponds to the first achievement of the user of the first external computer system) (e.g., is determined based on the first achievement and/or is responsive to the first achievement) and is different from the first set of visual content (e.g., quick send option 1006B in FIG. 10J). Automatically updating the appearance and function of the quick send option in response to satisfaction of a first set of conditions (e.g., in response to an achievement by a user of an external computer system participating in the shared workout session) provides the user with the ability to send visual content to other computer systems that is responsive to the first set of conditions with reduced user inputs. Performing an operation when a set of conditions has been met without requiring further user input and/or reducing the number of inputs required to perform an action enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, in response to detecting the one or more user inputs (e.g., 1008, 1014), the computer system ceases to display the user interface corresponding to the workout session (e.g., 1004B) (e.g., ceases display of the one or more physical activity metrics corresponding to the workout session) (e.g., regardless of whether or not the workout session is a shared workout session). Ceasing display of the user interface corresponding to the workout session in response to detecting the one or more user inputs provides the user with feedback about the current state of the device (e.g., that the device has detected the one or more user inputs). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first option (e.g., 1018A-1018D, 1028A-1028I), when selected, further causes at least one of the one or more external computer systems participating in the shared workout session to output a haptic output (e.g., a tactile output) (e.g., a vibration) (e.g., device 1000A in FIGS. 10D, 10E, 10G, 10K). In some embodiments, the first set of one or more options includes a second option different from the first option that, when selected, causes the one or more external computer systems participating in the shared workout session to output a haptic output. Causing an external computer system to output a haptic output in response to user selection of the first option provides the user of the external computer system with feedback about the current state of the external computer system (e.g., that the external computer system has received information indicative of selection of the first option by a user of the computer system). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first option (e.g., 1018A-1018D, 1028A-1028I), when selected, further causes the one or more external computer systems participating in the shared workout session to output an audio output (e.g., a first set of audio output (e.g., a first set of audio output corresponding to the first option)) (e.g., device 1000A in FIGS. 10D, 10E, 10G, 10K). In some embodiments, the first set of one or more options includes a second option different from the first option that, when selected, causes the one or more external computer systems participating in the shared workout session to output an audio output (e.g., a second set of audio output) (e.g., a second set of audio output that is the same as the first set of audio output or different from the first set of audio output). Causing an external computer system to output an audio output in response to user selection of the first option provides the user of the external computer system with feedback about the current state of the external computer system (e.g., that the external computer system has received information indicative of selection of the first option by a user of the computer system). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first option (e.g., 1018A-1018D, 1028A-1028I), when selected, causes: a first external electronic device (e.g., 800, 1000A) (e.g., an external computer system) corresponding to a first remote user (e.g., a watch, a wearable device) to display the visual content corresponding to the first option (e.g., 1022-1, 1022-2, 1026-1, 1026-2, 1032-1, 1032-2, 1044-1, 1044-2); and a second external electronic device corresponding to the first remote user (e.g., 800, 1000A) (e.g., a phone, a tablet, a media player, a television) and different from the first external electronic device to display the visual content corresponding to the first option (e.g., 1022-1, 1022-2, 1026-1, 1026-2, 1032-1, 1032-2, 1044-1, 1044-2). In some embodiments, the first external electronic device displays a first user interface corresponding to the workout session for the first remote user, including one or more physical activity metrics for the first remote user in the workout session; and the second external electronic device displays video content corresponding to the workout session (e.g., an instructional video demonstrating a workout) for the first remote user. In some embodiments, the first external computer system and the second external computer system display different user interfaces corresponding to the workout session for the first remote user. Causing an external electronic device to display visual content corresponding to the first option in response to user selection of the first option provides the user of the external computer system with feedback about the current state of the device (e.g., that the external electronic device has received information pertaining to selection of the first option by a user of the computer system). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first option (e.g., 1018A-1018D, 1028A-1028I), when selected, causes the first external electronic device corresponding to the first remote user to output a haptic output (e.g., a tactile output and/or a vibration) (e.g., device 1000A in FIGS. 10D, 10E, 10G, 10K) without causing the second external electronic device corresponding to the first remote user to output a haptic output (e.g., device 800 in FIGS. 10D, 10E, 10G, 10K). Causing an external computer system to output a haptic output in response to user selection of the first option provides the user of the external computer system with feedback about the current state of the external computer system (e.g., that the external computer system has received information indicative of selection of the first option by a user of the computer system). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first option (e.g., 1018A-1018D, 1028A-1028I), when selected, further causes the computer system (e.g., 1000B) to display, via the display generation component, the visual content corresponding to the first option (e.g., 1022-3, 1026-3, 1032-3, 1044-3). Causing the computer system to display visual content corresponding to the first option in response to selection of the first option by a user provides the user with feedback about the current state of the device (e.g., that the device has detected selection of the first option by the user). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first option (e.g., 1018A-1018D, 1028A-1028I), when selected, causes the one or more external computer systems (e.g., 800, 1000A) participating in the shared workout session to display a visual indication of a user of the computer system (e.g., 1024-1, 1024-2, 1024-3) (e.g., causes the one or more external computer systems to display a username and/or user profile picture corresponding to the computer system and/or the user of the computer system). Causing an external computer system to display a visual indication of a user of the computer system in response to the user of the computer system selecting the first option provides the user of the external computer system with feedback about the current state of the external computer system (e.g., that the external computer system has received information indicating that the user of the computer system has selected the first option). Providing improved feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first set of one or more options and/or the quick send option includes one or more of the following: one or more emoji options corresponding to different emojis (e.g., different emotions) (e.g., a smiling emoji, a laughing emoji, a sad emoji, an angry emoji, a tired emoji); a profile picture option that is selectable to cause the one or more external computer systems to display a profile picture corresponding to the computer system and/or a user of the computer system; a calories option that is selectable to cause the one or more external computer systems to display an indication of the number of calories burned by a user of the computer system (e.g., during the workout session and/or in the current day); a heartrate option that is selectable to cause the one or more external computer systems to display an indication of a heartrate (e.g., a current heartrate) of a user of the computer system; one or more options corresponding to messages of congratulations, support, and/or appreciation; and/or one or more options corresponding to messages of competition and/or trash talk.

Note that details of the processes described above with respect to method 1100 (e.g., FIG. 11) are also applicable in an analogous manner to the methods described above. For example, methods 700, 750, and 900 optionally include one or more of the characteristics of the various methods described above with reference to method 1100. For example, the communication session of the first type recited in methods 700, 750, 900, and 1100 are the same communication session in all three methods. For brevity, these details are not repeated above.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of workout content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver workout suggestions that are of greater interest to the user. Accordingly, use of such personal information data enables users to have calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of workout suggestions and/or shared workout content, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content, such as workout content and/or workout suggestions, can be selected and delivered to users by inferring preferences based on non-personal information data or a bare minimum amount of personal information, such as the content being requested by the device associated with a user, other non-personal information available to the content delivery services, or publicly available information.

What is claimed is:

1. A computer system that is configured to communicate with a display generation component and one or more input devices, comprising:
one or more processors; and
memory storing one or more programs configured to be executed by the one or more processors, the one or more programs including instructions for:
while the computer system is participating in a communication session of a first type with one or more external computer systems including a first external computer system:
receiving an indication that the first external computer system has initiated a shared workout session;
in response to receiving the indication that the first external computer system has initiated the shared workout session, displaying, via the display generation component, a user interface object corresponding to the shared workout session;
while displaying a first user interface and the user interface object corresponding to the shared workout session, detecting, via the one or more input devices, a user input; and
in response to detecting the user input while displaying the first user interface and the user interface object corresponding to the shared workout session:
in accordance with a determination that the user input corresponds to a request to join the shared workout session:
ceasing displaying the first user interface, while maintaining the communication session of the first type; and
displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and
in accordance with a determination that the user input does not correspond to a request to join the shared workout session, forgo displaying the content corresponding to the shared workout session, while maintaining the communication session of the first type;
after forgoing displaying the content corresponding to the shared workout session and while the computer system continues to participate in the communication session of the first type with one or more external computer systems, receiving a first set of one or more inputs corresponding to a request to display a user interface of a workout application; and
in response to the first set of one or more inputs, displaying the user interface of the workout application, wherein the user interface of the workout application includes a second user interface object corresponding to the shared workout session that, when selected, causes display, via the display generation component, of the content corresponding to the shared workout.

2. The computer system of claim 1, wherein:
while displaying the content associated with the shared workout session and while the computer system is participating in the communication session of the first type with one or more external computer systems, the computer system is configured to communicate with the one or more external computer systems via a communication modality of the communication session of the first type selected from the group consisting of: audio communication, video communication, text communication, screen content sharing communication, and a combination thereof.

3. The computer system of claim 1, the one or more programs further including instructions for:
while displaying the content corresponding to the shared workout session and while the computer system is participating in the communication session of the first type with one or more external computer systems, receiving notification data; and
in response to receiving the notification data:
in accordance with a determination that the notification data is associated with the communication session of the first type, displaying a first notification at a first location of the display generation component; and
in accordance with a determination that the notification data is associated with the shared workout session, displaying a second notification at a second location of the display generation component, different than the first location.

4. The computer system of claim 3, wherein the first notification indicates that a second external computer system is, via the communication session of the first type, joining the shared workout session or leaving the shared workout session.

5. The computer system of claim 3, wherein the first notification indicates that a third external computer system is joining the communication session of the first type or leaving the communication session of the first type.

6. The computer system of claim 3, wherein the second notification is a notification that includes first information related to the shared workout session for the computer system or for one or more external computer systems that are participating in the shared workout session.

7. The computer system of claim 6, wherein the first information is an indication that a user of a fourth external computer system that is in the communication session of the first type and that is participating in the shared workout session has achieved a predetermined physical activity goal or has achieved a change in status relative to one or more other participants for a first workout that corresponds to the shared workout session.

8. The computer system of claim 1, the one or more programs further including instructions for:
while displaying the content corresponding to the shared workout session and while the computer system is engaged in the communication session of the first type with one or more external computer systems, receiving a user input corresponding to a request to initiate a process for ending the display of content corresponding to the shared workout session;

in response to receiving the user input corresponding to a request to initiate a process for ending the display of content corresponding to the shared workout session, displaying:
- a first end option that, when selected, causes the computer system to cease displaying the content corresponding to the shared workout session, without causing at least one external computer system that is in the communication session of the first type and that is displaying the content corresponding to the shared workout session to cease displaying the content corresponding to the shared workout session; and
- a second end option that, when selected, causes the computer system to cease displaying the content corresponding to the shared workout session and causes at least one external computer system that is in the communication session of the first type and that is displaying the content corresponding to the shared workout session to cease displaying the content corresponding to the shared workout session.

9. The computer system of claim 8, the one or more programs further including instructions for:
receiving a user input corresponding to the first end option; and
in response to receiving the user input corresponding to the first end option, ceasing to display, via the display generation component in communication with the computer system, the content corresponding to the shared workout session, wherein the content corresponding to the shared workout session continues to be displayed via a display generation component that is in communication with at least one external computer system that is in the communication session of the first type after the computer system ceases to display the content corresponding to the shared workout session.

10. The computer system of claim 9, the one or more programs further including instructions for:
subsequent to ceasing to display the content corresponding to the shared workout session via the display generation component in communication with the computer system, receiving a first set of user inputs corresponding to a request to re-join the shared workout session; and
in response to receiving the first set of user inputs, displaying, via the display generation component in communication with the computer system, content corresponding to the shared workout session, wherein the content corresponding to the shared workout session that is displayed via the display generation component in communication with the computer system is synchronized with content corresponding to the shared workout session that is displayed via the display generation component that is in communication with the at least one external computer system that is in the communication session of the first type.

11. The computer system of claim 8, the one or more programs further including instructions for:
receiving a user input corresponding to the second end option;
in response to receiving the user input corresponding to the second end option:
ceasing to display, via the display generation component, the content corresponding to the shared workout session; and
causing at least one external computer system that is in the communication session of the first type and that is displaying the content corresponding to the shared workout session to cease displaying the content corresponding to the shared workout session.

12. The computer system of claim 1, the one or more programs further including instructions for:
while displaying the content corresponding to the shared workout session and while the computer system is engaged in the communication session of the first type with one or more external computer systems that includes a fifth external computer system that is displaying the content corresponding to the shared workout session, receiving a user input corresponding to a request to pause the shared workout session;
in response to receiving the user input corresponding to the request to pause the shared workout session:
pausing the shared workout session; and
causing the fifth external computer system to pause display of the content corresponding to the shared workout session.

13. The computer system of claim 1, the one or more programs further including instructions for:
while displaying the content corresponding to the shared workout session and while the computer system is engaged in the communication session of the first type with one or more external computer systems including a sixth external computer system that is displaying the content corresponding to the shared workout session, receiving a request from the sixth external computer system to end the shared workout session and to cease displaying the content corresponding to the shared workout session; and
in response to receiving the request from the sixth external computer system, ending the workout session on the computer system.

14. The computer system of claim 1, the one or more programs further including instructions for:
while displaying the content corresponding to the shared workout session and while the computer system is engaged in the communication session of the first type with one or more external computer systems including a seventh external computer system that is displaying the content corresponding to the shared workout session, receiving a request from the seventh external computer system to pause displaying the content corresponding to the shared workout session; and
in response to receiving the request from the seventh external computer system, pausing display of the content corresponding to the shared workout session.

15. The computer system of claim 1, the one or more programs further including instructions for:
after completing the shared workout session, displaying, via the display generation component, a workout summary user interface that includes:
physical activity data collected by the computer system for a user of the computer system; and
an indication of one or more external computer systems that were in the communication session of the first type with the computer system and participated in the shared workout session.

16. The computer system of claim 1, the one or more programs further including instructions for:

while displaying, via the display generation component, the content corresponding to the shared workout session, receiving a request to cause a second display generation component that is in communication with the computer system to display the content corresponding to the shared workout session; and in response to the request to cause a second display generation component that is in communication with the computer system to display the content corresponding to the shared workout session, causing the second display generation component to display the content corresponding to the shared workout session.

17. The computer system of claim 16, the one or more programs further including instructions for:

while causing display of the content corresponding to the shared workout session at the second display generation component, receiving second notification data; and in response to the second notification data:

in accordance with a determination that the second notification data is associated with the communication session of the first type, displaying a third notification via the display generation component; and in accordance with a determination that the second notification data is associated with the shared workout session, causing display of a fourth notification at the second display generation component.

18. A non-transitory computer-readable storage medium storing one or more programs configured to be executed by one or more processors of a computer system that is in communication with a display generation component and one or more input devices, the one or more programs including instructions for:

while the computer system is participating in a communication session of a first type with one or more external computer systems including a first external computer system:

receiving an indication that the first external computer system has initiated a shared workout session;

in response to receiving the indication that the first external computer system has initiated the shared workout session, displaying, via the display generation component, a user interface object corresponding to the shared workout session;

while displaying a first user interface and the user interface object corresponding to the shared workout session, detecting, via the one or more input devices, a user input; and in response to detecting the user input while displaying the first user interface and the user interface object corresponding to the shared workout session:

in accordance with a determination that the user input corresponds to a request to join the shared workout session:

ceasing displaying the first user interface, while maintaining the communication session of the first type; and displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and in accordance with a determination that the user input does not correspond to a request to join the shared workout session, forgo displaying the content corresponding to the shared workout session, while maintaining the communication session of the first type;

after forgoing displaying the content corresponding to the shared workout session and while the computer system continues to participate in the communication session of the first type with one or more external computer systems, receiving a first set of one or more inputs corresponding to a request to display a user interface of a workout application; and in response to the first set of one or more inputs, displaying the user interface of the workout application, wherein the user interface of the workout application includes a second user interface object corresponding to the shared workout session that, when selected, causes display, via the display generation component, of the content corresponding to the shared workout.

19. A method, comprising:

at a computer system that is in communication with a display generation component and one or more input devices:

while the computer system is participating in a communication session of a first type with one or more external computer systems including a first external computer system:

receiving an indication that the first external computer system has initiated a shared workout session;

in response to receiving the indication that the first external computer system has initiated the shared workout session, displaying, via the display generation component, a user interface object corresponding to the shared workout session;

while displaying a first user interface and the user interface object corresponding to the shared workout session, detecting, via the one or more input devices, a user input; and in response to detecting the user input while displaying the first user interface and the user interface object corresponding to the shared workout session:

in accordance with a determination that the user input corresponds to a request to join the shared workout session:

ceasing displaying the first user interface, while maintaining the communication session of the first type; and displaying, via the display generation component, content corresponding to the shared workout session, while maintaining the communication session of the first type, wherein display of the content corresponding to the shared workout session is initiated from a first playback position based on a playback position of corresponding content being displayed at the first external computer system; and in accordance with a determination that the user input does not correspond to a request to join the shared workout session, forgo displaying the content corresponding to the shared workout session, while maintaining the communication session of the first type;

after forgoing displaying the content corresponding to the shared workout session and while the computer system continues to participate in the communication session of the first type with one or more external computer systems, receiving a first set of one or more inputs corresponding to a request to display a user interface of a workout application; and in response to the first set of one or more inputs, displaying the user interface of the workout application, wherein the user interface of the workout application includes a second user interface object corresponding to the shared workout session that, when selected, causes display, via the display generation component, of the content corresponding to the shared workout.

20. The non-transitory computer-readable storage medium of claim 18, wherein:

while displaying the content associated with the shared workout session and while the computer system is participating in the communication session of the first type with one or more external computer systems, the computer system is configured to communicate with the one or more external computer systems via a communication modality of the communication session of the first type selected from the group consisting of: audio communication, video communication, text communication, screen content sharing communication, and a combination thereof.

21. The non-transitory computer-readable storage medium of claim 18, the one or more programs further including instructions for:

while displaying the content corresponding to the shared workout session and while the computer system is participating in the communication session of the first type with one or more external computer systems, receiving notification data; and in response to receiving the notification data:
in accordance with a determination that the notification data is associated with the communication session of the first type, displaying a first notification at a first location of the display generation component; and
in accordance with a determination that the notification data is associated with the shared workout session, displaying a second notification at a second location of the display generation component, different than the first location.

22. The non-transitory computer-readable storage medium of claim 21, wherein the first notification indicates that a second external computer system is, via the communication session of the first type, joining the shared workout session or leaving the shared workout session.

23. The non-transitory computer-readable storage medium of claim 21, wherein the first notification indicates that a third external computer system is joining the communication session of the first type or leaving the communication session of the first type.

24. The non-transitory computer-readable storage medium of claim 21, wherein the second notification is a notification that includes first information related to the shared workout session for the computer system or for one or more external computer systems that are participating in the shared workout session.

25. The non-transitory computer-readable storage medium of claim 24, wherein the first information is an indication that a user of a fourth external computer system that is in the communication session of the first type and that is participating in the shared workout session has achieved a predetermined physical activity goal or has achieved a change in status relative to one or more other participants for a first workout that corresponds to the shared workout session.

26. The non-transitory computer-readable storage medium of claim 18, the one or more programs further including instructions for:

while displaying the content corresponding to the shared workout session and while the computer system is engaged in the communication session of the first type with one or more external computer systems, receiving a user input corresponding to a request to initiate a process for ending the display of content corresponding to the shared workout session;

in response to receiving the user input corresponding to a request to initiate a process for ending the display of content corresponding to the shared workout session, displaying:
a first end option that, when selected, causes the computer system to cease displaying the content corresponding to the shared workout session, without causing at least one external computer system that is in the communication session of the first type and that is displaying the content corresponding to the shared workout session to cease displaying the content corresponding to the shared workout session; and
a second end option that, when selected, causes the computer system to cease displaying the content corresponding to the shared workout session and causes at least one external computer system that is in the communication session of the first type and that is displaying the content corresponding to the shared workout session to cease displaying the content corresponding to the shared workout session.

27. The non-transitory computer-readable storage medium of claim 26, the one or more programs further including instructions for:

receiving a user input corresponding to the first end option; and in response to receiving the user input corresponding to the first end option, ceasing to display, via the display generation component in communication with the computer system, the content corresponding to the shared workout session, wherein the content corresponding to the shared workout session continues to be displayed via a display generation component that is in communication with at least one external computer system that is in the communication session of the first type after the computer system ceases to display the content corresponding to the shared workout session.

28. The non-transitory computer-readable storage medium of claim 27, the one or more programs further including instructions for:

subsequent to ceasing to display the content corresponding to the shared workout session via the display generation component in communication with the computer system, receiving a first set of user inputs corresponding to a request to re-join the shared workout session; and in response to receiving the first set of user inputs, displaying, via the display generation component in communication with the computer system, content corresponding to the shared workout session, wherein the content corresponding to the shared workout session that is displayed via the display generation component in communication with the computer system is synchronized with content corresponding to the shared workout session that is displayed via the display generation component that is in communication with the at least one external computer system that is in the communication session of the first type.

29. The non-transitory computer-readable storage medium of claim 26, the one or more programs further including instructions for:
receiving a user input corresponding to the second end option;
in response to receiving the user input corresponding to the second end option:
ceasing to display, via the display generation component, the content corresponding to the shared workout session; and
causing at least one external computer system that is in the communication session of the first type and that is displaying the content corresponding to the shared workout session to cease displaying the content corresponding to the shared workout session.

30. The non-transitory computer-readable storage medium of claim 18, the one or more programs further including instructions for:
while displaying the content corresponding to the shared workout session and while the computer system is engaged in the communication session of the first type with one or more external computer systems that includes a fifth external computer system that is displaying the content corresponding to the shared workout session, receiving a user input corresponding to a request to pause the shared workout session;
in response to receiving the user input corresponding to the request to pause the shared workout session:
pausing the shared workout session; and
causing the fifth external computer system to pause display of the content corresponding to the shared workout session.

31. The non-transitory computer-readable storage medium of claim 18, the one or more programs further including instructions for:
while displaying the content corresponding to the shared workout session and while the computer system is engaged in the communication session of the first type with one or more external computer systems including a sixth external computer system that is displaying the content corresponding to the shared workout session, receiving a request from the sixth external computer system to end the shared workout session and to cease displaying the content corresponding to the shared workout session; and
in response to receiving the request from the sixth external computer system, ending the workout session on the computer system.

32. The non-transitory computer-readable storage medium of claim 18, the one or more programs further including instructions for:
while displaying the content corresponding to the shared workout session and while the computer system is engaged in the communication session of the first type with one or more external computer systems including a seventh external computer system that is displaying the content corresponding to the shared workout session, receiving a request from the seventh external computer system to pause displaying the content corresponding to the shared workout session; and
in response to receiving the request from the seventh external computer system, pausing display of the content corresponding to the shared workout session.

33. The non-transitory computer-readable storage medium of claim 18, the one or more programs further including instructions for:
after completing the shared workout session, displaying, via the display generation component, a workout summary user interface that includes:
physical activity data collected by the computer system for a user of the computer system; and
an indication of one or more external computer systems that were in the communication session of the first type with the computer system and participated in the shared workout session.

34. The non-transitory computer-readable storage medium of claim 18, the one or more programs further including instructions for:
while displaying, via the display generation component, the content corresponding to the shared workout session, receiving a request to cause a second display generation component that is in communication with the computer system to display the content corresponding to the shared workout session; and
in response to the request to cause a second display generation component that is in communication with the computer system to display the content corresponding to the shared workout session, causing the second display generation component to display the content corresponding to the shared workout session.

35. The non-transitory computer-readable storage medium of claim 34, the one or more programs further including instructions for:
while causing display of the content corresponding to the shared workout session at the second display generation component, receiving second notification data; and
in response to the second notification data:
in accordance with a determination that the second notification data is associated with the communication session of the first type, displaying a third notification via the display generation component; and
in accordance with a determination that the second notification data is associated with the shared workout session, causing display of a fourth notification at the second display generation component.

36. The method of claim 19, wherein:
while displaying the content associated with the shared workout session and while the computer system is participating in the communication session of the first type with one or more external computer systems, the computer system is configured to communicate with the one or more external computer systems via a communication modality of the communication session of the first type selected from the group consisting of: audio communication, video communication, text communication, screen content sharing communication, and a combination thereof.

37. The method of claim 19, the further comprising:
while displaying the content corresponding to the shared workout session and while the computer system is participating in the communication session of the first type with one or more external computer systems, receiving notification data; and
in response to receiving the notification data:
in accordance with a determination that the notification data is associated with the communication session of the first type, displaying a first notification at a first location of the display generation component; and in accordance with a determination that the notification data is associated with the shared workout session, displaying a second notification at a second location of the display generation component, different than the first location.

38. The method of claim 37, wherein the first notification indicates that a second external computer system is, via the communication session of the first type, joining the shared workout session or leaving the shared workout session.

39. The method of claim 37, wherein the first notification indicates that a third external computer system is joining the communication session of the first type or leaving the communication session of the first type.

40. The method of claim 37, wherein the second notification is a notification that includes first information related to the shared workout session for the computer system or for one or more external computer systems that are participating in the shared workout session.

41. The method of claim 40, wherein the first information is an indication that a user of a fourth external computer system that is in the communication session of the first type and that is participating in the shared workout session has achieved a predetermined physical activity goal or has achieved a change in status relative to one or more other participants for a first workout that corresponds to the shared workout session.

42. The method of claim 19, further comprising:
while displaying the content corresponding to the shared workout session and while the computer system is engaged in the communication session of the first type with one or more external computer systems, receiving a user input corresponding to a request to initiate a process for ending the display of content corresponding to the shared workout session;
in response to receiving the user input corresponding to a request to initiate a process for ending the display of content corresponding to the shared workout session, displaying:
  a first end option that, when selected, causes the computer system to cease displaying the content corresponding to the shared workout session, without causing at least one external computer system that is in the communication session of the first type and that is displaying the content corresponding to the shared workout session to cease displaying the content corresponding to the shared workout session; and
  a second end option that, when selected, causes the computer system to cease displaying the content corresponding to the shared workout session and causes at least one external computer system that is in the communication session of the first type and that is displaying the content corresponding to the shared workout session to cease displaying the content corresponding to the shared workout session.

43. The method of claim 42, further comprising:
receiving a user input corresponding to the first end option; and
in response to receiving the user input corresponding to the first end option, ceasing to display, via the display generation component in communication with the computer system, the content corresponding to the shared workout session, wherein the content corresponding to the shared workout session continues to be displayed via a display generation component that is in communication with at least one external computer system that is in the communication session of the first type after the computer system ceases to display the content corresponding to the shared workout session.

44. The method of claim 43, further comprising:
subsequent to ceasing to display the content corresponding to the shared workout session via the display generation component in communication with the computer system, receiving a first set of user inputs corresponding to a request to re-join the shared workout session; and
in response to receiving the first set of user inputs, displaying, via the display generation component in communication with the computer system, content corresponding to the shared workout session, wherein the content corresponding to the shared workout session that is displayed via the display generation component in communication with the computer system is synchronized with content corresponding to the shared workout session that is displayed via the display generation component that is in communication with the at least one external computer system that is in the communication session of the first type.

45. The method of claim 42, further comprising:
receiving a user input corresponding to the second end option;
in response to receiving the user input corresponding to the second end option:
  ceasing to display, via the display generation component, the content corresponding to the shared workout session; and
  causing at least one external computer system that is in the communication session of the first type and that is displaying the content corresponding to the shared workout session to cease displaying the content corresponding to the shared workout session.

46. The method of claim 19, further comprising:
while displaying the content corresponding to the shared workout session and while the computer system is engaged in the communication session of the first type with one or more external computer systems that includes a fifth external computer system that is displaying the content corresponding to the shared workout session, receiving a user input corresponding to a request to pause the shared workout session;
in response to receiving the user input corresponding to the request to pause the shared workout session:
  pausing the shared workout session; and
  causing the fifth external computer system to pause display of the content corresponding to the shared workout session.

47. The method of claim 19, further comprising:
while displaying the content corresponding to the shared workout session and while the computer system is engaged in the communication session of the first type with one or more external computer systems including a sixth external computer system that is displaying the content corresponding to the shared workout session, receiving a request from the sixth external computer system to end the shared workout session and to cease displaying the content corresponding to the shared workout session; and
in response to receiving the request from the sixth external computer system, ending the workout session on the computer system.

48. The method of claim 19, further comprising:
while displaying the content corresponding to the shared workout session and while the computer system is engaged in the communication session of the first type with one or more external computer systems including a seventh external computer system that is displaying the content corresponding to the shared workout session, receiving a request from the seventh external computer system to pause displaying the content corresponding to the shared workout session; and in response to receiving the request from the seventh external computer system, pausing display of the content corresponding to the shared workout session.

49. The method of claim 19, further comprising:

after completing the shared workout session, displaying, via the display generation component, a workout summary user interface that includes:

physical activity data collected by the computer system for a user of the computer system; and an indication of one or more external computer systems that were in the communication session of the first type with the computer system and participated in the shared workout session.

50. The method of claim 19, further comprising:

while displaying, via the display generation component, the content corresponding to the shared workout session, receiving a request to cause a second display generation component that is in communication with the computer system to display the content corresponding to the shared workout session; and in response to the request to cause a second display generation component that is in communication with the computer system to display the content corresponding to the shared workout session, causing the second display generation component to display the content corresponding to the shared workout session.

51. The method of claim 50, further comprising:

while causing display of the content corresponding to the shared workout session at the second display generation component, receiving second notification data; and in response to the second notification data:
- in accordance with a determination that the second notification data is associated with the communication session of the first type, displaying a third notification via the display generation component; and
- in accordance with a determination that the second notification data is associated with the shared workout session, causing display of a fourth notification at the second display generation component.

\* \* \* \* \*